(12) United States Patent
Sun et al.

(10) Patent No.: US 8,680,137 B2
(45) Date of Patent: Mar. 25, 2014

(54) AGENTS AND METHODS FOR TREATING ISCHEMIC AND OTHER DISEASES

(75) Inventors: Xiujun Sun, Toronto (CA); Michael Tymianski, Toronto (CA); Jonathan David Garman, Thornhill (CA)

(73) Assignee: Nono Inc. (CA)

( * ) Notice: Subject to any disclaimer, the term of this patent is extended or adjusted under 35 U.S.C. 154(b) by 151 days.

(21) Appl. No.: 12/966,871

(22) Filed: Dec. 13, 2010

(65) Prior Publication Data
US 2011/0251182 A1    Oct. 13, 2011

Related U.S. Application Data

(60) Provisional application No. 61/312,154, filed on Mar. 9, 2010, provisional application No. 61/285,954, filed on Dec. 11, 2009.

(51) Int. Cl.
| | | |
|---|---|---|
| *A01N 43/12* | (2006.01) | |
| *A61K 31/38* | (2006.01) | |
| *A01N 43/06* | (2006.01) | |
| *C07D 333/00* | (2006.01) | |
| *C07D 311/02* | (2006.01) | |

(52) U.S. Cl.
USPC .............. 514/443; 514/445; 549/57; 549/283

(58) Field of Classification Search
USPC .............................. 514/443, 445; 549/57, 283
See application file for complete search history.

(56) References Cited

U.S. PATENT DOCUMENTS

2009/0004209 A1    1/2009  Ruchelman et al.

FOREIGN PATENT DOCUMENTS

KR       10-0821683 B1    4/2008

OTHER PUBLICATIONS

PCT Search Report and Written Opinion of the International Searching Authority for application PCT/US2010/059976 mailed Oct. 18, 2011.

*Primary Examiner* — Samira Jean-Louis
(74) *Attorney, Agent, or Firm* — Alston & Bird LLP

(57) ABSTRACT

This invention relates to methods of screening for modulators of mammalian cell injury cause by TRPM7 gene and protein activity, compounds that modulate TRPM7 gene and protein activity and methods of treatment of mammalian cell injury using modulators of TRPM7 gene and protein activity.

3 Claims, 85 Drawing Sheets

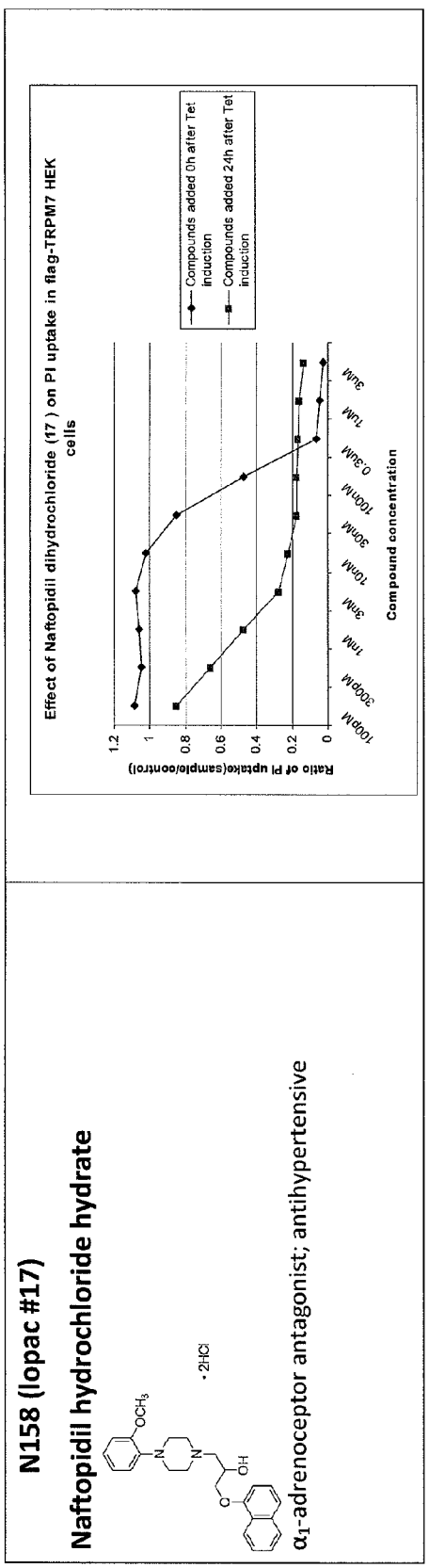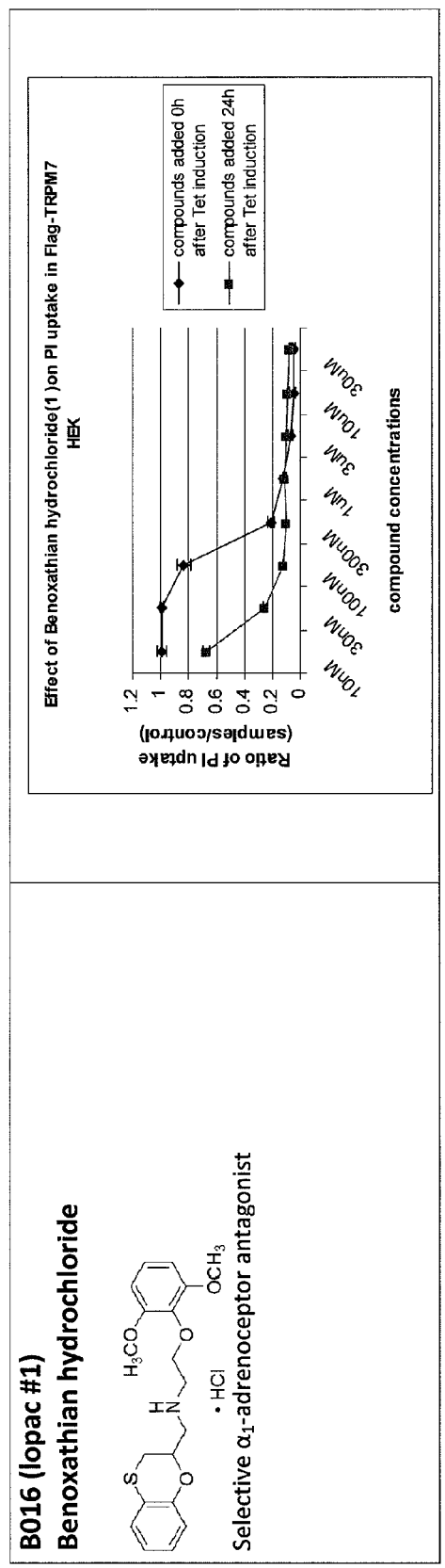

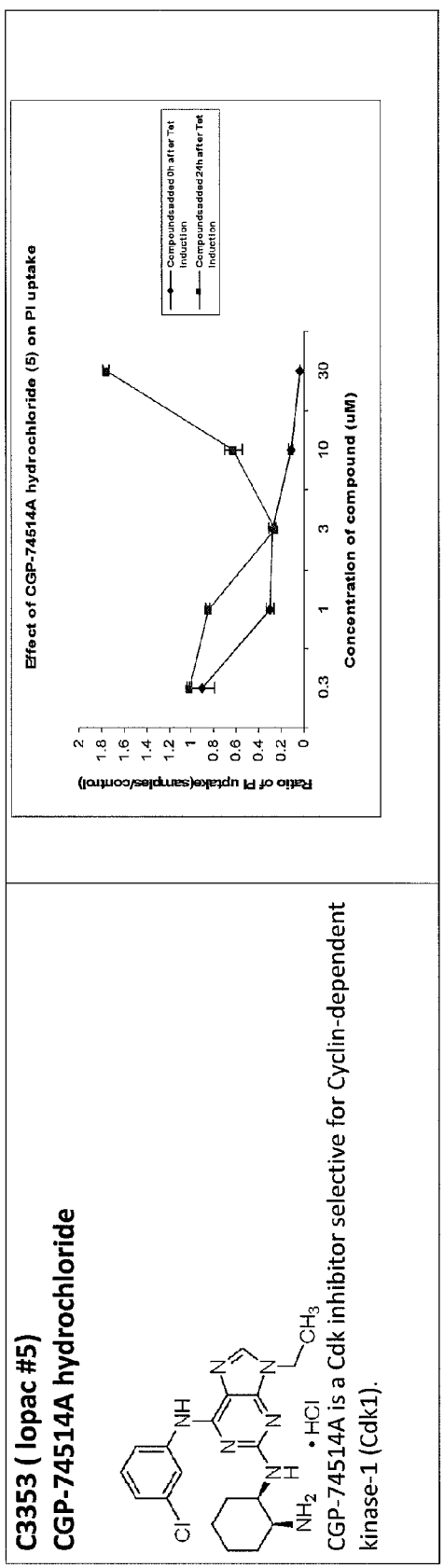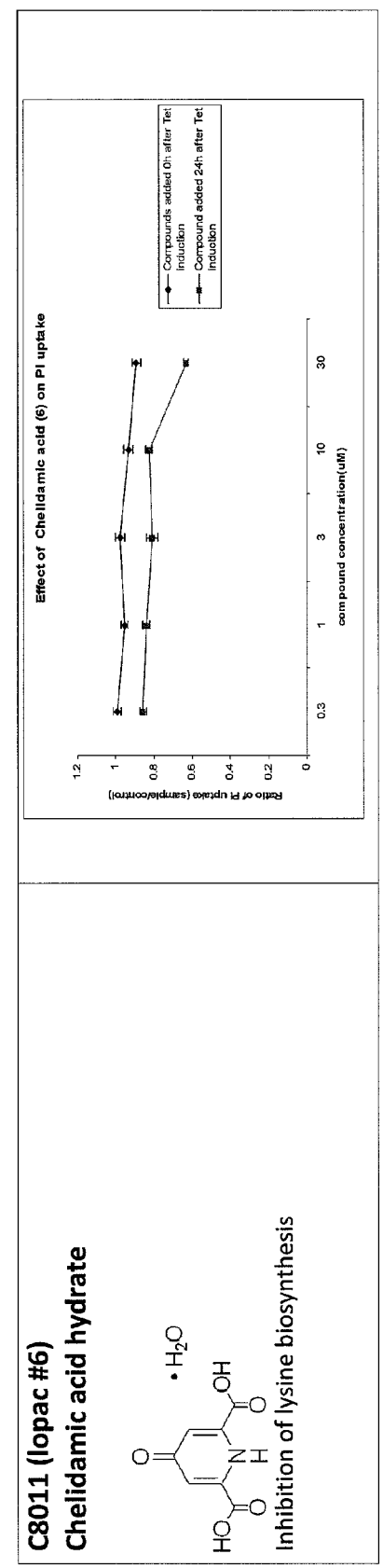
Fig. 3A
Fig. 3B

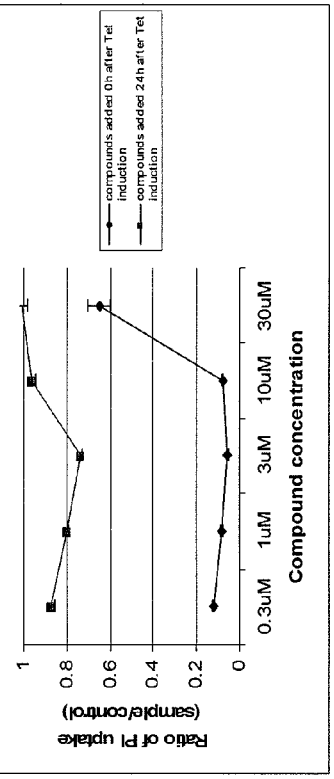
Fig. 4A
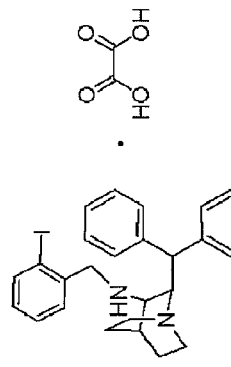
L119 (lopac #11)
L-703,606 oxalate salt hydrate
Potent and selective non-peptide NK-1 tachykinin receptor antagonist
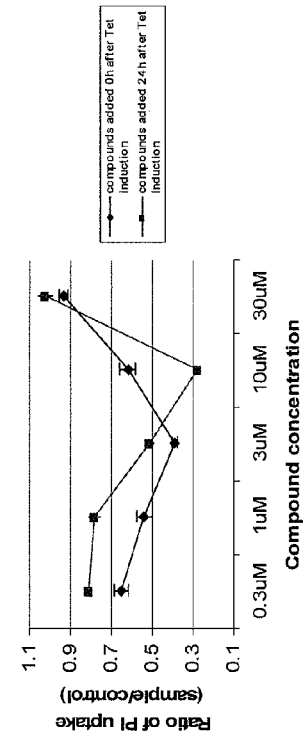
Fig. 4B
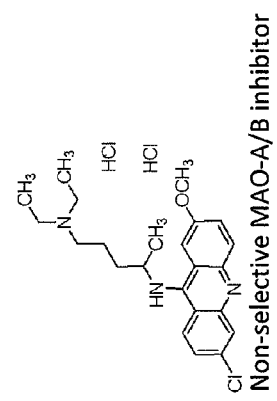
Q3251 (lopac #19)
Quinacrine dihydrochloride
Non-selective MAO-A/B inhibitor

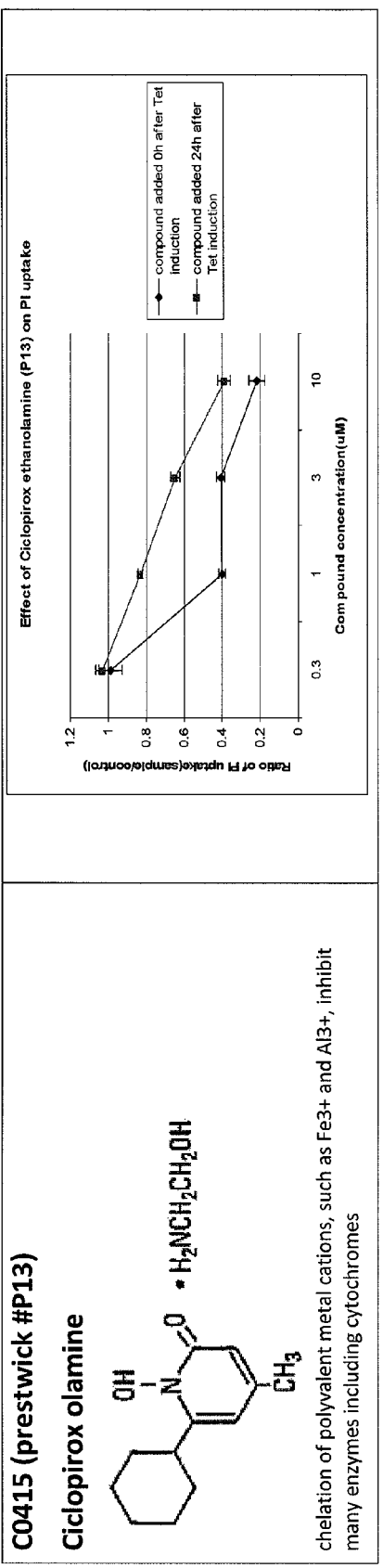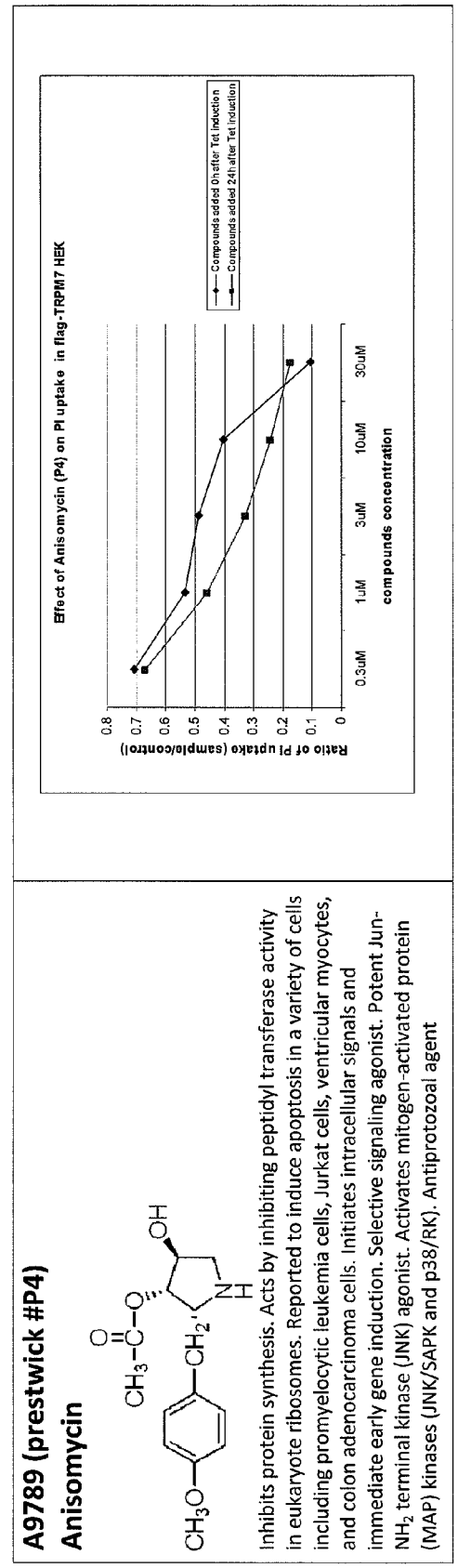

| Drug | Structure | Titration | #'s |
|---|---|---|---|
| M1 | 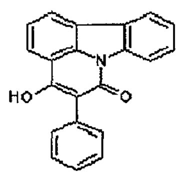 | | A |
| M2 | 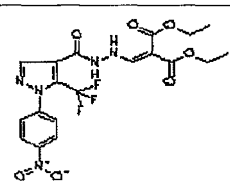 | | A |
| M3 | 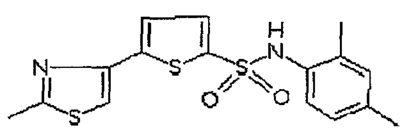 | | A |
| M4 | 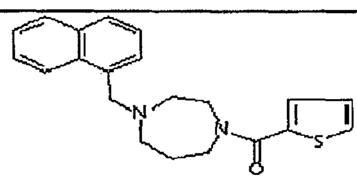 | | A |

Fig. 11

| Drug | Structure | Titration | #'s |
|---|---|---|---|
| M5 | 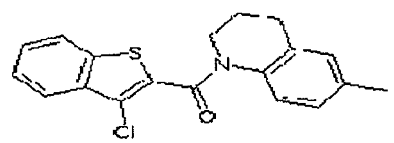 | | A B C D |
| M6 | 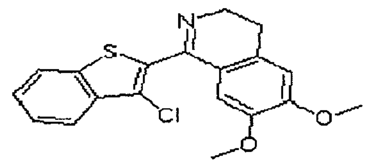 | | A B C D |
| M7 | 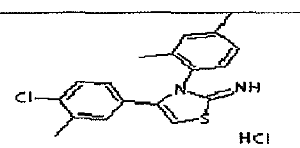 | | A B C D |
| M8 | 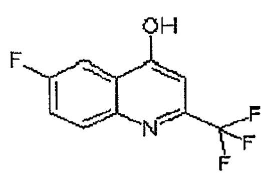 | | A |
| M9 | 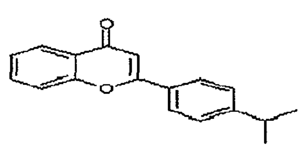 | | A |

Fig. 12

| Drug | Structure | Titration | #'s |
|---|---|---|---|
| M10 | 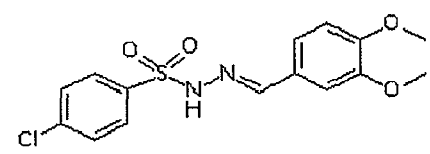 | | A |
| M11 | 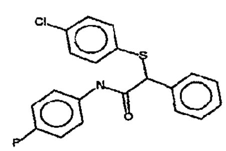 | | A B C D |
| M12 | 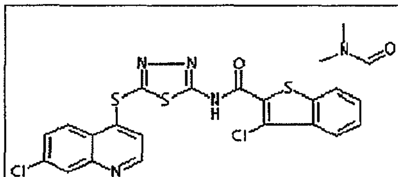 | | A |
| M13 | 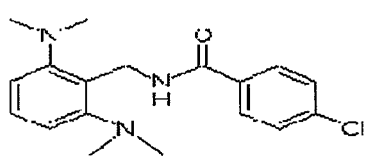 | | A |
| M14 | 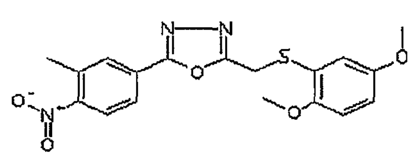 | | A B C D |

Fig. 13

| Drug | Structure | Titration | #'s |
|---|---|---|---|
| M15 | 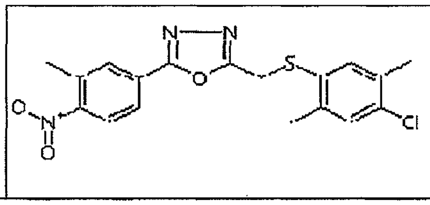 | | A |
| M16 | 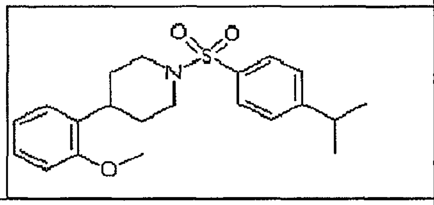 | | A |
| M17 | 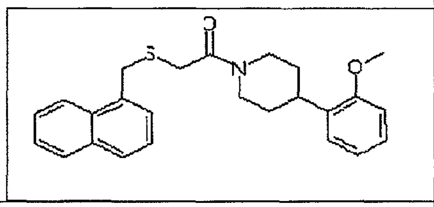 | | A |
| M18 | 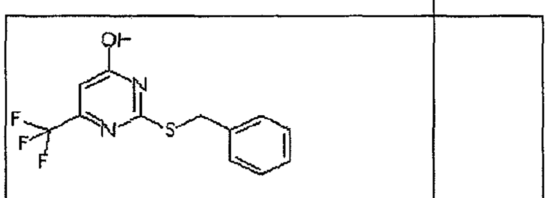 | | A |
| M19 | 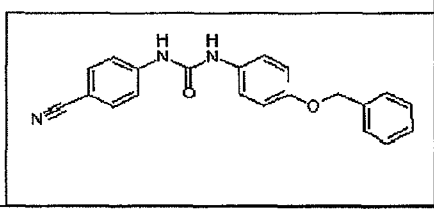 | | A |

Fig. 14

| Drug | Structure | Titration | #'s |
|---|---|---|---|
| M25 | 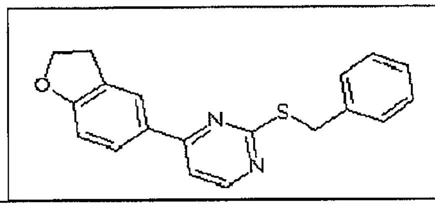 | | A |
| M26 | 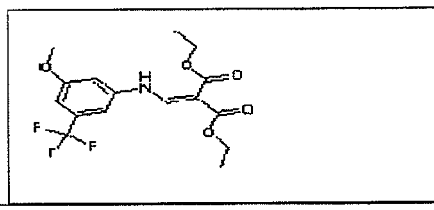 | | A |
| M27 | 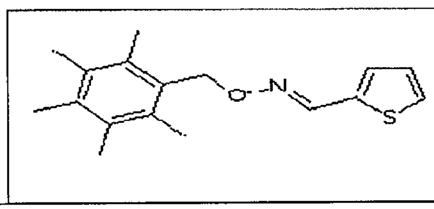 | | A |
| M28 | 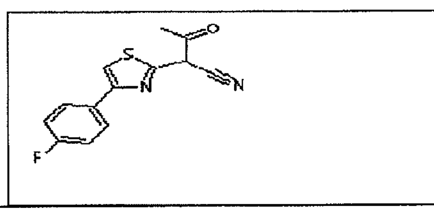 | | A |
| M29 | 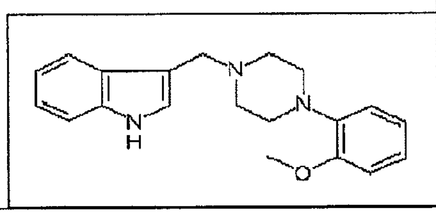 | | A |
| M30 | 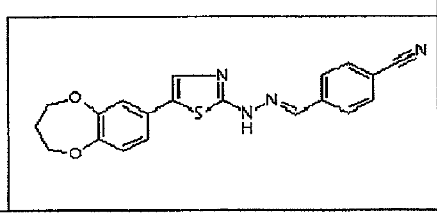 | | A |

Fig. 16

PI uptake in flag-TRPM7 HEK293T in 24-well plate
PI uptake in Flag-TRPM7 transfected HEK293 Incubated at 37°C without $CO_2$
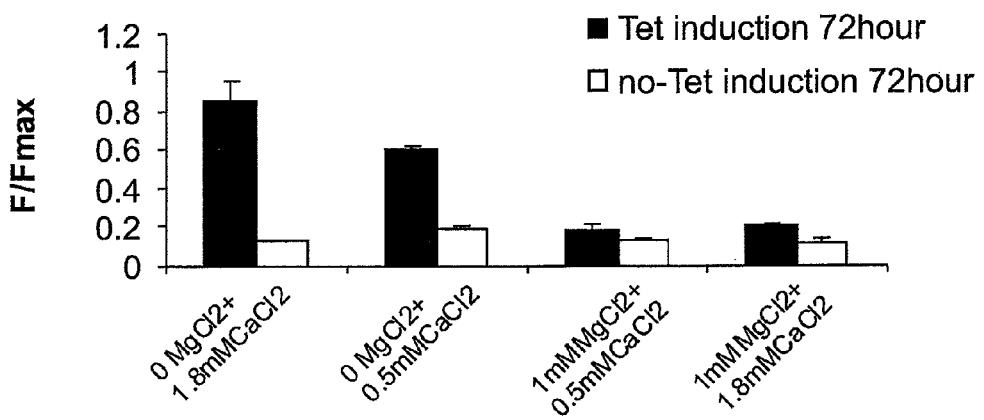
PI uptake in Flag-TRPM7 transfected HEK293 Incubated at 37°C with 5% $CO_2$
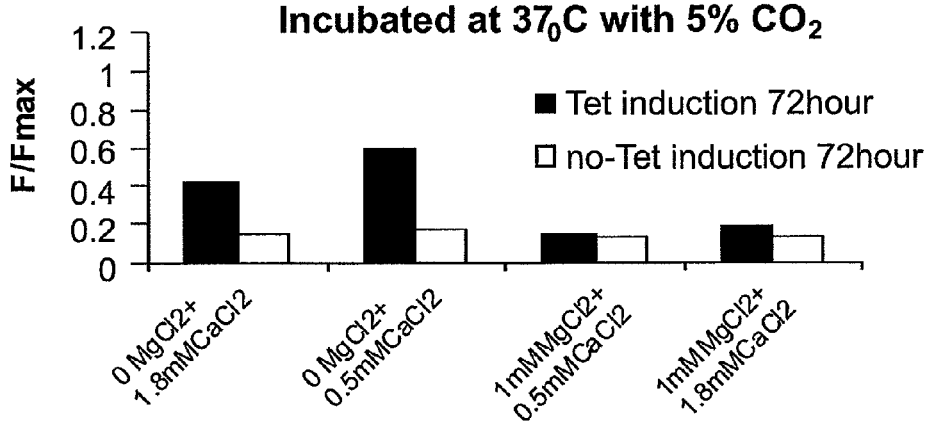
Figure 18

Fig. 21
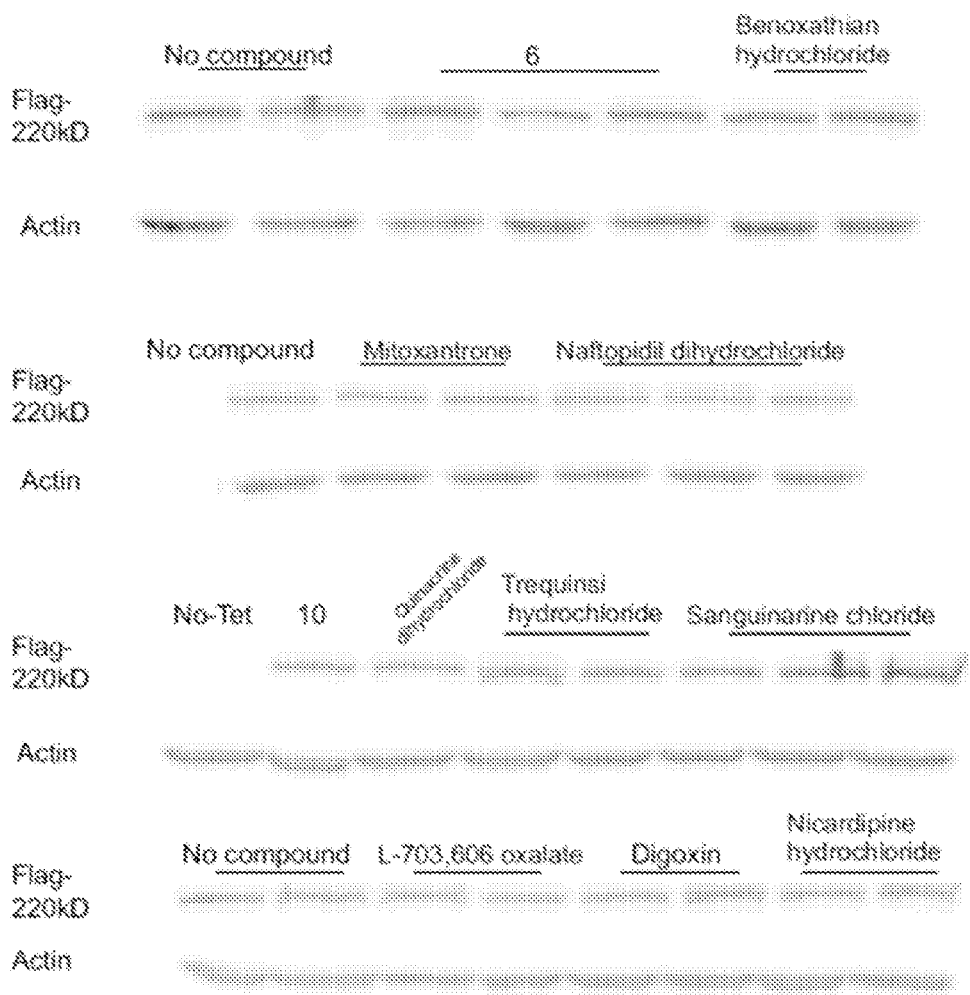
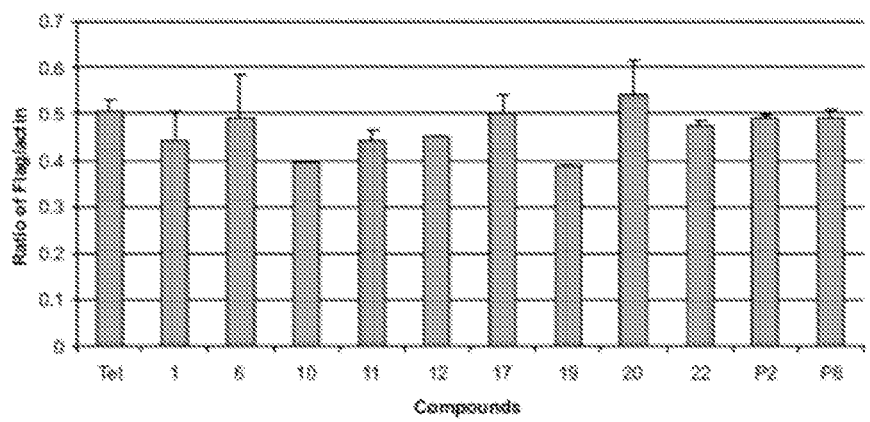

Scatterplots of B-scorse obtained using screening in 384 well plates
Plate 1 to 79
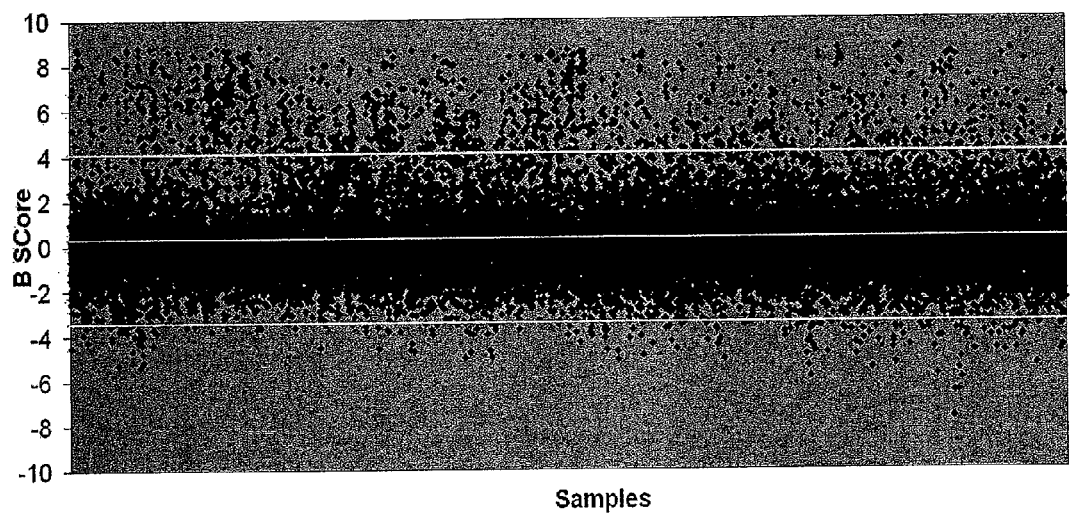
Plate 80 to 157
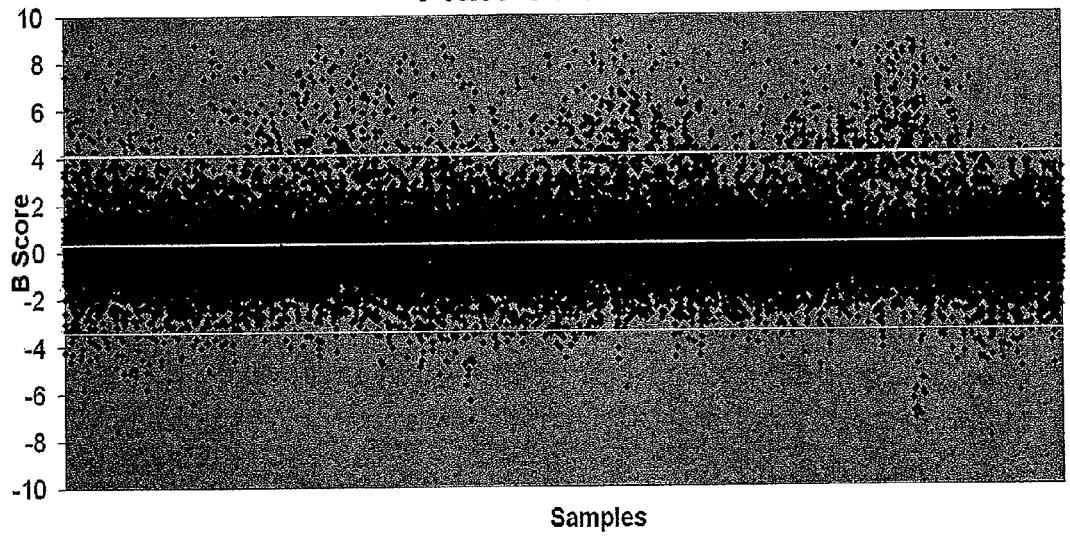
Figure 22

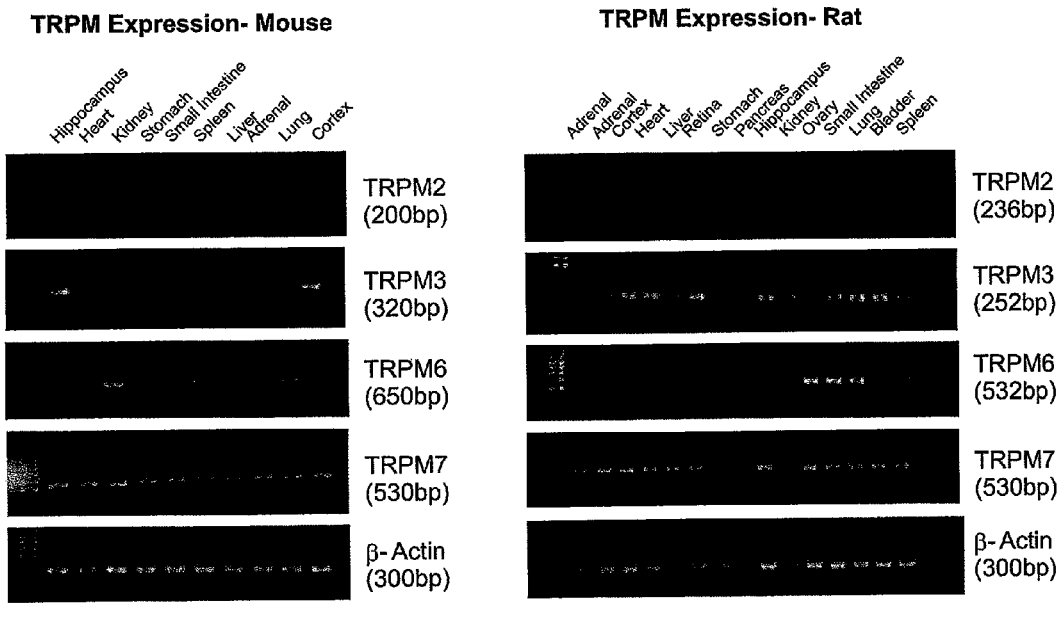
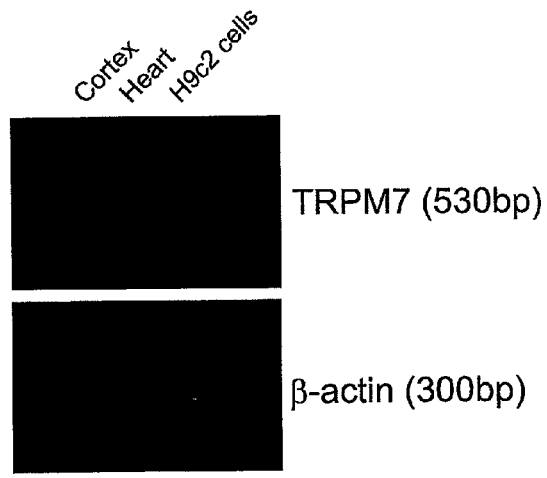
Figure 23

TRPM7 antibody (NeuroMab N74/25 + GAM Alexa488)   H9c2 cardiac myocytes
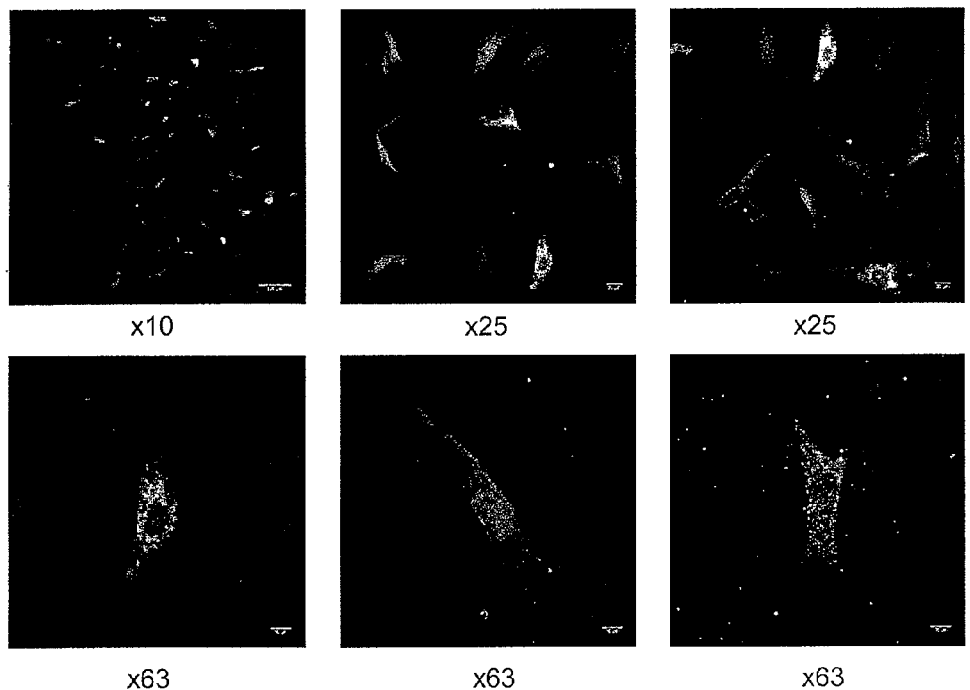
TRPM7 antibody (NeuroMab N74/25 + GAM Alexa568)   H9c2 cardiac myocytes
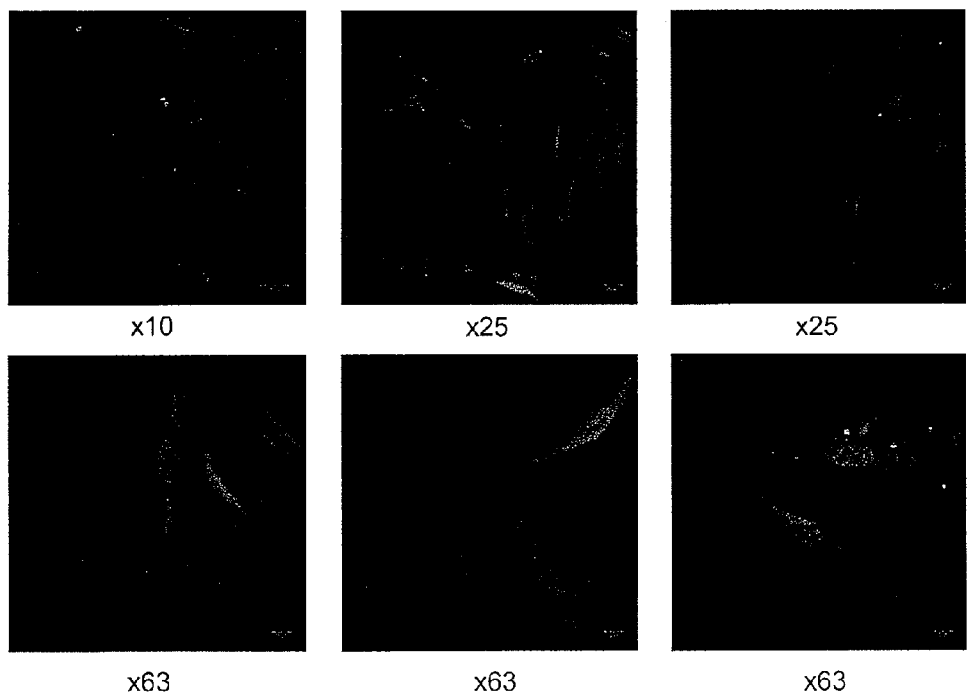
Figure 24

A
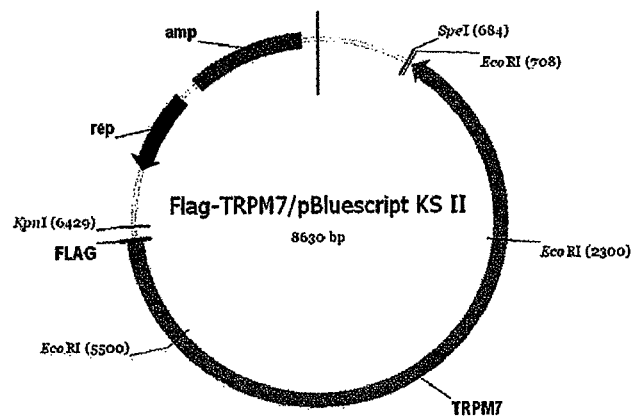
B
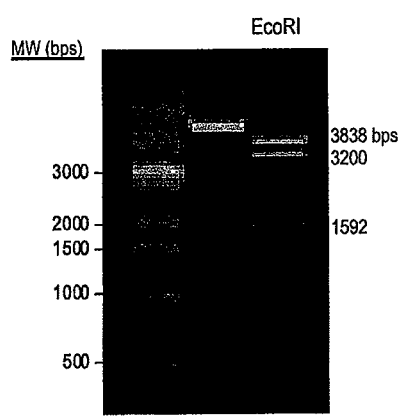
Figure 27

A
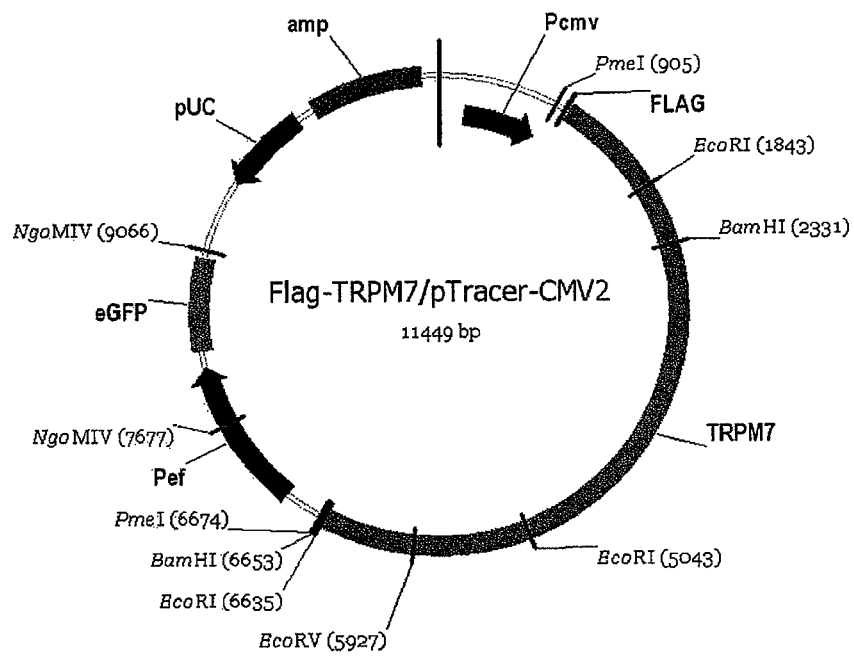
B
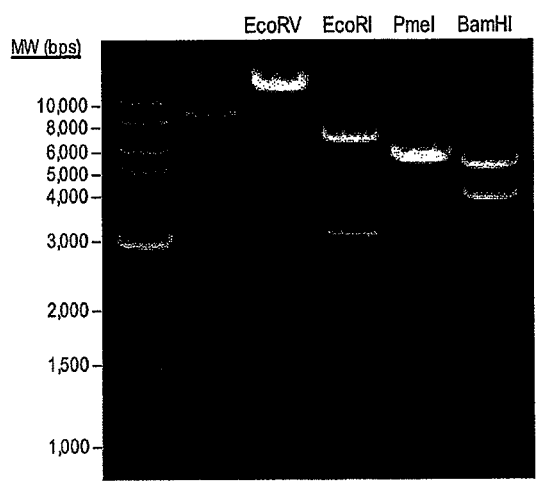
Figure 28

A
TRPM7/pTracer
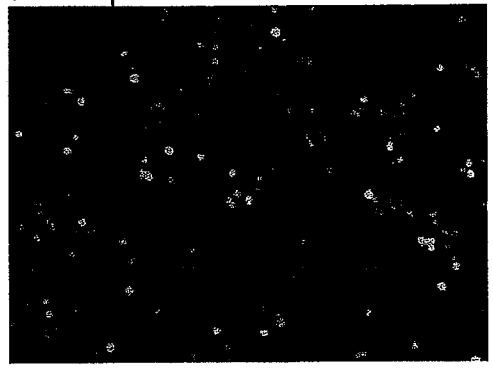
B
Untransfected
TRPM7-transfected
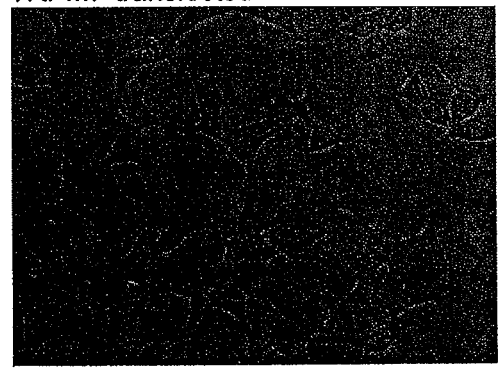
Figure 29

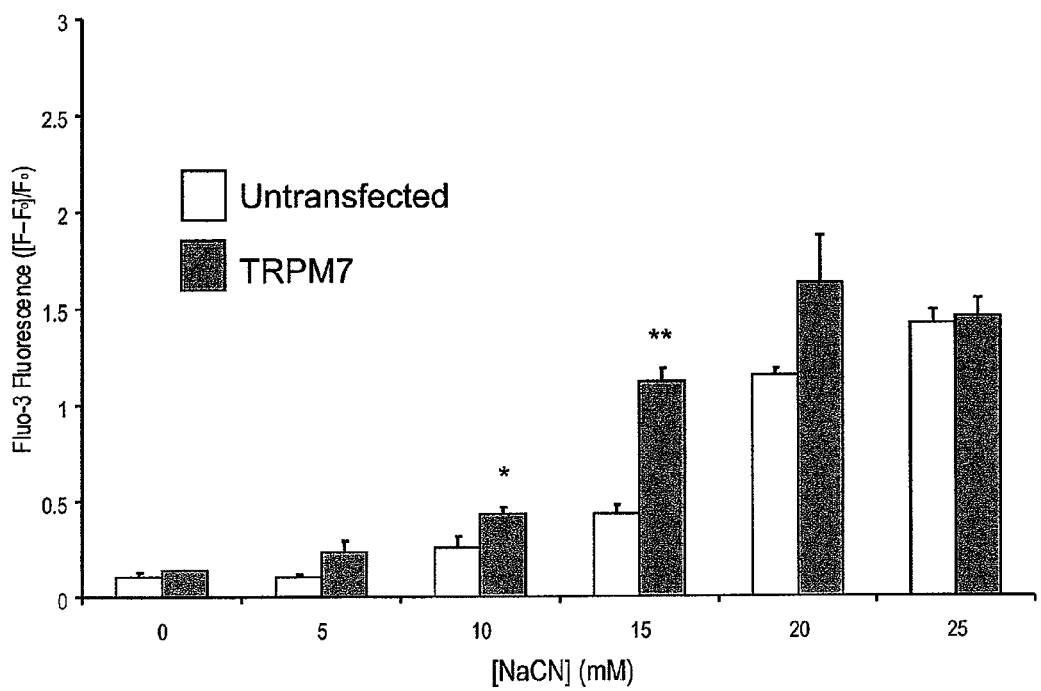
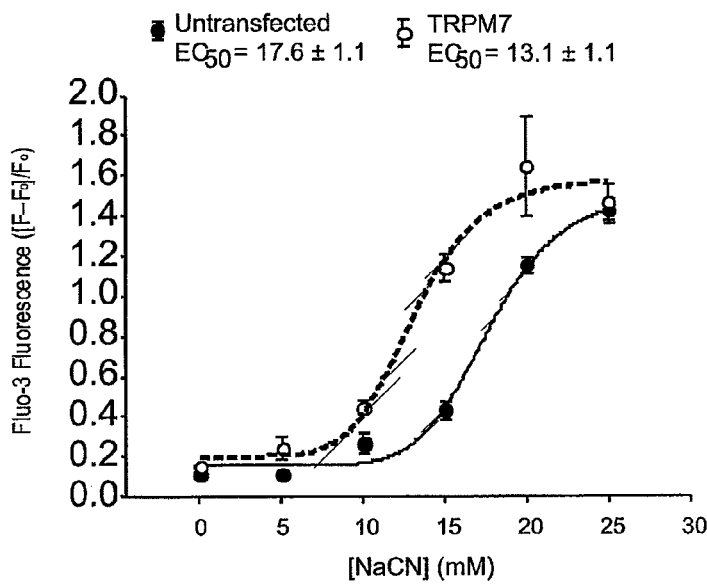
Figure 30

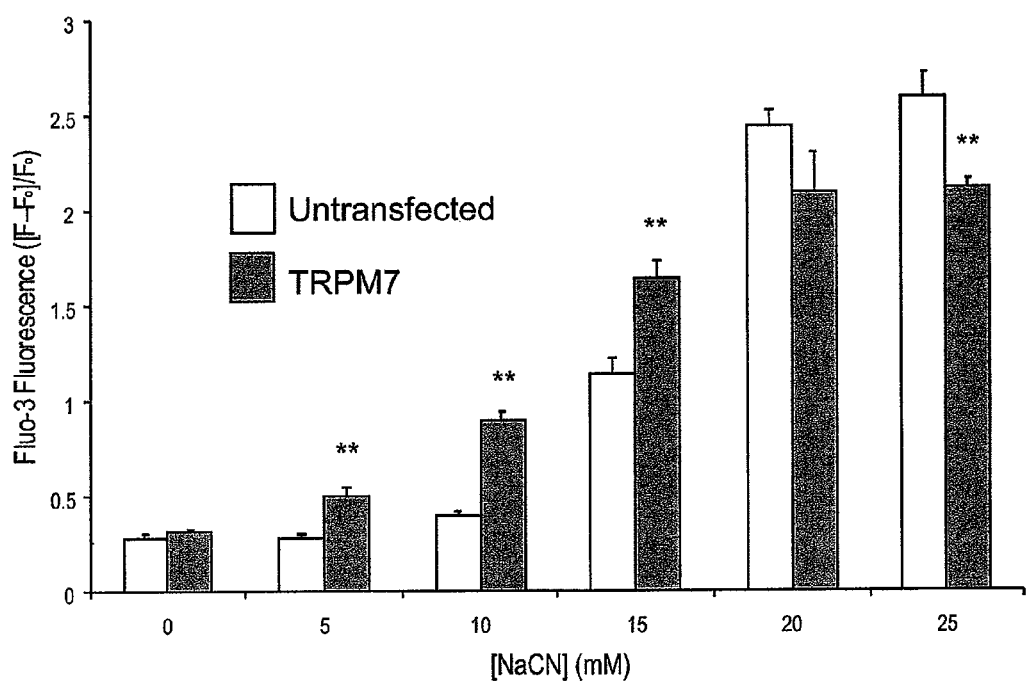
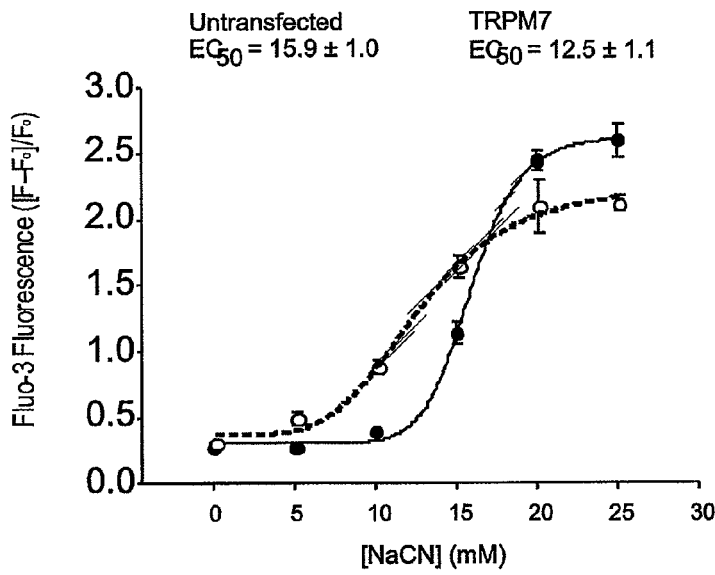
Figure 31

| Item | M5 |
|---|---|
| MW | 341.86 |
| Formula | C19H16ClNOS |
Structure 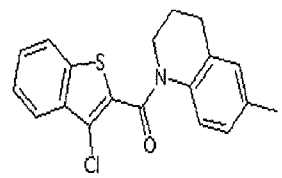
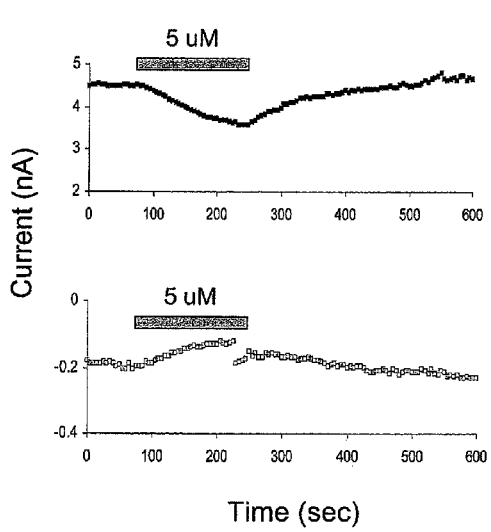
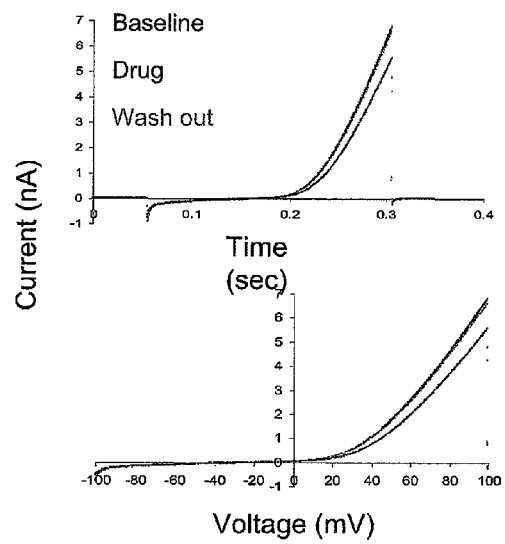
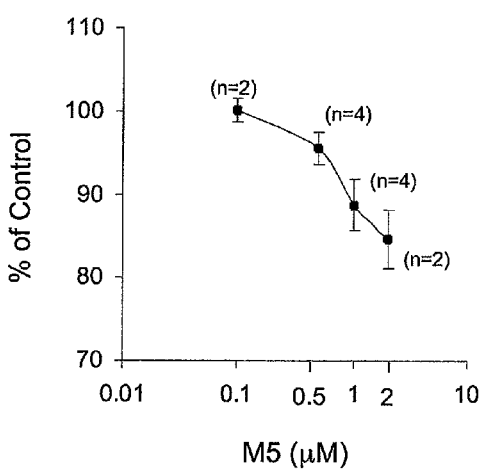
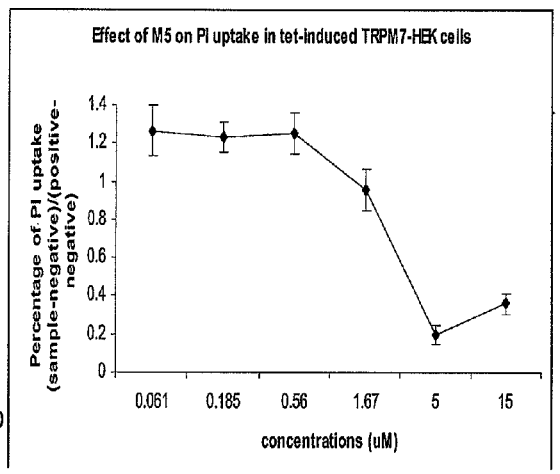
Figure 35

| Item | M6 |
|---|---|
| MW | 357.85 |
| Formula | C19H16ClNO2S |
Structure
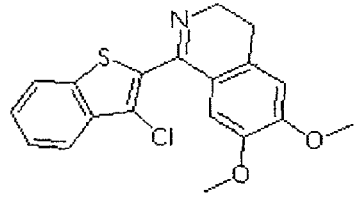
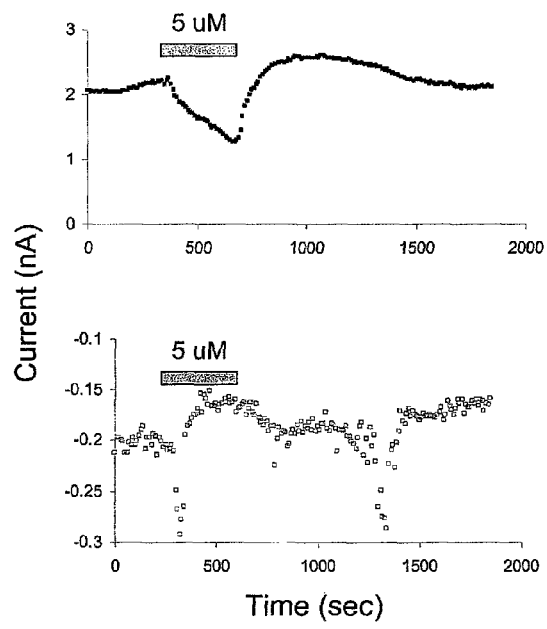
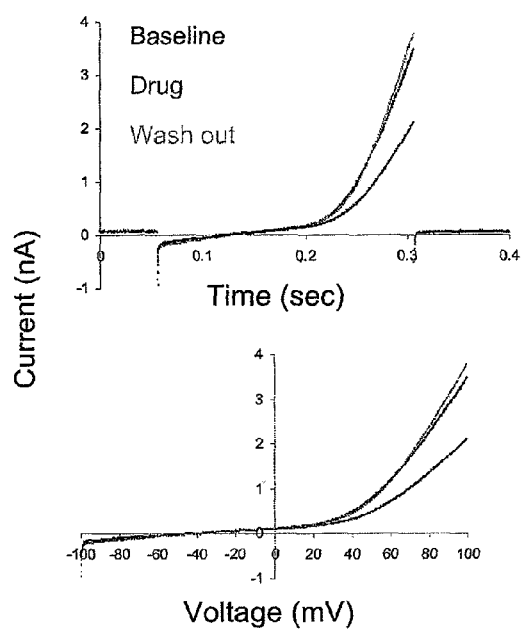
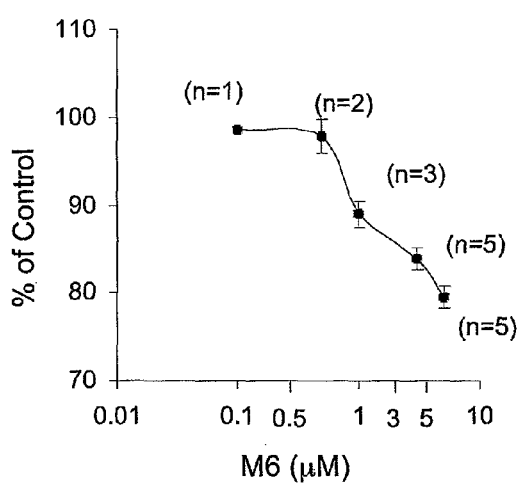
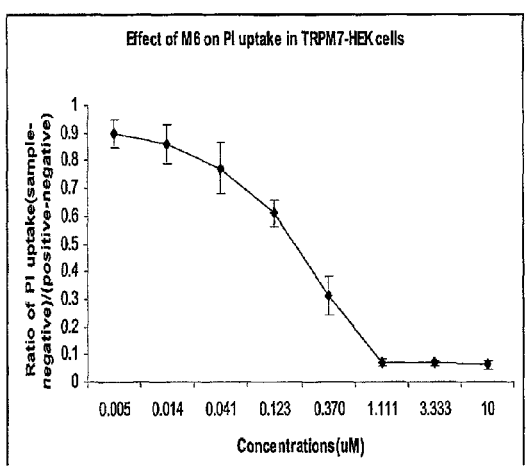
Figure 36

| Item | M14 | Structure | 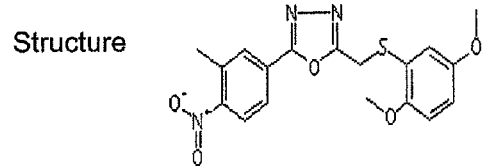 |
|---|---|---|---|
| MW | 387.41 | | |
| Formula | C18H17N3O5S | | |
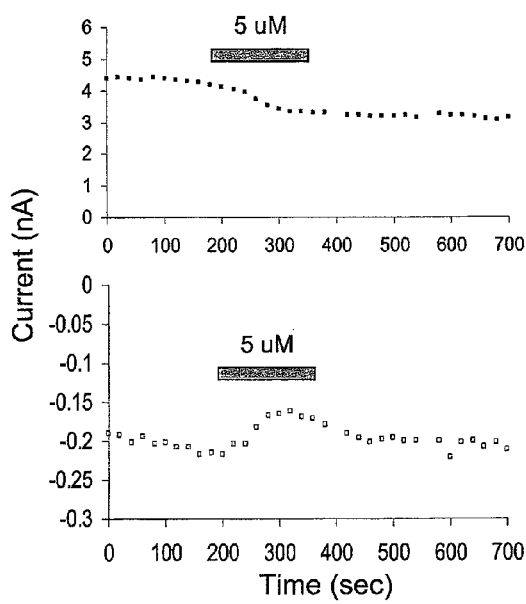
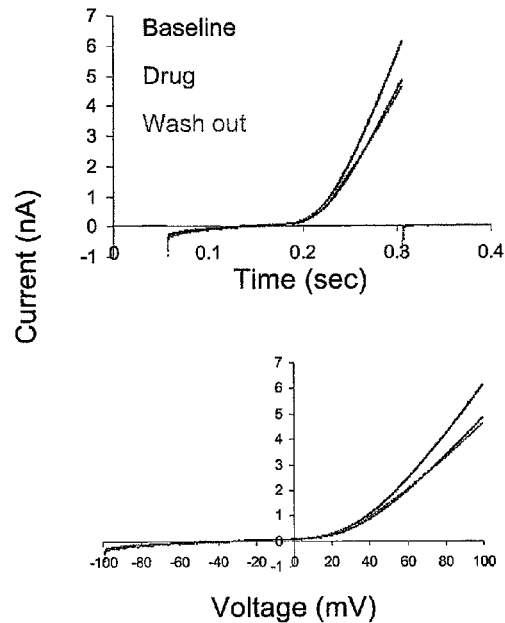
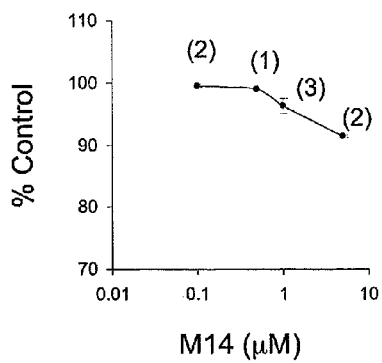
(dose response test is still undergoing)
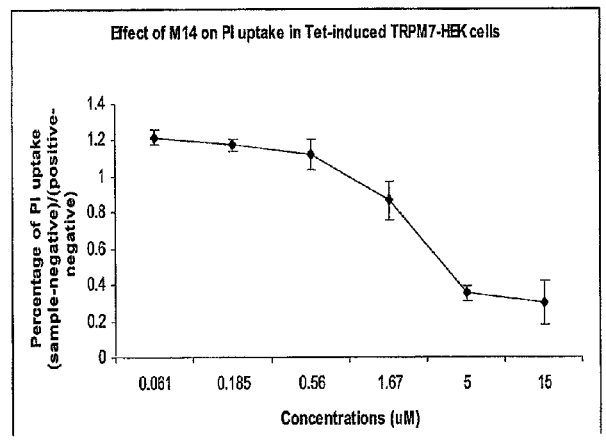
Figure 39

| Item | M21 |
|---|---|
| MW | 335.18 |
| Formula | C17H12Cl2O3 |
Structure 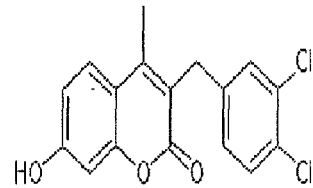
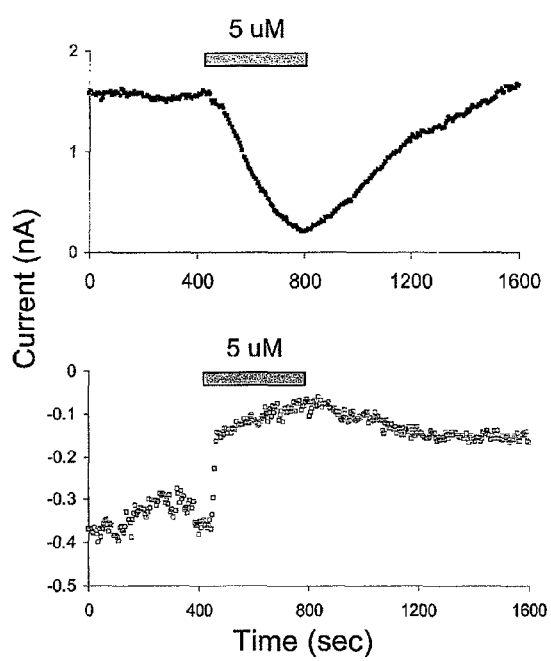
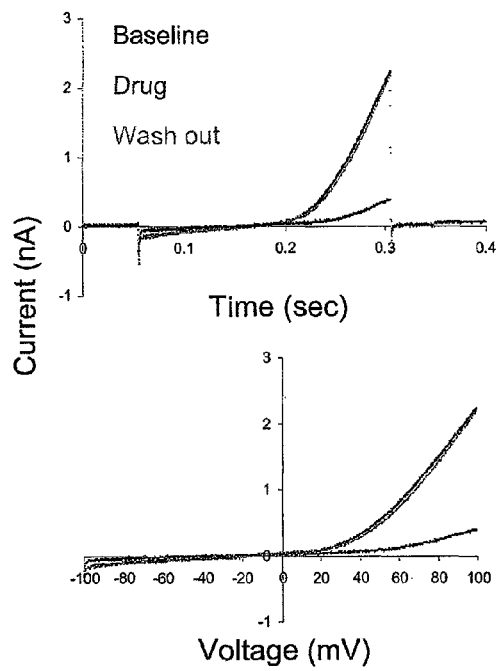
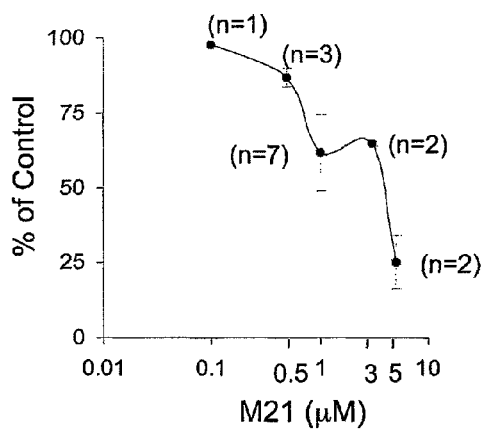
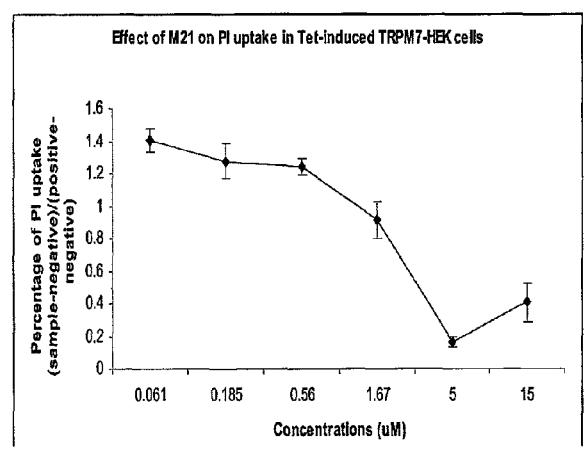
Figure 40

Effect of Compounds on PI uptake in TRPM7-HEK cell (M1, M2, M3, M4)

Figure 52: Effect of Compounds on PI uptake in TRPM7-HEK cell (M29, M30)

Effect of compounds on PI uptake in Primary cultured mouse cortical cells 20h after 2h OGD (M5)

Figure 56. Effect of compounds on PI uptake in Primary cultured mouse cortical cells 20h after 2h OGD (M6)

Effect of compounds on PI uptake in Primary cultured mouse cortical cells 20h after 2h OGD (M7, M11)

Figure 58. Effect of compounds on PI uptake in Primary cultured mouse cortical cells 20h after 2h OGD (M14, M21)

Toxicity of compounds treated for 24h(M11, M14, M21)

FIG. 66
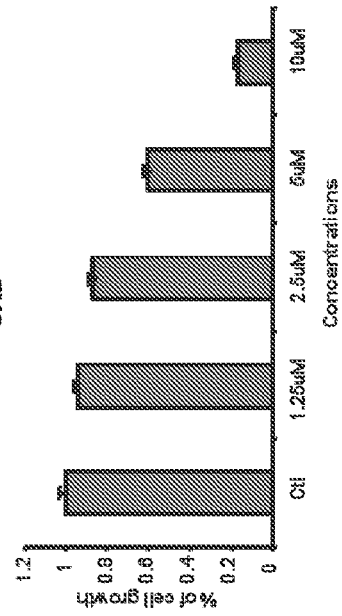
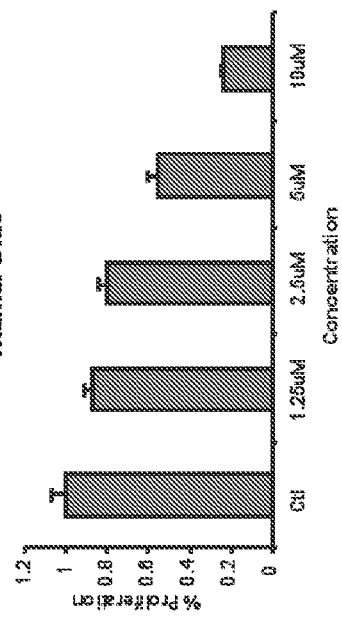
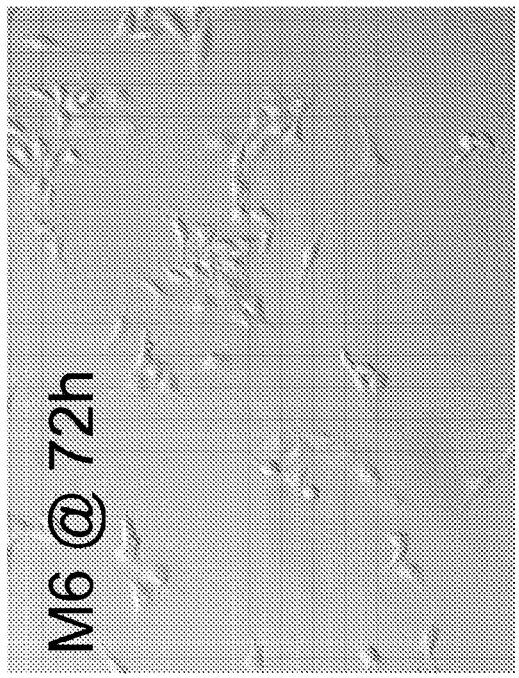

FIGS. 69 A, B, C
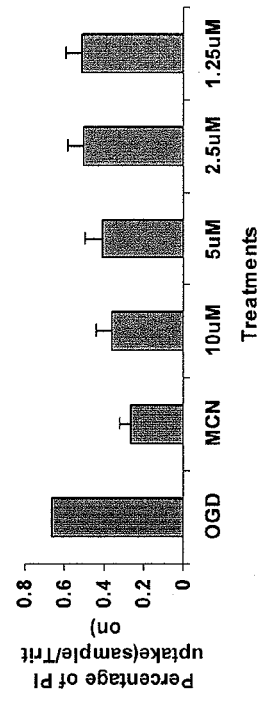
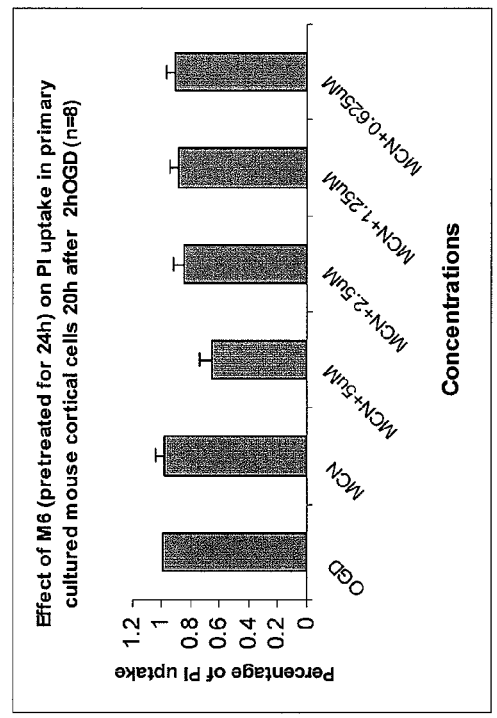
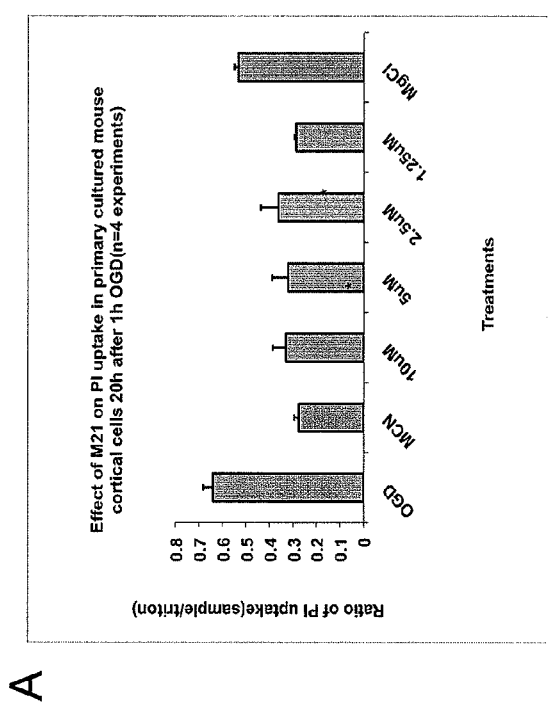

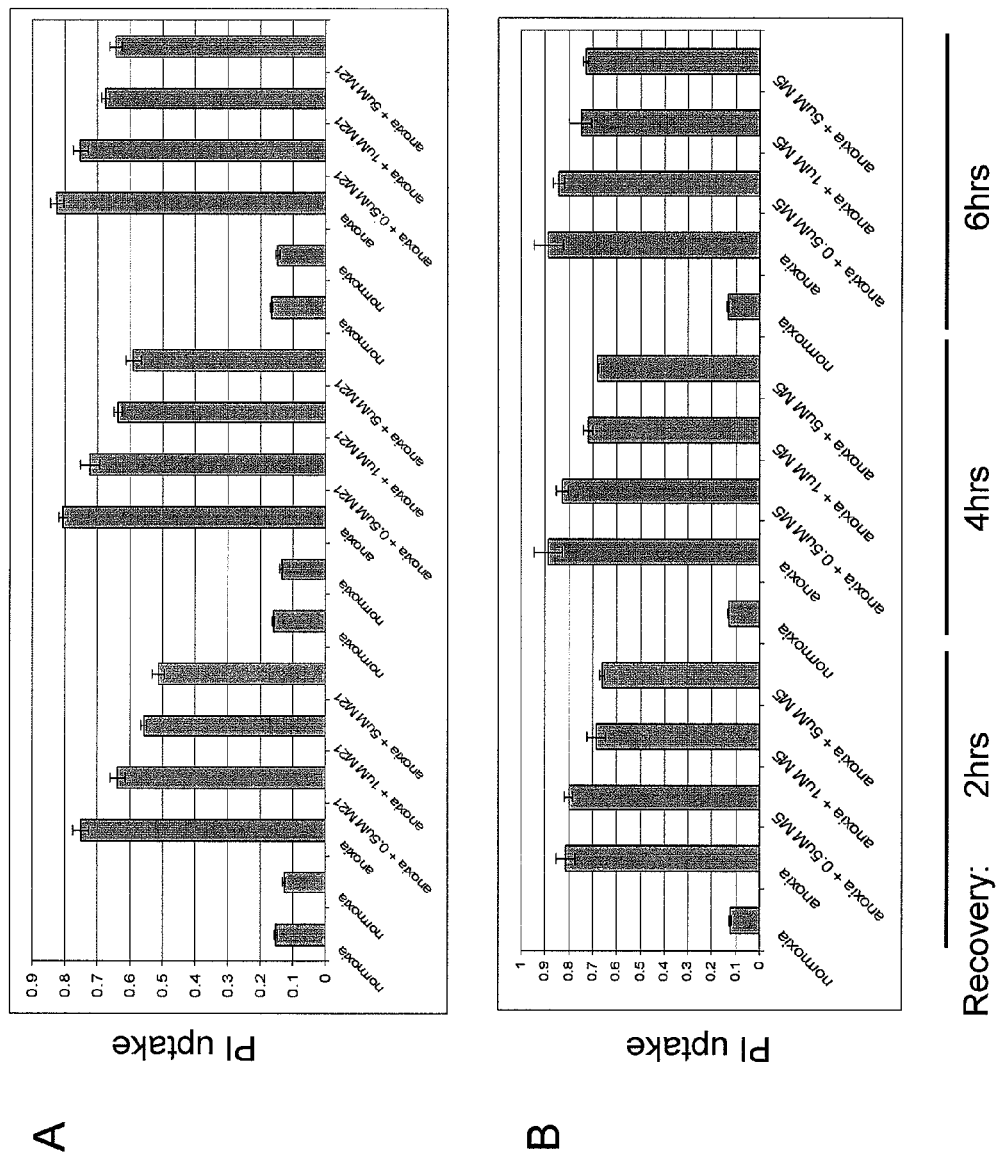
FIGS. 70 A, B

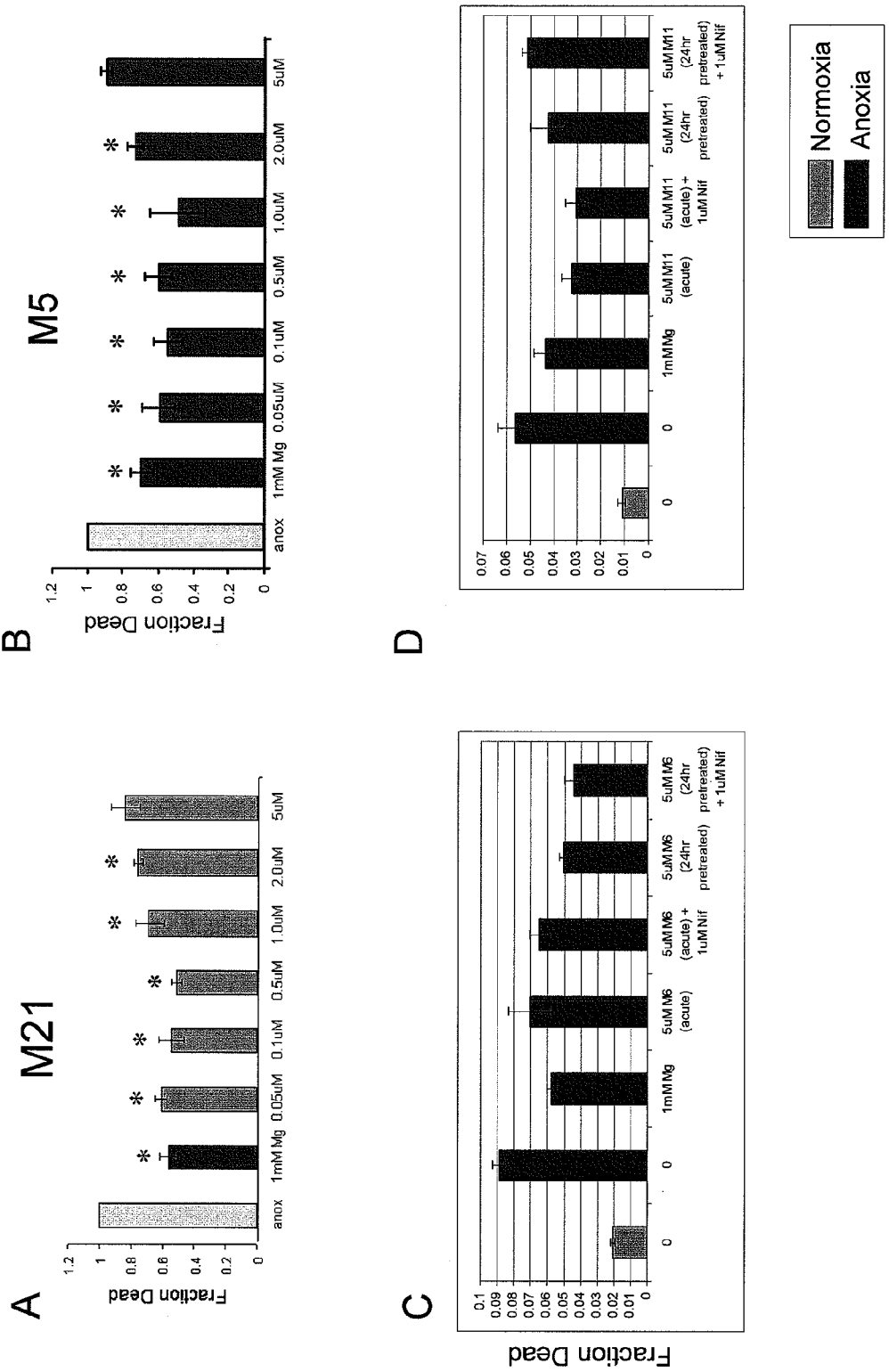
FIGS. 71 A, B, C, D

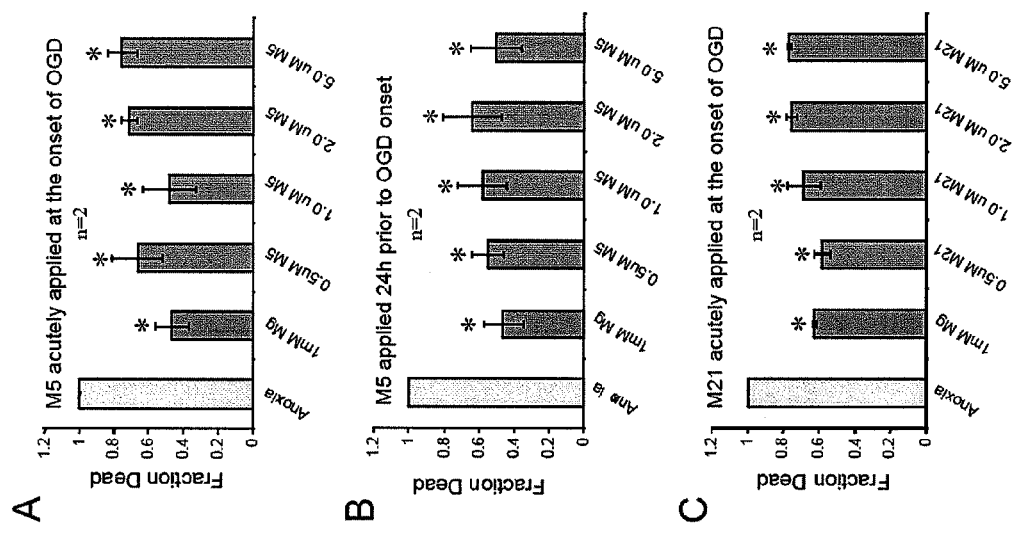
FIGS. 72 A, B, C

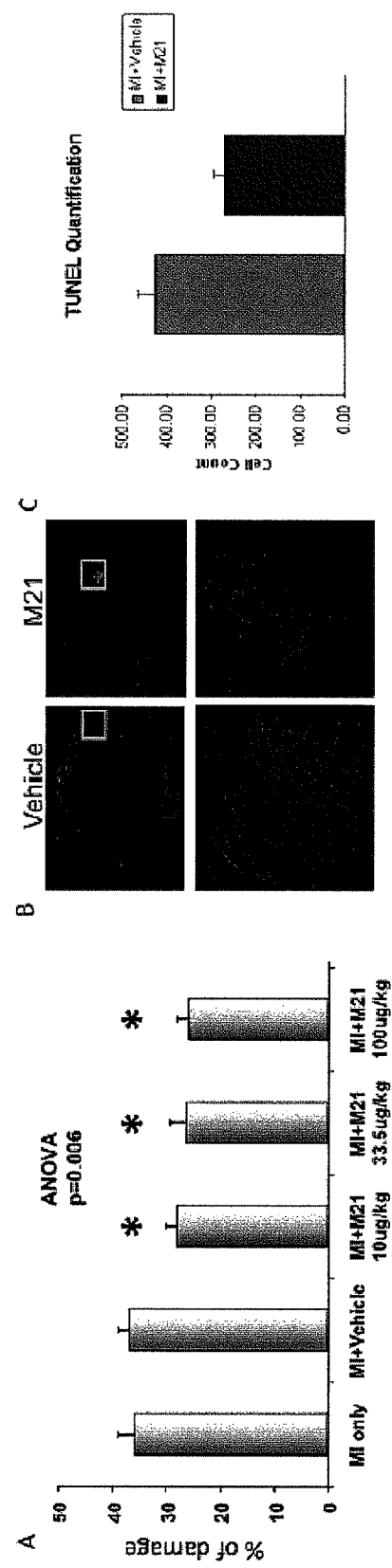
FIGS. 73, A, B, C

FIGS. 74 A, B
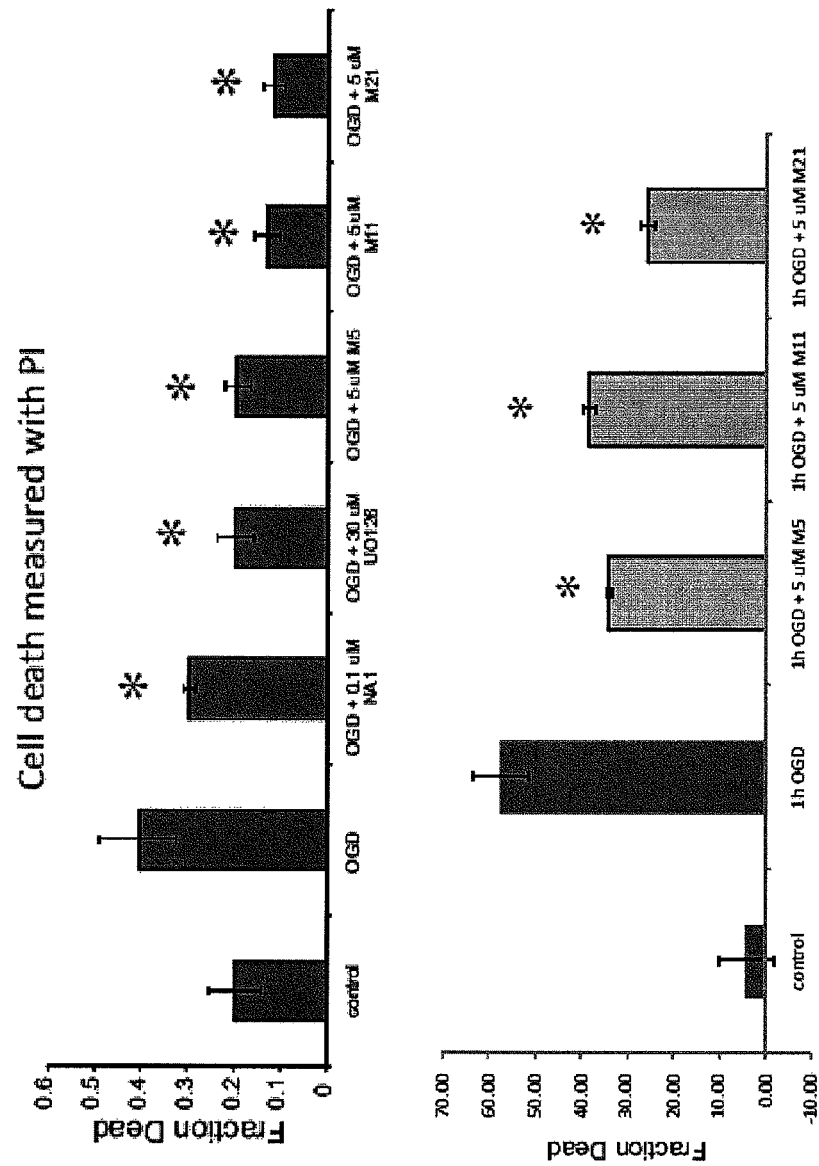

FIGS. 75 A, B
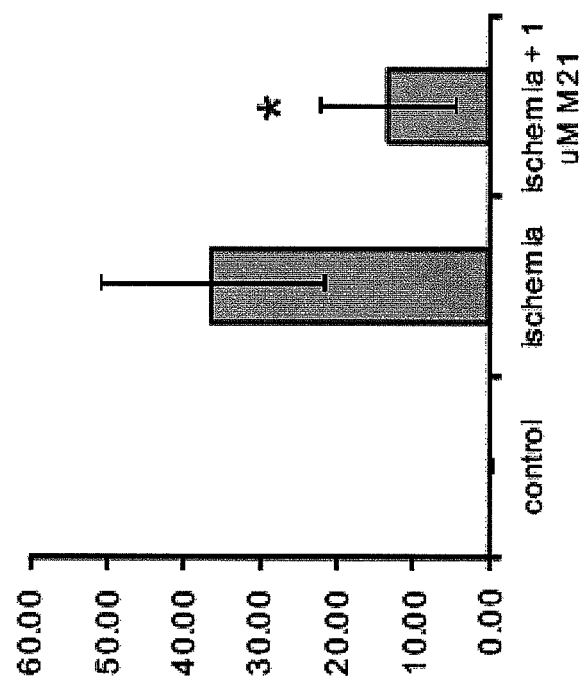
A
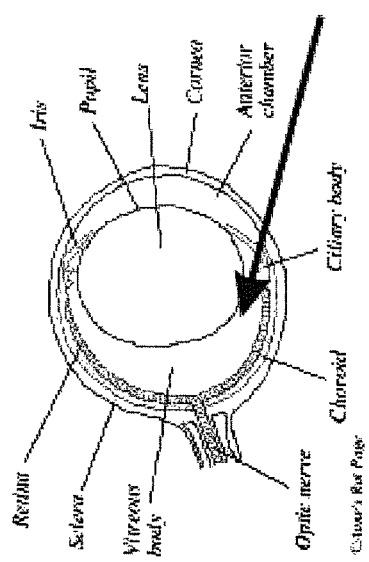
B

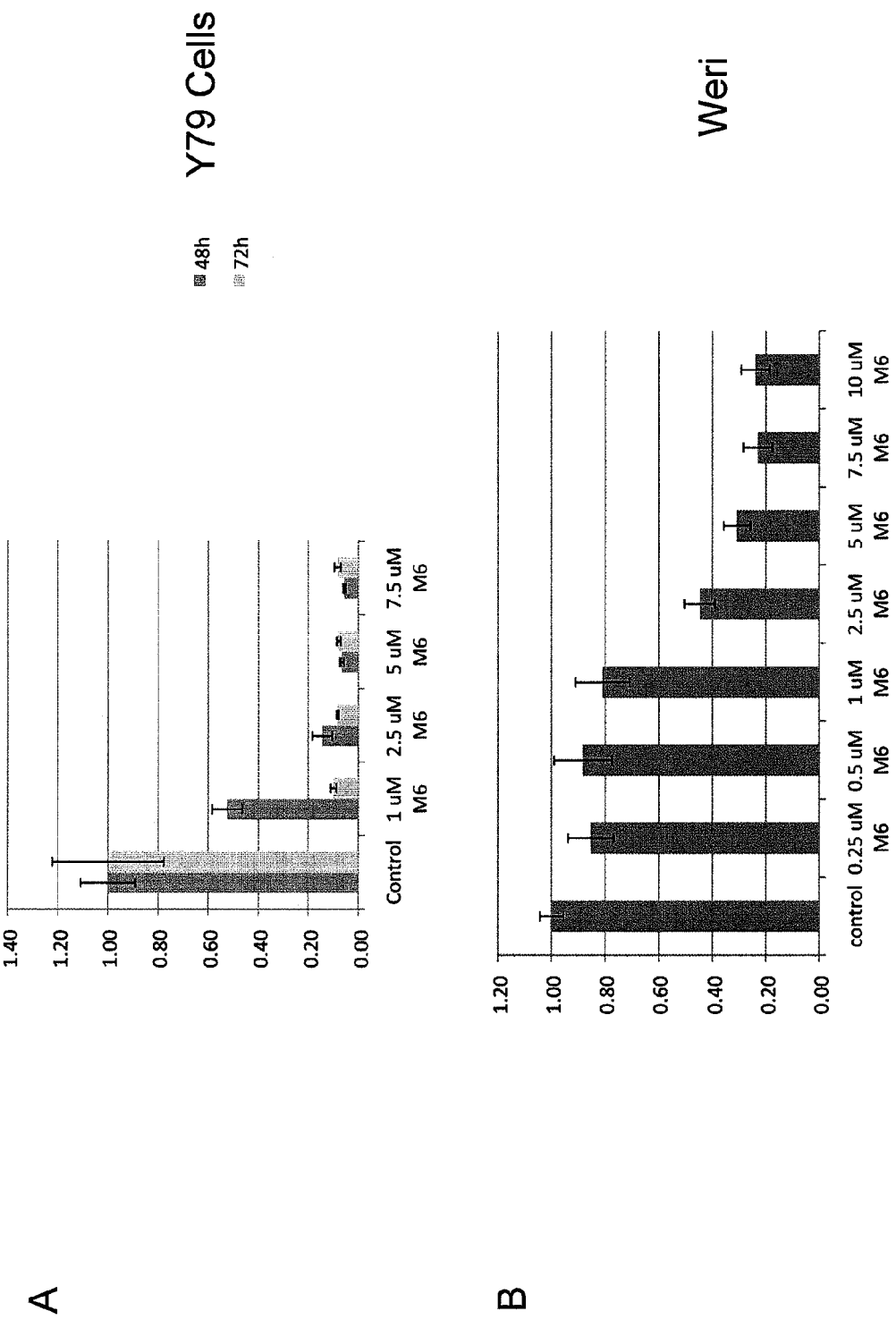
FIGS. 76 A, B

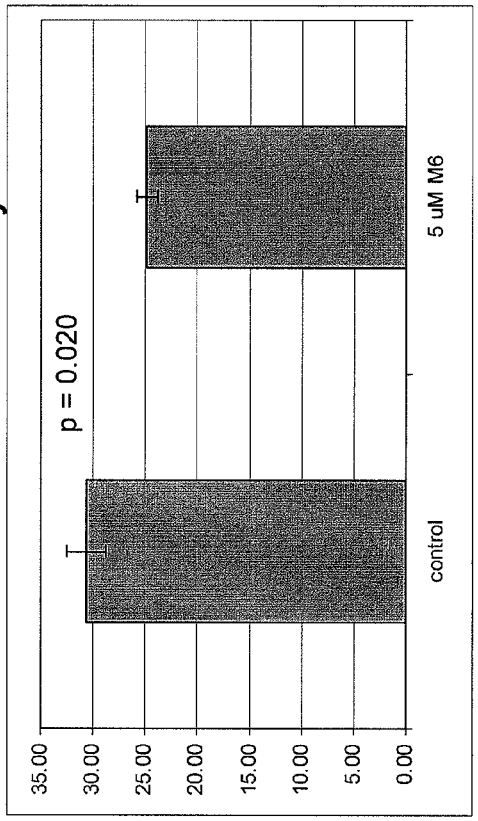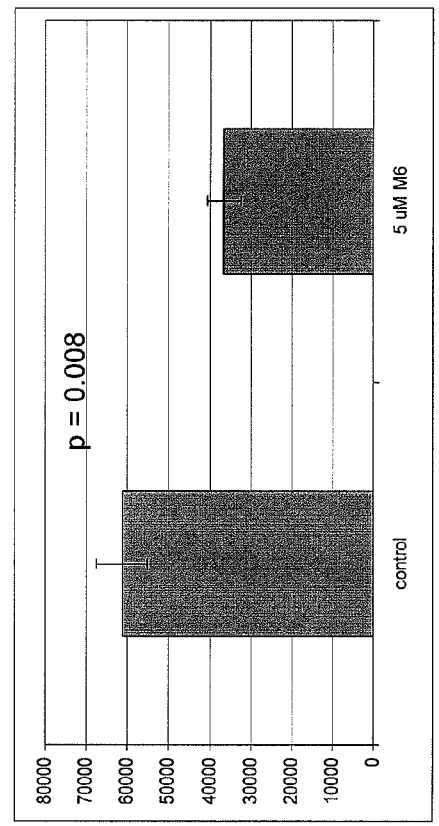
FIGS. 77 A, B
A
B

FIG. 79 A - D
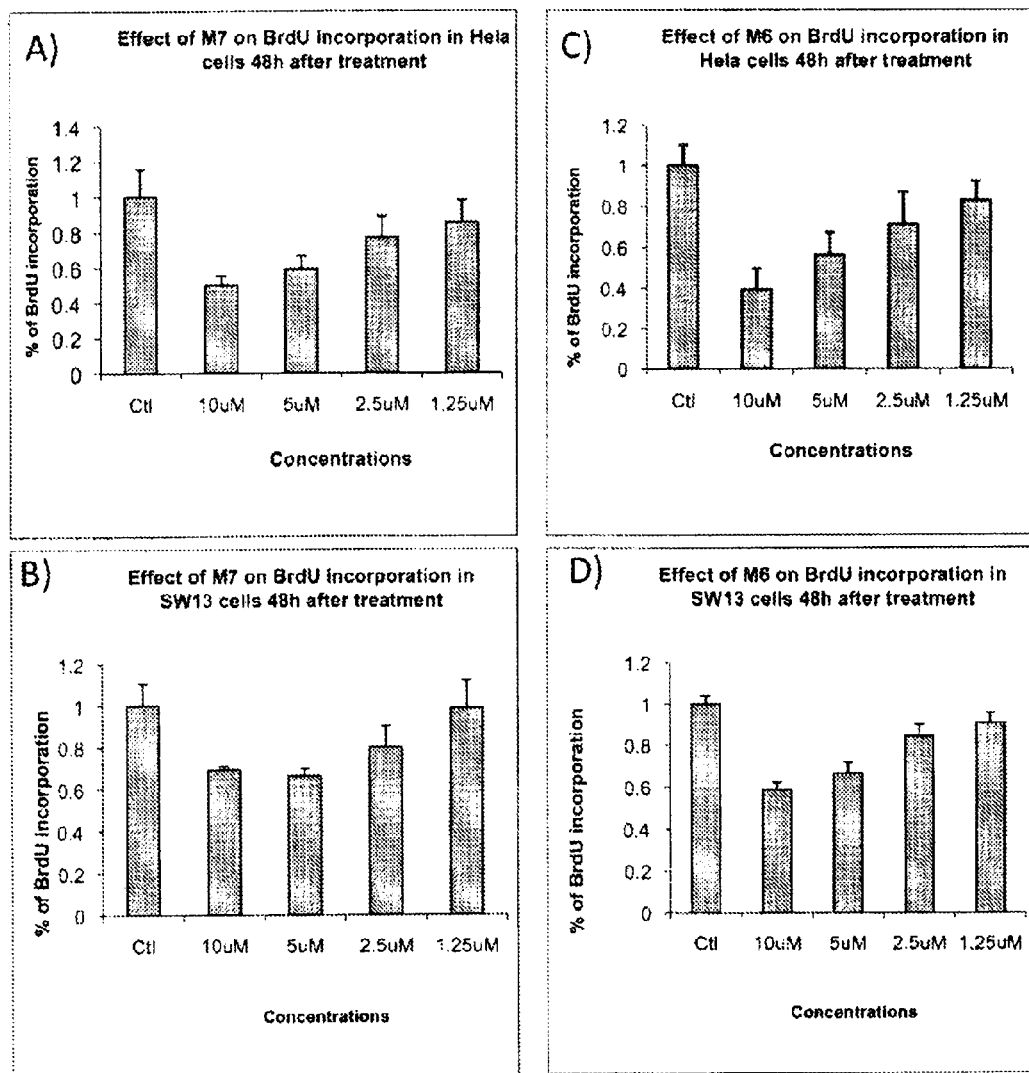

FIG. 80 A - F
SRB (MCF-7)
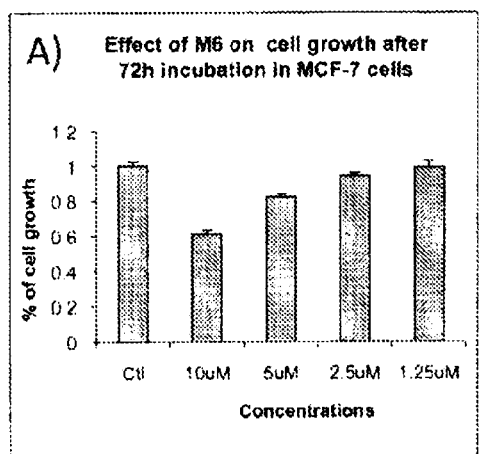
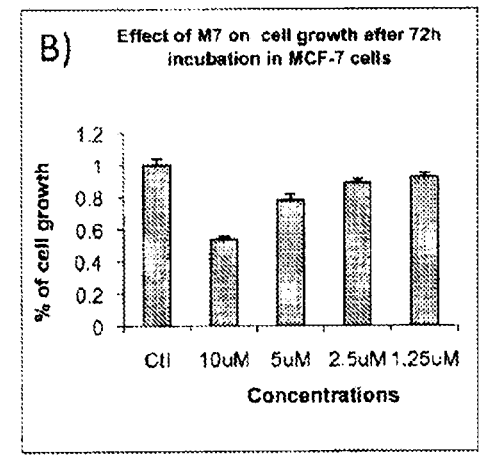
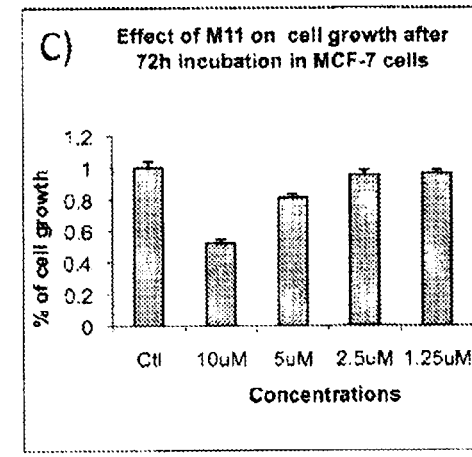
SRB (MDA-MB231)
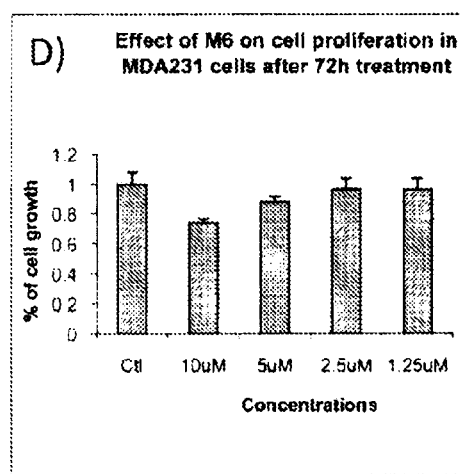
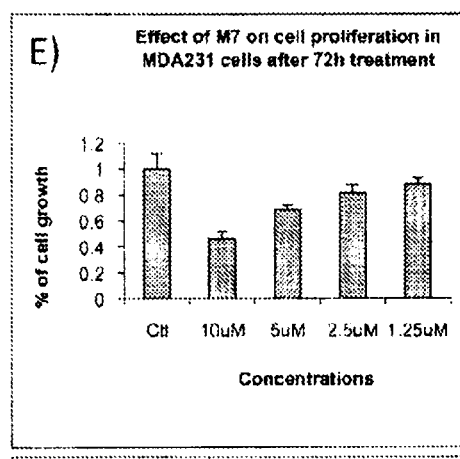
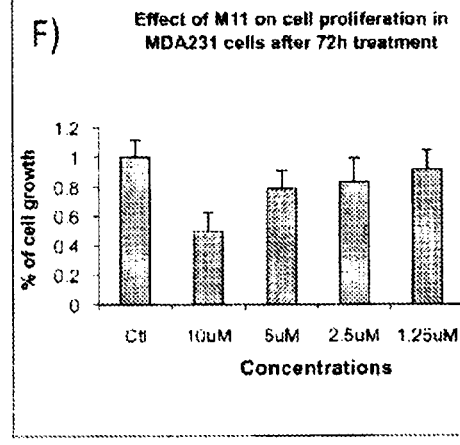

FIG. 81 A - F
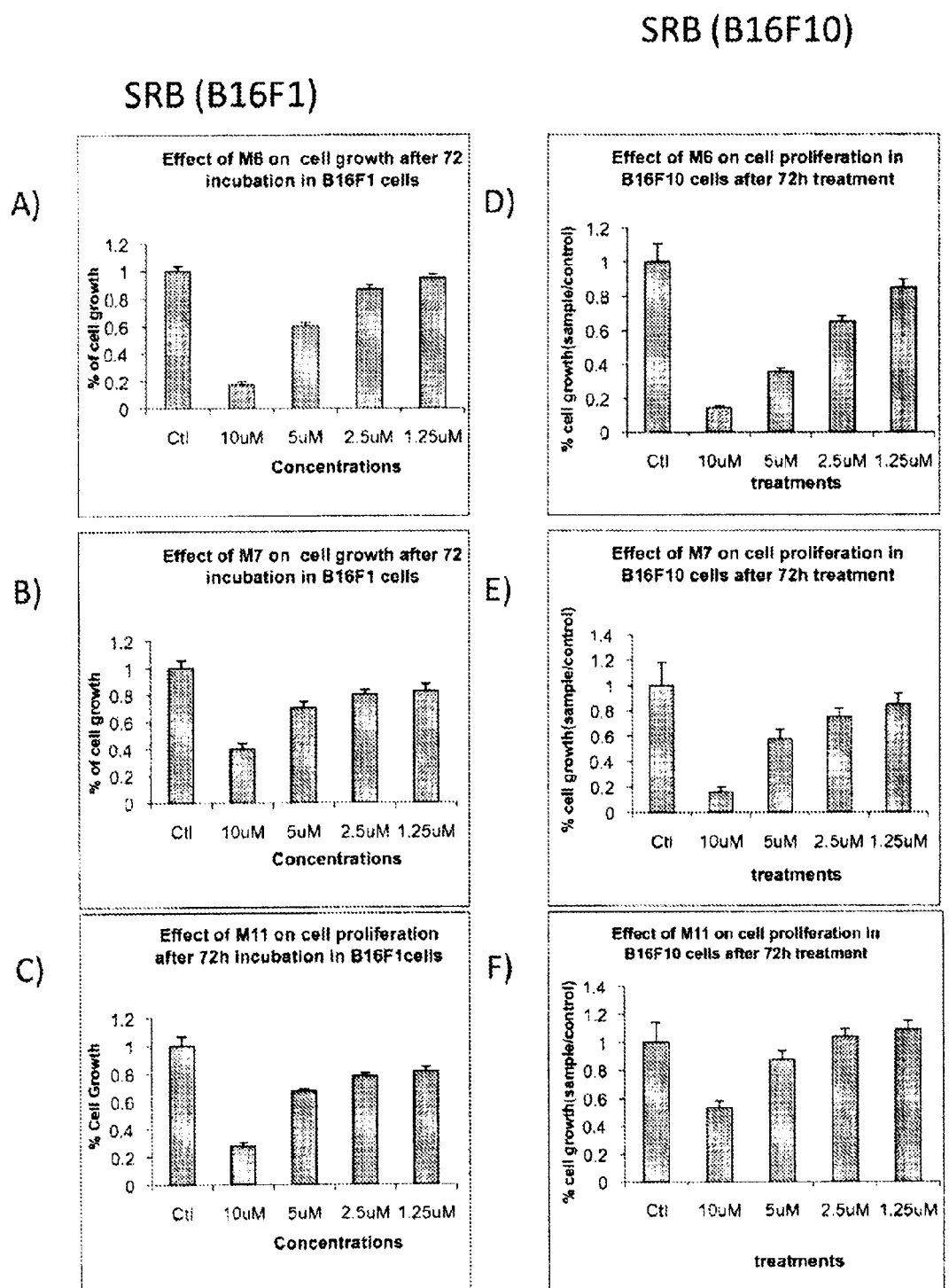

FIGS. 84 A-D  MTT and SRB assays in B16F1 and B16F10 mouse melanoma cell lines 48hrs following TRPM7 siRNA

US 8,680,137 B2

AGENTS AND METHODS FOR TREATING ISCHEMIC AND OTHER DISEASES

CROSS-REFERENCES TO RELATED APPLICATIONS

The present application is a nonprovisional and claims the benefit of 61/312,154 filed Mar. 9, 2010 and 61/285,954 filed Dec. 11, 2009, each of which is incorporated by reference in its entirety for all purposes.

BACKGROUND OF THE INVENTION

The transient receptor potential channel TRPM7 is a member of the TRP superfamily of cation channels that comprises greater than 20 cation channels that play critical roles in varied processes within the body. TRP channels are integral membrane proteins in which the ion-conducting pores are formed by six membrane-spanning helical segments that are similar to those of voltage-gated potassium channels and cyclic nucleotide-gated channels. TRP channels are divided into three families based on their homology. The families are the short TRP channel family, the osm TRP family, and the long TRP family. Long TRP channels can be distinguished by their having particularly long extensions outside the channel segment. Long TRP channels are involved in critical control mechanisms regulating cell growth, differentiation and death ((Montell et al., 2002, Harteneck et al., 2000).

The TRPM7 channel belongs to the long TRP family. The human TRPM7 protein was first identified by Runnels et al (2001)) and was identified as a bifunctional protein with kinase and ion channel activities. In another study by Nadler et al. (2001), TRPM7 was identified as a Mg-ATP regulated cation channel required for cell viability. Runnels et al. (2002) reported that TRPM7 is a calcium-permeant ion channel. It was also reported that the kinase domain of TRPM7 directly associates with the C2 domain of phospholipase C (PLC) and that 4,5-biphophate ($PIP_2$), the substrate of PLC, is a key regulator of TRPM7. The TRPM7 channel produces pronounced outward currents at nonphysiological voltages ranging from +50 to +100 mV and small inward currents at negative potentials between −100 to −40 mV when expressed heterologously in mammalian cells (Jiang et al., 2005) The basal activity of TRPM7 was originally reported to be regulated by millimolar levels of intracellular mgATP and $Mg^{2+}$. It is now recognized that the TRPM7 channel is unlikely to be gated by ATP (it was the Mg2+ in the MgATP that, when depleted, caused the channel to open). TRPM7 is activated by depletion of intracellular $Mg^{2+}$, and is inhibited by high concentrations of $Mg^{2+}$ with an $IC_{50}$ of about 0.6 mM (Nadler et al., supra, Jiang et al., supra). The TRPM7 channel is also known as the CHAK, CHAK1, LTRPC7, FLJ20117 or TRPPLIK channel. The TRPM7 channel is also activated by a reduction in extraellular divalent cation levels, especially Mg2+ and Va2+. More recently, the TRPM7 channel has been shown to be involved in ischemic CNS injury and anoxic neuronal cell death (Aarts et al., 2003; Aarts and Tymianski, 2005a, Aarts and Tymianski, 2005b).

Excitotoxicity in brain ischemia triggers neuronal death and neurological disability, and yet these are not prevented by antiexcitotoxic therapy (AET) in humans. Aarts et al. (2003) have shown that in murine neurons subjected to prolonged oxygen glucose deprivation (OGD), AET unmasks a dominant death mechanism perpetuated by a Ca2+-permeable nonselective cation conductance (IOGD). IOGD was activated by reactive oxygen/nitrogen species (ROS), and permitted neuronal Ca2+ overload and further ROS production despite AET. IOGD currents corresponded to those evoked in HEK-293 cells expressing the nonselective cation conductance TRPM7. In cortical neurons, blocking IOGD or suppressing TRPM7 expression blocked TRPM7 currents, anoxic 45Ca2+ uptake, ROS production, and anoxic death. TRPM7 suppression eliminated the need for AET to rescue anoxic neurons and permitted the survival of neurons previously destined to die from prolonged anoxia. Thus, excitotoxicity may be is a subset of a greater overall anoxic cell death mechanism, in which TRPM7 channels play a key role.

Exposure to low Ca(2+) and/or Mg(2+) is tolerated by cardiac myocytes, astrocytes, and neurons, but restoration to normal divalent cation levels paradoxically causes Ca(2+) overload and cell death. This phenomenon has been called the "Ca(2+) paradox" of ischemia-reperfusion. The mechanism by which a decrease in extracellular Ca(2+) and Mg(2+) is "detected" and triggers subsequent cell death is unknown. Transient periods of brain ischemia are characterized by substantial decreases in extracellular Ca(2+) and Mg(2+) that mimic the initial condition of the Ca(2+) paradox. Wei et al. (2007) have shown that In CA1 hippocampal neurons, lowering extracellular divalents stimulates a nonselective cation current. They showed that this current resembles TRPM7 currents in several ways. Both (i) respond to transient decreases in extracellular divalents with inward currents and cell excitation, (ii) demonstrate outward rectification that depends on the presence of extracellular divalents, (iii) are inhibited by physiological concentrations of intracellular Mg(2+), (iv) are enhanced by intracellular phosphatidylinositol 4,5-bisphosphate (PIP(2)), and (v) can be inhibited by Galphaq-linked G protein-coupled receptors linked to phospholipase C beta1-induced hydrolysis of PIP(2). Furthermore, suppression of TRPM7 expression in hippocampal neurons strongly depressed the inward currents evoked by lowering extracellular divalents. Finally, they show that activation of TRPM7 channels by lowering divalents significantly contributes to cell death. Together, the results suggest that TRPM7 contributes to the mechanism by which hippocampal neurons "detect" reductions in extracellular divalents and provide a means by which TRPM7 contributes to neuronal death during transient brain ischemia.

BRIEF SUMMARY OF THE INVENTION

The invention provides methods of screening for compounds that modulate the injurious effects of TRPM7 gene and protein activity on mammalian cells, classes and specific compounds that modulate the injurious effects of TRPM7 activity on mammalian cells, and methods of treating the injurious effects of TRPM7 activity and ischemic damage on mammalian cells.

The invention provides pharmaceutical compositions comprising a compound according to any of Formulae I to XIX, or any other compound or genera of compounds disclosed herein, or pharmaceutically acceptable salts of such compounds. Preferred compounds are designated M5, M6, M11, M14 and M21. Some compounds inhibit inhibit TRPM7-mediated cell death in mammalian cells by at least 50, 60, 70 or 80% relative to a control assay lacking the compound.

In some pharmaceutical composition the compound or pharmaceutically acceptable salt thereof is at least 95 or 99% w/w pure of contaminants from its production. Some compositions further comprise a carrier acceptable for human administration. Some compositions contain a unit dose of the compound or pharmaceutically acceptable salt thereof. Some pharmaceutical compositions are formulated for oral administration. Some such pharmaceutical composition are formulated as a pill or capsule. Some pharmaceutical compositions are formulated for patenteral administration. Some such pharmaceutical compositions are packaged in a vial containing a unit dose of the agent. Any of these pharmaceutical compositions can be used in prophylaxis of treatment of disease.

The invention provides methods of treating or effecting prophylaxis of a damaging effect of ischemia in a patient, comprising administering to a patient having or at risk of ischemia an effective regime of a pharmaceutical composition, compound or a pharmaceutically acceptable salt thereof as specified above or herein. Optionally, the ischemia is cardiac, renal, retinal or CNS ischemia.

The invention provides methods of treating or effecting prophylaxis of cancer in a patient, comprising administering to a patient having a cancer or at risk of cancer an effective regime of a pharmaceutical composition, compound or a pharmaceutically acceptable salt thereof as specified above or herein. Optionally, the cancer is renal cancer, small lung cell cancer, non-small lung cell cancer, colon cancer, retinoblastoma, breast cancer, melanoma, adrenal carcinoma, cervical cancer, or osteosarcoma.

The invention further provides method of treating or effecting prophylaxis of ischemia, pain, glaucoma or cancer comprising administering to a patient an effective regime of a compound of formula V or a pharmaceutically acceptable salt thereof and thereby effecting prophylaxis of treatment of ischemia, pain, glaucoma or cancer.

In some such methods, the patient has or is at risk of ischemia and the administration reduces or inhibits a damaging effect of the ischemia. In some methods, the patient has glaucoma and the administration reduces or inhibits a damaging effect of the glaucoma. In some methods, the damaging effect of glaucoma or ischemia is cell death. In some methods, the patient is in pain and the administration reduces or inhibits a symptom of the pain. In some methods, the patient has had a stroke and the administration reduces or inhibits a damaging effect of the stroke. In some methods, the patient has a cancer, and the administration inhibits or reduces proliferation, toxicity and/or metastasis of the cancer.

The invention further provides methods of treating or effecting prophylaxis of cancer comprising administering an effective regime of a compound of formula III or a pharmaceutically acceptable salt thereof thereby inhibiting or reducing proliferation, toxicity and/or metastasis of the cancer.

The invention further provides methods of treating or effecting prophylaxis of cancer or ischemia, comprising administering an effective regime of a compound of formula IX thereby effecting treatment or prophylaxis of the cancer or ischemia.

The invention further provides methods of treating or effecting prophylaxis of cancer or ischemia, comprising administering an effective regime of a compound of formula XI thereby effecting treatment or prophylaxis of the cancer or ischemia.

The invention further provides a method of screening for an inhibitor of TRPM7, comprising activating TRPM7 in cells expressing TRPM7; contacting the cells with an agent; determining whether the agent inhibits death of the cells; and if the compound inhibits death of the cells, determining whether the agent inhibits an ion current through the TRPM7 channel; inhibition of an ion current indicating the agent is an inhibitor of TRPM7 channel. Optionally, the method further comprises determining whether the agent inhibits a damaging effect of ischemia in a cell or animal model of ischemic injury.

The invention further provides for use of host cells or progeny of the host cells. In certain aspects, the host cell is a eukaryote. In certain aspects, the host cell comprises an expression vector that comprises a murine TRPM7 polynucleotide in which the nucleotide sequence of the polynucleotide is operatively linked with a regulatory sequence that controls expression of the polynucleotide in a host cell or progeny of the host cell. In certain aspects, the invention provides a host cell comprising a murine TRPM7 polynucleotide, wherein the nucleotide sequence of the polynucleotide is operatively linked with a regulatory sequence that controls expression of the polynucleotide in a host cell, or progeny of the cell. The nucleotide sequence of the polynucleotide can be operatively linked to the regulatory sequence in a sense or antisense orientation.

The invention further provides a method of screening bioactive agents comprising: a) providing a cell that expresses an inducible or constitutively expressed murine TRPM7 gene as described herein; b) inducing the expression of the TRPM7 protein if needed, c) activating the channel d) adding a bioactive agent candidate to the cell; and e) determining the effect of the bioactive agent candidate on the cellular injury produced by the expression product of the TRPM7 gene under said ionic environment. In some methods, the determining comprises comparing the level of cellular injury in the absence of the bioactive agent candidate to the level of injury in the presence of the bioactive agent candidate. In some methods, the determining comprises comparing the level of cellular injury in the presence of the bioactive agent candidate but in the absence of induction of the TRPM7 gene to the level of injury in the presence of the bioactive agent candidate also in the presence of induction of the TRPM7 gene.

The invention further provides a method of screening bioactive agents for modulating cellular injury as described herein, but in a robotic system intended to achieve high-throughput screening.

The invention further provides a method for screening for a bioactive agent that increases or decreases the activity of a TRPM7 channel, the method comprising: a) providing a cell that expresses an inducible or constitutively expressed murine TRPM7 gene as described herein; b) inducing the expression of the TRPM7 protein (if needed), c) loading the cell with a fluorescent ion indicator compound to which TRPM7 protein-containing ion channels are permeable d) activating the channel, e) adding a bioactive agent candidate to the cell; and f) determining the effect of the bioactive agent candidate on the fluorescence of the ion indicator in the cell under said ionic environment. In some methods, the determining comprises comparing the level of fluorescence in the absence of the bioactive agent candidate to the level of fluorescence in the presence of the bioactive agent candidate. In some methods, the determining comprises comparing the level of the fluorescence in the presence of the bioactive agent candidate but in the absence of induction of the TRPM7 gene to the level of fluorescence in the presence of the bioactive agent candidate also in the presence of induction of the TRPM7 gene.

The invention further provides a method of screening bioactive agents for modulating the fluorescence of an ion indicator compound as described herein, but in a robotic system intended to achieve high-throughput screening.

The invention further provides a method for screening for a bioactive agent that modulates the monovalent or divalent cationic permeability of a channel comprising a TRPM7 protein comprising a) providing a recombinant cell comprising a recombinant nucleic acid encoding a TRPM7 protein and an inducible or constitutive promoter operably linked thereto; b) inducing the recombinant cell to express the TRPM7 protein and form a channel comprising the TRPM7 protein (if needed); c) contacting the recombinant cell with a candidate bioactive agent; d) activating the channel; and e) detecting modulation of TRPM7-mediated cellular injury. In one aspect, the TRPM7-mediated cellular injury is increased by contacting the cell with the bioactive agent. In another aspect, the TRPM7-mediated cellular injury is decreased by contacting the cell with the bioactive agent. In another aspect, contacting the cell with the bioactive agent alters the fluorescence of an ion indicator compound loaded into the cell.

The invention further provides a method for screening for a bioactive agent that increases or decreases ion flux through a murine TRPM7 channel, the method comprising: a) contacting a candidate bioactive agent with a TRPM7 protein wherein the TRPM7 protein forms a TRPM7 channel; and b) determining the functional effect of the bioactive agent on the TRPM7 channel-mediated ion flux as determined by a fluorescent ion indicator. In one aspect, the determining step comprising comparing the indicators' fluorescence in the absence of the bioactive agent to the indicator's fluorescence in the presence of the bioactive agent.

The invention further provides an expression cassette comprising a polynucleotide encoding a murine TRPM7 polypeptide, wherein said polynucleotide is under the control of a promoter operable in eukaryotic cells. In some expression cassettes, the promoter is heterologous to the coding sequence. In some such expression cassettes, the promoter is a tissue specific promoter. In other such expression cassettes, the promoter is an inducible promoter. In some such expression cassette is contained in a viral vector. In some such expression cassettes, the viral vector is selected from the group consisting of a retroviral vector, an adenoviral vector, and adeno-associated viral vector, a vaccinia viral vector, and a herpes viral vector. Some such expression cassette further comprises a polyadenylation signal.

The invention further provides a cell comprising an expression cassette comprising a polynucleotide encoding a murine TRPM7 polypeptide, wherein said polynucleotide is under the control of a promoter operable in eukaryotic cells, said promoter being heterologous to said polynucleotide.

The invention further provides a method of screening for a modulator of ischemic injury, said method comprising: contacting a recombinant cell or cell line that expresses the inducible or transiently expressed TRPM7 gene with a test compound under conditions that activate TRPM7 channel activity; and detecting an increase or a decrease in the amount of cell death.

The invention further provides a method of screening for a modulator of ischemic injury, said method comprising: producing a stroke in a rat or mouse, administering to said murine an effective amount of said modulator, and determining the impact on the size of the stroke. In one aspect, the determining step comprising determining the area of ischemic tissue in a standardized section of the murine brain. In another aspect, the determining step comprising determining the volume of ischemic tissue in the murine brain. In another aspect, the determining comprises comparing the size of the stroke in the absence of the bioactive agent candidate to the size of the stroke in the presence of the bioactive agent candidate. Analogous assays can be performed in a mouse or rat model of myocardial infarction or glaucoma or any of the animal models described herein.

BRIEF DESCRIPTION OF THE DRAWINGS

FIGS. 1, 2A, 2B, 3A, 3B, 4A, 4B, 5A, 5B, 6, 7A, 7B, 8, 9 and 10A, 10B: Compounds from Lopac and Prestwick libraries, FIGS. 11-16: M1-M30 structures

FIG. 18: Effect of Tet Induction and the indicated different buffer conditions on cell death as measured by propidium iodide (PI) fluorescence in TRPM7-expressing HEK293 cells at the indicated times in an assay performed in a 24 well plate format.

FIG. 21: Effect of adding a candidate test compound at the same time as Tet induction on the expression of FLAG-TRPM7 in HEK293 cells.

FIG. 22: Scatterplots of B-scores obtained by screening the Maybridge compound library for the ability of the test compounds to reduce TRPM7-mediated cell death in stably-transfected, Tet-inducible HEK293 cells.

FIG. 23: TRPM7 expression in rat tissues, mouse tissues and H9c2 cardiac myocytes. RNA from rat tissues, mouse tissues, and H9c2 cells was reverse-transcribed and PCR carried out using rat- and mouse-TRPM7-specific primers. TRPM7 expression was visualized as a 530 bp band on a 1% agarose gel. β-actin served as a loading control.

FIG. 24: Immunocytochemical analysis of TRPM7 immunofluorescence in H9c2 cells. The cells were stained with the indicated primary and secondary antibodies, and viewed with a confocal microscope at the indicated magnification.

FIG. 27: Schematic of Flag-TRPM7/pBluescript KS II. (A) Schematic of the Flag-TRPM7/pBluescript construct depicting sites of EcoRI, KpnI, and SpeI digest. Abbreviations:

Figure 1:
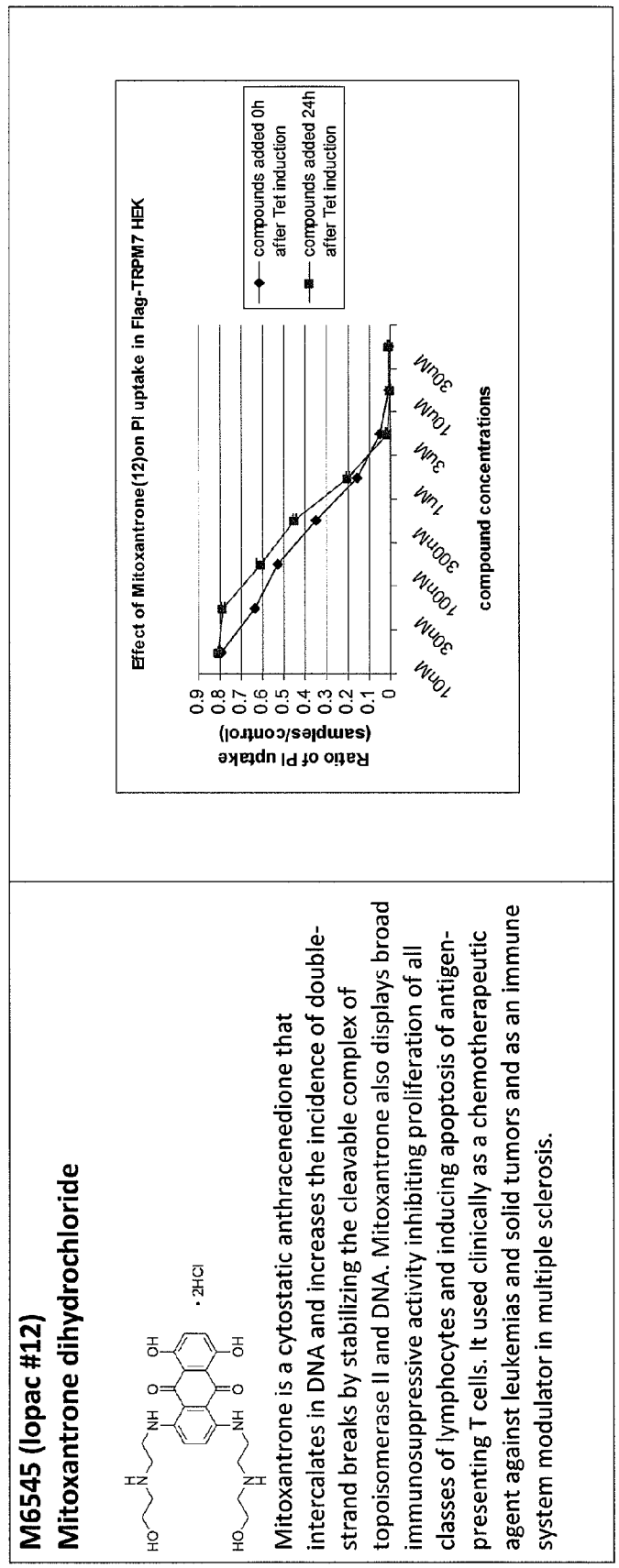
Figure 5A:
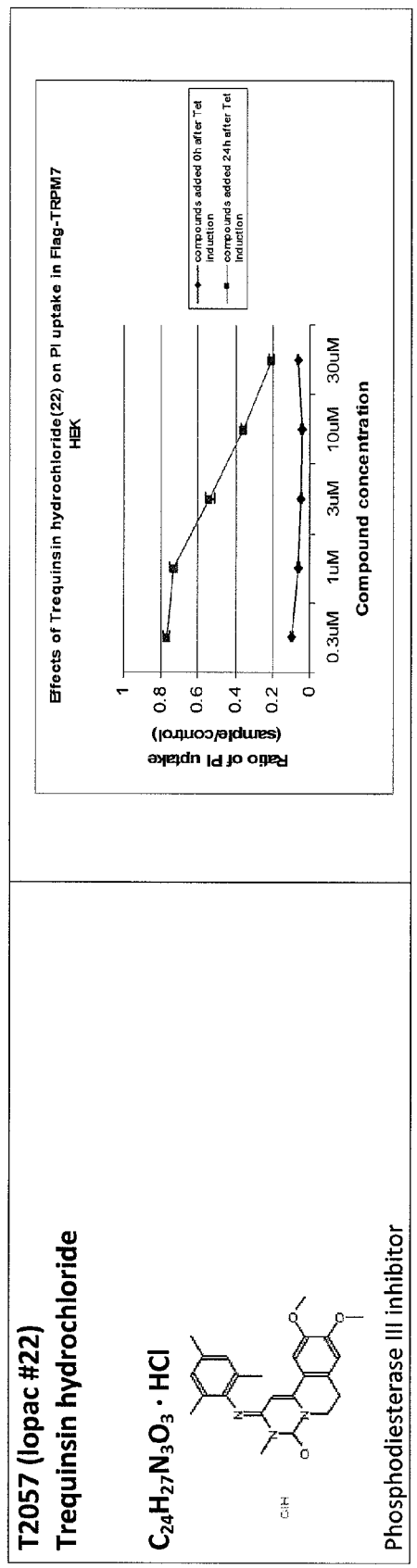
Figure 5B:
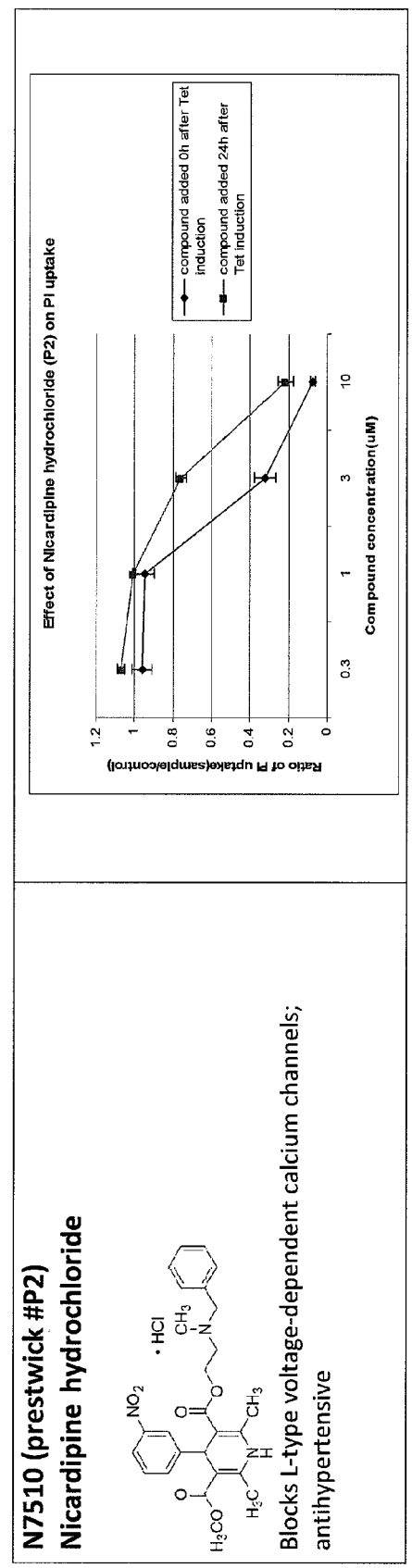
Figure 6:
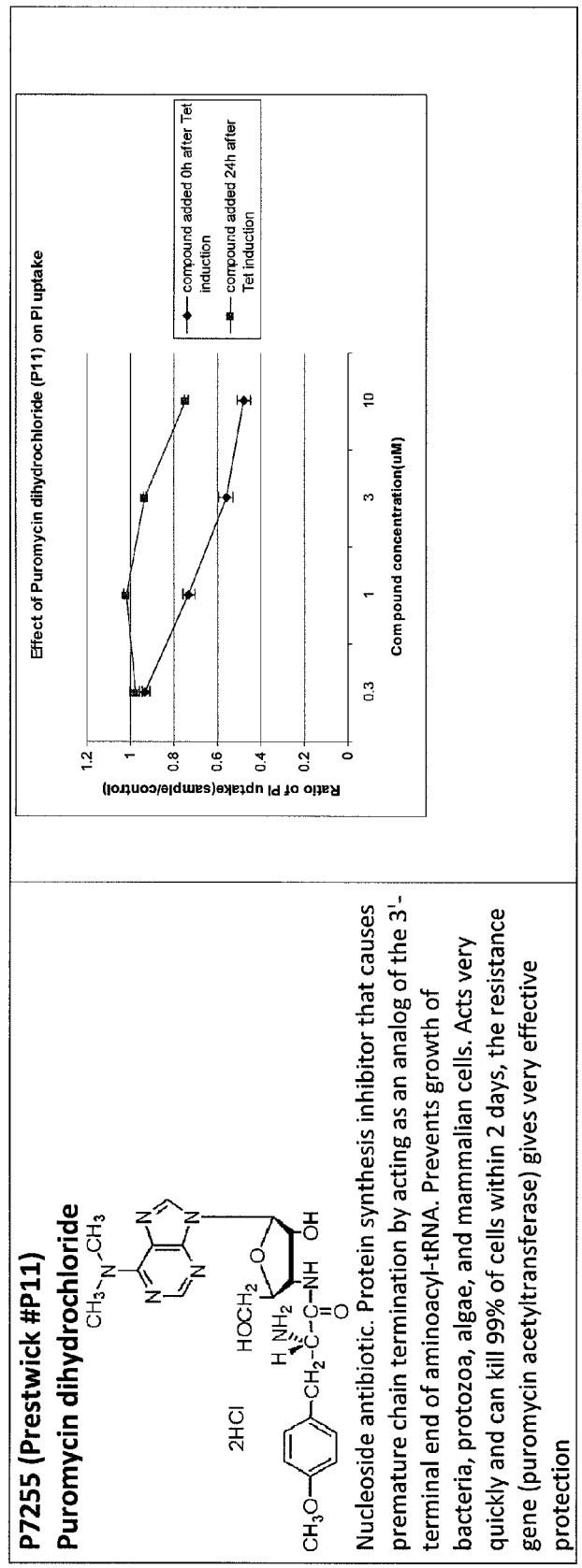
Figure 8:
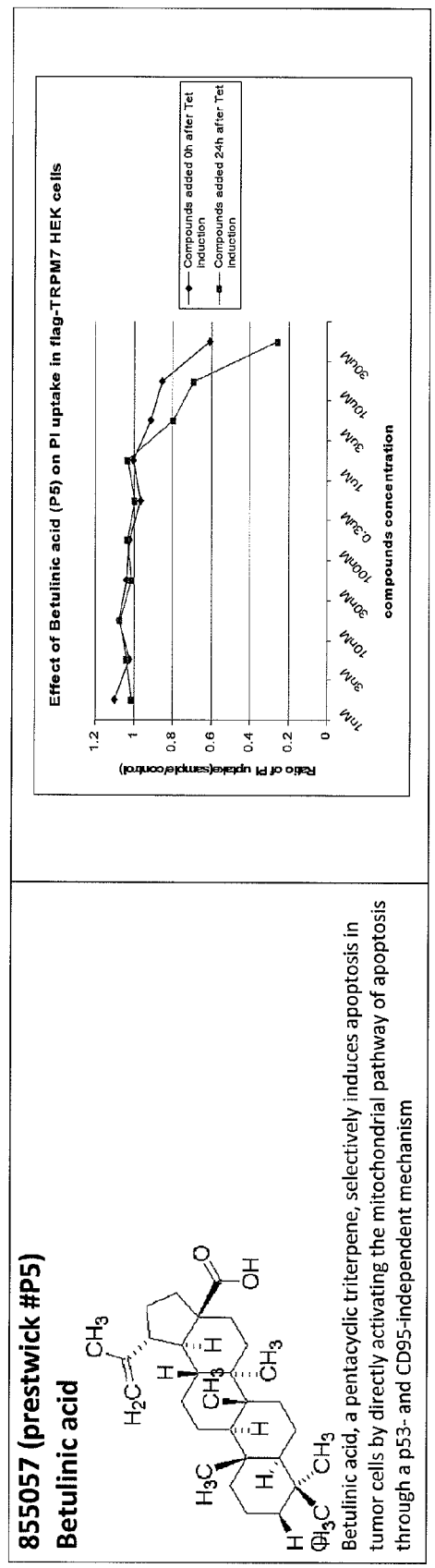
Figure 9:
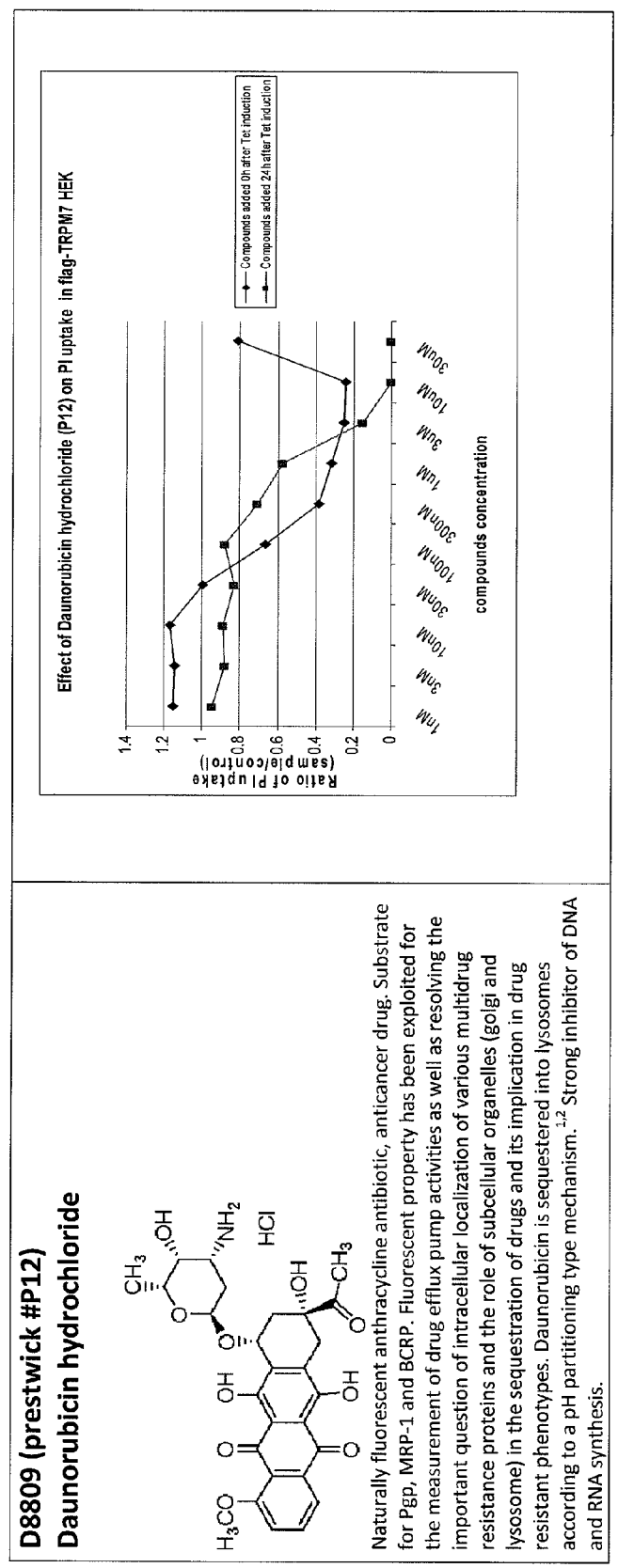
Figure 10A:
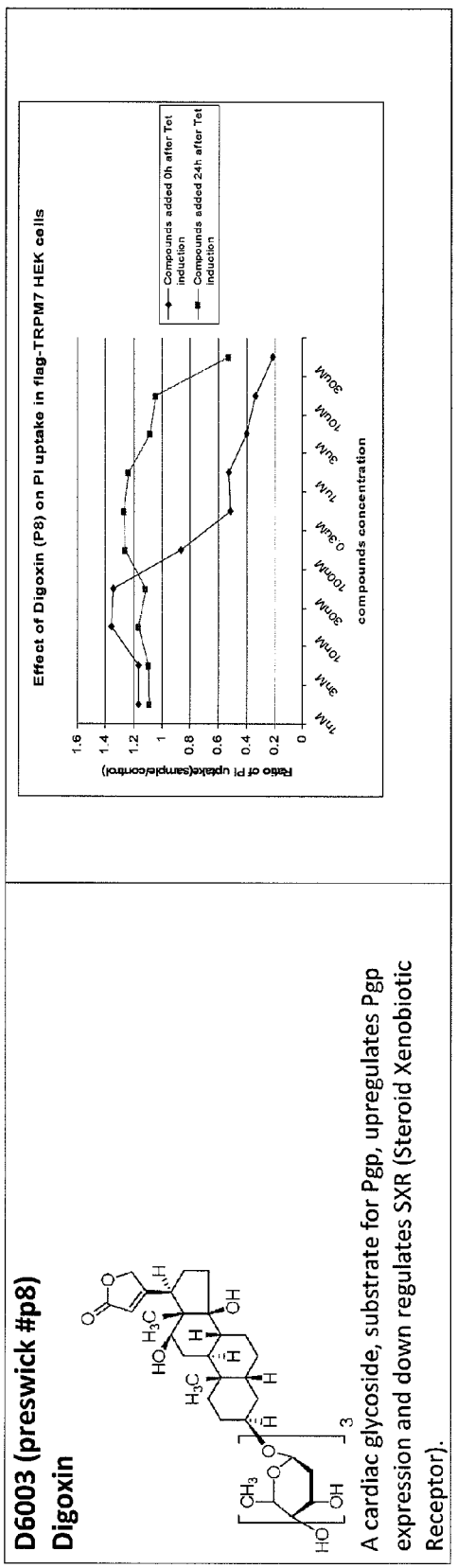
Figure 10B:
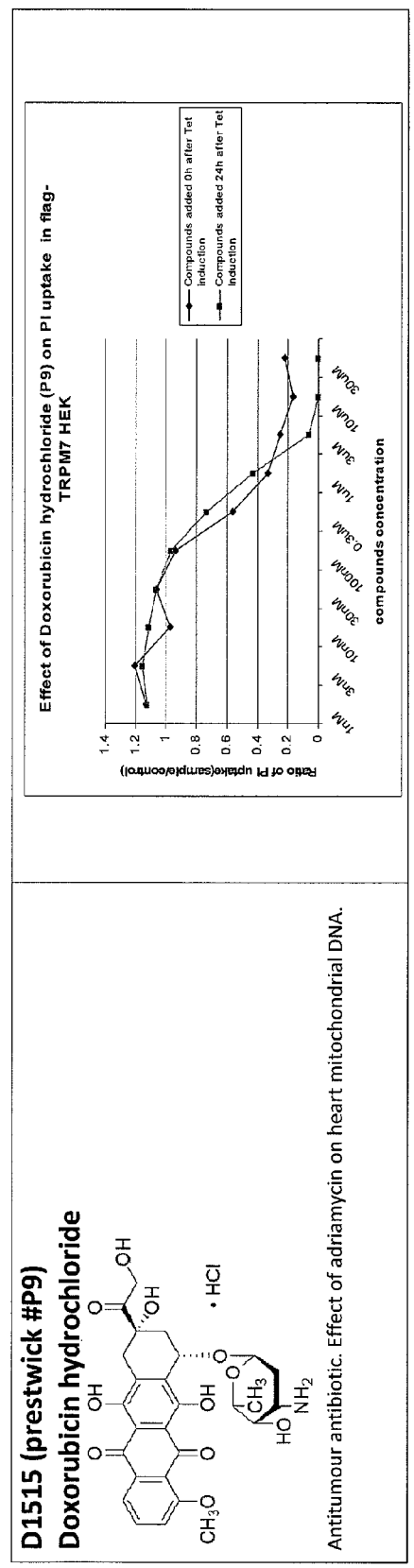
Figure 15:
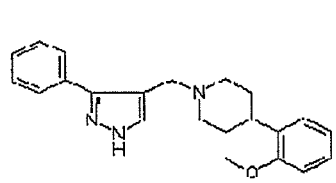

TRPM7, TRPM7 cDNA; Flag, Flag tag sequence; rep, promotes replication of the plasmid; Amp, ampicillin resistance gene. (B) Restriction enzyme digest with EcoRI produced 3 fragments corresponding to a 3'→5' direction of insert in the pBluescript vector (lane 3), length in bps: 3838, 3200, 1592. Lane 1:1 kb DNA ladder; lane 2: control, undigested plasmid.

FIG. 28: Schematic of Flag-TRPM7/pTracer-CMV2. (A) Schematic of the Flag-TRPM7/pTracer eGFP(+) construct depicting the expected sites of BamHI, EcoRI, EcoRV, and PmeI digest. The region encompassed by the NgoMIV restriction sites are absent from the eGFP(−) construct. Abbreviations: Pcmv, CMV promoter; TRPM7, TRPM7 cDNA; P¬ ef, EF-1α promoter; eGFP, enhanced green fluorescent protein cDNA; pUC, origin of replication; Amp, ampicillin resistance gene. (B) Restriction digest of the eGFP (+) construct. Lane 1:1 kb DNA ladder; lane 2: control, undigested plasmid. Fragment lengths, in bps, for EcoRV: 11449; EcoRI: 6657, 3200, 1592; PmeI: 5769, 5680; BamHI: 5857, 4000, 1592.

FIG. 29: Transient transfection of HEK-293T cells with the full-length TRPM7 construct. (A) Representative images of eGFP and Hoechst fluorescence 48 hours post-transfection. Green: eGFP expression; blue: Hoechst. (B) Representative phase images of untransfected cells and of cells transfected with the TRPM7/pTraceeGFP-constructs 48 hours post-transfection.

FIG. 30: TRPM7 expression increases calcium uptake induced by chemical anoxia (1 hour). Untransfected cells and cells expressing the full-length TRPM7 channel were exposed to NaCN treatment and calcium uptake monitored by fluo-3. (A) Bars represent mean±sem of 4-5 separate experiments. * indicates significant difference from untransfected controls by Student's t test, $p<0.05$; ** $p<0.01$. (B) Fitted dose-response curves of calcium uptake induced by NaCN treatment at 1 hour. Symbols represent mean±sem of 4-5 separate experiments.

FIG. 31: TRPM7 expression increases calcium uptake induced by chemical anoxia (2 hours). Untransfected cells and cells expressing the full-length TRPM7 channel were exposed to NaCN treatment and uptake monitored by fluo-3. (A) Bars represent mean±sem of 4-5 separate experiments. * indicates significant difference from untransfected controls by Student's t test, $p<0.05$; ** $p<0.01$. (B) Fitted dose-response curves of calcium uptake induced by NaCN treatment at 2 hours. Symbols represent mean±sem of 4-5 separate experiments.

Figure 32:
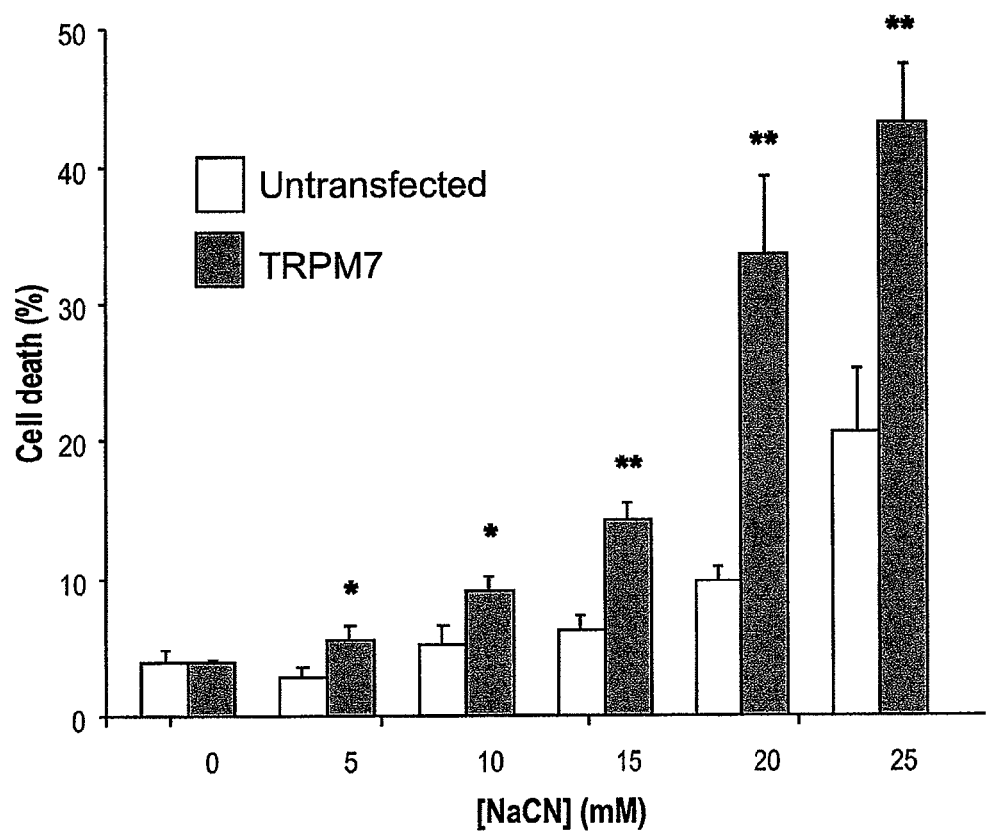

FIG. 32: Expression of full-length TRPM7 increases cell death induced by chemical anoxia. Cells were treated with NaCN for 2 hours and cell death assessed by PI uptake. PI uptake values are normalized to Fmax by the addition of 0.05% Triton X-100. Bars represent mean±sem of 4-5 separate experiments. * indicates significant difference from untransfected controls, ANOVA followed by post hoc Holm-Sidak pairwise multiple comparisons, $p<0.05$; ** $p<0.01$. # indicates significant difference from TRPM7-transfected cells, $p<0.05$; ## $p<0.01$.

Figure 33:
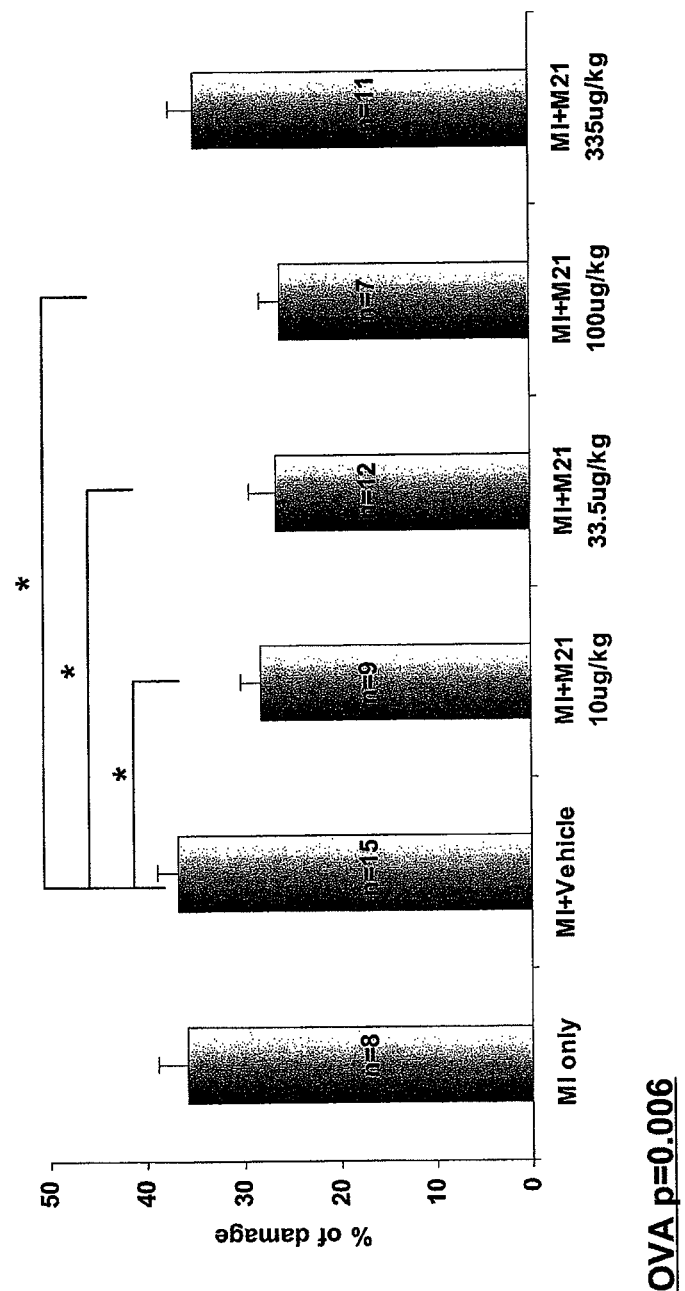

FIG. 33: Drug M21 reduces the damage to the heart in an in vivo mouse model of myocardial infarction.

Figure 34:
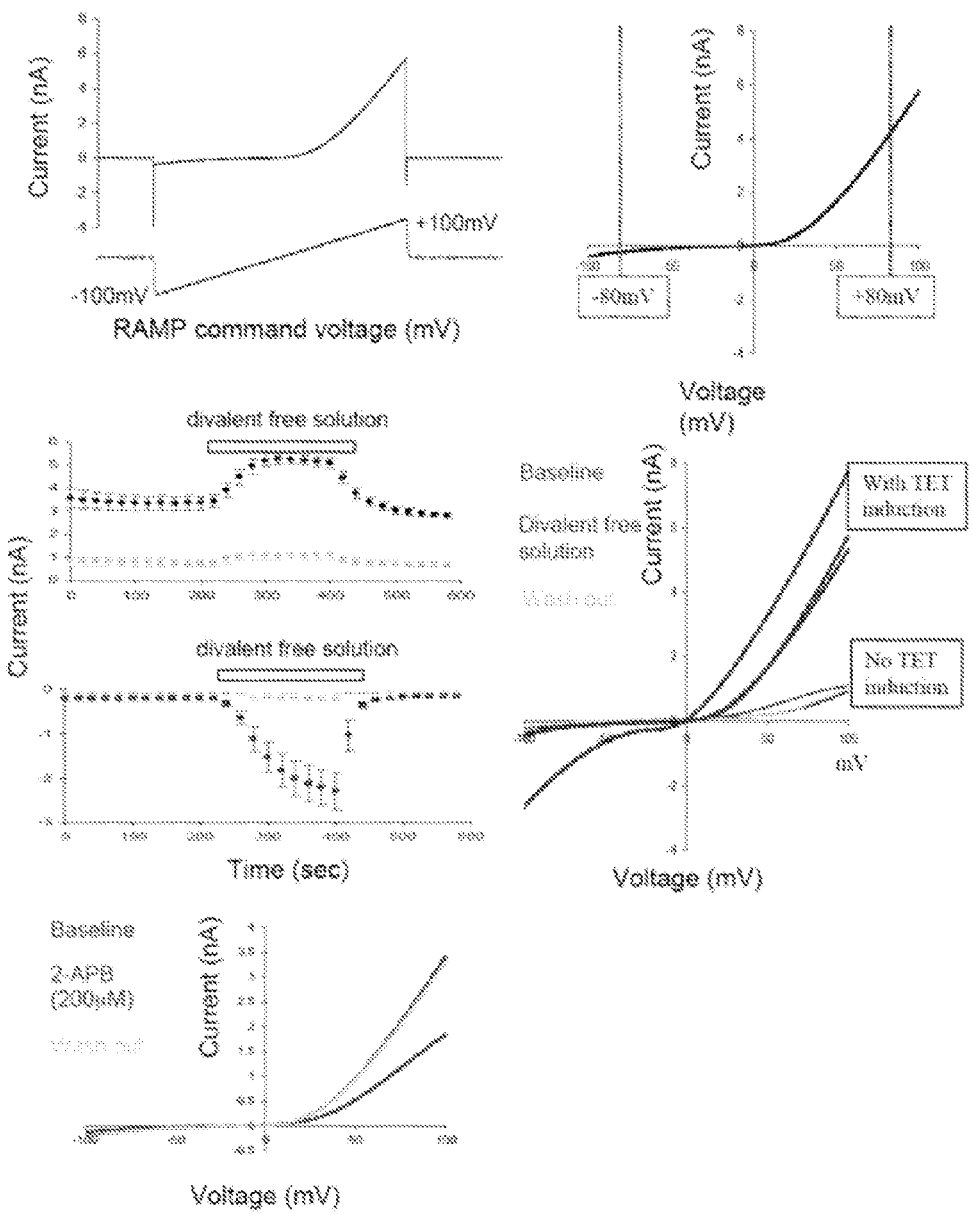

FIG. 34: Characterization of TRPM7-like currents in HEK293 cells.

FIG. 35: Effect of Compound M5 on TRPM7 Currents, % of control, and cell survival following tet-induced TRPM7 in HEK293 cells.

FIG. 36: Effect of Compound M6 on TRPM7 Currents, % of control, and cell survival following tet-induced TRPM7 in HEK293 cells.

Figure 37:
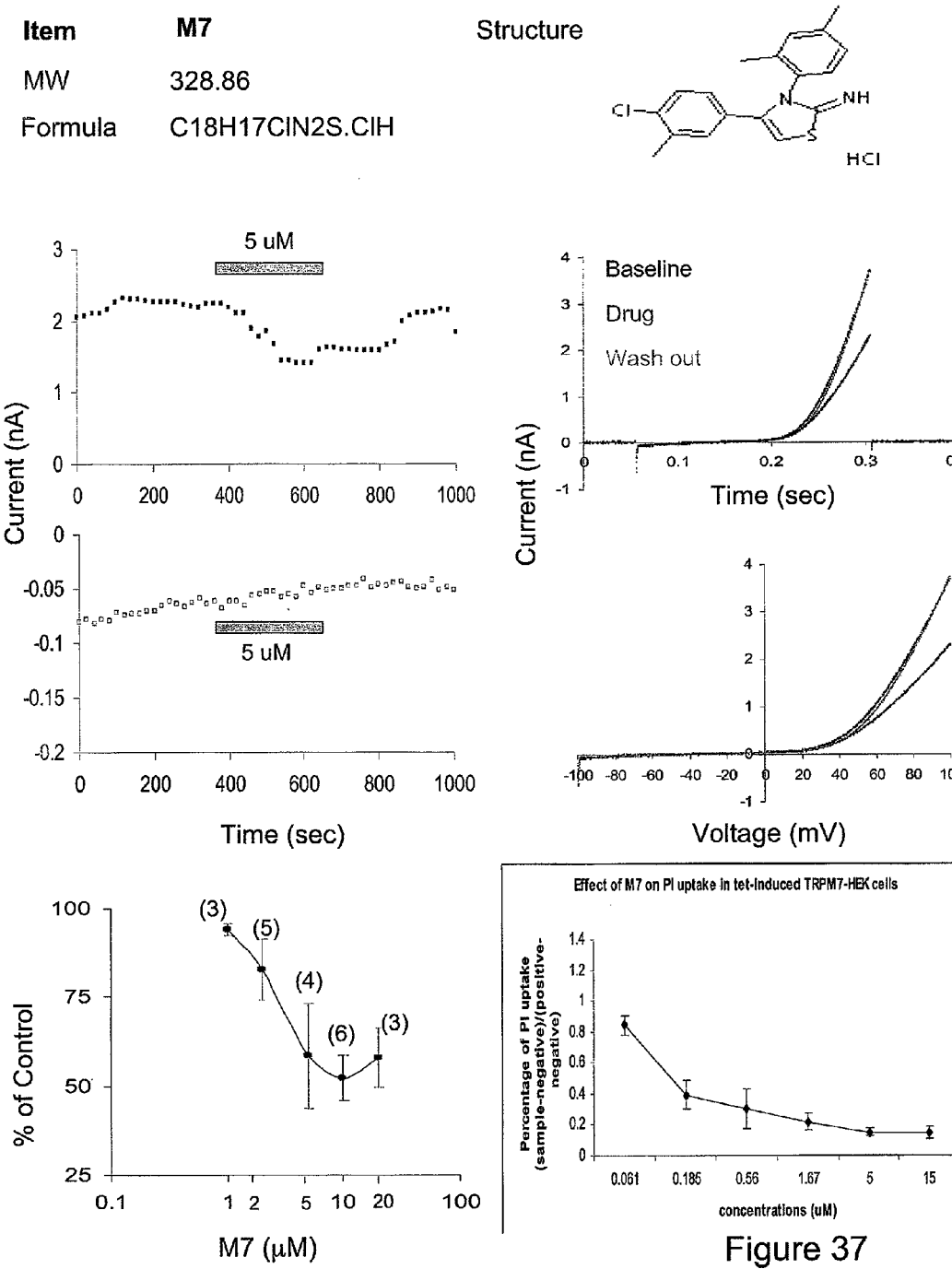

FIG. 37: Effect of Compound M7 on TRPM7 Currents, % of control, and cell survival following tet-induced TRPM7 in HEK293 cells.

Figure 38:
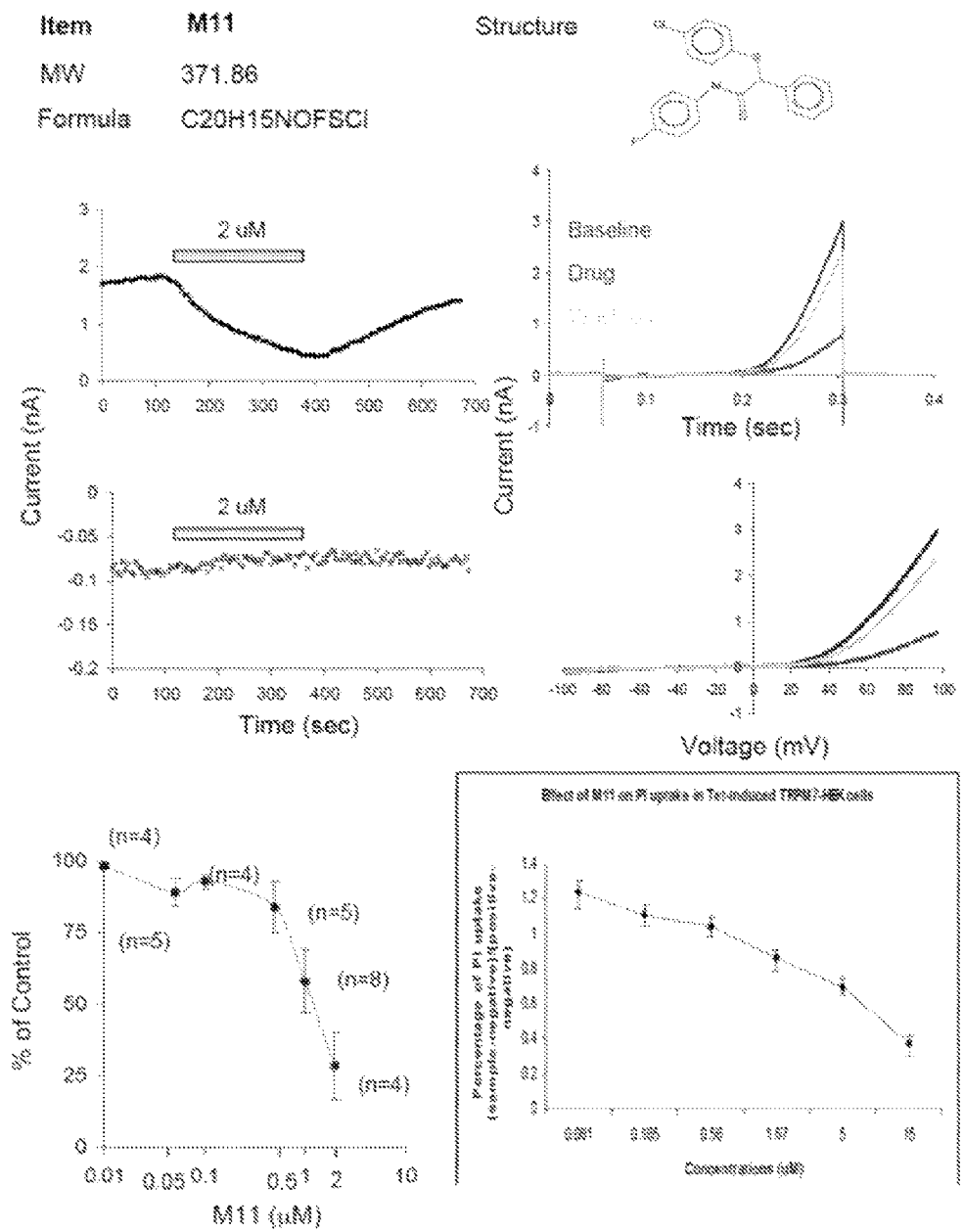

FIG. 38: Effect of Compound M11 on TRPM7 Currents, % of control, and cell survival following tet-induced TRPM7 in HEK293 cells.

FIG. 39: Effect of Compound M14 on TRPM7 Currents, % of control, and cell survival following tet-induced TRPM7 in HEK293 cells.

FIG. 40: Effect of Compound M21 on TRPM7 Currents, % of control, and cell survival following tet-induced TRPM7 in HEK293 cells.

Figure 41:
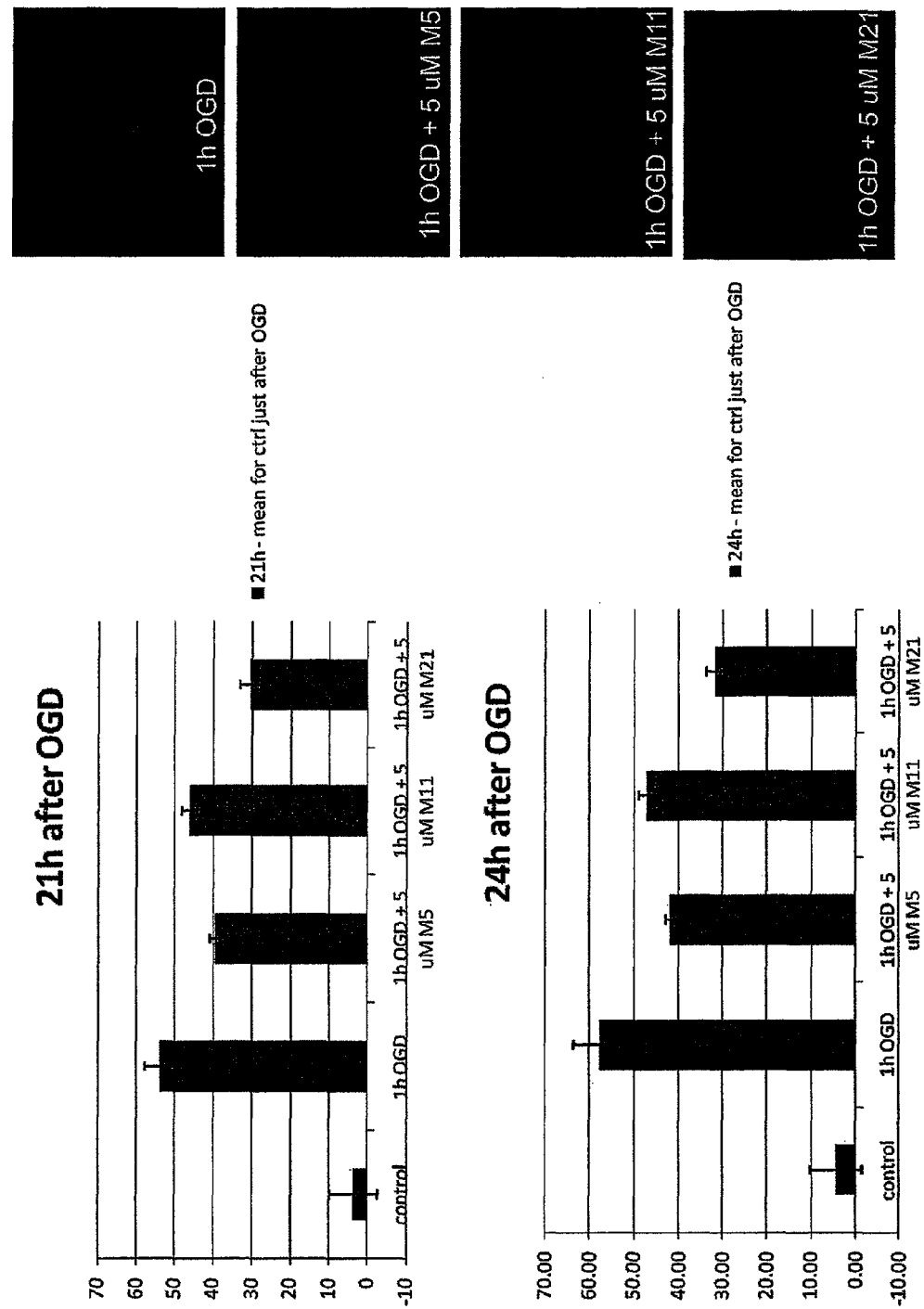

FIG. 41: Compounds M5, M11 and M21 are able to reduce retinal ischemia in rat retinal explants subjected to oxygen-glucose deprivation (OGD).

Figure 42:
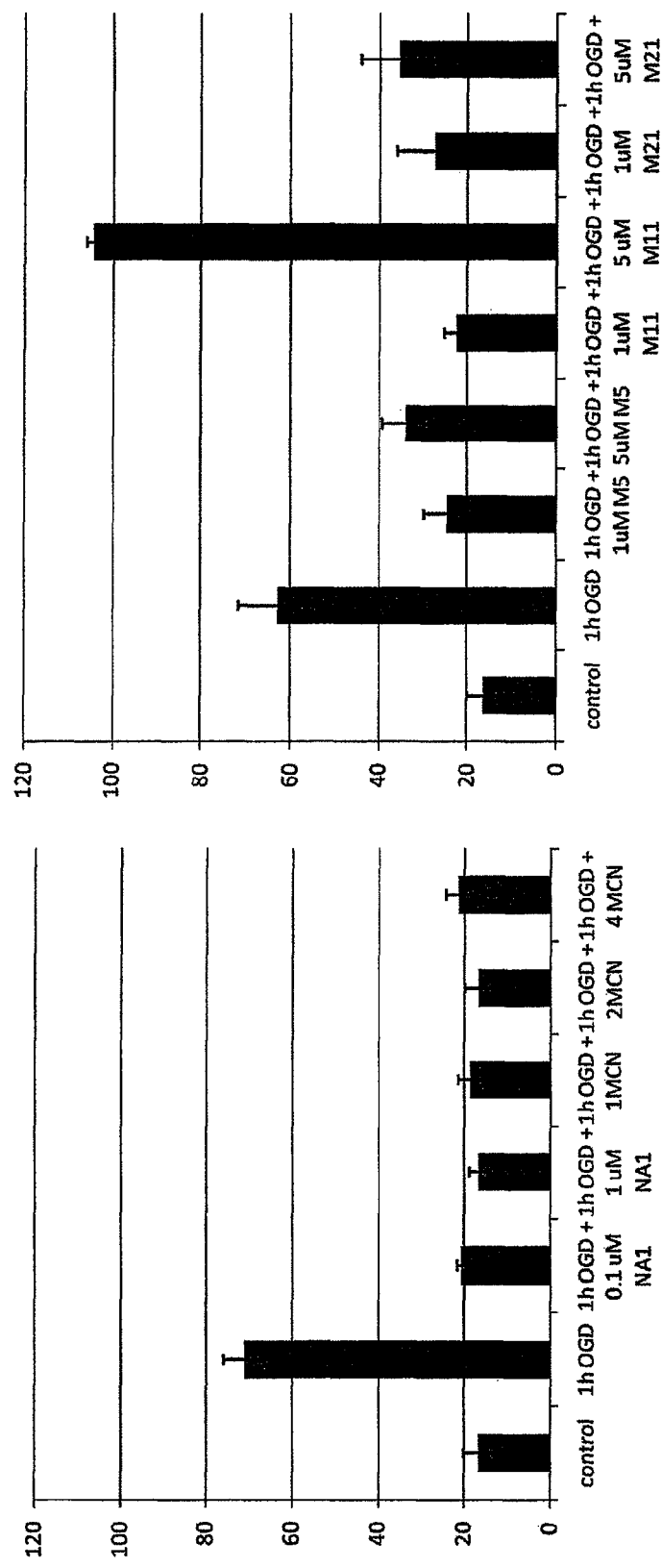

FIG. 42: Compounds M5, M11 and M21 can reduce retinal cell death in rat retinal explants that have been dissociated and subjected to oxygen-glucose deprivation (OGD).

Figure 43:
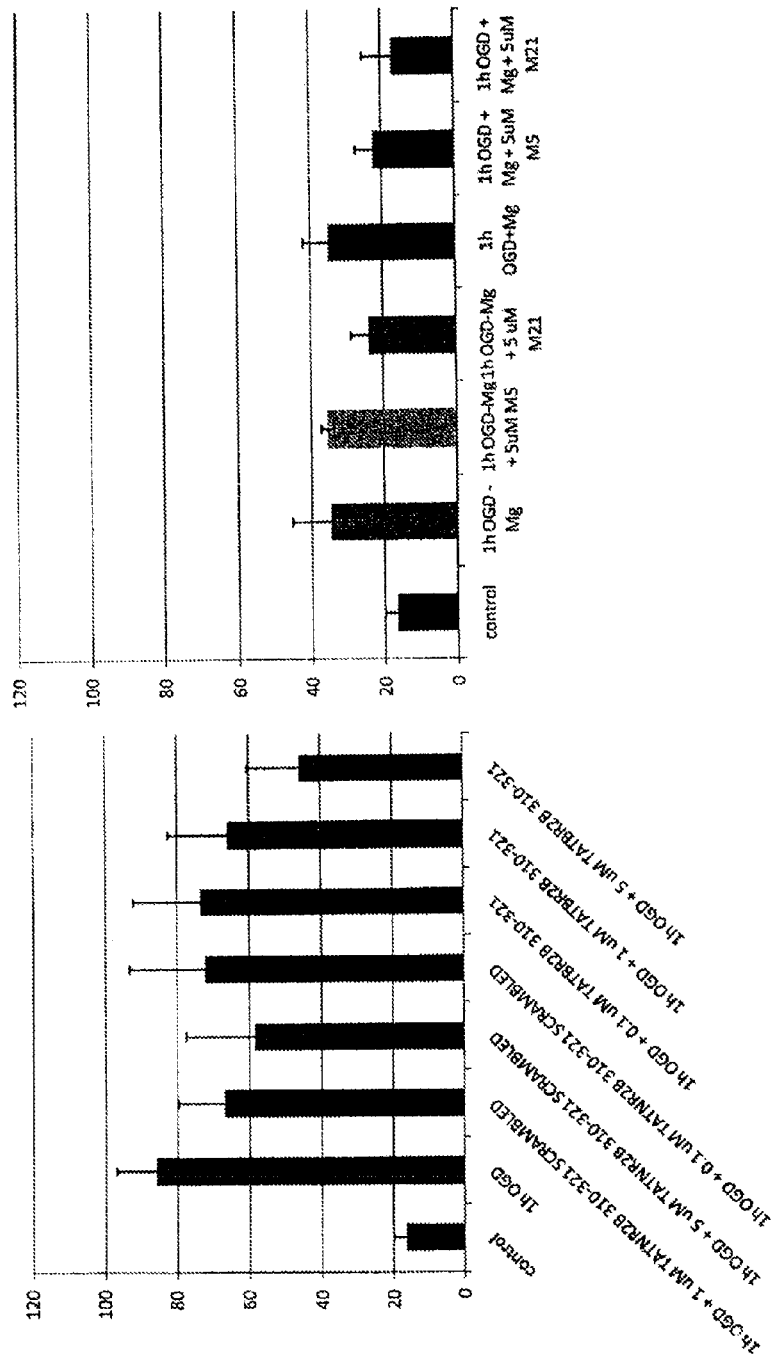

FIG. 43: Percent cell death in dissociated mixed rat retinal cultures subjected to OGD in the presence or absence of different compounds.

Figure 44:
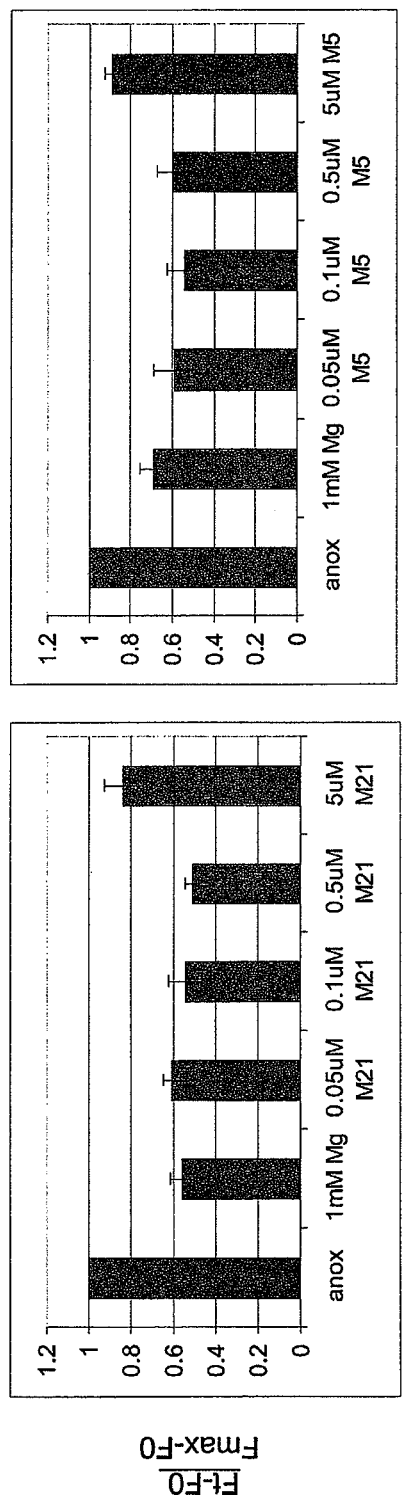

FIG. 44: Compounds M5 and M21 significantly reduce the amount of cell death following OGD in the rat ventricular myoblast cell line H9c2

Figure 45:
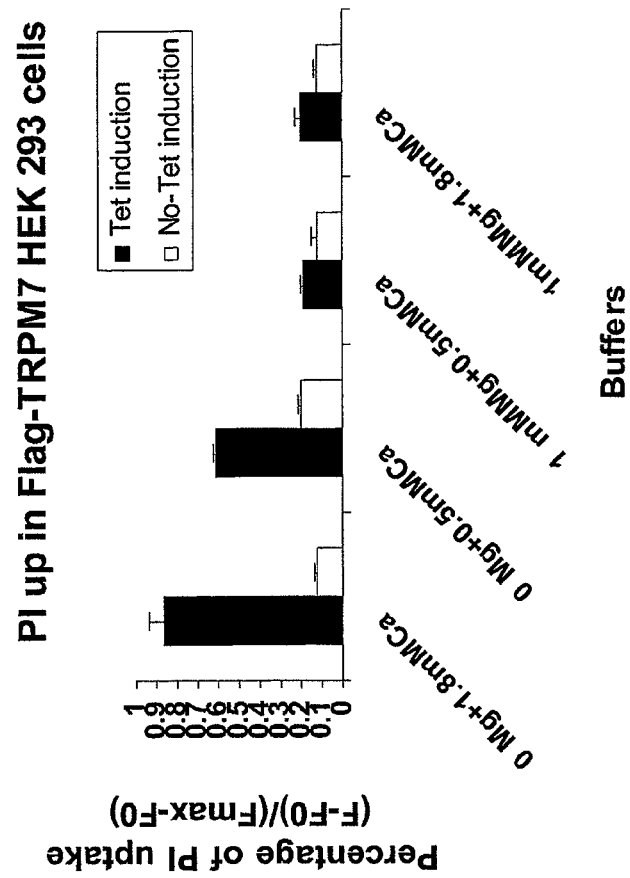

FIG. 45: Optimization of Screening buffer conditions for TRPM7 expression under a tet on/off expression system in HEK293 cells.

Figure 46:
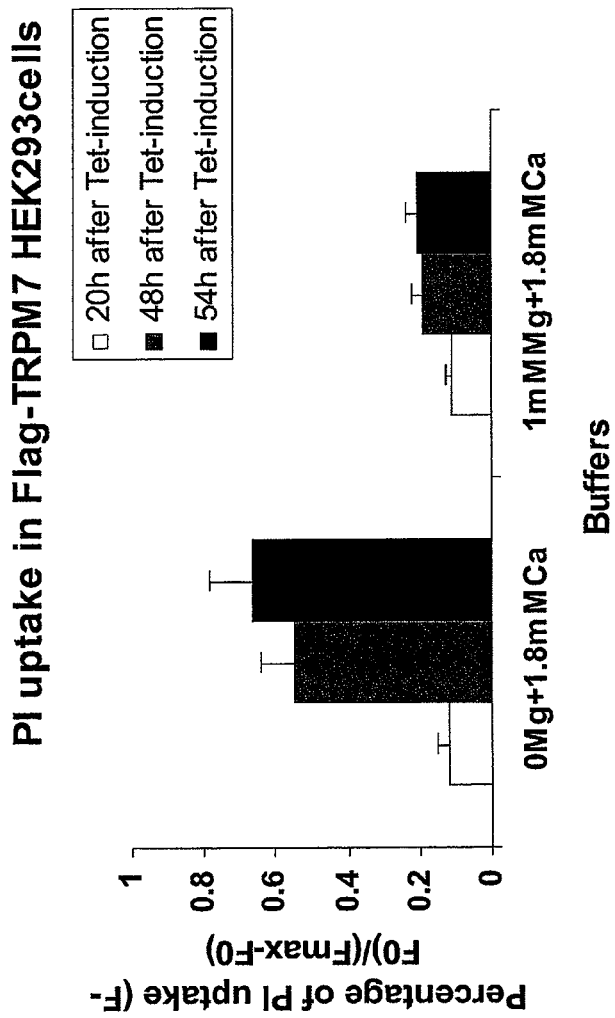

FIG. 46: Optimization of the duration of tet induction of TRPM7 in HEK293 cells.

Figure 47:
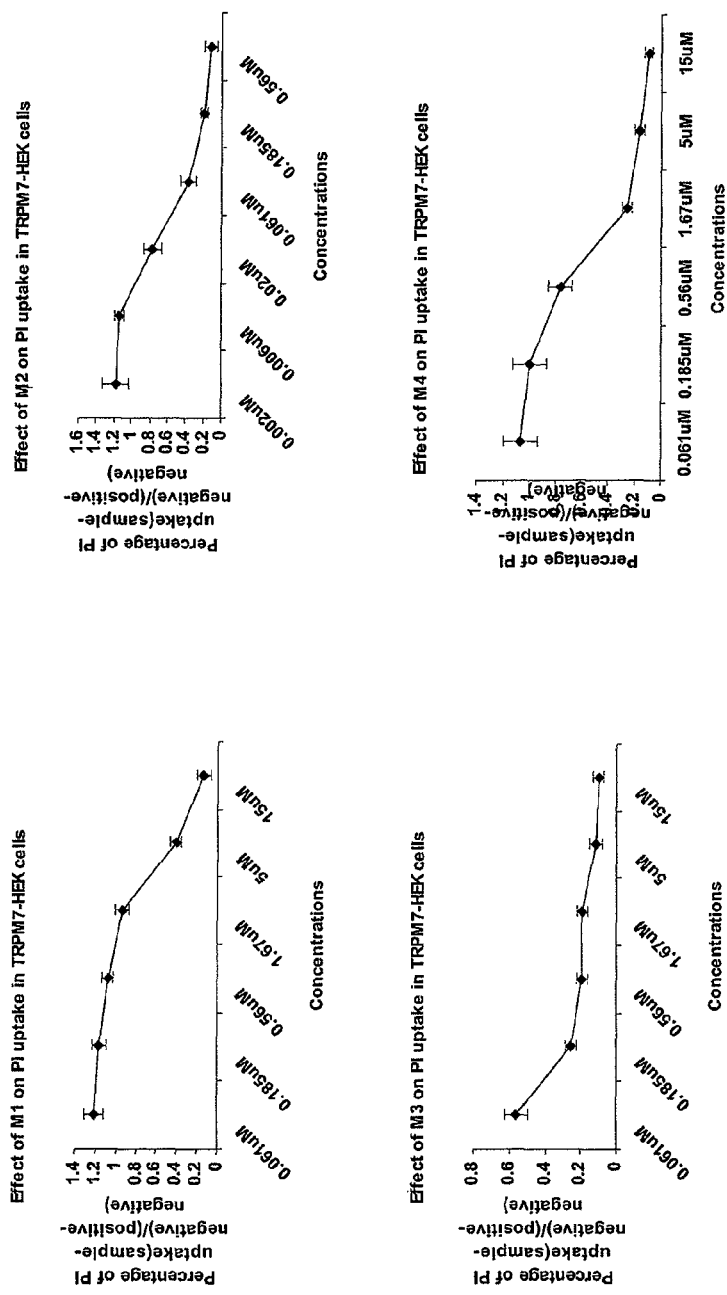

FIG. 47: Titrations of compounds identified in chemical screens that inhibit TRPM7-induced cell death.

Figure 48:
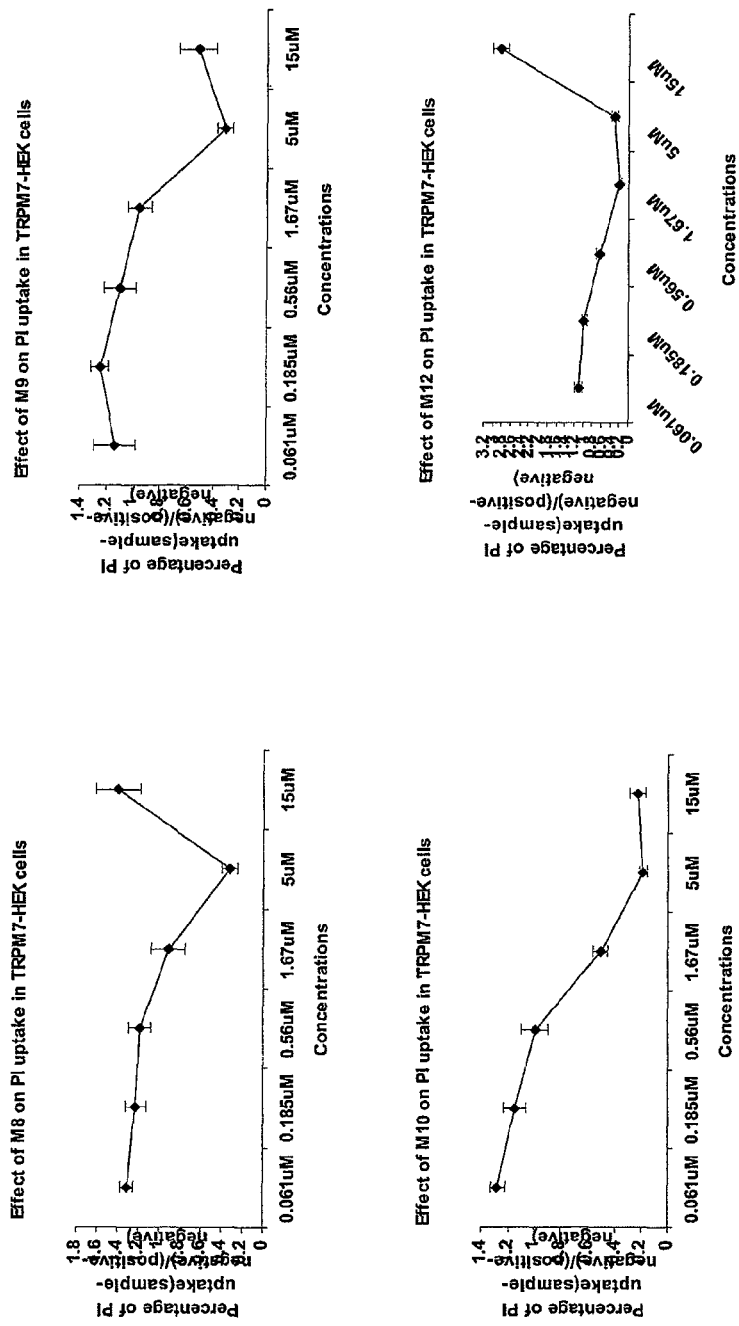

FIG. 48: Titrations of compounds identified in chemical screens that inhibit TRPM7-induced cell death.

Figure 49:
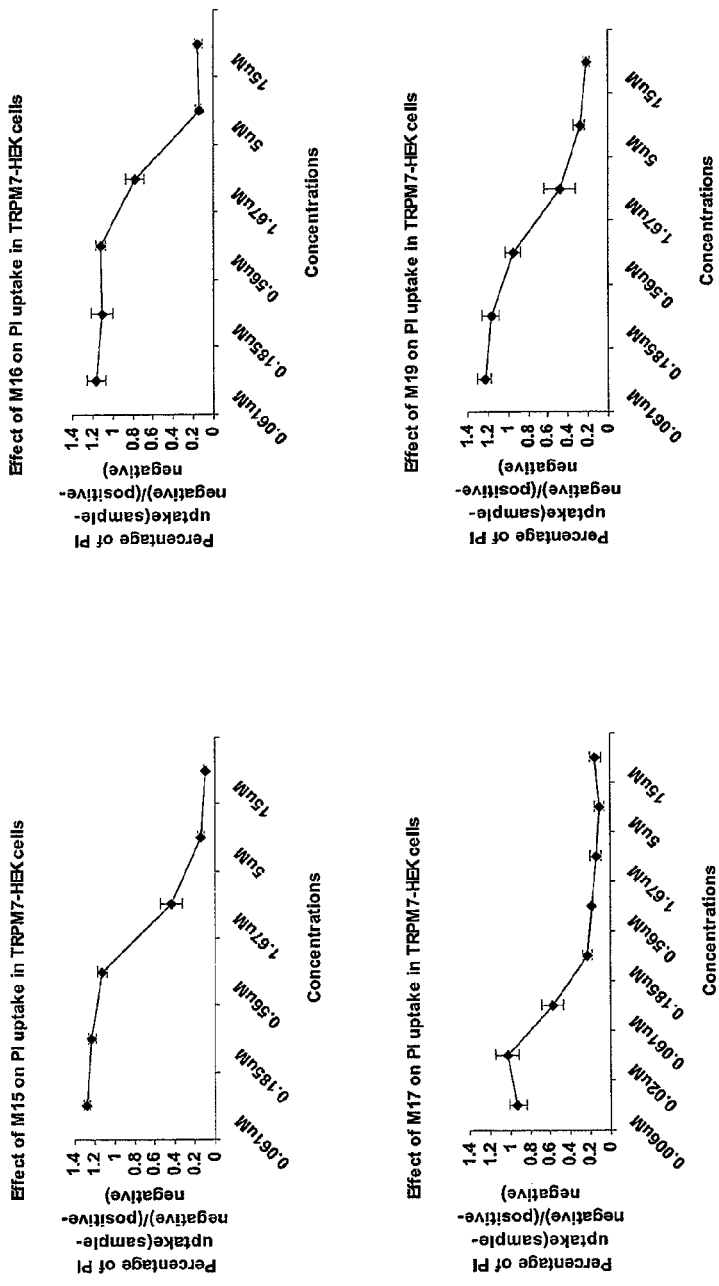

FIG. 49: Titrations of compounds identified in chemical screens that inhibit TRPM7-induced cell death.

Figure 50:
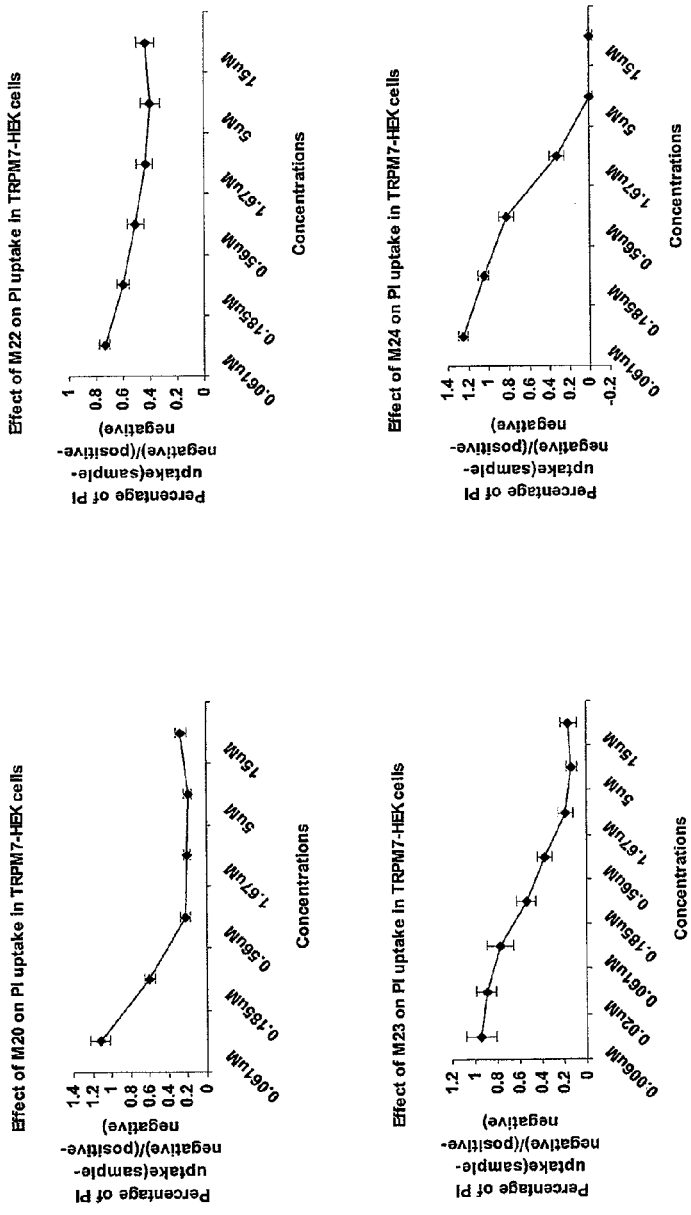

FIG. 50: Titrations of compounds identified in chemical screens that inhibit TRPM7-induced cell death.

Figure 51:
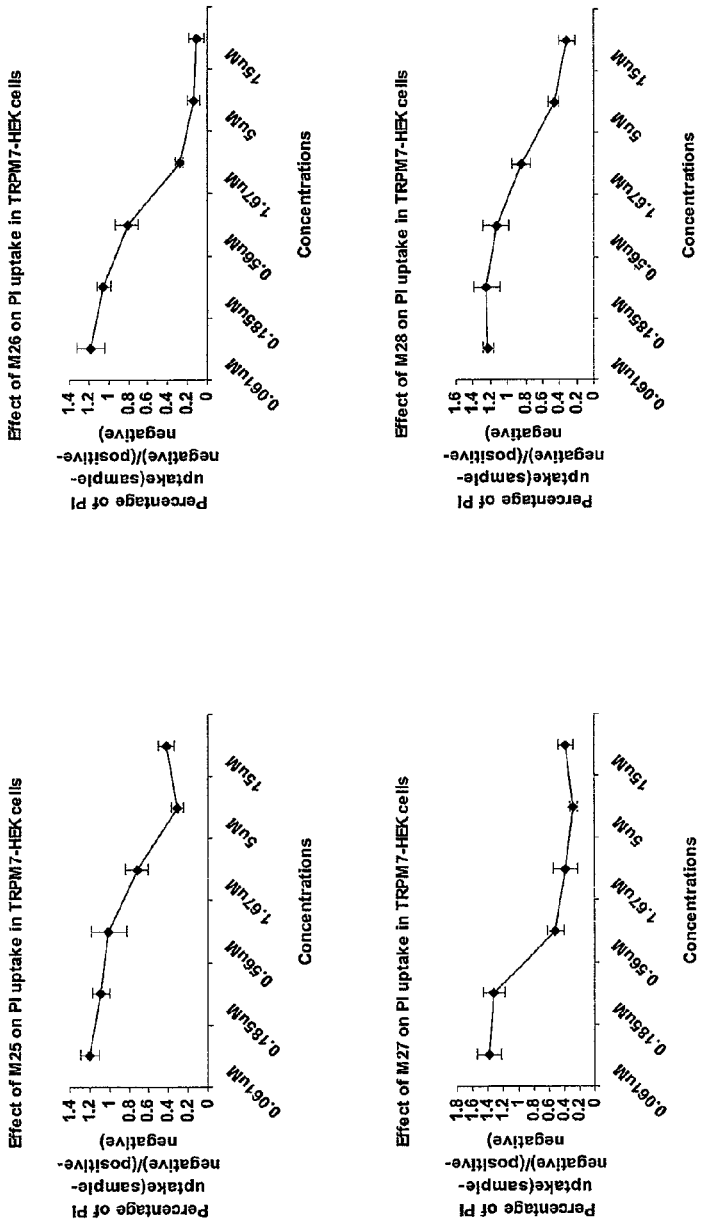

FIG. 51: Titrations of compounds identified in chemical screens that inhibit TRPM7-induced cell death.

Figure 52:
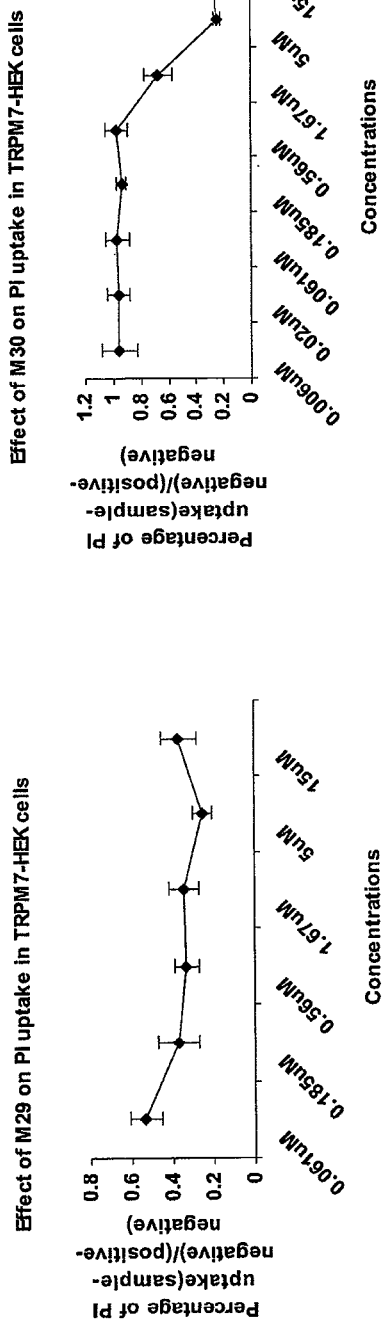

FIG. 52: Titrations of compounds identified in chemical screens that inhibit TRPM7-induced cell death.

Figure 53:
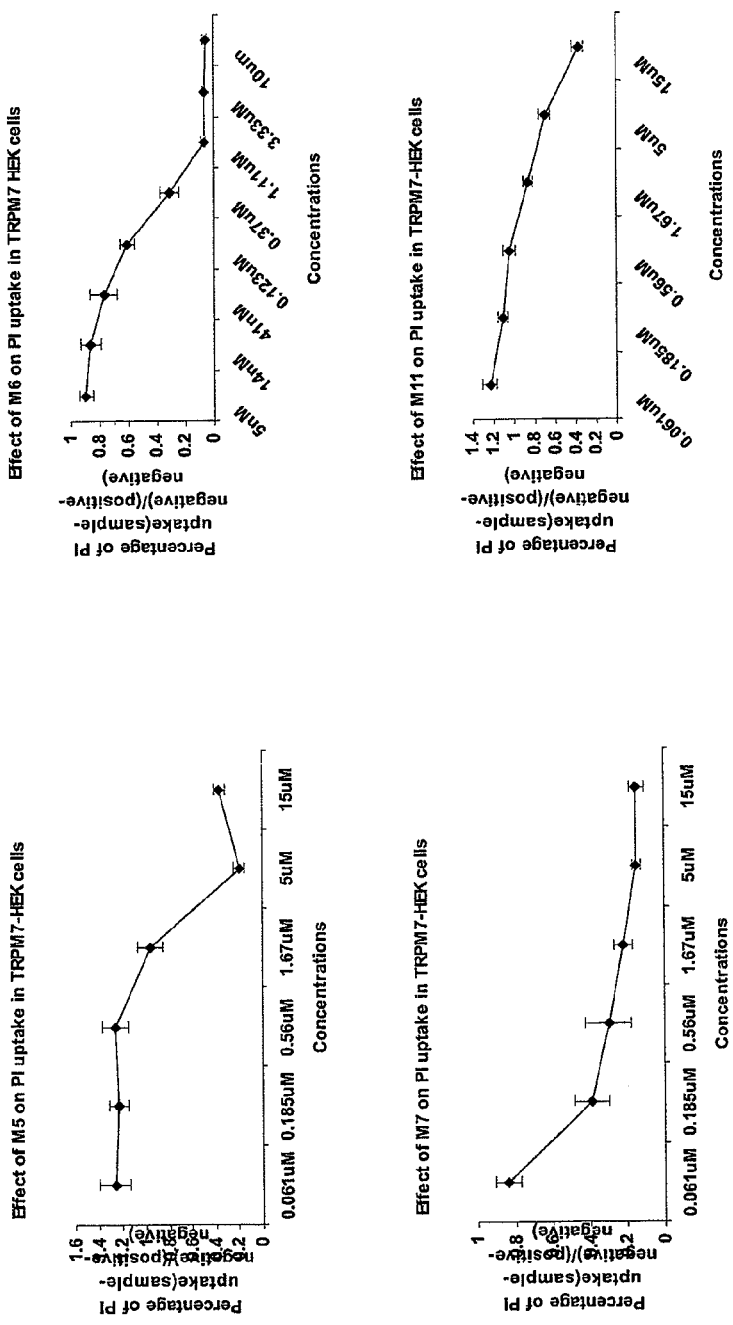

FIG. 53: Titrations of compounds identified in chemical screens that inhibit TRPM7-induced cell death.

Figure 54:
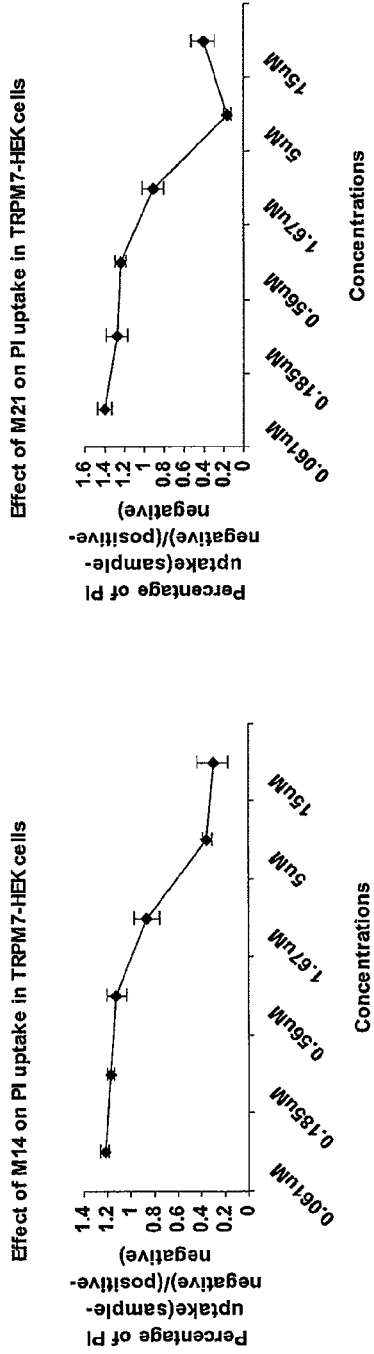

FIG. 54: Titrations of compounds identified in chemical screens that inhibit TRPM7-induced cell death.

Figure 55:
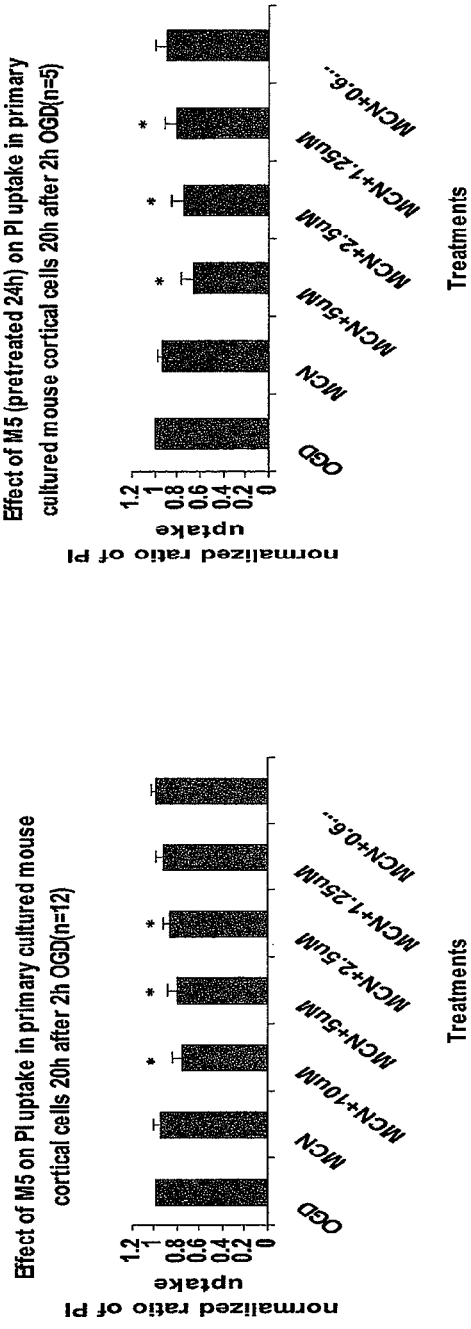

FIG. 55: Effect of compounds on PI uptake in Primary cultured mouse cortical cells 20 h after OGD.

Figure 56:
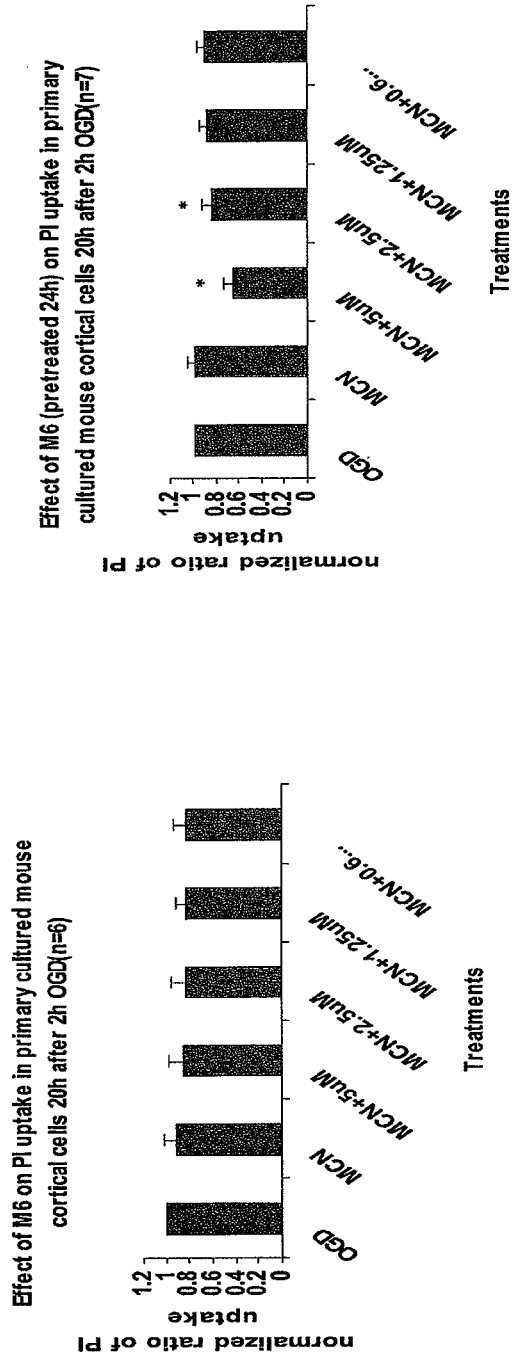

FIG. 56: Effect of compounds on PI uptake in Primary cultured mouse cortical cells 20 h after OGD.

Figure 57:
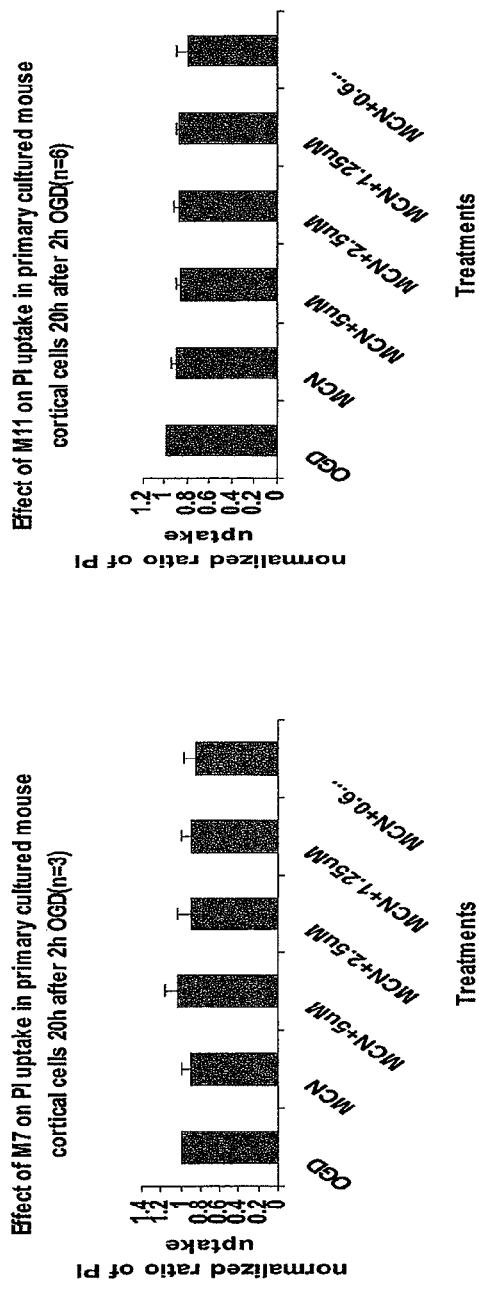

FIG. 57: Effect of compounds on PI uptake in Primary cultured mouse cortical cells 20 h after OGD.

Figure 58:
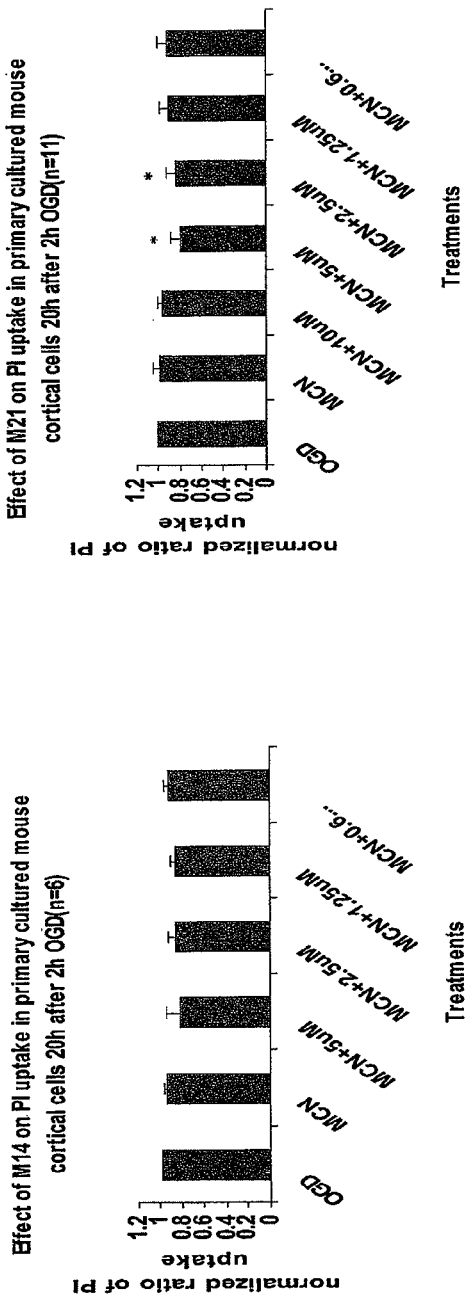

FIG. 58: Effect of compounds on PI uptake in Primary cultured mouse cortical cells 20 h after OGD.

Figure 59:
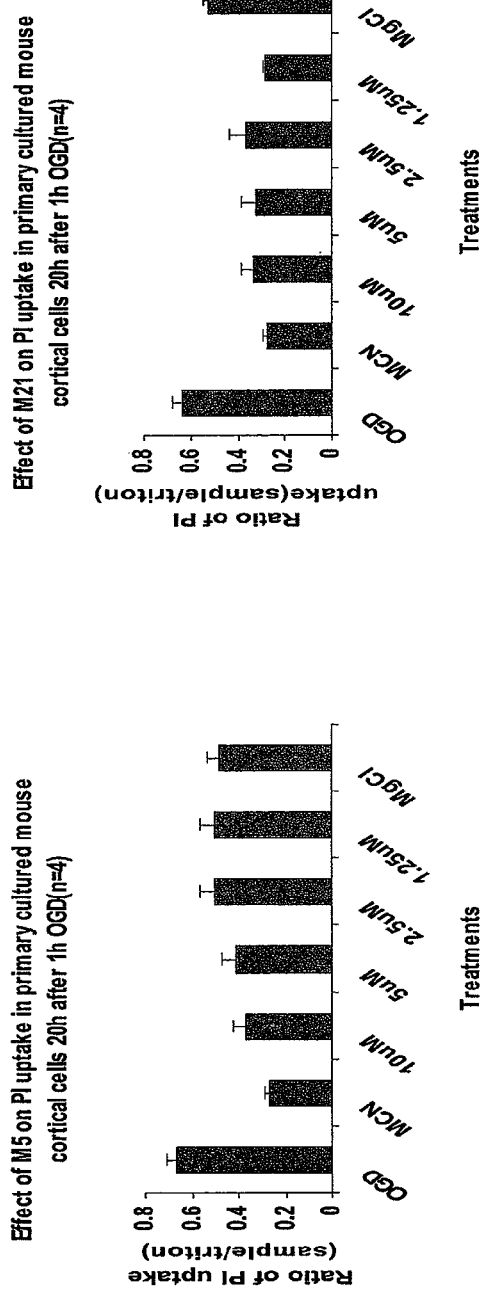

FIG. 59: Effect of compounds on PI uptake in Primary cultured mouse cortical cells 20 h after OGD.

Figure 60:
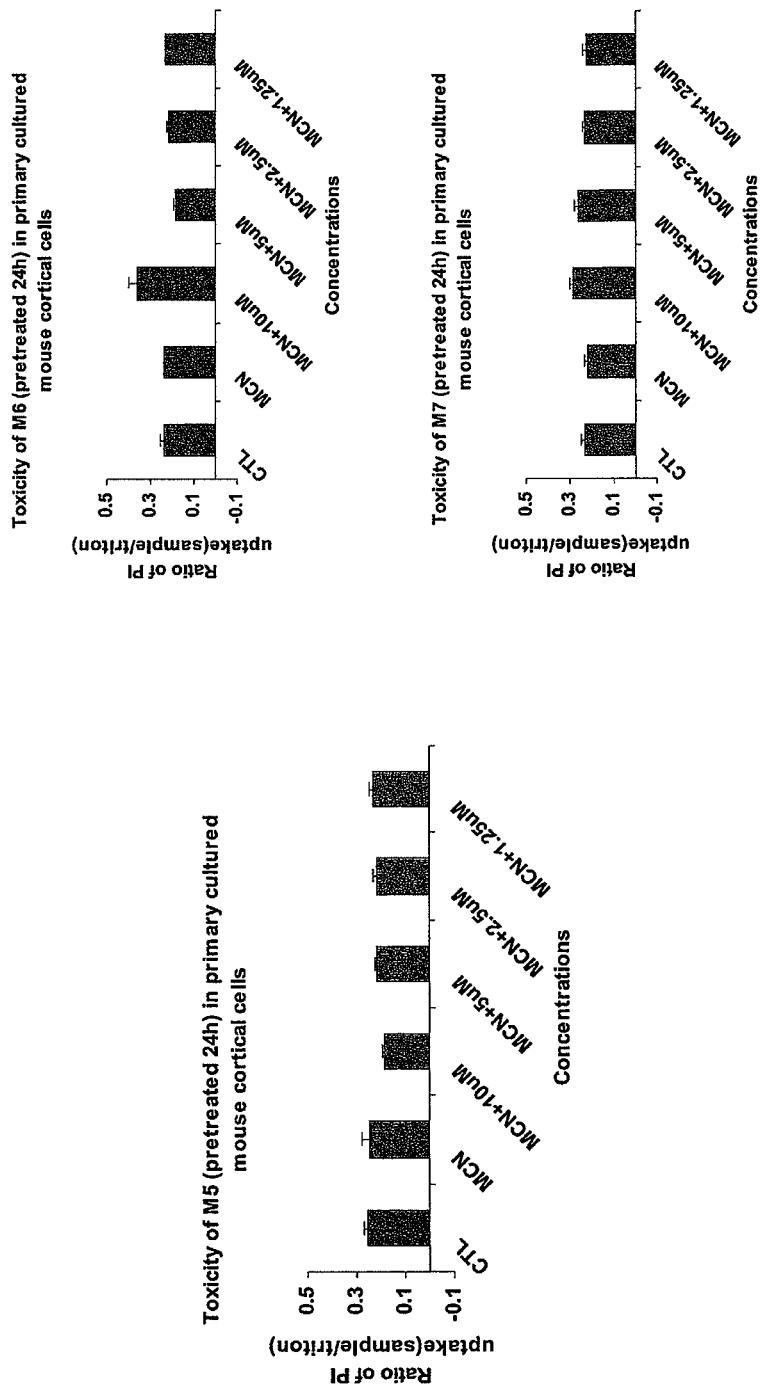

FIG. 60: Toxicity of compounds applied to mouse primary cultured cortical cells for 24 hours.

Figure 61:
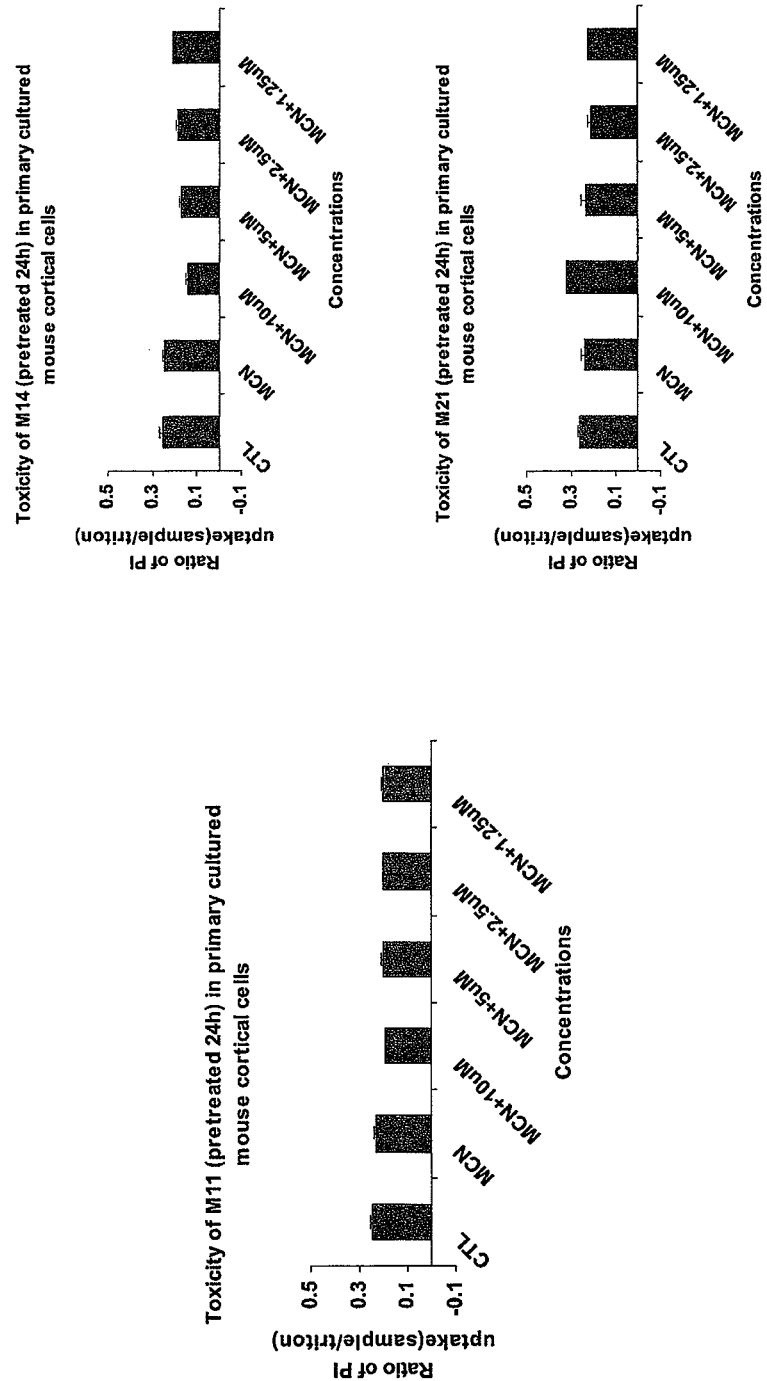

FIG. 61: Toxicity of compounds applied to mouse primary cultured cortical cells for 24 hours.

Figure 62:
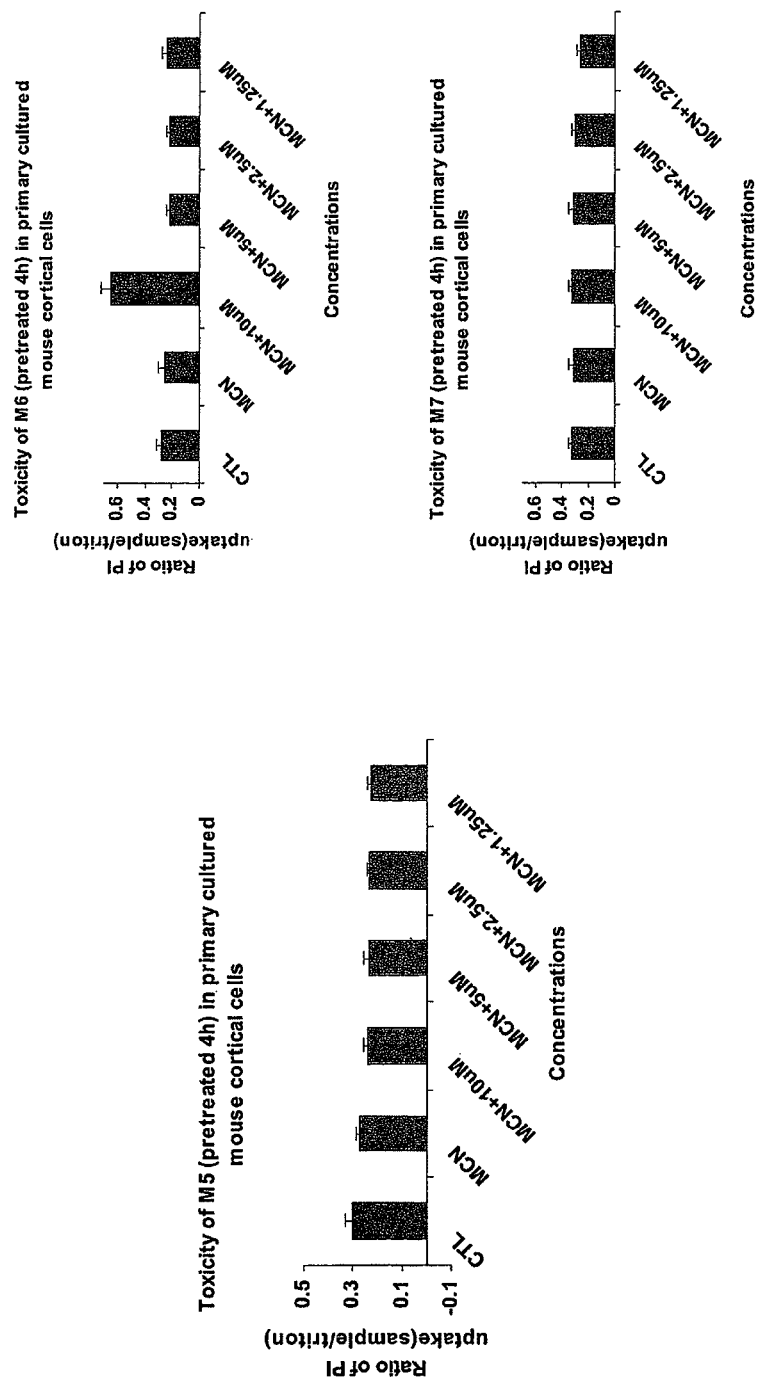

FIG. 62: Toxicity of compounds applied to mouse primary cultured cortical cells for 4 hours.

Figure 63:
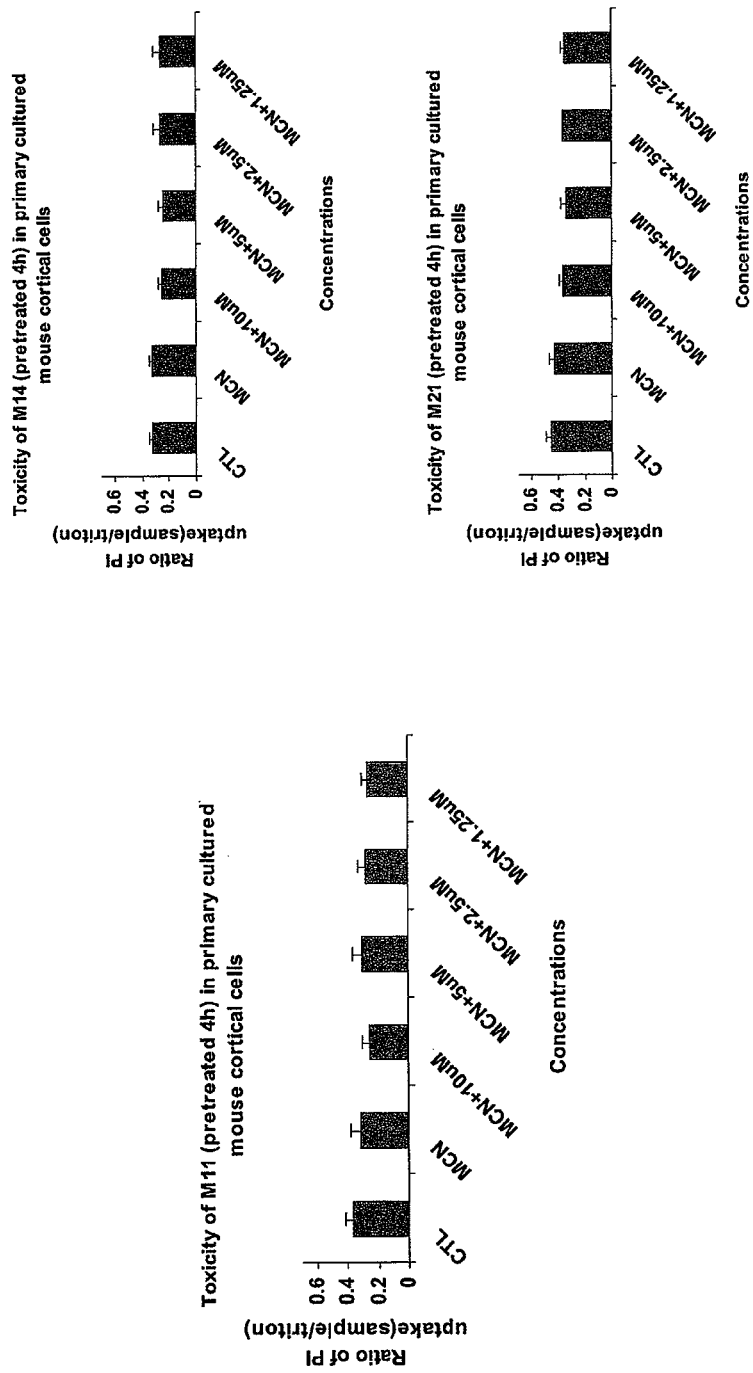

FIG. 63: Toxicity of compounds applied to mouse primary cultured cortical cells for 4 hours.

Figure 64:
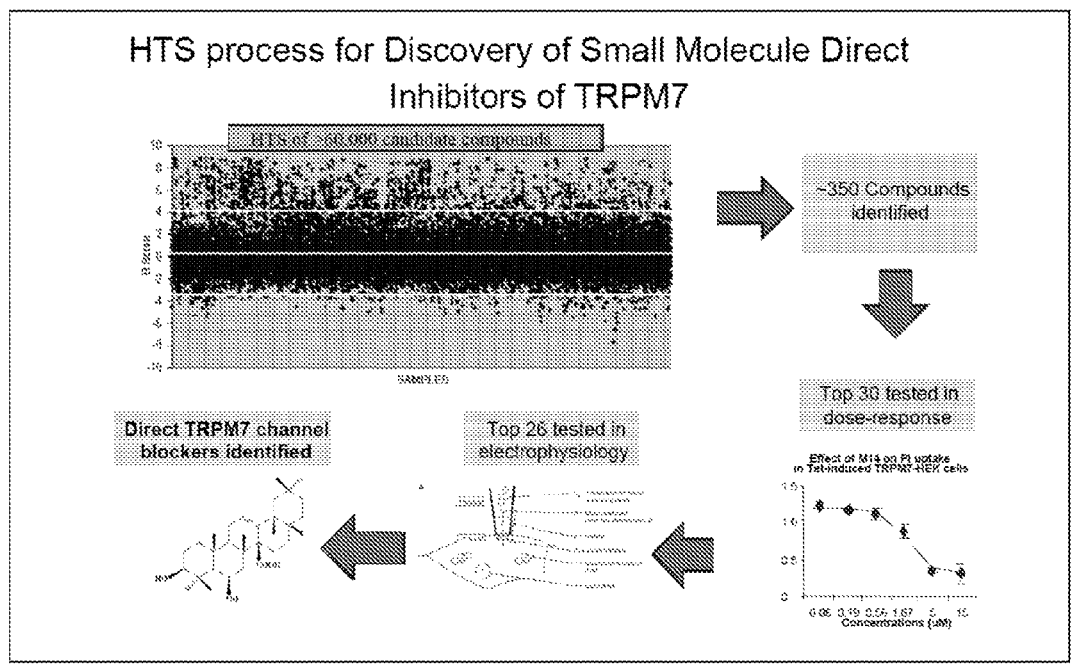

FIG. 64: Scheme for high throughput screening.

Figure 65:
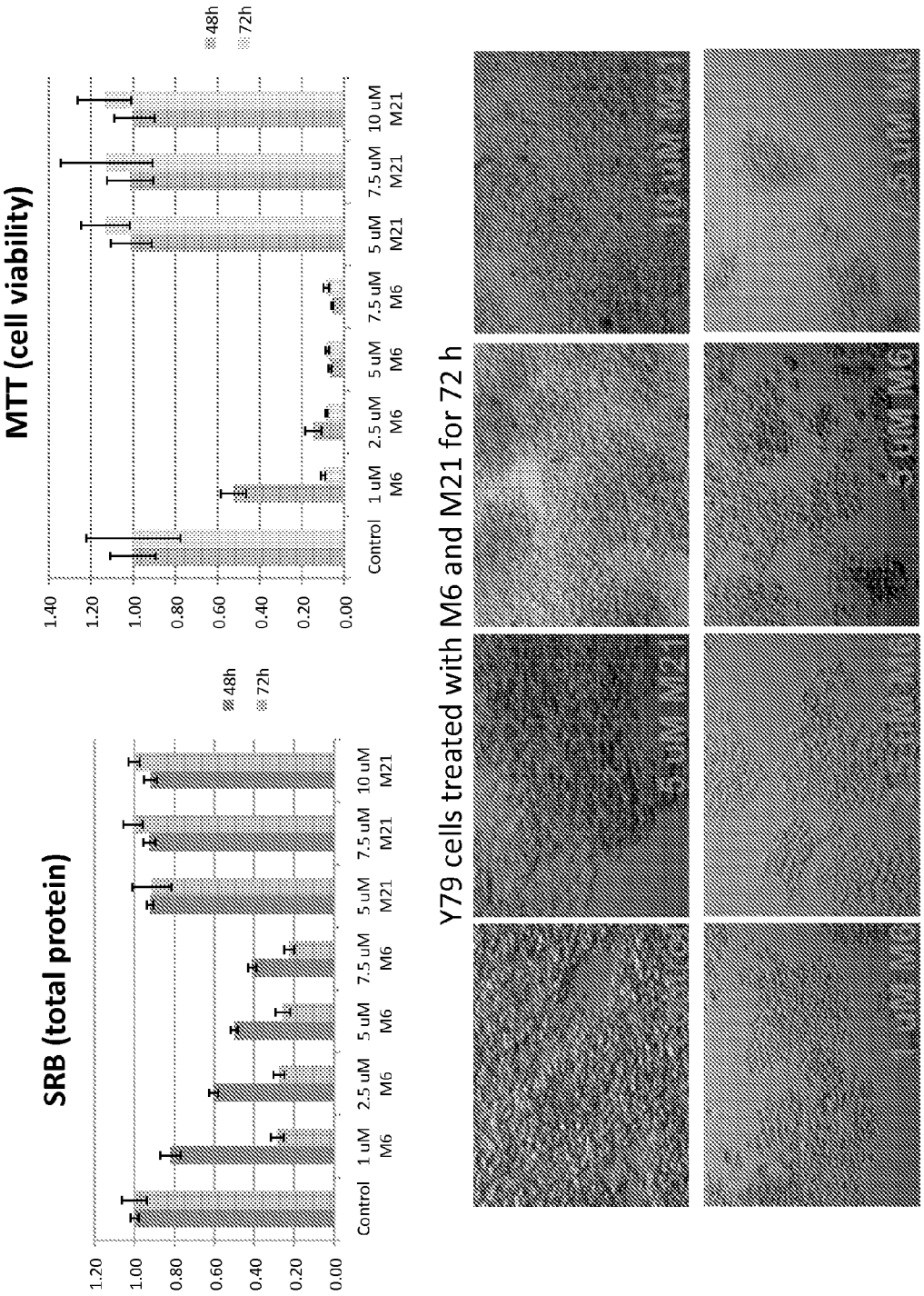

FIG. 65: Top portion: Effect of Compounds M6 and M21 on SRB (total protein) and MTT (cell viability) of Y79 retinoblastoma cell line. Bottom: state of Y79 cells treated for 72 hours with M21 (top row, from left to right: untreated, 5 micromolar M21, 7.5 micromolar M21 and 10 micromolar M21) and M6 (bottom row, from left to right: 1 micromolar M6, 2.5 micromolar M6, 5 micromolar M6 and 7.5 micromolar M6).

FIG. 66: Effect of Compound M6 on B16F1 (melanoma) cell proliferation and growth after 72 hours of treatment.

Figure 67:
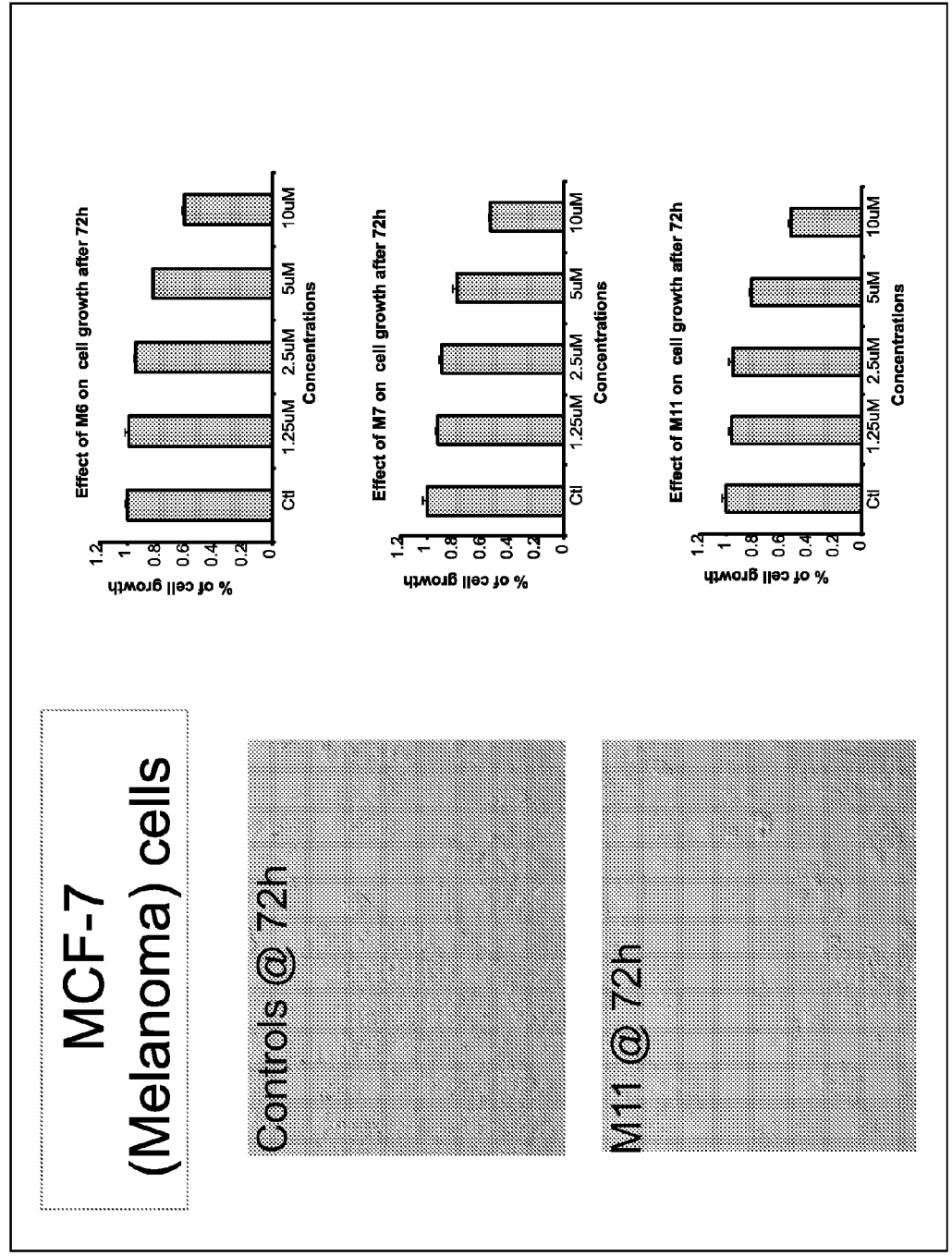

FIG. 67: Effect of Compound M6, M7 and M11 on MCF-7 (breast) cell growth after 72 hours of treatment.

Figure 68:
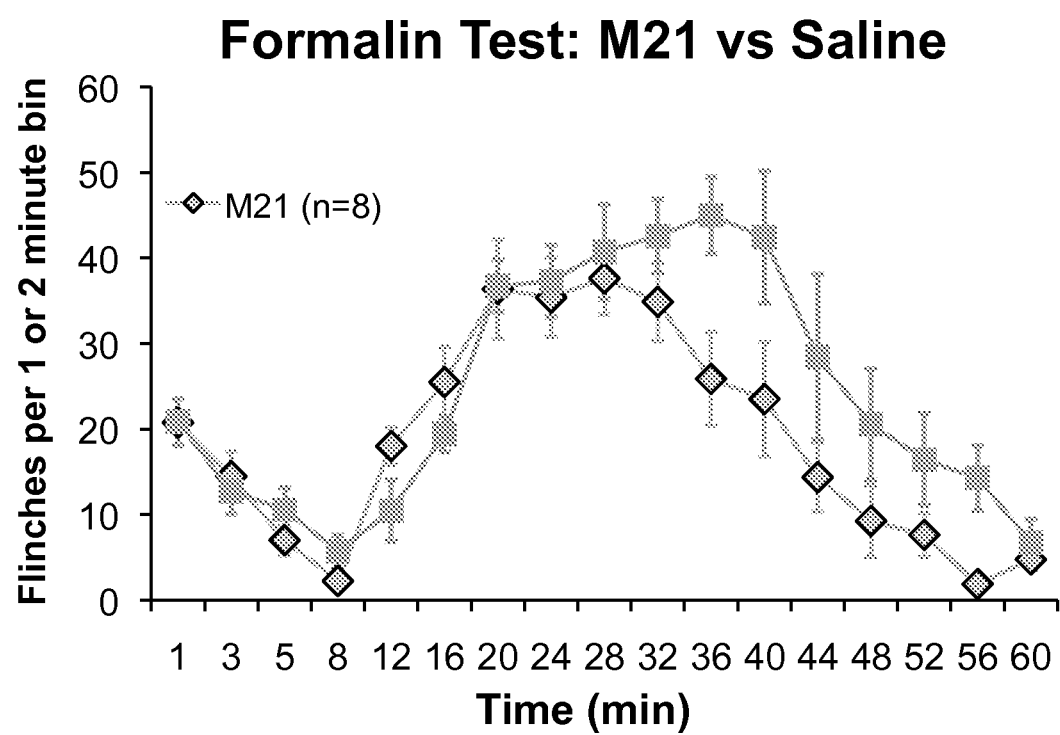

FIG. 68: M21 reduces formalin-induced pain in experimental animals.

FIG. 69: TRPM7 inhibitors protect against death induced by Oxygen-Glucose Deprivation (OGD) in primary mouse cultured cortical cells. A) M21; B) M5; C) M6.

FIG. 70: TRPM7 inhibitors protect against death induced by Oxygen-Glucose Deprivation (OGD) in mouse AML12 hepatocytes. A) M21; B) M5.

FIG. 71: TRPM7 inhibitors protect against death induced by Oxygen-Glucose Deprivation (OGD) in H9c2 cardiomyocytes. A) M21; B) M5; C) M6; D) M11.

FIG. 72: TRPM7 inhibitors protect against death induced by Oxygen-Glucose Deprivation (OGD) in H9c2 cardiomyocytes when given before or during the OGD. A) M5 during OGD; B) M5 prior to OGD; C) M21 during OGD FIG. 73: A) TRPM7 reduces infarct volumes following LAD occlusion of rodent hearts. B) Representative TUNEL staining (red) in a heart cross section from vehicle and M21 treated mice. C) M21 significantly reduces dead cells following LAD restriction of the heart.

FIG. 74: Effect of TRPM7 inhibitor on cell death. A) Drug effects 24 hours following a 3 hour OGD insult in cultured retinal ganglion cells. B) TRPM7 inhibitors reduce cell death following 1 hr OGD in retinal explants.

FIG. 75: M21 reduces retinal cell death in a rat model of acute glaucoma. A) Method of saline injection to increase intra-ocular pressure (TOP). B) Average number of TUNEL-stained cells in retinas exposed to 1 hr increased IOP.

FIG. 76: M6 reduces cell proliferation of retinoblastoma cells in culture by the MTT assay. A) Y79 retinoblastoma cells. B) Weri's retinoblastoma cells.

FIG. 77: Effect of TRPM7 inhibitors on Y79 retinoblastoma cells cultured on retinal explants. A) M6 reduces the number of viable Y79 cells on retinal explants. B) M6 reduces the ability of Y79 retinoblastoma cells to migrate away from the retina in cultured explants.

Figure 78:
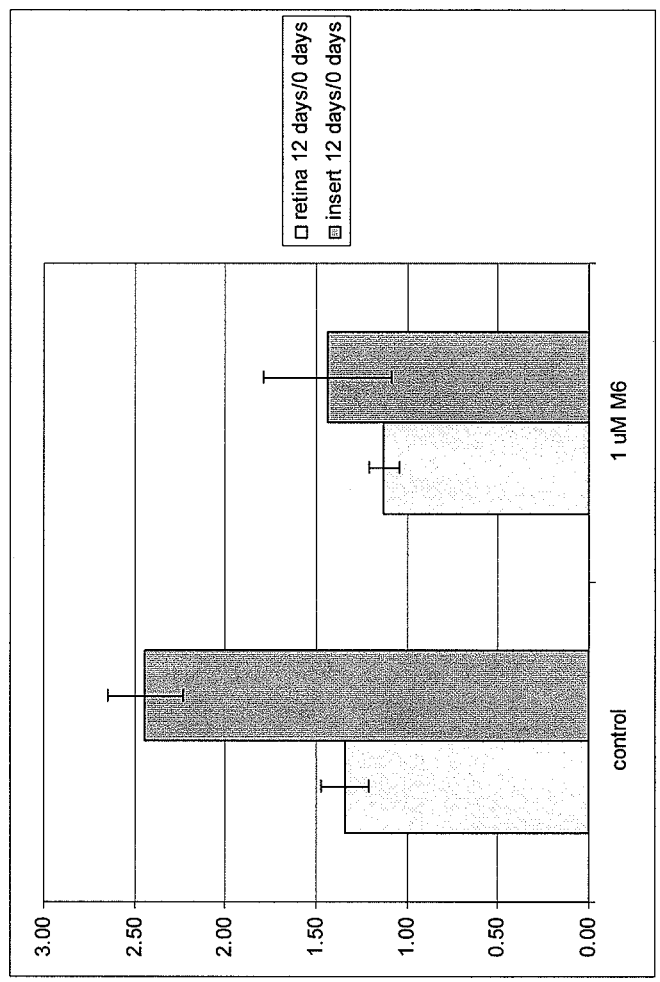

FIG. 78: M6 reduces the ability of Weri retinoblastoma cells to migrate away from the retina in cultured explants.

FIG. 79: TRPM7 inhibitors reduce proliferation of cancer cell lines. A) M7 reduces proliferation of HeLa cervical cancer cells. B) M7 reduces proliferation of SW13 adrenal carcinoma cells. C) M6 reduces proliferation of HeLa cervical cancer cells. D) M6 reduces proliferation of SW13 adrenal carcinoma cells.

FIG. 80: TRPM7 inhibitors M5, M6 and M11 inhibit proliferation of MCF-7 and MDA-MB231 breast cancer cells.

FIG. 81: TRPM7 inhibitors M5, M6 and M11 inhibit proliferation of B16F1 and B16F10 melanoma cells.

Figure 82:
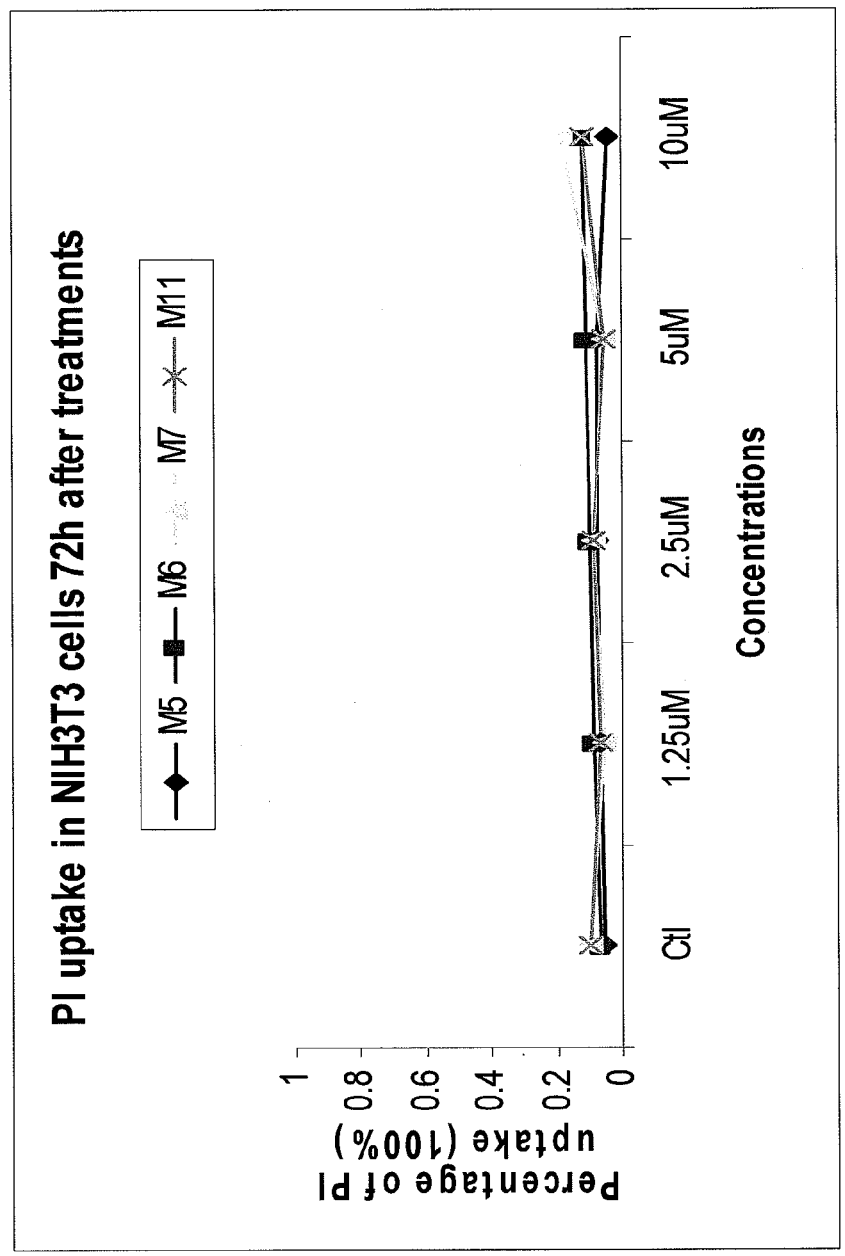

FIG. 82: TRPM7 inhibitors M5, M6, M7 and M11 do not show toxicity on NIH3T3 fibroblast cells at concentrations that reduce proliferation of cancerous cells.

Figure 83:
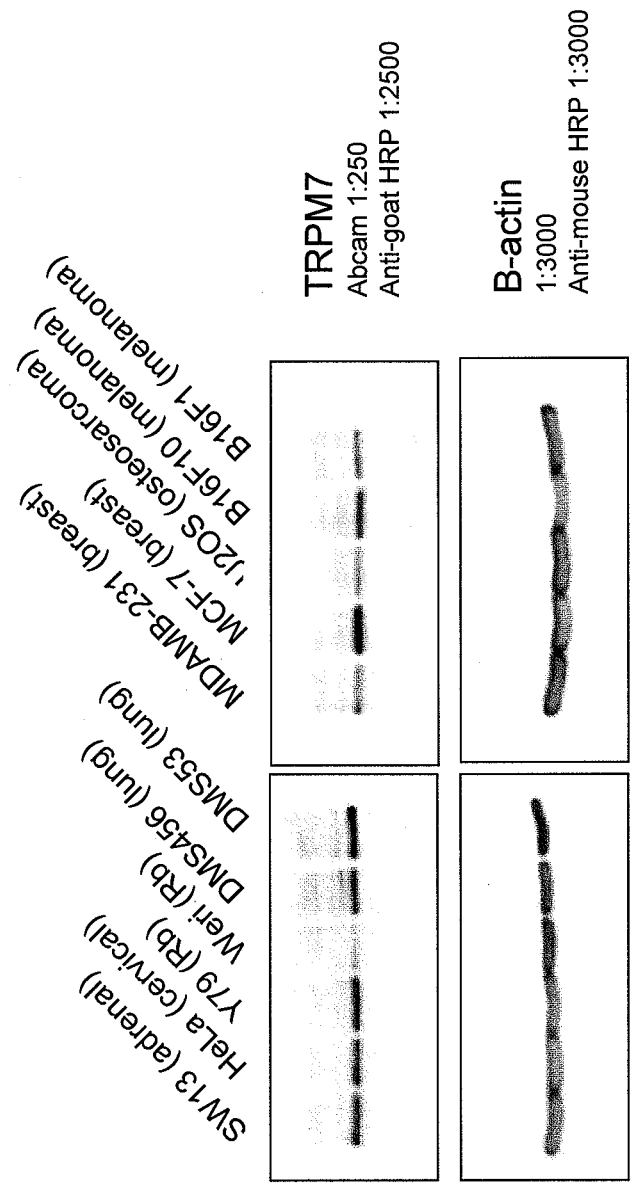

FIG. 83: TRPM7 is expressed in all cancer cell lines tested.

Figure 84:
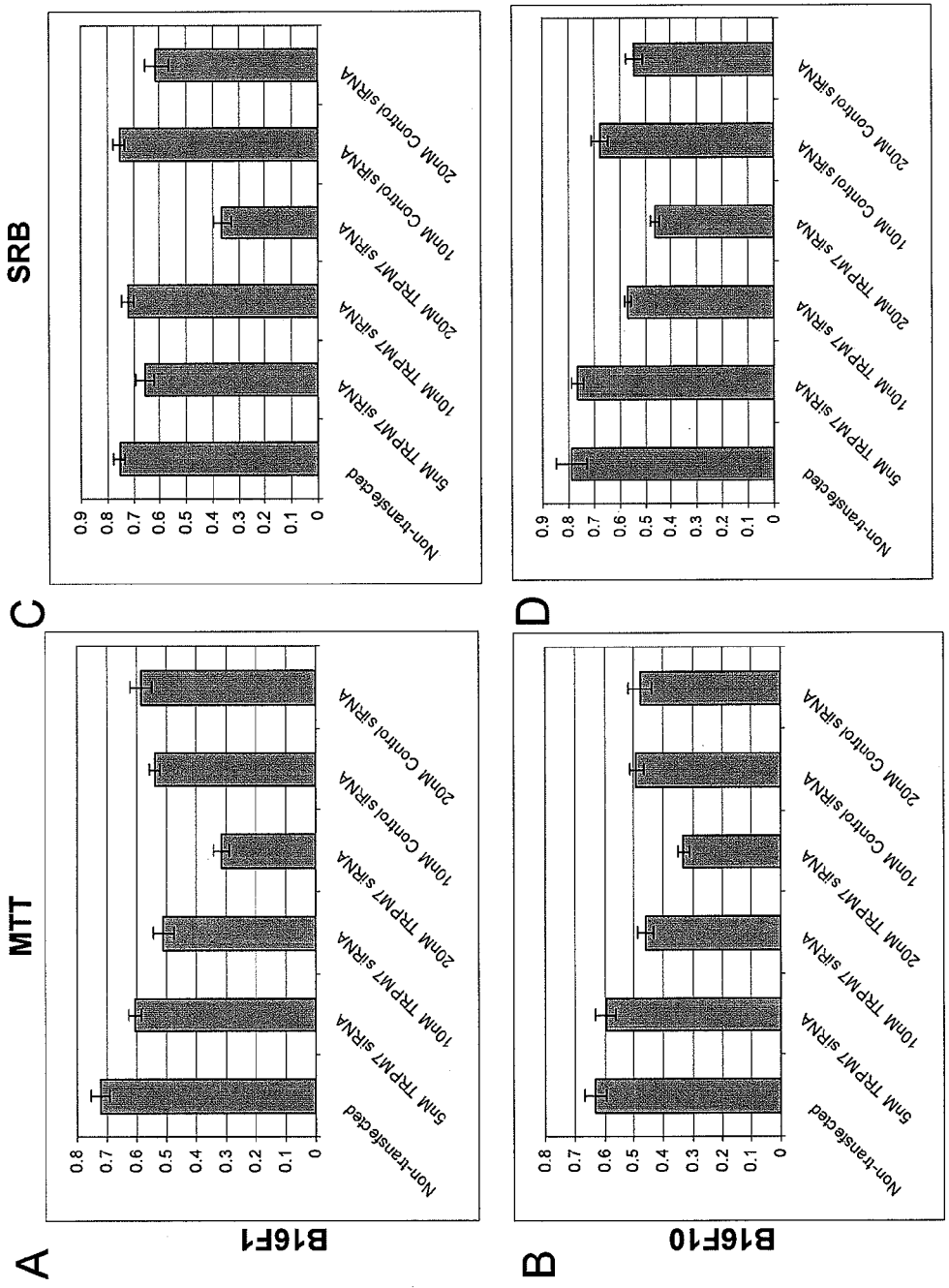

FIG. 84: siRNA knockdown of TRPM7 in mouse B16F1 and B16F10 melanoma cell lines reduces proliferation by MTT and SRB assays.

Figure 85:
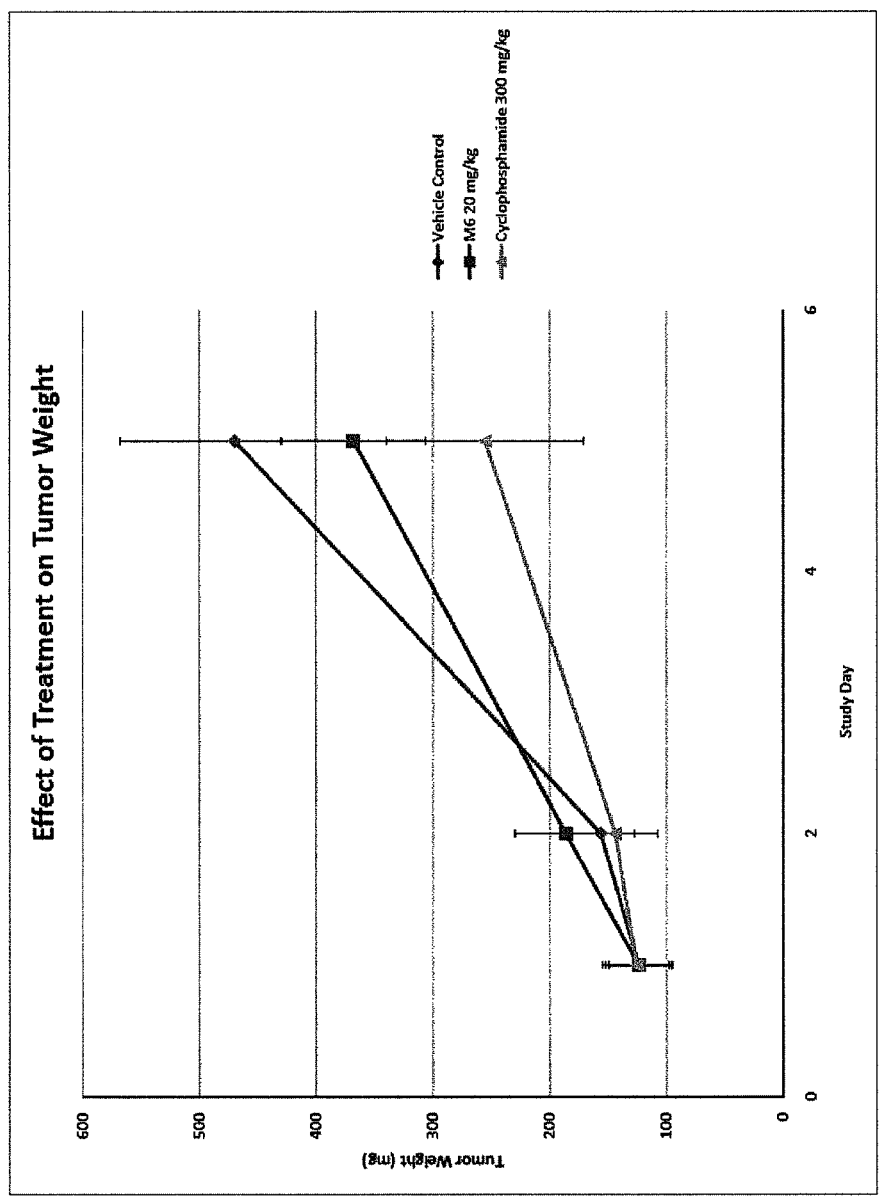

FIG. 85: M6 is able to slow tumor formation in an in vivo murine model of cancer.

DETAILED DESCRIPTION OF THE INVENTION

1. Introduction

The present invention provides, inter alia, modulators (sometimes referred to as compounds or agents) and methods of screening for other modulators (e.g., activators, inhibitors, stimulators, enhancers, agonists, and antagonists) of TRPM7 proteins. Such modulators can be used in the prophylactic or therapeutic treatment of ischemic and cytodegenerative diseases and conditions, including neurological diseases and conditions, such as stroke, traumatic brain injury, Alzheimer's disease, Parkinson's disease, Huntington's disease, dementia, epilepsy, spinocerebellar ataxia, spinal and bulbar muscular dystrophy, dentatorubropallidoluysian atrophy, brain injury, spinal cord injuries, prion-based diseases, and other traumatic, ischemic or neurodegenerative nervous system injuries. Such modulators can also be used in the prophylactic or therapeutic treatment of non-neurological diseases, including ischemic and degenerative disorders and conditions of other tissues, such as those of the CNS, brain, heart, liver, kidneys, muscles, retina, skin, intestines, pancreas, gall bladder, thyroid, thymus, spleen, bone, cartilage, joints, lungs, diaphragm, adrenal glands, salivary and lacrimal glands, blood vessels, and cells of endodermal, mesodermal and ectodermal origin. Such modulators can also be used in the prophylactic or therapeutic treatment of ocular disorders including macular degeneration, diabetic retinopathy, glaucoma, ischemic retinopathy. Such modulators can further be used in the prophylactic or therapeutic treatment of cancer and other proliferative disorders, including breast cancer, retinoblastoma, head and neck cancers, gastric cancer, adrenal cancer, cervical cancer, osteosarcoma, colon cancer, renal cancer, lung cancer including small or non-small cell lung cancer, melanoma, leukemia and lymphoma. The modulators can also be used to for prophylaxis or therapeutic treatment of pain. The modulators can also be used to preserve or enhance memory, in the prophylaxis or therapeutic treatment of hypertension, autoimmune disorders, arrhythmia, depressive disorders, stress disorders or immune disorders.

The use of cells, cell lines, primary neuronal cultures, whole tissue preparations and whole animals provides a means for assaying for modulators for TRPM7 activity that can then be tested in animal models of diseases, including animal models of diseases modulated by TRPM7 activity, including stroke.

Related methodology is described in U.S. Application No. 20080119412, filed Dec. 22, 2004, and Sun et al., Nat Neurosci. 2009 October; 12(10):1300-7, each incorporated by reference in its entirety for all purposes.

As used in this specification and the appended claims, the singular forms "a", "an" and "the" include plural referents unless the content clearly dictates otherwise. Thus, for example, reference to "a cell" includes a combination of two or more cells, and the like.

"About" as used herein when referring to a measurable value such as an amount, a temporal duration, and the like, is meant to encompass variations of +/−20% or +/−110%, more preferably +/−5%, even more preferably +/−1%, and still more preferably +/−0.1% from the specified value, as such variations are appropriate to perform the disclosed methods.

Unless defined otherwise, all technical and scientific terms used herein have the same meaning as commonly understood by those of ordinary skill in the art to which this invention pertains. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); and Hale & Marham, THE HARPER COLLINS DICTIONARY OF BIOLOGY (1991).

Unless otherwise indicated TRPM7 includes reference to human and/or murine TRPM7 proteins.

"Murine TRPM7 protein" refers to an amino acid sequence that has at least 80%, at least 90%, at least 95%, preferably at least 99% amino acid sequence identity, including at least 99.1%, 99.2%, 99.3%, 99.4%, 99.5%, 99.6%, 99.7%, 99.8%, or at least 99.9%, identity to an amino acid sequence encoded by a murine TRPM7 nucleic acid, e.g., a murine TRPM7 protein of Swiss-Prot Q923J1.

"Nucleic acid encoding murine TRPM7 protein" or "TRPM7 gene" or "TRPM7 nucleic acid" refers to a nucleic acid sequence that has at least 96% nucleic acid sequence identity, or at least 90%, 95%, 96.5%, 97%, 97.5%, 98%, 98.5%, 99%, 99.1%, 99.2%, 99.3%, 99.4%, 99.5%, 99.6%, 99.7%, 99.8%, or at least 99.9%, to a murine TRPM7 nucleic acid as shown in e.g., EMBL AY032951, their complements, or conservatively modified variants thereof.

A murine TRPM7 polynucleotide or polypeptide sequence can be naturally occurring or non-naturally occurring. It can be isolated from murine or synthetically constructed.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The phrase "functional effects" in the context of assays for testing compounds that affect a TRPM7 gene, TRPM7 protein or TRPM7-mediated cellular injury includes the determination of any parameter that is indirectly or directly under the influence of the TRPM7 gene or protein. It includes changes in ion flux and membrane potential, changes in ligand binding, changes in gene expression, changes in the fluorescence of ion indicator molecules, changes in cellular viability markers, changes in cellular integrity markers, changes in cellular metabolism markers, and changes in the quantity or function of ischemic tissue in a tissue preparation or in a whole animal "Functional effects" also means all physiological and pathological effects such as increases or decreases in cell death following administration of a test compound.

By "determining the functional effect" refers to determining the functional effect of a compound on a physiological or pathological process mediated by TRPM7 gene or protein. Such functional effects can be measured by any known means, e.g., cell death assays, cell viability assays, ion-sensitive fluorescent probes, electrophysiological techniques, and animal models of disease, and the like.

"TRPM7 activity" refers to one or more of: TRPM7 gene function, TRPM7 protein expression, TRPM7 protein activity as measured by electrophysiological measurements of ion channel activity, TRPM7 protein activity as measured by fluorescent ion indicators, and TRPM7 protein activity as measured using assays of cell metabolism or cell death or cell survival.

The term "modulation" as used herein refers to both upregulation, (i.e., activation or stimulation) for example by agonizing, and downregulation (i.e., inhibition or suppression) for example by antagonizing, TRPM7 activity as measured using the assays described herein. An inhibitor or agonist may cause partial or complete modulation of binding.

"Inhibitors," "activators," and "modulators" (sometimes referred to simply as agents or compounds), of TRPM7 activity, TRPM7 genes and their gene products in cells also refer to inhibitory or activating molecules identified using assays for TRPM7 activity Inhibitors are compounds that decrease, block, prevent, delay activation, inactivate, desensitize, or down regulate the TRPM7 activity. Activators are compounds that increase, open, activate, facilitate, enhance activation, sensitize or up regulate the TRPM7 activity. Such assays for inhibitors and activators include e.g., expressing TRPM7 in cells or cell membranes and then inferring the flux of ions through the use of fluorescent ion indicators, or through measuring cell survival or cell death, after contacting a cell expressing TRPM7 with a putative modulator of TRPM7 activity. To examine the extent of inhibition, samples or assays comprising a TRPM7 protein are treated with a potential activator or inhibitor and are compared to control samples without the activator inhibitor. Control samples (untreated with inhibitors) are assigned a relative TRPM7 activity value of 100% Inhibition of TRPM7 is achieved when the TRPM7 activity value relative to the control is about 90% or less, optionally about 80% or less, 70% or less, 60% or less, 50% or less, 40% or less, 30% or less; or 25-0%. Activation of TRPM7 is achieved when the TRPM7 activity value relative to the control is about 110%, optionally 120%, 130%, 140%, 150% or more, 200-500% or more, 1000-3000% or more.

A "TRPM7 inhibitor," used interchangeably with "TRPM7 competitive inhibitor," (also sometimes referred to simply as a compound or agent), means that the subject compound reduces TRPM7 activity by at least 20%, e.g., at least 30%, at least 40%, at least 50%, at least 60%, at least 70%, at least 80%, at least 90%, at least 95%, up to about 99% or 100%, as compared to controls that do not include the test compound. In general, agents of interest are those which exhibit IC50 values in a particular assay in the range of about 1 mM or less. Compounds that exhibit lower IC50s, for example, have values in the range of about 250 µM, 100 µM, 50 µM, 25 µM, 10 µM, 5 µM, 2 µM, 1 µM, 500 nM, 250 nM, 100 nM, 50 nM, 25 nM, 10 nM, 5 nM, 1 nM, or even lower, and compounds with these attributes are presently preferred.

The term "analog" is used herein to refer to a small molecule that structurally resembles a molecule of interest but which has been modified in a targeted and controlled manner, by replacing a specific substituent of the reference molecule with an alternate substituent. Compared to the starting molecule, an analog may exhibit the same, similar, or improved utility in modulating a TRPM7 activity. Synthesis and screening of analogs, to identify variants of known compounds having improved traits (such as higher binding affinity, or higher selectivity of binding to a target and lower activity levels to non-target molecules) is an approach that is well known in pharmaceutical chemistry.

As used herein, "contacting" has its normal meaning and refers to bringing two or more agents into contact, e.g., by combining the two or more agents (e.g., two proteins, a protein and a small molecule, etc.). Contacting can occur in vitro, in situ or in vivo.

"Recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription.

A "constitutive" promoter is a promoter that is active under most environmental and developmental conditions. An "inducible" promoter is a promoter that is active under environmental or developmental regulation.

The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

"Recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A host cell is any cell suitable for expression of subject polypeptide-encoding nucleic acid. Usually, an animal host cell line is used, examples of which are as follows: monkey kidney cells (COS cells), monkey kidney CVI cells transformed by SV40 (COS-7, ATCC CRL 165 1); human embryonic kidney cells (HEK-293); HEK-293T cells; baby hamster kidney cells (BHK, ATCC CCL 10); chinese hamster ovary-cells (CHO); mouse sertoli cells (TM4); monkey kidney cells (CVI ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (hep G2, HB 8065); mouse mammary tumor (MMT 060562, ATCC CCL 51); TRI cells; NIH/3T3 cells (ATCC CRL-1658); and mouse L cells (ATCC CCL-1). Additional cell lines are available from the American Type Culture Collection, 10801 University Boulevard, Manassas, Va. 20110-2209.

"A monovalent cation indicator" refers to a molecule that is readily permeable to a cell membrane or otherwise amenable to transport into a cell e.g., via liposomes, etc., and upon entering a cell, exhibits a fluorescence signal, or other detectable signal, that is either enhanced or quenched upon contact with a monovalent cation. Examples of monovalent cation indicators useful in the invention are set out in Haugland, R. P. Handbook of Fluorescent Probes and Research Chemicals., 9th ed. Molecular Probes, Inc Eugene, Oreg., (2001).

"A divalent cation indicator" refers to a molecule that is readily permeable to a cell membrane or otherwise amenable to transport into a cell e.g., via liposomes, etc., and upon entering a cell, exhibits a fluorescence signal, or other detectable signal, that is either enhanced or quenched upon contact with a divalent cation.

"Specifically bind(s)" or "bind(s) specifically" when referring to a peptide refers to a peptide molecule which has intermediate or high binding affinity, exclusively or predominately, to a target molecule. The phrases "specifically binds to" refers to a binding reaction which is determinative of the presence of a target protein in the presence of a heterogeneous population of proteins and other biologics. Thus, under designated assay conditions, the specified binding moieties bind preferentially to a particular target protein and do not bind in a significant amount to other components present in a test sample. Specific binding to a target protein under such conditions can require a binding moiety that is selected for its specificity for a particular target antigen. A variety of assay formats can be used to select ligands that are specifically reactive with a particular protein. For example, solid-phase ELISA immunoassays, immunoprecipitation, Biacore and Western blot are used to identify peptides that specifically react with the antigen. Typically a specific or selective reaction is at least twice background signal or noise and more typically more than 10 times background.

"Naturally-occurring" as applied to an object refers to the fact that an object can be found in nature. For example, a polypeptide or polynucleotide sequence that is present in an organism (including viruses) that can be isolated from a source in nature and which has not been intentionally modified in the laboratory is naturally-occurring.

The term "assessing" includes any form of measurement, and includes determining if an element is present or not. The terms "determining," "measuring," "evaluating," "assessing" and "assaying" are used interchangeably and may include quantitative and/or qualitative determinations. Assessing may be relative or absolute. "Assessing binding" includes, e.g., determining the amount of binding, the KD for binding affinity and/or determining whether binding has occurred (i.e., whether binding is present or absent).

The terms "treatment," "treating," "treat," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting or slowing its development or onset; and (c) relieving the disease, i.e., causing regression of the disease and/or relieving one or more disease symptoms. "Treatment" is also meant to encompass delivery of an agent to provide for a pharmacologic effect, even in the absence of a disease or condition.

"Subject," "individual," "host" and "patient" are used interchangeably herein, to refer to an animal, human or non-human, amenable to a treatment according to a method of the invention. Generally, the subject is a mammalian subject. Exemplary subjects include humans, domestic and non-domestic animals: e.g., non-human primates, mice, rats, cattle, sheep, goats, pigs, dogs, cats, and horses; with humans being of particular interest.

For any molecule described as containing one or more optional substituents only sterically practical and/or synthetically feasible compounds are meant to be included. Further, combinations of substituents and/or variables are permissible only if such combinations result in stable compounds.

"Optionally substituted" refers to all subsequent modifiers in a term, for example in the term "optionally substituted phenyl ($C_{1-6}$)alkyl," optional substitution may occur on both the alkyl portion and the phenyl portion of the molecule. Preferably, the alkyl groups herein can have one hydrogen on the alkyl backbone substituted with aromatic and heteroaromatice ring systems that are described herein, which themselves can be further optionally substituted. Another example is "optionally substituted $C_{5-7}$ aryl-$(C_{1-6})$alkyl can be a fluoro, chloro-benzyl group.

Another preferred alkyl is a "haloalkyl." Haloalkyl refers to any of the alkyl groups disclosed herein that is substituted by one or more chlorine, bromine, fluorine or iodine with fluorine and chlorine being preferred, such as chloromethyl, iodomethyl, trifluoromethyl, 2,2,2-trifluoroethyl, and 2-chloroethyl. A haloalkyl can have other substitutions in addition to the halogen.

"Substituted" alkyl, aryl, and heterocyclyl, refer respectively to alkyl, aryl, and heterocyclyl, wherein one or more (for example up to about five, in another example, up to about three) hydrogen atoms are replaced by a substituent independently selected. Examples include fluoromethyl, hydroxypropyl, nitromethyl, aminoethyl or and the like, optionally substituted aryl (for example, 4-hydroxyphenyl, 2,3-difluorophenyl, and the like), optionally substituted arylalkyl (for example, 1-phenyl-ethyl, para-methoxyphenylethyl and the like), optionally substituted heterocyclylalkyl (for example, 1-pyridin-3-yl-ethyl, N-ethylmorphonlino and the like), optionally substituted heterocyclyl (for example, 5-chloropyridin-3-yl, 1-methyl-piperidin-4-yl and the like), optionally substituted alkoxy (for example methoxyethoxy, hydroxypropyloxy, methylenedioxy and the like), optionally substituted amino (for example, methylamino, diethylamino, trifluoroacetylamino and the like), optionally substituted amidino, optionally substituted aryloxy (for example, phenoxy, para-chlorophenoxy, meta-aminophenoxy, para-phenoxyphenoxy and the like), optionally substituted arylalkyloxy (for example, benzyloxy, 3-chlorobenzyloxy, meta-phenoxybenzyloxy and the like), carboxy (—$CO_2H$), optionally substituted carboalkoxy (that is, acyloxy or —OC(=O)R), optionally substituted carboxyalkyl (that is, esters or —$CO_2$)), optionally substituted carboxamido, optionally substituted benzyloxycarbonylamino (CBZ-amino), cyano, optionally substituted acyl, halogen, hydroxy, nitro, optionally substituted alkylsulfanyl, optionally substituted alkylsulfinyl, optionally substituted alkylsulfonyl, thiol, oxo, carbamyl, optionally substituted acylamino, optionally substituted hydrazino, optionally substituted hydroxylamino, and optionally substituted sulfonamido.

An "alkyl" group refers to a saturated aliphatic hydrocarbon, including straight-chain, branched chain, and cyclic alkyl groups. Alkyl groups can comprise any combination of acyclic and cyclic subunits. Further, the term "alkyl" as used herein expressly includes saturated groups as well as unsaturated groups. Unsaturated groups contain one or more (e.g., one, two, or three), double bonds and/or triple bonds. The term "alkyl" includes substituted and unsubstituted alkyl groups. "Lower alkyl" is defined as having 1-7 carbons. Preferably, the alkyl group has 1 to 18 carbons and is straight-chain or branched. The term can include a saturated linear or branched-chain monovalent hydrocarbon radical of a specified number of carbon atoms, wherein the alkyl radical may be optionally substituted independently with one or more substituents described herein. Substituents can be chosen form any of the radicals, groups or moieties described herein. Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), and the like. Thus, when an alkyl residue having a specific number of carbons is named, all geometric isomers having that number of carbons are intended to be encompassed; thus, for example, either "butyl" or "$C_4$ alkyl" is meant to include n-butyl, sec-butyl, isobutyl, t-butyl, isobutenyl and but-2-yne radicals; and for example, "propyl" includes n-propyl, propenyl, and isopropyl. The term "$C_1$-$C_6$ alkyl" encompasses alkyl groups of 1 to 6 carbons. Preferably, the carbon number is one to three in all embodiments.

The term "alkoxy" means a straight or branched chain alkyl radical, as defined above, unless the chain length is limited thereto, bonded to an oxygen atom, including, but not limited to, methoxy, ethoxy, n-propoxy, isopropoxy, and the like. Preferably the alkoxy chain is 1 to 6 carbon atoms in length, more preferably 1-4 carbon atoms in length. The substitutions on alkoxy groups are similar to those on alkyl groups. Haloalkoxy groups are preferred optionally substituted alkoxy groups, for example, trifluormethoxy.

The term "alkylamine" by itself or as part of another group refers to an amino group which is substituted with one alkyl group as defined above.

The term "dialkylamine" by itself or as part of another group refers to an amino group which is substituted with two alkyl groups as defined above.

The term "halo" or "halogen" by itself or as part of another group refers to chlorine, bromine, fluorine or iodine, unless defined otherwise in specific uses in the text and/or claims.

The term "carbonyl" refers to a C double bonded to an O, wherein the C is further covalently bound.

The term "heterocycle" or "heterocyclic ring", as used herein except where noted, represents a stable 5- to 7-membered mono-heterocyclic ring system which may be saturated or unsaturated, and which consists of carbon atoms and from one to three heteroatoms selected from the group consisting of N, O, and S, and wherein the nitrogen and sulfur heteroatom may optionally be oxidized. Especially useful are rings contain one nitrogen combined with one oxygen or sulfur, or two nitrogen heteroatoms. Examples of heterocyclyl radicals include, but are not limited to, azetidinyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, tetrahydrofuryl, tetrahydropyranyl, thienyl, benzothieliyl, thiamorpholinyl, thiamorpholinyl sulfoxide, thiamorpholinyl sulfone, dioxaphospholanyl, and oxadiazolyl, most preferably piperazinyl and morpholinyl.

The term "aryl," "aromatic" and "heteroaromatic" refer to aromatic six- to fourteen-membered carbocyclic ring, for example, benzene, naphthalene, indane, tetralin, fluorene and the like. The "aryl" "aromatic" and "heteroaromatic" group may be substituted with substituents including lower alkyl, hydroxyl, halo, haloalkyl, nitro, cyano, alkoxy and lower alkylamino, and the like.

The term "heteroatom" is used herein to mean an oxygen atom ("O"), a sulfur atom ("S") or a nitrogen atom ("N"). When the heteroatom is nitrogen, it may form an NRR moiety, wherein each R is independently from one another hydrogen or a substitution.

The term "alkenyl" refers to linear or branched-chain hydrocarbon radical of two to six carbon atoms with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH=CH$_2$), allyl (—CH$_2$CH=CH$_2$), and the like.

An "alkenyl" group refers to an unsaturated hydrocarbon group containing at least one carbon-carbon double bond, including straight-chain, branched-chain, and cyclic groups. Preferably, the alkenyl group has 1 to 18 carbons. The alkenyl group may be substituted or unsubstituted. The term includes a linear or branched monovalent hydrocarbon radical of two to twelve carbon atoms with at least one site of unsaturation, i.e., a carbon-carbon, sp triple bond, wherein the alkynyl radical may be optionally substituted independently with one or more substituents described herein. Examples include ethynyl (—C≡CH), propynyl (propargyl, —CH$_2$C≡CH), and the like.

The terms "cyclic," "bicyclic" and "heterobycyclic" refer to a saturated or partially unsaturated ring having from 5 to 12 carbon atoms as a monocyclic ring or 7 to 12 carbon atoms as a bicyclic ring. Bicyclic rings having 7 to 12 atoms can be arranged, for example, as a bicyclo [4,5], [5,5], [5,6] or [6,6] system, and bicyclic carbocycles having 9 or 10 ring atoms can be arranged as a bicyclo [5,6] or [6,6] system, or as bridged systems such as bicyclo[2.2.1]heptane, bicyclo [2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. Included in this definition are bicyclic radicals comprising an aromatic ring fused to a saturated, partially unsaturated ring, or aromatic carbocyclic or heterocyclic ring. Typical aryl groups include, but are not limited to, radicals derived from benzene (phenyl), substituted benzenes, biphenyl, benzoamidazoles, indole, coumarin, pyranopyrole, benzothiophene, indazole, indenyl, indanyl, 1,2-dihydronapthalene, 1,2,3,4-tetrahydronapthyl, and the like. Aryl groups are optionally substituted independently with one or more substituents described herein.

An "Acyl" refers to groups of from one to ten carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like.

An "alkynyl" group refers to an unsaturated hydrocarbon group containing at least one carbon-carbon triple bond, including straight-chain, branched chain, and cyclic groups. Preferably, the alkynyl group has 1 to 18 carbons. The alkynyl group may be substituted or unsubstituted.

As used herein, the term "acute insult to the central nervous system" includes short-term events that pose a substantial threat of neuronal damage mediated by glutamate excitotoxicity, or caused by trauma, inflammation TRPM7 channels, TRPM2 or other channels as well as, longer-term propagation of stroke-induced ischemic damage mediated e.g. by inflammation Ischemic events may also involve inadequate blood flow, such as a stroke or cardiac arrest, hypoxic events (involving inadequate oxygen supply, such as drowning, suffocation, or carbon monoxide poisoning), trauma to the brain or spinal cord (in the form of mechanical or similar injury), certain types of food poisoning which involve an excitotoxic poison such as domoic acid, and seizure-mediated neuronal degeneration, which includes certain types of severe epileptic seizures. It can also include trauma that occurs to another part of the body, if that trauma leads to sufficient blood loss to jeopardize blood flow to the brain (for example, as might occur following a shooting, stabbing, or automobile accident).

"Cardiovascular ischemia" which is used interchangeably with "myocardial ischemia" or cardiac or heart ischemia is intended to mean acute and chronic damage in the circulatory system with cell death resulting, e.g., from hypoxia, e.g., heart attack, suffocation, carbon monoxide poisoning, trauma, pulmonary dysfunction and the like; decreased blood flow, e.g., from occlusion, atherosclerosis, diabetic microvascular insufficiency and the like; dysregulation of nitric oxide; dysfunction of the endothelium or vascular smooth muscle; and the like.

7. Assays for Modulators of Murine TRPM7 Production or TRPM7 Activity

TRPM7 has been identified as a Mg2+ and Ca2+-regulated and calcium-permeant ion channel required for cell viability. As an ion channel, TRPM7 conducts calcium, Mg2+ and monovalent cations to depolarize cells and increase intracellular calcium. TRPM7 currents are activated at low intracellular Mg levels or low extracellular levels of divalent cations and are blocked by a number of divalent and polyvalent cations, including magnesium, zinc, spermine, 2-aminophenoxyborate, Mn(III) tetrakis (4-benzoic acid) porphyrin chloride, and lanthanum (Harteneck, Arch Pharamcol 2005 371"307-314). Both $Mg^{2+}$ and $Zn^2$ permeate TRPM7 channels and block the monovalent cation flow through them (Kozak et al., Biophys. 2003 84:2293-2305). The TRPM7 channel produces pronounced outward currents at nonphysiological voltages ranging from +50 to +100 mV and small inward currents at negative potentials between −100 to −40 mV when expressed heterologously in mammalian cells (Jiang et al, J. Gen. Physiol. 2005 126(2), 137-150) TRPM7 has also been shown to be modulated by Src-family kinases (Jiang et al., J. Biol. Chem. 2003 278:42867-42876), phosphatidylinositol 4,5-biphosphate (PIP.sub.2) (Runnels et al., Nat Cell Biol 2002 4:329-336), and its own .alpha.-kinase domain (Takezawa et al., PNAS USA 2004 101:6009-6014). Heterologously expressed TRPM7 channels, e.g., TPRM7 channels expressed in HEK-293 cells, exhibit currents with a high $Ca^{2+}$ permeability, an outwardly rectifying I-V curve, enhancement by low $Ca^{2+}$ concentration and a block of current by the polyvalent cation gadolinium. Overexpression of TRPM7 channels has been shown to be lethal to HEK-293 cells. The lethality can be prevented by increasing extracellular $Mg^{2+}$ to restore $Mg.^{2+}$ homeostasis (Aarts et al., Cell 2003 115:863-877).

The present invention provides, inter alia, cell based systems that can be used to identify modulators, for example, inhibitors or activators of TRPM7 production or TRPM7 activity. The amount or activity of a TRPM7 channel can be assessed using a variety of assays, including measuring current, measuring membrane potential, measuring ion flux, measuring ligand binding, measuring second messengers and transcription levels or physiological effects such as cell survival.

Modulators of the TRPM7 channels can be tested using biologically active TRPM7, either recombinant or naturally occurring. Murine TRPM7 can be isolated, co-expressed or expressed in a cell, or expressed in a membrane derived from a cell. Samples or assays that are treated with a potential TRPM7 channel inhibitor or activator can be compared to control samples without the test compound, to examine the extent of modulation. Control samples (untreated with activators or inhibitors) are assigned a relative TRPM7 activity value of 100% Inhibition of channels comprising TRPM7 is achieved when the ion channel activity value relative to the control is, for example, about 90%, preferably about 50%, more preferably about 25%. Activation of channels comprising TRPM7 is achieved when the ion channel activity value relative to the control is 110%, more preferably 150%, more preferable 200% higher.

Changes in ion flux can be assessed by determining changes in polarization (i.e., electrical potential) of the cell membrane expressing the TRPM7 channel. A preferred means to determine changes in cellular polarization is by measuring changes in current (thereby measuring changes in polarization) with voltage-clamp and patch-clamp techniques, e.g., the "cell-attached" mode, the "inside-out" mode, and the "whole cell" mode (see, e.g., Runnels et al. Science 2001 291:1043-1047, Jiang et al, J. Gen. Physiol. 2005 126 (2), 137-150). Whole cell currents are conveniently determined using the standard methodology (see, e.g., Hamil et al., PFlugers. Archiv. 1981, 391:85). Other known assays include: radiolabeled rubidium flux assays and fluorescence assays using ion-sensitive dyes, voltage-sensitive dyes (see, e.g., Vestergarrd-Bogind et al., J. Membrane Biol. 1988, 88:67-75; Daniel et al., J. Pharmacol. Meth. 1991, 25:185-193; Holevinsky et al., J Membrane Biology 1994, 137:59-70). Generally, the compounds to be tested are present in the range from about 1 pM to about 100 mM.

The present invention provides, inter alia, methods of identifying molecules that bind TRPM7, methods of identifying molecules that modulate TRPM7 ion channel activity, and/or methods of identifying molecules that alter expression of TRPM7 within a cell. These molecules are candidate bioactive agents that can be useful for treating conditions or diseases regulated by TRPM7 activity. Such modulators can be used in the therapeutic or prophylactic treatment of any of the diseases and disorders described herein including ischemic injuries as described herein, as well as neurodegenerative conditions, including neurological diseases and conditions, such as stroke, traumatic brain injury, Alzheimer's disease, Parkinson's disease, Huntington's disease, dementia, epilepsy, spinocerebellar ataxia, spinal and bulbar muscular dystrophy, dentatorubropallidoluysian atrophy, brain injury, spinal cord injury, and other traumatic nervous system injuries. Such modulators can also be used in the therapeutic treatment of non-neurological diseases, including ischemic disorders and conditions of other tissues, such as ischemia of the heart, liver, kidneys, muscles, retina, skin, intestines, pancreas, gall bladder, thyroid, thymus, spleen, bone, cartilage, joints, lungs, diaphragm, adrenal glands, salivary and lacrimal glands, blood vessels, and cells of endothelial, mesanchymal and neural origin. In a preferred embodiment, these methods can be used to identify drug candidates that inhibit murine TRPM7 activity.

The present invention provides methods of screening for a candidate bioactive agent capable of reducing TRPM7-mediated cellular injury. In some embodiments, the candidate bioactive agent binds to a particular domain of the TRPM7 protein, such as, the C-terminal kinase domain. In other embodiments, the candidate bioactive agent acts on a downstream signaling pathway that is associated and/or activated by TRPM7 activity, and that mediate the injurious consequences of TRPM7 activity on the cell.

In one embodiment for binding assays, either TRPM7 or a candidate bioactive agent is labeled. The label can be any detectable label, such as those described herein. The label provides a means of detecting the binding of the candidate agent to TRPM7. In some binding assays, TRPM7 is immobilized or covalently attached to a surface and contacted with a labeled candidate bioactive agent. In other assays, a library of candidate bioactive agents are immobilized to a surface or covalently attached to a surface, e.g., biochip and contacted with a labeled TRPM7.

The present invention provides methods for blocking or reducing murine TRPM7 gene expression as well as methods for screening for a candidate bioactive agent capable of blocking or reducing TRPM7 gene expression and thus, TRPM7 activity.

Expression of TRPM7 can be specifically suppressed by methods such as RNA interference (RNAi) (Science, 288: 1370-1372 (2000)). Briefly, traditional methods of gene suppression, employing anti-sense RNA or DNA, operate by binding to the reverse sequence of a gene of interest such that binding interferes with subsequent cellular processes and therefore blocks synthesis of the corresponding protein. RNAi also operates on a post-translational level and is sequence specific, but suppresses gene expression far more efficiently. In RNA interference methods, post-transcriptional gene silencing is brought about by a sequence-specific RNA degradation process which results in the rapid degradation of transcripts of sequence-related genes. Small nucleic acid molecules, such as short interfering nucleic acid (siNA), short interfering RNA (siRNA), double-stranded RNA (dsRNA), micro-RNA (mRNA), and short hairpin RNA (shRNA) molecules can all be used to modulate the expression of TRPM7 genes. Small nucleic acid molecules capable of suppressing TRPM7 through RNA interference can be prepared by methods known in the art. See, for example, US Publication No. 2005/0124567 and Aarts et al., Cell 2003 115:863-877.

Accordingly, the present invention provides molecules capable of modulating e.g., blocking or reducing murine TRPM7 activity, as well as methods of screening for a candidate bioactive agent capable of modulating murine TRPM7 activity, such as anti-sense RNAs and DNAs, ribozymes, and other small nucleic acid molecules such as those described herein. All of these agents can be used as therapeutic agents for blocking the expression of certain TRPM7 genes in vivo. In some embodiments, they can be used to prevent TRPM7 gene transcription into mRNAs, to inhibit translation of TRPM7 mRNAs into proteins, and to block activities of preexisting TRPM7 proteins. Standard immunoassays, such as western blotting, ELISA, and the like, can be performed to confirm that the candidate bioactive agent has an effect on TRPM7 gene expression. Alternatively, TRPM7 expression can be determined by RT-PCR. Methods of performing RT-PCR are known in the art and are thus, not described herein. The effect of these molecules on TRPM7 channel activity can be assessed using a variety of assays described herein, including measuring current, measuring membrane potential, measuring ion flux, and measuring cell survival.

In some embodiments, the present invention provides methods for identifying molecules that modulate the divalent or monovalent cationic permeability of the TRPM7 channel.

Modulation of the monovalent cationic permeability of the TRPM7 channel can, for example, be determined by measuring the inward and outward currents in whole cell patch clamp assays or single-channel membrane patch assays in the presence and absence of the candidate bioactive agent. In an alternative embodiment, the modulation of monovalent cation activity can be monitored as a function of cation currents and/or membrane-potential of a cell comprising a TRPM7 channel. For example, the modulation of membrane potential can be detected with the use of a membrane potential-sensitive probe, such as bis-(1,3-dibutylbarbituric acid)trimethine oxonol (DiBAC4(3)) (Handbook of Fluorescent Probes and Research Chemicals, 9th ed. Molecular Probes). The use of a fluorescent membrane potential-sensitive probe allows rapid detection of change in membrane potential by monitoring change in fluorescence with the use of such methods as fluorescence microscopy, flow cytometry and fluorescence spectroscopy, including use of high through-put screening methods utilizing fluorescence detection (Alvarez-Barrientos, et al., "Applications of Flow Cytometry to Clinical Microbiology", Clinical Microbiology Reviews, 13(2): 167-195, (2000)).

Modulation of the monovalent cationic permeability of the TRPM7 channel by a candidate agent can be determined by contacting a cell that expresses TRPM7 with a monovalent cation and a monovalent cation indicator that reacts with the monovalent cation to generate a signal. The intracellular levels of the monovalent cation can be measured by detecting the indicator signal in the presence and absence of a candidate bioactive agent. Additionally, the intracellular monovalent cation levels in cells that express TRPM7 with cells that do not express TRPM7 can be compared in the presence and absence of a candidate bioactive agent.

The monovalent cation indicator can be, for example, a sodium or potassium indicator. Examples of sodium indicators include SBFI, CoroNa Green, CoroNa Red, and Sodium Green (Handbook of Fluorescent Probes and Research Chemicals, 9th ed. Molecular Probes). Examples of potassium indicators include PBFI (Handbook of Fluorescent Probes and Research Chemicals, 9th ed. Molecular Probes).

The present invention provides methods for identifying molecules that modulate the divalent cationic permeability of the TRPM7 channel. The TRPM7 channel is permeable to the divalent cations, zinc, nickel, barium, cobalt, magnesium, manganese, strontium, cadmium, and calcium (Harteneck, Arch Pharmacol 2005 371:307-314). Modulation of the divalent cationic permeability of the TRPM7 channel can, for example, be determined by measuring the inward and outward currents in whole cell patch clamp assays or single-channel membrane patch assays in the presence and absence of the candidate bioactive agent. In an alternative embodiment, the modulation of divalent cation activity can be monitored as a function of cation currents and/or membrane-potential of a cell comprising a TRPM7 channel.

Modulation of the divalent cationic permeability of the TRPM7 channel by a candidate agent can be determined by contacting a cell that expresses TRPM7 with a divalent cation and a divalent cation indicator that reacts with the divalent cation to generate a signal. The intracellular levels of the divalent cation can be measured by detecting the indicator signal in the presence and absence of a candidate bioactive agent. Additionally, the intracellular divalent cation levels in cells that express TRPM7 with cells that do not express TRPM7 can be compared in the presence and absence of a candidate bioactive agent.

The divalent cation indicator can be, for example, a fluorescent magnesium indicator. Examples of magnesium indicators include furaptra or Magfura (commercially available from Molecular Probes™, Invitrogen Detection Technologies).

Many forms of neurodegenerative disease are attributed to calcium ions. Excessive Ca2+ influx or release from intracellular stores can elevate Ca2+ loads to levels that exceed the capacity of Ca2+-regulator mechanisms (Aarts et al., Cell 2003 115:863-877). The methods of the present invention include methods of detecting Ca2+ flux through TRPM7 channels. The levels of intracellular Ca2+ levels are detectable, for example, using indicators specific for Ca2+. Indicators that are specific for Ca2+ include, but are not limited to, fura-2, indo-1, rhod-2, fura-4F, fura-5F, fura-6F and fura-FF, fluo-3, fluo-4, Oregon Green 488 BAPTA, Calcium Green, X-rhod-1 and fura-red (Handbook of Fluorescent Probes and Research Chemicals, 9th ed. Molecular Probes). Ca2+ loading can be determined by measuring Ca2+ accumulation in the cells. See, for example, Sattler et al., J. Neurochem, 1998 71, 2349-2364 and Aarts et al., Cell 2003 115:863-877.

Both the levels of monovalent and divalent cations into the cell can be measured either separately or simultaneously. For example, a Ca2+ specific indicator can be used to detect levels of Ca2+ and a monovalent cation specific indicator can be used to detect levels of monovalent cation. In some embodiments, the Ca2+ indicator and the monovalent cation specific indicator are chosen such that the signals from the indicators are capable of being detected simultaneously. For example, in some embodiments, both indicators have a fluorescent signal but the excitation and/or emission spectra of both indicators are distinct such that the signal from each indicator can be detected at the same time.

Both the levels of divalent or monovalent cations and the change in membrane potential can be measured simultaneously. In this embodiment a Ca2+ specific indicator can be used to detect levels of Ca2+ and a membrane potential sensitive probe can be used to detect changes in the membrane potential. The Ca2+ indicator and the membrane potential sensitive probe can be chosen such that the signals from the indictors and probes are capable of being detected simultaneously. For example, in some embodiments, both the indicator and probe have a fluorescent signal but the excitation and/or emission spectra of both indicators are distinct such that the signal from each indicator can be detected at the same time.

Before modulation of the TRPM7 channel is measured, TRPM7 is preferably activated. RPM7 channels are activated by millimolar levels of MgATP levels (Nadler et al., Nature 2001 411:590-595). TRPM7 can be activated by altering extracellular divalent cation concentrations prior to measuring the modulation of TRPM7 activity by a candidate modulating agent. Preferably, extracellular Ca2+ concentration, extracellular Mg2+ concentration, or both are altered. More preferably, such alteration comprise the lowering of extracellular Mg2+ concentration by at least at least 10%, at least 20%, at least 30% at least 40% at least 50%, at least 60%, at least 70%, at least 80%, at least 90%, at least 95%, preferably at least 99%. Also preferably, such alteration comprise the lowering of extracellular Ca2+ concentration by at least at least 10%, at least 20%, at least 30% at least 40% at least 50%, at least 60%, at least 70%, at least 80%, at least 90%, at least 95%, preferably at least 99%. Also preferably, such alteration comprise the simultaneous lowering of the extracellular Ca2+ and Mg2+ concentration to the extents described herein.

The TRPM7 activity can be measured in intact cells, e.g., HEK-293 cells, that are transformed with a vector comprising nucleic acid encoding TRPM7 and an inducible promoter operably linked thereto. After inducement of the promoter, the TRPM7 polypeptides are produced and form a TRPM7 channel. Endogenous levels of TRPM7 activity can be measured prior to inducement and then compared to the levels of TRM7 activity measured subsequent to inducement. In one embodiment, fluorescent molecules can be used to detect intracellular monovalent and divalent cation levels.

In certain embodiments, the candidate bioactive agents can, for example, open TRPM7 channels in a variety of cells such as cells of the nervous systems of vertebrates. In a preferred embodiment, the candidate bioactive agents close, e.g., inhibit, TRPM7 channels in a variety of cells such as cells of the nervous system. Preferred candidate bioactive agents close or inhibit TRPM7 channels. The closing or inhibition of the TRPM7 channels can, for example, prevent or significantly decrease neuronal cell death following ischemic injury.

In yet other embodiments, the candidate bioactive agents can, for example, increase the expression of TRPM7 channels in a variety of cells such as cells of the nervous systems of vertebrates. In a preferred embodiment, the candidate bioactive agents reduce, e.g., inhibit, the expression of TRPM7 channels in a variety of cells such as cells of the nervous system. Preferred candidate bioactive agents inhibit the expression of TRPM7 channels. The inhibition of expression of TRPM7 channels can, for example, prevent or significantly decrease neuronal cell death following ischemic injury.

In yet other certain embodiments, the candidate bioactive agents can, for example, potentiate the activity of downstream signaling pathways that depend on TRPM7 channel activity in a variety of cells such as cells of the nervous systems of vertebrates. In a preferred embodiment, the candidate bioactive agents inhibit the activity of downstream signaling pathways that depend on TRPM7 channel activity in a variety of cells such as cells of the nervous system. Preferred candidate bioactive agents inhibit the activity of downstream signaling pathways that depend on TRPM7 channel activity. The inhibition of downstream signaling pathways that depend on TRPM7 channel activity can, for example, prevent or significantly decrease neuronal cell death following ischemic injury.

The present provides methods for identifying candidate bioactive agents that modulate expression levels of TRPM7 within cells. Candidate agents can be used that wholly or partially suppress or enhance the expression of TRPM7 within cells, thereby altering the cellular phenotype. Examples of these candidate agents include naturally occurring or synthetic small molecules, antisense cDNAs and DNAs, regulatory binding proteins and/or nucleic acids, as well as any of the other candidate bioactive agents herein described that modulate transcription or translation of nucleic acids encoding TRPM7.

A particularly useful assay for use in the present invention measures the effect that a compound of interest has on cells expressing TRPM7 that have been exposed to conditions that activate TRPM7 channels as described herein. For example, such cells may be exposed to conditions of low extracellular Mg2+, low extracellular Ca2+ or both (Wei et al., 2007). By measuring cell survival or cell death after the activation of TRPM7 channels and comparing the amount of cell survival in a control cell sample versus the amount of cell survival in a cell sample treated with a test compound, it can be determined whether the test compound is a modulator of TRPM7 activity and of TRPM7-mediated cellular injury. Assays for measuring cell survival are known in the art and include, for example, assays for measuring lactate dehydrogenase which is released from dying cells and assays for measuring ATP in living cells. A preferred candidate bioactive agent rescue cells that have undergone TRPM7 channel activation. If desired, further tests can be performed to confirm that the compound had an effect on TRPM7 gene expression or biological activity of the protein. Standard immunoassays can be used, such as western blotting, ELISA and the like. For measurement of mRNA, amplification, e.g., using PCR, LCR, or hybridization assays, e.g., northern hybridization, RNase protection, dot blotting, are preferred. The level of protein or mRNA can be detected, for example, using directly or indirectly labeled detection agents, e.g., fluorescently or radioactively labeled nucleic acids, radioactively or enzymatically labeled antibodies, and the like, as described herein. After a compound is determined to have an effect on murine TRPM7 activity or/and gene or protein expression or/and cell survival, the compound can be used in an animal model, in particular a murine model, for ischemic injury, including, for example, stroke.

Another useful assay for use in the present invention measures the effect that a compound of interest has on cells expressing TRPM7 that have been denied oxygen and glucose. By measuring cell survival or cell death after the denial of oxygen and glucose and comparing the amount of cell survival in a control cell sample versus the amount of cell survival in a cell sample treated with a test compound, it can be determined whether the test compound is a modulator of TRPM7 activity and of ischemic death. Assays for measuring cell survival are known in the art and include, for example, assays for measuring lactate dehydrogenase which is released from dying cells and assays for measuring ATP in living cells. A preferred candidate bioactive agent rescue cells that have been denied oxygen and glucose. If desired, further tests can be performed to confirm that the compound had an effect on TRPM7 gene expression or biological activity of the protein as described herein.

In certain embodiments of the assays described herein are conducted in cells in which TRPM7 expression is inducible. The effects of a compound of interest has on the cells expressing TRPM7 is compared between the effect measured when the compound of interest is contacted with the cells prior to the induction of TRPM7 expression, preferably at a time ranging from 0 to 3 days prior to induction of TRPM7 expression, with the effects that the same compound of interest has on the cells expressing TRPM7 when the compound of interest is applied at or after the activation of TRPM7, preferably at a time ranging from 0 to 36 hours after the activation of TRPM7.

In some preferred embodiments of the current invention, the TRPM7 used in these assays has at least 99% identity to the amino acid sequence as set forth in Swiss-Prot Q923J1 [mouse], Q925B3 [rat], or Q96QT4 [human].

The various screening methods described vary in length of time needed to perform and information generated. For screening large numbers of agents (e.g., greater than 10,000) methods can be combined with a primary highthroughput screen performed on random compounds, and a secondary screen performed on agents showing a positive result in the first screen. A useful primary screen is to measure the effect of an agent on cell death/survival of cells expressing TRPM7 (either naturally or recombinantly). Typically TRPM7 is activated before performing the assay by decreasing the concentration of bivalent ion (e.g., Ca or Mg) in the culture media.

The concentration can be changed by changing the culture media or simply by dilution. In the absence of an agent, a significant portion of cells die. However, some agents have a protective function against cell death. This protective function can be assessed from any measure of cell death or survival. Because cell death and survival are reciprocal events, a measurement of one effectively serves as a measure of the other. Some agents identified by the assay inhibit cell death or in other words promote cell survival. Other agents have the opposite effect of promoting cell death or inhibiting cell survival. Other agents have no effect in such an assay. Such effects are typically demonstrated relative to a control assay in which the agent being tested is not present. Agents identified by the primary screen are inhibitors or activators of TRPM7-mediated cell death. However, the agents need not act directly to inhibit expression or functional activity of TRPM7. For example, some agents may upstream or downstream in a molecular pathway by which TRPM7 mediated cells death occurs.

A secondary assay can be performed on agents found to inhibit or promote TRPM7-mediated cell death in the primary assay. The secondary assay measure an effect on ion currents through a TRPM7 ion channel as described in the examples. An ability to inhibit or promote such ion currents demonstrates the agent has a specific effect on TRPM7 activity, which may be directly on the channel although could also be indirect via upstream activation.

Additional tertiary assays can be performed on agents found to inhibit or promote ion currents in a TRPM7 channel can be further tested for pharmacological activity in treatment or prophylaxis of disease in cellular or animal models of disease, including any of the diseases described herein. Such models include cellular and animal models of ischemia, including stroke. Agents having positive activity in disease models (e.g., which reduce infarct size or reduce cognitive deficit), cancer, pain or glaucoma can be carried forward into clinical trials and then used as pharmaceuticals in indications, such as those described herein.

Additional assays can be performed in combination with the primary, second and tertiary assays described above. For example, following the primary assay, it can be useful to perform a dose response analysis on agents showing positive results from the primary assay. Existence of a dose response provides a safeguard against false positives as well as allowing more accurate comparison of potency of different agents and selection of which agents to carry forward to the secondary assay.

Other assays that can be performed include determining whether an agent binds to a TRPM7 protein, optionally in competition, with a compound known to inhibit TRPM7 or inhibits expression of a TRPM7 protein. Such assays can performed before or after the primary screen described above and are useful in selecting from a larger pool, agents that act specifically on TRPM7 or its expression.

A. Candidate Bioactive Agents

The term "modulator", "candidate substance", "candidate bioactive agent", "drug candidate", "agent," "compound" or grammatical equivalents as used herein describes any molecule, e.g., protein, oligopeptide, small organic molecule, polysaccharide, polynucleotide or oligonucleotide (e.g., antisense, siRNA), to be tested for bioactive agents that are capable of directly or indirectly altering the activity of a target gene, protein, or cell. Accordingly, the term "candidate bioactive agent" as used herein describes any molecule that binds to TRPM7, modulates the activity of a TRPM7 ion channel, alters the expression of TRPM7 within cells, or reduces the damaging effects of TRPM7 channel activation on cells by inhibiting TRPM7-dependent downstream pathways. Candidate agents may be bioactive agents that are known or suspected to bind to ion channel proteins or known to modulate the activity of ion channel proteins, or alter the expression of ion channel proteins within cells. Candidate agents can also be mimics of bioactive agents that are known or suspected to bind to ion channel proteins or known to modulate the activity of ion channel proteins, or alter the expression of ion channel proteins within cells. In a particularly preferred method, the candidate agents induce a response, or maintain such a response as indicated, for example, reduction of neuronal cell death following ischemic injury.

Candidate agents encompass numerous chemical classes, though typically they are organic molecules. Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents can be subjected to directed or random chemical modifications, such as acylation, alkylation, esterification, amidification to produce structural analogs.

B. Combinatorial Chemical Libraries

The invention provides methods for identifying/screening for modulators (e.g., inhibitors, activators) of murine TRPM7 activity. In practicing the screening methods of the invention, a candidate compound is provided. Combinatorial chemical libraries are one means to assist in the generation of new chemical compound leads for, e.g., compounds that inhibit a murine TRPM7 activity. A combinatorial chemical library is a collection of diverse chemical compounds generated by either chemical synthesis or biological synthesis by combining a number of chemical "building blocks" such as reagents. For example, a linear combinatorial chemical library such as a polypeptide library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. For example, the systematic, combinatorial mixing of 100 interchangeable chemical building blocks results in the theoretical synthesis of 100 million tetrameric compounds or 10 billion pentameric compounds. (See, e.g., Gallop et al., J. Med. Chem. 1994, 37: 1233-1250). Preparation and screening of combinatorial chemical libraries are well known to those of skill in the art, (see, e.g., U.S. Pat. Nos. 6,004,617; 5,985,356). Such combinatorial chemical libraries include, but are not limited to, peptide libraries. (see, e.g., U.S. Pat. No. 5,010,175; Furka, Int. J. Pept. Prot. Res. 1991, 37: 487-493; Houghton et al., Nature 1991, 354: 84-88). Other chemistries for generating chemical diversity libraries include, but are not limited to: peptoids (see, e.g., WO 91/19735), encoded peptides (see, e.g., WO 93/20242), random bio-oligomers (see, e.g., WO 92/00091), benzodiazepines (see, e.g., U.S. Pat. No. 5,288,514), diversomers such as hydantoins, benzodiazepines and dipeptides (see, e.g., Hobbs, Proc. Nat. Acad. Sci. USA 1993, 90: 6909-6913), vinylogous polypeptides (see, e.g., Hagihara, J. Amer. Chem. Soc. 1992, 114: 6568), non-peptidal peptidomimetics with a Beta-D-Glucose scaffolding (see, e.g., Hirschmann, J. Amer. Chem. Soc. 1992, 114: 9217-9218), analogous organic syntheses of small compound libraries (see, e.g., Chen, J. Amer. Chem. Soc. 1994, 116: 2661), oligocarbamates (see, e.g., Cho, Science 1993, 261:1303), and/or peptidyl phosphonates (see, e.g., Campbell, J. Org. Chem. 1994, 59: 658). See also (Gordon, J. Med. Chem. 1994, 37: 1385); for nucleic acid libraries, peptide nucleic acid libraries, (see, e.g., U.S. Pat. No. 5,539,083); for antibody libraries, (see, e.g., Vaughn, Nature Biotechnology 1996, 14: 309-314); for carbohydrate libraries, (see, e.g., Liang et al., Science 1996, 274: 1520-1522, U.S. Pat. No. 5,593,853); for small organic molecule libraries, (see, e.g., for isoprenoids U.S. Pat. No. 5,569,588); for thiazolidinones and metathiazanones, (U.S. Pat. No. 5,549,974); for pyrrolidines, (U.S. Pat. Nos. 5,525,735) and 5,519,134; for morpholino compounds, (U.S. Pat. No. 5,506, 337); for benzodiazepines (U.S. Pat. No. 5,288,514).

Devices for the preparation of combinatorial libraries are commercially available (see, e.g., U.S. Pat. Nos. 6,045,755; 5,792,431; 357 MPS, 390 MPS), (Advanced Chem Tech, Louisville Ky., Symphony, Rainin, Woburn, Mass., 433A Applied Biosystems, Foster City, Calif., 9050 Plus, Millipore, Bedford, Mass.). A number of robotic systems have also been developed for solution phase chemistries. These systems include automated workstations, e.g., like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) that mimic the manual synthetic operations performed by a chemist. Any of the above devices are suitable for use with the present invention. In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., and the like).

The compounds tested as modulators of murine TRPM7 genes or gene products can be any small organic molecule, or a biological entity, such as a protein, e.g., an antibody or peptide, a sugar, a nucleic acid, e.g., an antisense oligonucleotide or RNAi, or a ribozyme, or a lipid. Alternatively, modulators can be genetically altered versions of a murine TRPM7 protein. Typically, test compounds are small organic molecules (molecular weight no more than 1000 and usually no more than 500 Da), peptides, lipids, and lipid analogs.

Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays that are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one embodiment, high throughput screening methods involve providing a combinatorial small organic molecule or peptide library containing a large number of potential therapeutic compounds (potential modulator or ligand compounds). Such "combinatorial chemical libraries" or "ligand libraries" (as described above) are then screened in one or more assays, as described herein, to identify those library members (particular chemical species or subclasses) that display a desired characteristic activity. The compounds thus identified can serve as conventional "lead compounds" or can themselves be used as potential or actual therapeutics.

C. Solid State and Soluble High Throughput Assays

In certain embodiments, the invention provide soluble assays using molecules such as a domain such as ligand binding domain, an active site, and the like; a domain that is covalently linked to a heterologous protein to create a chimeric molecule; murine TRPM7; a cell or tissue expressing murine TRPM7, either naturally occurring or recombinant. In another embodiment, the invention provides solid phase based in vitro assays in a high throughput format, where the domain, chimeric molecule, murine TRPM7, or cell or tissue expressing murine TRPM7 is attached to a solid phase substrate.

In exemplary high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100-1500 different compounds. It is possible to assay several different plates per day; assay screens for up to about 6,000-20,000 different compounds is possible using the integrated systems of the invention.

The molecule of interest can be bound to the solid state component, directly or indirectly, via covalent or non covalent linkage, e.g., via a tag. The tag can be any of a variety of components. In general, a molecule that binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, and the like) Antibodies to molecules with natural binders such as biotin are also widely available and appropriate tag binders; see, SIGMA Immunochemicals 1998 catalogue SIGMA, St. Louis Mo.

Similarly any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody that recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott et al., The Adhesion Molecule Facts Book I, 1993. Similarly, toxins and venoms, viral epitopes, hormones (e.g., opiates, steroids, and the like), intracellular receptors (e.g. that mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages.

Tag binders can be fixed to solid substrates using any of a variety of methods currently available. Solid substrates are commonly derivatized or functionalized by exposing all or a portion of the substrate to a chemical reagent that fixes a chemical group to the surface that is reactive with a portion of the tag binder. For example, groups that are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. (See, e.g., Merrifield, J. Am. Chem. Soc. 1963 85: 2149-2154 (describing solid phase synthesis of, e.g., peptides); Geysen et al., J. Immun. Meth. 1987 102: 259-274 (describing synthesis of solid phase components on pins); Frank et al., Tetrahedron 1988, 44: 6031-6040, (describing synthesis of various peptide sequences on cellulose disks); Fodor et al., Science, 1991, 251: 767-777; Sheldon et al., Clinical Chemistry 1993, 39: 718-719; and Kozal et al., Nature Medicine 1996, 7: 753-759 (all describing arrays of biopolymers fixed to solid substrates). Non-chemical approaches for fixing tag binders to substrates include other common methods, such as heat, cross-linking by UV radiation, and the like.

D. Computer-Based Assays

Compounds that modulate murine TRPM7 activity can also be determined by computer assisted drug design, in which a computer system is used to generate a three-dimensional structure of murine TRPM7 based on the structural information encoded by the amino acid sequence. The input amino acid sequence interacts directly and actively with a preestablished algorithm in a computer program to yield secondary, tertiary, and quaternary structural models of the protein. The models of the protein structure are then examined to identify regions of the structure that have the ability to bind, e.g., ligands. These regions are then used to identify ligands that bind to the protein.

The three-dimensional structural model of the protein is generated by entering murine TRPM7 amino acid sequences of at least 10 amino acid residues or corresponding nucleic acid sequences encoding a murine TRPM7 polypeptide into the computer system. The amino acid sequence of the polypeptide or the nucleic acid encoding the polypeptide is selected from the group consisting of the sequences provided herein, and conservatively modified versions thereof. The amino acid sequence represents the primary sequence or subsequence of the protein, which encodes the structural information of the protein. At least 10 residues of the amino acid sequence (or a nucleotide sequence encoding 10 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the protein is then generated by the interaction of the amino acid sequence and the computer system, using software known to those of skill in the art. The three-dimensional structural model of the protein can be saved to a computer readable form and be used for further analysis (e.g., identifying potential ligand binding regions of the protein and screening for mutations, alleles and interspecies homologs of the gene).

The amino acid sequence represents a primary structure that encodes the information necessary to form the secondary, tertiary and quaternary structure of the protein of interest. The software looks at certain parameters encoded by the primary sequence to generate the structural model. These parameters are referred to as "energy terms," and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential ligand binding regions are identified by the computer system. Three-dimensional structures for potential ligands are generated by entering amino acid or nucleotide sequences or chemical formulas of compounds, as described above. The three-dimensional structure of the potential ligand is then compared to that of the murine TRPM7 protein to identify ligands that bind to murine TRPM7. Binding affinity between the protein and ligands is determined using energy terms to determine which ligands have an enhanced probability of binding to the protein. The software can then also be used to modify the structure of a candidate ligand in order to modify (e.g., enhance or diminish) its affinity to the protein. Thus, each candidate ligand may be used as a "lead compound" for the generation of other candidate ligands by the computer system. The results, such as three-dimensional structures for potential ligands and binding affinity of ligands, can also be saved to a computer readable form and can be used for further analysis (e.g., generating a three dimensional model of mutated proteins having an altered binding affinity for a ligand, or generating a list of additional candidate ligands for chemical synthesis).

9. Preferred Compounds of the Invention

The invention provides several genera and examples of compounds. The compounds can be provided as they are as a pharmaceutically acceptable salt or as pharmaceutical composition. Functional properties of compounds include any or all of specific binding to TRPM7, inhibiting TRPM7-mediated cell death, inhibiting TRPM7 currents, inhibiting damaging effects of ischemia (e.g., cell death) in any of the tissues disclosed herein, as demonstrated in any of the assays of the Examples (among others), inhibiting proliferation, toxicity or metastasis of cancers of any of the types disclosed herein, as demonstrated by any of the assays in the Examples (among others), inhibiting pain, and/or inhibiting damaging effects of glaucoma (e.g., cell death). Preferred compounds exhibit any or all of the properties of TRPM7 inhibitors or candidate bioactive molecules described herein. For example, a preferred compound inhibits TRPM7-mediated cell death in a mammalian cell by at least 30, 40, 50, 60, 70 or 80% as illustrated by the compounds in Table 3. The TRPM7 used in such assays can be human (Swiss prot Q96QT4), mouse or other mammalian origin. Likewise, cellular or animal systems used to demonstrate functional properties can be human, mouse or other mammalian. Because the primary therapeutic use of the compounds is usually in treating humans, it is preferred that binding and other functional effects occur on materials of human origin.

Some compounds are of Formula I:

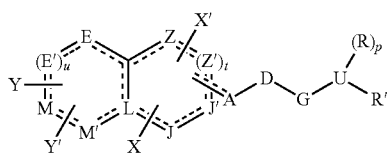

I wherein

――― is a single or double bond,

Z, Z', J, J', E, E', L, M and M' are each independently S, O, N or C, wherein N or C in each instance can be further covalently bound to X, X', Y or Y', X and X' are each independently selected from the group consisting of hydrogen, hydroxyl, optionally substituted, saturated or unsaturated $C_1$-$C_6$ alkyl, $C_1$-$C_6$ alkenyl, $C_1$-$C_6$ alkynyl, $C_1$-$C_6$ alkoxy, $C_1$-$C_6$ alkoxycarbonyl, amino, $C_1$-$C_6$ alkylamino, di-($C_1$-$C_6$) alkylamino, halogen, thiol, cyano, nitro, and optionally substituted 5- to 7-member cyclic, heterocyclic, bicyclic or heterobicyclic ring, wherein said ring may be aromatic or heteroaromatic, or is O, which taken together with a C to which it is attached forms a carbonyl, Y and Y' are each independently selected from the group consisting of hydrogen, hydroxyl, optionally substituted, saturated or unsaturated $C_1$-$C_6$ alkyl, $C_1$-$C_6$ alkenyl, $C_1$-$C_6$ alkynyl, $C_1$-$C_6$ alkoxy, $C_1$-$C_6$ alkoxycarbonyl, amino, $C_1$-$C_6$ alkylamino, di-($C_1$-$C_6$) alkylamino, halogen, thiol, cyano, nitro, and optionally substituted 5- to 7-member cyclic, heterocyclic, bicyclic or heterobicyclic ring, wherein said ring may be aromatic or heteroaromatic, or is O, which taken together with a C to which it is attached forms a carbonyl, A is $NR^a$, $SO_2$, $(CR^1R^2)_x$ or —$(CR^1=CR^2)$—$_x$, wherein x is an integer from zero to four, D is carbonyl, sulfoxide, O, S or $(CR^3R^4)_y$, wherein y is an integer from zero to four, G is $NR^b$, $SO_2$, $(CR^5R^6)_z$ or —$(CR^5=CR^6)$—$_z$, wherein z is an integer from zero to four, U is C—$(R^7)_q$ or N, wherein C—$R^7$ can be taken together to form a carbonyl when p is zero, or $R^7$ is as described below, p is one or zero, q is one or zero, t is one or zero, u is one or zero, R is selected from the group consisting of hydrogen, optionally substituted $C_1$-$C_6$ alkyl, optionally substituted phenyl ($C_1$-$C_6$) alkyl, and optionally substituted 5- to 10-member cyclic, heterocyclic, bicyclic or heterobicyclic ring, wherein said ring may be aromatic or heteroaromatic, R' is selected from the group consisting of optionally substituted $C_1$-$C_6$ alkyl, optionally substituted phenyl ($C_1$-$C_6$) alkyl, and optionally substituted 5- to 10-member cyclic, heterocyclic, bicyclic or heterobicyclic ring, wherein said ring may be aromatic or heteroaromatic, or R and R' are taken together with U to form an optionally substituted 5- to 10-member cyclic, bicyclic, heterocyclic or heterobicyclic ring, wherein said ring may be aromatic or heteroaromatic, and $R^1$, $R^2$, $R^3$, $R^4$, $R^5$, $R^6$, $R^7$, $R^a$ and $R^b$ are each independently selected from the group consisting of hydrogen, optionally substituted $C_1$-$C_6$ alkyl, $C_1$-$C_6$ alkenyl, $C_1$-$C_6$ alkynyl, optionally substituted phenyl ($C_1$-$C_6$) alkyl, optionally substituted 5- to 10-member cyclic, heterocyclic, bicyclic or heterobicyclic ring, wherein said ring may be aromatic or heteroaromatic.

Examples of such compounds include M4, M5, M6, M9, M17, M21, M29 (FIGS. 11-16) and CO4, CO6, C10, C07, C08, C13, C15, D03, D11, D19, E07, E09, G17, G18, H06, H16, H21, I04, I14, I08, I10, I20, J08, K06, K16, C07, C11, C20, D09, D19, E18, F18, G11, G16, H19, and H20 (Table 3).

Some such compounds are of Formula II

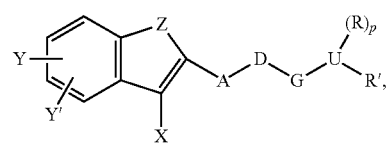

II wherein

Z is S, O, N—H or C—H,

X is halogen,

Y and Y' are each independently selected from the group consisting of hydrogen, hydroxyl, optionally substituted saturated or unsaturated $C_1$-$C_6$ alkyl, $C_1$-$C_6$ alkenyl, $C_1$-$C_6$ alkynyl, $C_1$-$C_6$ alkoxy, amino, $C_1$-$C_6$ alkylamino, di-($C_1$-$C_6$) alkylamino, halogen, thiol, cyano, nitro, and optionally substituted 5- to 7-member cyclic, heterocyclic, bicyclic or heterobicyclic ring, wherein said ring may be aromatic or heteroaromatic, or is O, which taken together with a C to which it is attached forms a carbonyl, A is $NR^a$ or $(CR^1R^2)_x$, wherein x is an integer from zero to four, D is carbonyl or $(CR^3R^4)_y$, wherein y is an integer from zero to four, G is $NR^b$ or $(CR^5R^6)_z$, wherein z is an integer from zero to four, U is C—$(R^7)_q$ or N, wherein C—$R^7$ taken together are carbonyl and p is zero, or $R^7$ is as described below, p is one or zero, q is one or zero, R is hydrogen, optionally substituted $C_1$-$C_6$ alkyl, $C_1$-$C_6$ alkenyl, $C_1$-$C_6$ alkynyl, optionally substituted phenyl ($C_1$-$C_6$) alkyl, or an optionally substituted 5- to 10-member cyclic, heterocyclic, bicyclic or heterobicyclic ring, wherein said ring may be aromatic or heteroaromatic, R' is selected from the group consisting of optionally substituted $C_1$-$C_6$ alkyl, optionally substituted phenyl ($C_1$-$C_6$) alkyl, $C_1$-$C_6$ alkenyl, $C_1$-$C_6$ alkynyl, optionally substituted 5- to 10-member cyclic, heterocyclic, bicyclic or heterobicyclic ring, wherein said ring may be aromatic or heteroaromatic, or R and R' are taken together with U to form an optionally substituted 5- to 10-member cyclic, bicyclic, heterocyclic or heterobicyclic ring, wherein said ring may be aromatic or heteroaromatic, and $R^1$, $R^2$, $R^3$, $R^4$, $R^5$, $R^6$, $R^7$, $R^a$ and $R^b$ are each independently selected from the group consisting of substituted $C_1$-$C_6$ alkyl, $C_1$-$C_6$ alkenyl, $C_1$-$C_6$ alkynyl, optionally substituted phenyl ($C_1$-$C_6$) alkyl, optionally substituted 5- to 10-member cyclic, heterocyclic, bicyclic or heterobicyclic ring, wherein said ring may be aromatic or heteroaromatic.

Some such compounds have a structure wherein R, R' and U are taken together to form a ring selected from the group consisting of

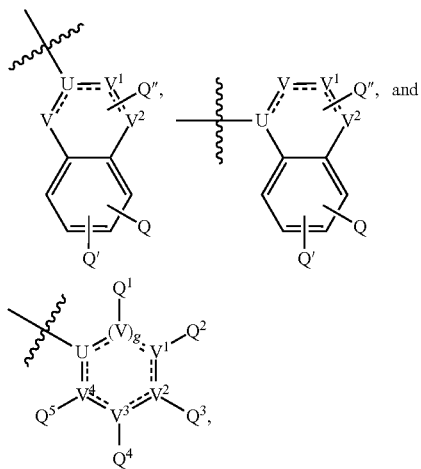

wherein V, $V^1$, $V^2$, $V^3$ and $V^4$ in each instance are independently selected from the group consisting of N, C and O, wherein N or C can be further covalently bound to Q", $Q^1$, $Q^2$, $Q^3$, $Q^4$ or $Q^5$, g is zero, one or two and Q, Q', Q", $Q^1$, $Q^2$, $Q^3$, $Q^4$ and $Q^5$ are each independently selected from the group consisting of hydrogen, hydroxyl, optionally substituted $C_1$-$C_6$ alkyl, $C_1$-$C_6$ alkenyl, $C_1$-$C_6$ alkynyl, optionally substituted phenyl ($C_1$-$C_6$) alkyl, $C_1$-$C_6$ alkoxy, amino, $C_1$-$C_6$ alkylamino, di-($C_1$-$C_6$) alkylamino, halogen, thiol, cyano, nitro, and optionally substituted 5- to 7-member cyclic, heterocyclic, bicyclic or heterobicyclic ring, wherein said ring may be aromatic or heteroaromatic, optionally substituted $C_5$-$C_7$ aryl- or heteroaryl-thiamide, optionally substituted $C_5$-$C_7$ aryl- or heteroaryl-carboxy, optionally substituted $C_5$-$C_7$ aryl- or heteroaryl-($C_1$-$C_6$) alkyl, or is O, which taken together with a C to which it is attached forms a carbonyl.

In some such compounds, the ring has the following structure

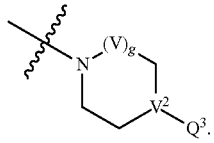

In some such compounds, Z in Formula II is S, and/or X is chlorine and/or Y and Y' are each hydrogen and/or D is carbonyl, x is zero and y is zero. In some such compounds, Q and Q' are each independently selected from the group consisting of hydrogen, hydroxyl, optionally substituted $C_1$-$C_6$ alkyl, optionally substituted phenyl ($C_1$-$C_6$) alkyl, $C_1$-$C_6$ alkoxy, amino, $C_1$-$C_6$ alkylamino, di-($C_1$-$C_6$) alkylamino and halogen. For example, Q can be hydrogen, methoxy, ethoxy, propoxy, methyl, ethyl or propyl and Q' can be methoxy, ethoxy, propoxy, methyl, ethyl or propyl.

Compounds C10, C07, C08 and D08 from Table 3 have the following structures.

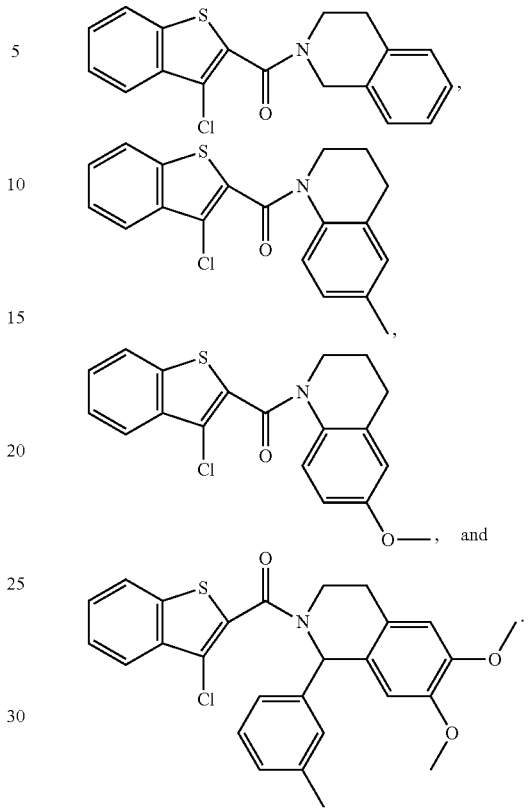

M6 and some related compounds can be represented by the compound of Formula III

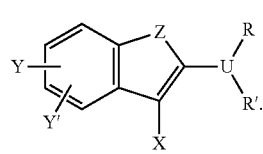

In some such compounds, Z is S, X is chlorine, Y and Y' are each hydrogen, and U is C—$(R^7)_q$. In some compounds R and R' are taken together with U to form an optionally substituted 5- to 10-member cyclic, bicyclic, heterocyclic or heterobicyclic ring, wherein said ring may be aromatic or heteroaromatic. M6 has the structure

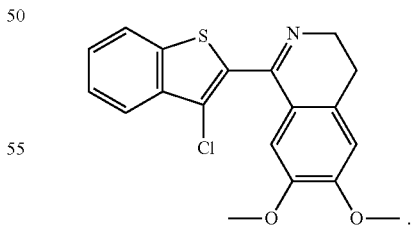

In some compounds of formula II, D is carbonyl, X is zero, Z is zero, and U is N. In some such compounds R is selected from the group consisting of hydrogen, optionally substituted $C_1$-$C_6$ alkyl, optionally substituted phenyl ($C_1$-$C_6$) alkyl, $C_1$-$C_6$ alkenyl, $C_1$-$C_6$ alkynyl, and optionally substituted 5- to 10-member cyclic, heterocyclic, bicyclic or heterobicyclic ring, wherein the ring may be aromatic or heteroaromatic, and R' is selected from the group consisting of optionally substituted $C_1$-$C_6$ alkyl, optionally substituted phenyl ($C_1$-$C_6$)

alkyl, $C_1$-$C_6$ alkenyl, $C_1$-$C_6$ alkynyl, and optionally substituted 5- to 10-member cyclic, heterocyclic, bicyclic or heterobicyclic ring, wherein said ring may be aromatic or heteroaromatic. In some such compounds, R is hydrogen or $C_1$-$C_6$ alkyl, and R' is a substituted $C_1$-$C_6$ alkyl. Some exemplary compounds having such a structure are C15 and D03 from Table 3.

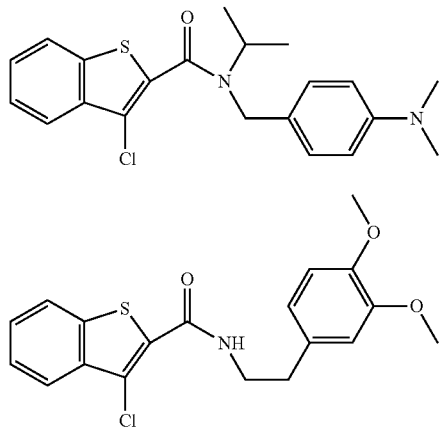

Some compounds of Formula I have a structure of Formula IV

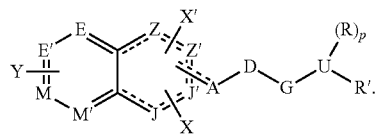

In some such compounds, one of E, E', M and M' is C—Y, and the others are C—H. In some such compounds, Y is selected from the group consisting of hydrogen, hydroxyl, and optionally substituted, saturated or unsaturated $C_1$-$C_6$ alkyl, $C_1$-$C_6$ alkoxy and $C_1$-$C_6$ alkoxycarbonyl, or is O, which taken together with a C to which it is attached forms a carbonyl, and X and X' are each independently selected from the group consisting of hydrogen, hydroxyl, and optionally substituted, saturated or unsaturated $C_1$-$C_6$ alkyl, $C_1$-$C_6$ alkoxy and $C_1$-$C_6$ alkoxycarbonyl, or is O, which taken together with a C to which it is attached forms a carbonyl. M21 and related compounds are a preferred example of this formula and can be represented by Formula V

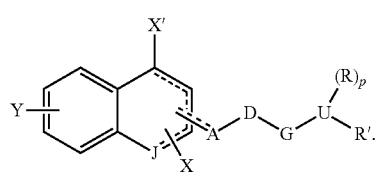

In some such compounds of Formula V, Y is hydrogen, hydroxyl, $C_1$-$C_6$ alkoxy, $C_1$-$C_6$ alkyl, amino, $C_1$-$C_6$ alkylamino, di-($C_1$-$C_6$) alkylamino or halogen, X' is hydrogen, hydroxyl, $C_1$-$C_6$ alkoxy, $C_1$-$C_6$ alkyl, amino, $C_1$-$C_6$ alkylamino, di-($C_1$-$C_6$) alkylamino or halogen, or is O, which taken together with a C to which it is attached forms a carbonyl, X is hydrogen, hydroxyl, $C_1$-$C_6$ alkoxy, $C_1$-$C_6$ alkyl, amino, $C_1$-$C_6$ alkylamino, di-($C_1$-$C_6$) alkylamino or halogen, or is O, which taken together with a C to which it is attached forms a carbonyl, J is C—H, $CH_2$ or O. In some such compounds, A is $(CR^1R^2)_x$ or $—(CR^1=CR^2)—_x$, wherein x is an integer from zero to one D is $(CR^3R^4)_y$, wherein y is zero, G is $(CR^5R^6)_z$, wherein z is zero. In some such compounds, R and R' are taken together with U to form an optionally substituted 5- to 10-member cyclic, bicyclic, heterocyclic or heterobicyclic ring, wherein said ring may be aromatic or heteroaromatic. Some such compounds are of Formula VI

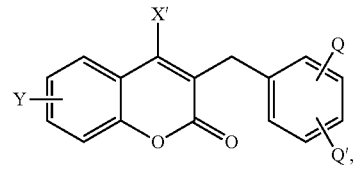

wherein
X' is hydrogen, hydroxyl, $C_1$-$C_6$ alkoxy or $C_1$-$C_6$ alkyl,
Y is hydrogen, hydroxyl, $C_1$-$C_6$ alkoxy or $C_1$-$C_6$ alkyl, and
Q and Q' are each independently selected from the group consisting of hydrogen, hydroxyl, optionally substituted $C_1$-$C_6$ alkyl, $C_1$-$C_6$ alkenyl, $C_1$-$C_6$ alkynyl, optionally substituted phenyl ($C_1$-$C_6$) alkyl, $C_1$-$C_6$ alkoxy, amino, $C_1$-$C_6$ alkylamino, di-($C_1$-$C_6$) alkylamino, halogen, thiol, cyano, nitro, and optionally substituted 5- to 7-member cyclic, heterocyclic, bicyclic or heterobicyclic ring, wherein said ring may be aromatic or heteroaromatic.

A preferred example of such compounds is M21 having the structure

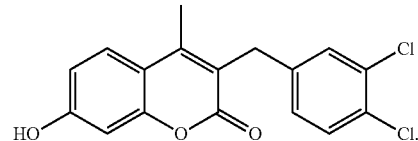 [SMILES: Cc1c(Cc2ccc(Cl)c(Cl)c2)c(=O)oc2cc(O)ccc12]

Other preferred examples of such compounds have the Formula VII or VIII

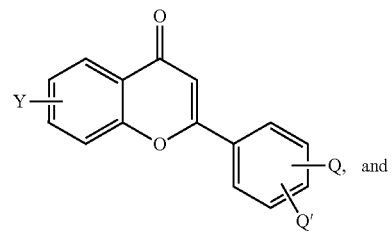

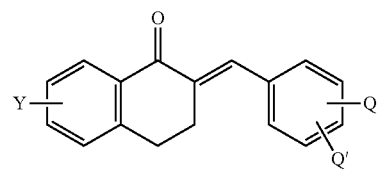

wherein
Y is hydrogen, hydroxyl, $C_1$-$C_6$ alkoxy or $C_1$-$C_6$ alkyl, and
Q and Q' are each independently selected from the group consisting of hydrogen, hydroxyl, optionally substituted $C_1$-$C_6$ alkyl, $C_1$-$C_6$ alkenyl, $C_1$-$C_6$ alkynyl, optionally substituted phenyl ($C_1$-$C_6$) alkyl, $C_1$-$C_6$ alkoxy, amino, $C_1$-$C_6$ alkylamino, di-($C_1$-$C_6$) alkylamino, halogen, thiol, cyano, cyano ($C_1$-$C_6$)alkyl, nitro, optionally substituted 5- to 7-member cyclic, heterocyclic, bicyclic or heterobicyclic ring, wherein said ring may be aromatic or heteroaromatic, optionally substituted $C_5$-$C_7$ aryl- or heteroaryl-thiamide, optionally substituted $C_5$-$C_7$ aryl- or heteroaryl-carboxy, optionally substituted $C_5$-$C_{10}$ aryl-S—, optionally substituted phenyl-$SO_2$—, optionally substituted phenyl-NH(CO)—, and optionally substituted $C_5$-$C_7$ aryl-($C_1$-$C_6$) alkyl or heteroaryl-($C_1$-$C_6$) alkyl, or is O, which taken together with a C to which it is attached forms a carbonyl.

In some such compounds Q and Q' are each independently selected from the group consisting of hydrogen, hydroxyl, optionally substituted $C_1$-$C_6$ alkyl, $C_1$-$C_6$ alkenyl, $C_1$-$C_6$ alkynyl, optionally substituted phenyl ($C_1$-$C_6$) alkyl, $C_1$-$C_6$ alkoxy, amino, $C_1$-$C_6$ alkylamino, di-($C_1$-$C_6$) alkylamino, halogen, thiol, cyano, nitro, and optionally substituted 5- to 7-member cyclic, heterocyclic, bicyclic or heterobicyclic ring, wherein said ring may be aromatic or heteroaromatic Two exemplary such compounds are I20 and E09 as shown in Table 3.

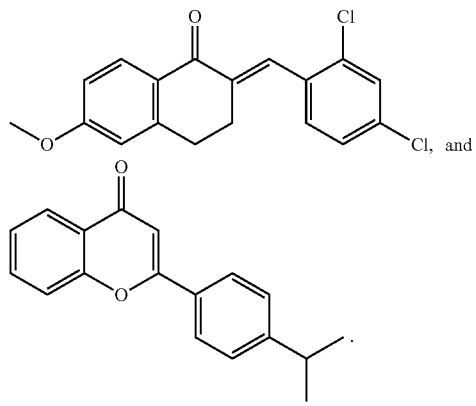

Other compounds represented by M11 and related compounds are represented by Formula IX:

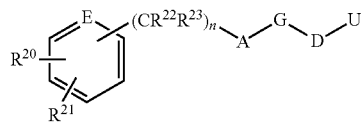

IX wherein

E is C—$R^{20}$, N, S or O, $R^{20}$, $R^{21}$, $R^{22}$ and $R^{23}$ are each independently selected from the group consisting of hydrogen, hydroxyl, optionally substituted, saturated or unsaturated $C_1$-$C_6$ alkyl, $C_1$-$C_6$ alkenyl, $C_1$-$C_6$ alkynyl, $C_1$-$C_6$ alkoxy, $C_1$-$C_6$ alkoxycarbonyl, amino, $C_1$-$C_6$ alkylamino, di-($C_1$-$C_6$) alkylamino, halogen, thiol, cyano, nitro, and optionally substituted 5- to 7-member cyclic, heterocyclic, bicyclic or heterobicyclic ring, wherein said ring may be aromatic or heteroaromatic, A is $NR^c$, $SO_2$ or carbonyl, G is $NR^c$, $SO_2$ or carbonyl, or $CR^{22}R^{23}$ and A together from a 6 or 7 member heterocyclic ring, D is $CR^{24}R^{25}$ or —$CR^{24}$=$CR^{25}$—, wherein $R^{24}$ and $R^{25}$ are each independently selected from the group consisting of hydrogen, hydroxyl, optionally substituted, saturated or unsaturated $C_1$-$C_6$ alkyl, $C_1$-$C_6$ alkenyl, $C_1$-$C_6$ alkynyl, $C_1$-$C_6$ alkoxy, $C_1$-$C_6$ alkoxycarbonyl, amino, $C_1$-$C_6$ alkylamino, di-($C_1$-$C_6$) alkylamino, halogen, thiol, cyano, nitro n is an integer from zero to 5, p is an integer from zero to 5, and U is $CR^{26}R^{27}R^{28}$ wherein $R^{26}$ is selected from the group consisting of hydrogen, hydroxyl, optionally substituted, saturated or unsaturated $C_1$-$C_6$ alkyl, $C_1$-$C_6$ alkenyl, $C_1$-$C_6$ alkynyl, $C_1$-$C_6$ alkoxy, $C_1$-$C_6$ alkoxycarbonyl, amino, $C_1$-$C_6$ alkylamino, di-($C_1$-$C_6$) alkylamino, halogen, thiol, cyano, nitro, and optionally substituted 5- to 7-member cyclic, heterocyclic, bicyclic or heterobicyclic ring, wherein said ring may be aromatic or heteroaromatic, $R^{27}$ is -T'-$R^{29}$, wherein T' is O, S or —(C≡C)—, and $R^{29}$ is an optionally substituted 5- to 7-member cyclic, heterocyclic, bicyclic or heterobicyclic ring, wherein said ring may be aromatic or heteroaromatic, $R^{28}$ is hydrogen, hydroxyl or $C_1$-$C_6$ alkyl, or U is an optionally substituted 5- to 7-member cyclic, heterocyclic, bicyclic or heterobicyclic ring, wherein said ring may be aromatic or heteroaromatic, provided that one of A and G is carbonyl or $SO_2$ and the other is $NR^c$.

In some such compounds U is $CR^{26}R^{27}R^{28}$. In some such compounds, $R^{26}$ is an optionally substituted 5- to 7-member cyclic, heterocyclic, bicyclic or heterobicyclic ring, wherein said ring may be aromatic or heteroaromatic, T' is S or —(C≡C)—, $R^{29}$ is an optionally substituted 5- to 7-member cyclic, heterocyclic, bicyclic or heterobicyclic ring, wherein said ring may be aromatic or heteroaromatic, and $R^{28}$ is hydrogen. In some such compounds, $R^{26}$ is an optionally substituted 6 member cyclic ring, wherein said ring may be aromatic or heteroaromatic, and $R^{29}$ is an optionally substituted 6 member cyclic ring, wherein said ring may be aromatic or heteroaromatic.

Some such compounds are represented by Formula X:

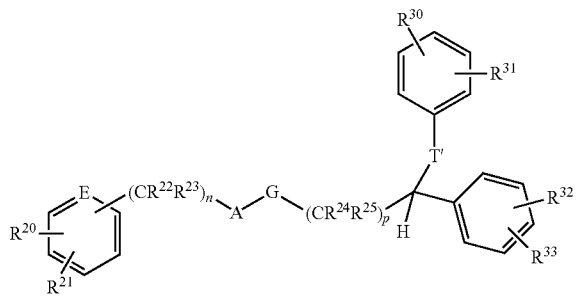

X wherein $R^{30}$, $R^{31}$, $R^{32}$ and $R^{33}$ are each independently selected from the group consisting of hydrogen, hydroxyl, optionally substituted, saturated or unsaturated $C_1$-$C_6$ alkyl, $C_1$-$C_6$ alkenyl, $C_1$-$C_6$ alkynyl, $C_1$-$C_6$ alkoxy, $C_1$-$C_6$ alkoxycarbonyl, amino, $C_1$-$C_6$ alkylamino, di-($C_1$-$C_6$) alkylamino, halogen, thiol, cyano and nitro. In some such compounds, $R^{21}$, $R^{30}$, $R^{31}$, $R^{32}$ and $R^{33}$ are each independently selected from the group consisting of hydrogen and halogen, n is zero, p is zero, and E is C—$R^{20}$, wherein $R^{20}$ is hydrogen.

M11 has the structure

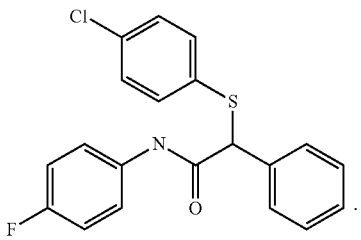 [SMILES: O=C(Nc1ccc(F)cc1)C(Sc1ccc(Cl)cc1)c1ccccc1]

Other compounds represented by M14 and M15 of FIGS. 11-16 and C21, D18, E06, F11, F14, F16, G10, I11, I17, M11, F11, F15, F20, F22, J03, J05, J14, J17, J21, L07, and L14 (Table 3) have the structure of Formula XI:

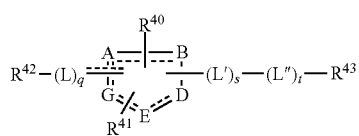

XI wherein

===== is a single or double bond,

A, B, D, E and G are each independently S, O, N or C, wherein N or C in each instance can be further covalently bound to L, L', $R^{40}$ or $R^{41}$, provided that at least two of A, B, D, E and G are other then C;

L is —$CR^{44}R^{45}$—, —$CR^{44}R^{45}$—$SO_2$—, —$CR^{44}R^{45}$—S—, $C_1$-$C_6$ alkenyl, carbonyl, $SO_2$ or —$CR^{44}$—, when ===== is a double bond, q is one or zero;

$R^{42}$ is an optionally substituted 5- to 7-member aromatic or heteroaromatic ring, $R^{40}$ and $R^{41}$ are each independently selected from the group consisting of hydrogen, hydroxyl, optionally substituted, saturated or unsaturated $C_1$-$C_6$ alkyl, ($C_1$-$C_6$)alkyl-S—($C_1$-$C_6$)alkyl, $C_1$-$C_6$ alkenyl, $C_1$-$C_6$ alkynyl, $C_1$-$C_6$ alkoxy, $C_1$-$C_6$ alkoxycarbonyl, amino, $C_1$-$C_6$ alkylamino, di-($C_1$-$C_6$) alkylamino, halogen, thiol, cyanomethyl, cyano and nitro, or is O, which taken together with a C to which it is attached forms a carbonyl, L' is carbonyl, (CO)O, $SO_2$, —$(CR^{46}R^{47})_m$—, piperidinyl, piperazinyl, m is an integer from one to four, L" is O, S, (CO)NH, (COO)NH or —$(CR^{46}=CR^{47})_n$—, n is an integer from one to four, s is one or zero, t is one or zero and $R^{43}$ is hydrogen or an optionally substituted 5- to 7-member aromatic or heteroaromatic ring.

In some such compounds, q is zero and $R^{42}$ is mono-, di- or tri-substituted 5 or 6 member aromatic or heteroaromatic ring. In some such compounds, $R^{42}$ is a mono-, di- or tri-substituted phenyl. Some such compounds have a structure of any of Formulae XII, XIII, XIV, XV, XVI, XVII, XVIII and XIX

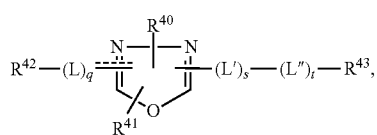

XII

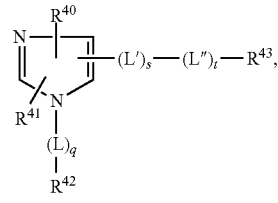

XIII

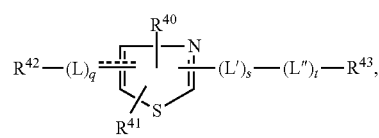

XIV

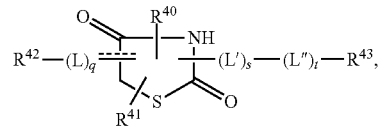

XV

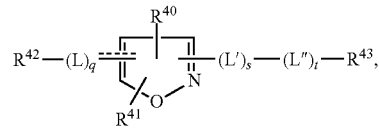

XVI

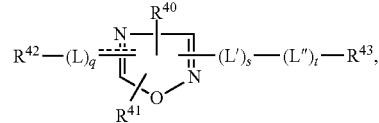

XVII

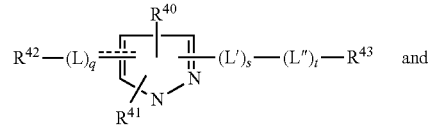

XVIII

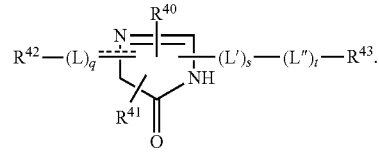

and

XIX

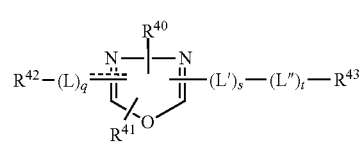

Some such compounds have a structure of Formula XII

XII

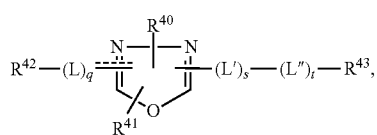

wherein, q is zero, $R^{42}$ is a mono-, di- or tri-substituted phenyl, $R^{40}$ and $R^{41}$ are each independently selected from the group consisting of hydrogen, hydroxyl, optionally substituted, saturated or unsaturated $C_1$-$C_6$ alkyl, ($C_1$-$C_6$)alkyl-S—($C_1$-$C_6$)alkyl, $C_1$-$C_6$ alkenyl, $C_1$-$C_6$ alkynyl, $C_1$-$C_6$ alkoxy, $C_1$-$C_6$ alkoxycarbonyl, amino, $C_1$-$C_6$ alkylamino, di-($C_1$-$C_6$) alkylamino, halogen, thiol, cyanomethyl and cyano, L' is —$(CR^{46}R^{47})_m$—, wherein m is an integer from one to three, L" is S or —$(CR^{46}=CR^{47})_n$—, s is one,
t is one and
R$^{43}$ is an optionally substituted 5- to 7-member aromatic or heteroaromatic ring. In some such compounds, R$^{40}$ and R$^{41}$ are each independently selected from the group consisting of hydrogen and C$_1$-C$_6$ alkyl, and
R$^{43}$ is a mono-, di- or tri-substituted phenyl.
M14 and M15 are examples of such structures as shown below.

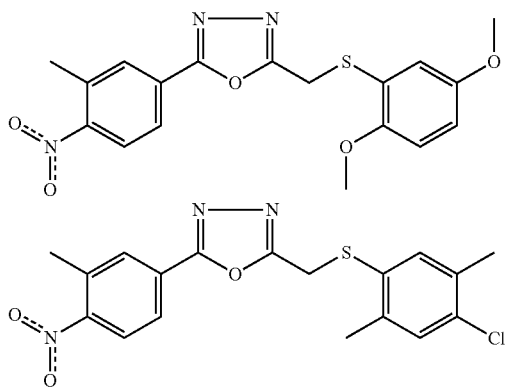

Thirty preferred agents that inhibit TRPM7-mediated cell death are shown in FIGS. 11-16. All of these agents inhibited TRPM7-mediated cell death in the primary screen described above. Most of these agents showed a distinct dose-response effect. Some of these agents including at least agents #'s 5, 6, 7, 11, 14 and 21 inhibited ion currents through TRPM7 (not all agents were tested). The agents were also tested in various cellular and animal disease models as indicated in the table. In each case, where the Figures show an assay was performed, the result was positive (i.e., the agent inhibited at above background levels). If the Figures do not show a particular assay for a compound, the assay was not performed.

M5 is effective in inhibiting proliferation of various cancer cell lines providing evidence of utility of M5 and related compounds in treatment or prophylaxis of cancer, particularly, retinoblastoma, breast cancer, melanoma, adrenal carcinoma and cervical cancer. M5 is also effective in increasing survival after anoxia in neurons, hepatocytes, cardiomyoctes, and retina providing evidence of utility of M5 and related compounds in treatment and prophylaxis of ischemia, particularly of the CNS, brain, liver, heart and retina.

M6 is also effective in inhibiting proliferation of various cancer cell lines providing evidence of utility of M6 and related compounds in treatment or prophylaxis of cancer, particularly of retinoblastoma, breast cancer, melanoma, adrenal carcinoma, cervical cancer, osteosarcoma, lung cancer, non-small cell lung cancer, colon cancer, and renal cancer. M6 is also effective in increasing survival after anoxia in neurons and cardiomyocytes providing evidence of utility of M6 and related compounds in treatment or prophylaxis of ischemia, particularly for the heart, CNS and brain.

M7 and M14 are effective in inhibiting proliferation of a retinoblastoma cell line providing evidence of utility of M7, M14 and related compounds in treatment of cancer, particularly retinoblastoma. M7 and M14 are also effective in increasing survival after anoxia in neurons providing evidence of utility of M7, M14 and related compounds in treatment and prophylaxis of ischemia, particularly of the brain and CNS.

M11 is effective in inhibiting proliferation of various cancer cell lines providing evidence of utility of M11 in treatment or prophylaxis of cancer, particularly retinoblastoma, breast cancer, melanoma, adrenal carcinoma, cervical cancer, osteosarcoma, and lung cancer. M11 is also effective in increasing survival after anoxia in neurons providing evidence of utility of M11 in treatment or prophylaxis of ischemia, particularly of the brain and CNS.

M21 is effective in inhibiting proliferation of a retinoblastoma cell line providing evidence of utility of M21 and related compounds in treatment or prophylaxis of cancer, particularly retinoblastoma. M21 is broadly effective in increasing survival after anoxia in various tissues providing evidence of utility of M21 and related compounds in treatment or prophylaxis of ischemia particularly of the CNS, brain, liver, heart and retina. M21 and related compounds are also effective for treatment or prophylaxis of pain or glaucoma.

10. Pharmaceutical Compositions and Regimes

The agents and compositions of the invention are useful for in treatment or prophylaxis of a variety of diseases and manufacture of a medicament for such purposes as described below and elsewhere herein, particularly neurological diseases, and especially diseases mediated in part by ischemia. The agents and compositions are also effective for treatment or prophylaxis of cancer and pain. The method are useful in treating subjects in which sign(s) and/or symptom(s) of disease are already present or in prophylaxis of subjects without known symptom(s) of disease but at enhanced risk of developing symptoms by virtue of one or more risk factors associated with the disease. Risk factors can be for example, genetic, biochemical or environment. Risk factors can also occur because the subject is about to undergo an event that carriers a known predisposition to development of disease (e.g., cardiac or brain surgery predisposes to development of ischemia).

Disease amenable to treatment prophylaxis include ischemic and cytodegenerative diseases and conditions, including neurological diseases and conditions, such as stroke, traumatic brain injury, Alzheimer's disease, Parkinson's disease, Huntington's disease, dementia, epilepsy, spinocerebellar ataxia, spinal and bulbar muscular dystrophy, dentatorubropallidoluysian atrophy, brain injury, spinal cord injury, and other traumatic, ischemic or neurodegenerative nervous system injuries, or pain. Other non-neurological diseases, including ischemic and degenerative disorders and other conditions of other tissues, such as those of the heart, liver, kidneys, muscles, retina, skin, intestines, pancreas, gall bladder, thyroid, thymus, spleen, bone, cartilage, joints, lungs, diaphragm, adrenal glands, salivary, lacrimal glands, blood vessels and cells of endodermal, mesodermal and ectodermal origin. As shown in Example 5, TRPM7 shows detectable expression by Western blot or RT-PCR in all cell types and tissues tested. Other disease and conditions are optical disorders, such as glaucoma, diabetic retinopathy, and macular degeneration. Other diseases amenable to treatment include cancer and other proliferative disorders including solid tumors and hematological malignancies. Some such cancers and proliferative disorders show detectable levels of TRPM7 measured at either the protein (e.g., as described in the present examples) or mRNA level. Some such cancers and proliferative disorders show elevated levels of TRPM7 relative to noncancerous tissue of the same type, preferably from the same patient. Optionally, a level of TRPM7 in a cancer is measured before performing treatment. Some examples of cancers treatable by the disclosed compounds include breast cancer, adrenal carcinoma, cervical cancer, osteosarcoma, lung cancer (small cell and nonsmall cell), colon cancer, f cancer, retinoblastoma, head and neck cancers, gastric cancer, melanoma, ovarian cancer, endometrial cancer, prostate cancer, pancreatic cancer, esophageal cancer, hepatocellular carcinoma (liver cancer), mesothelioma, sarcomas, and brain tumors (e.g., gliomas, such as glioblastomas), leukemia and lymphoma. Other disease amenable to treatment include autoimmune disorders and under undesired immune response, arrhythmia, depressive disorders, stress disorders, bone formation (using activators of TRPM7). Evidence supporting a role of TRPM7 in various types of cancer is provided by Guilbert, Am. J. Cell. Phys. 257, C943-501 (2009 (breast cancer); Hanaro. J. Pharmacol. Sci. 95, 403-419 (2004) (retinoblastoma); Jian, Cancer Cell. Res. 67, 10929-10938 (2007) (head and neck cancer); Kim, Cancer Sci. 99, 2502-2509 (2008) (gastric cancer); McNeil, J. Invest. Derm. 127, 2020-2030 200) (melanoma); Sahni, Cell Metabolism 8, 84-93 (2008) (blood cancers). TRPM7 has also been implicated in hypertension (Trouyz, Am. J. Physiol. Heart Circ. Physiol. 294: H1103-H1118 (2008)), myocardial fibrosis and heart failure.

As used herein, the term "disease" includes pain. Thus, the agents described herein, e.g., TRPM7 modulators, can be used in treatment or prophylaxis of pain.

In its broadest usage, "pain" refers to an experiential phenomenon that is highly subjective to the individual experiencing it, and is influenced by the individual's mental state, including environment and cultural background. "Physical" pain can usually be linked to a stimulus perceivable to a third party that is causative of actual or potential tissue damage. In this sense, pain can be regarded as a "sensory and emotional experience associated with actual or potential tissue damage, or described in terms of such damage," according to the International Association for the Study of Pain (IASP). However, some instances of pain have no perceivable cause. For example, psychogenic pain, including exacerbation of a pre-existing physical pain by psychogenic factors or syndromes of a sometimes-persistent, perceived pain in persons with psychological disorders without any evidence of a perceivable cause of pain.

Pain includes nociceptive pain, neuropathic/neurogenic pain, breakthrough pain, allodynia, hyperalgesia, hyperesthesia, dysesthesia, paresthesia, hyperpathia, phantom limb pain, psychogenic pain, anesthesia dolorosa, neuralgia, neuritis. Other categorizations include malignant pain, anginal pain, and/or idiopathic pain, complex regional pain syndrome I, complex regional pain syndrome II. Types and symptoms of pain need not be mutually exclusive. These terms are intended as defined by the IASP.

Nociceptive pain is initiated by specialized sensory nociceptors in the peripheral nerves in response to noxious stimuli, encoding noxious stimuli into action potentials. Nociceptors, generally on A-δ and C fibers, are free nerve endings that terminate just below the skin, in tendons, joints, and in body organs. The dorsal root ganglion (DRG) neurons provide a site of communication between the periphery and the spinal cord. The signal is processed through the spinal cord to the brainstem and thalamic sites and finally to the cerebral cortex, where it usually (but not always) elicits a sensation of pain. Nociceptive pain can result from a wide variety of a chemical, thermal, biological (e.g., inflammatory) or mechanical events that have the potential to irritate or damage body tissue, which are generally above a certain minimal threshold of intensity required to cause nociceptive activity in nociceptors.

Neuropathic pain is generally the result of abnormal functioning in the peripheral or central nervous system, giving rise to peripheral or central neuropathic pain, respectively. Neuropathic pain is defined by the International Association for the Study of Pain as pain initiated or caused by a primary lesion or dysfunction in the nervous system. Neuropathic pain often involves actual damage to the nervous system, especially in chronic cases. Inflammatory nociceptive pain is generally a result of tissue damage and the resulting inflammatory process. Neuropathic pain can persist well after (e.g., months or years) beyond the apparent healing of any observable damage to tissues.

In cases of neuropathic pain, sensory processing from an affected region can become abnormal and innocuous stimuli (e.g., thermal, touch/pressure) that would normally not cause pain may do so (i.e., allodynia) or noxious stimuli may elicit exaggerated perceptions of pain (i.e., hyperalgesia) in response to a normally painful stimulus. In addition, sensations similar to electric tingling or shocks or "pins and needles" (i.e., paresthesias) and/or sensations having unpleasant qualities (i.e., dysesthesias) may be elicited by normal stimuli. Breakthrough pain is an aggravation of pre-existing chronic pain. Hyperpathia is a painful syndrome resulting from an abnormally painful reaction to a stimulus. The stimulus in most of the cases is repetitive with an increased pain threshold, which can be regarded as the least experience of pain which a patient can recognize as pain.

Examples of neuropathic pain include tactile allodynia (e.g., induced after nerve injury) neuralgia (e.g., post herpetic (or post-shingles) neuralgia, trigeminal neuralgia), reflex sympathetic dystrophy/causalgia (nerve trauma), components of cancer pain (e.g., pain due to the cancer itself or associated conditions such as inflammation, or due to treatment such as chemotherapy, surgery or radiotherapy), phantom limb pain, entrapment neuropathy (e.g., carpal tunnel syndrome), and neuropathies such as peripheral neuropathy (e.g., due to diabetes, HIV, chronic alcohol use, exposure to other toxins (including many chemotherapies), vitamin deficiencies, and a large variety of other medical conditions). Neuropathic pain includes pain induced by expression of pathological operation of the nervous system following nerve injury due to various causes, for example, surgical operation, wound, shingles, diabetic neuropathy, amputation of legs or arms, cancer, and the like. Medical conditions associated with neuropathic pain include traumatic nerve injury, stroke, multiple sclerosis, syringomyelia, spinal cord injury, and cancer.

A pain-causing stimulus often evokes an inflammatory response which itself can contribute to an experience of pain. In some conditions pain appears to be caused by a complex mixture of nociceptive and neuropathic factors. For example, chronic pain often comprises inflammatory nociceptive pain or neuropathic pain, or a mixture of both. An initial nervous system dysfunction or injury may trigger the neural release of inflammatory mediators and subsequent neuropathic inflammation. For example, migraine headaches can represent a mixture of neuropathic and nociceptive pain. Also, myofascial pain is probably secondary to nociceptive input from the muscles, but the abnormal muscle activity may be the result of neuropathic conditions.

The agents discussed herein can alleviate or prevent at least one symptom of pain. Symptoms of pain experienced by a patient may or may not be accompanied by signs of pain discernable to a clinician. Conversely, pain can be manifested by clinical signs without the patient being aware of symptoms.

Symptoms of pain can include a response to pain, e.g., in the form of a behavioral change. Exemplary responses to pain can include conscious avoidance of a painful stimulus, a protective response intended to protect the body or body parts from the painful stimulus, responses intended to minimize pain and promote healing, communication of pain, and physiological responses. Communicative responses can involve vocalizations of pain or modifications of facial expression or posture. Physiological responses are include responses mediated by the autonomic nervous system or endocrine system. e.g., enhanced release of adrenalin and noradrenalin, increased output of glucagon and/or hormones and/or corticosteroids. Physiological changes that can be monitored include locomotor effects such as twitching, convulsions, paralysis, dilated pupils, shivering, hyperesthesia and/or altered reflexes. Physiological cardiovascular responses to pain can include changes in blood pressure, alterations in pulse rate and quality, decreased peripheral circulation, cyanosis and congestion. Increased muscle tension (tone) is also symptomatic of pain. Changes in brain function in response to pain can be monitored by various techniques such as electroencephalography (EEG), frontal electromyography (FEMG) or positron emission tomography (PET).

Another symptom of pain can be referred pain, which is a perception of pain as being localized at a site adjacent to or at a distance from the actual site of the pain-causing stimulus. Often, referred pain arises when a nerve is compressed or damaged at or near its origin. In this circumstance, the sensation of pain is generally felt in the territory that the nerve serves, even though the damage originates elsewhere. A common example occurs in intervertebral disc herniation, in which a nerve root arising from the spinal cord is compressed by adjacent disc material. Although pain may arise from the damaged disc itself, pain is also felt in the region served by the compressed nerve (for example, the thigh, knee, or foot).

Nociceptive activity is a symptom of nociceptive pain. Nociceptive activity, even in the absence of consciously-perceived pain, may trigger withdrawal reflexes and a variety of autonomic responses such as pallor, diaphoresis, bradycardia, hypotension, lightheadedness, nausea and fainting.

One patient class amenable to treatments are patients undergoing a surgical procedure that involves or may involve a blood vessel supplying the brain, or otherwise on the brain or CNS. Some examples are patients undergoing cardiopulmonary bypass, carotid stenting, diagnostic angiography of the brain or coronary arteries of the aortic arch, vascular or endovascular surgical procedures and neurosurgical procedures. Patients with a brain aneurysm are particularly suitable. Such patients can be treated by a variety of surgical procedures including clipping the aneurysm to shut off blood, or performing endovascular surgery to block the aneurysm with small coils or introduce a stent into a blood vessel from which an aneurysm emerges, or inserting a microcatheter. Endovascular procedures are less invasive than clipping an aneurysm but the outcome still includes a high incidence of small infarctions.

The agents of the invention can be formulated and administered in the form of a pharmaceutical composition. An agent included in such a composition is typically substantially pure of contaminants (i.e., contaminants resulting from production of an agent including synthesis and/or purification). For example, an agent can be at least 75, 90, 95 or 99% w/w free of such contaminants. However, substantial freedom from contaminants does not preclude the agent being formulated with one or more pharmaceutically acceptable carriers, diluents as further described below.

Pharmaceutical compositions are manufactured under GMP conditions. Pharmaceutical compositions can be provided in unit dosage form (i.e., the dosage for a single administration). For example, a pill, capsule or the like can provide a single oral dose and a vial can provide a single dose for parenteral administration. Pharmaceutical compositions can be manufactured by means of conventional mixing, dissolving, granulating, dragee-making, levigating, emulsifying, encapsulating, entrapping or lyophilizing processes.

Pharmaceutical compositions can be formulated in conventional manner using one or more pharmaceutically acceptable carriers (including diluents, excipients or other auxiliaries) that facilitate processing, storage or administration of agents. Proper formulation is dependent on the route of administration chosen.

Administration can be parenteral, intravenous, oral, subcutaneous, intraarterial, intracranial, intrathecal, intraperitoneal, topical, intranasal or intramuscular.

Pharmaceutical compositions for parenteral administration are preferably sterile and substantially isotonic. For injection, agents can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents.

Alternatively agents can be in powder form for constitution with a suitable vehicle, e.g., sterile pyrogen-free water, before use.

For transmucosal administration, penetrants appropriate to the barrier to be permeated are used in the formulation. This route of administration can be used to deliver the compounds to the nasal cavity or for sublingual administration.

For oral administration, agents can be formulated with pharmaceutically acceptable carriers as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents can be added, such as the cross-linked polyvinylpyrrolidone, agar, or alginic acid or a salt thereof such as sodium alginate. If desired, solid dosage forms can be sugar-coated or enteric-coated using standard techniques. For oral liquid preparations such as, for example, suspensions, elixirs and solutions, suitable carriers, excipients or diluents include water, glycols, oils, alcohols. Additionally, flavoring agents, preservatives, coloring agents and the like can be added.

In addition to the formulations described previously, the agents can also be formulated as a depot preparation. Such long acting formulations can be administered by implantation (for example subcutaneously or intramuscularly) or by intramuscular injection. Thus, for example, the agents can be formulated with suitable polymeric or hydrophobic materials (for example as an emulsion in an acceptable oil) or ion exchange resins, or as sparingly soluble derivatives, for example, as a sparingly soluble salt.

Alternatively other pharmaceutical delivery systems can be employed. Liposomes and emulsions can be used to deliver agents. Certain organic solvents such as dimethylsulfoxide also can be employed, although usually at the cost of greater toxicity. Additionally, the compounds can be delivered using a sustained-release system, such as semipermeable matrices of solid polymers containing the therapeutic agent. Sustained-release capsules can, depending on their chemical nature, release the chimeric peptides for a few weeks up to over 100 days. Depending on the chemical nature and the biological stability of the therapeutic reagent, additional strategies for protein stabilization can be employed.

Agents can be formulated as free acids or bases or as pharmaceutically acceptable salts (see generally Berg et al., 66 J. PHARM. SCI. 1-19 (1977), and C. G. Wermuth and P. H. Stahl (eds.) "Pharmaceutical Salts: Properties, Selection, and Use" Verlag Helvetica Chimica Acta, 2002 [ISBN 3-906390-26-8]. Pharmaceutically acceptable salts are those salts which substantially retain the biologic activity of the free bases and which are prepared by reaction with inorganic acids. Pharmaceutical salts tend to be more soluble in aqueous and other protic solvents than are the corresponding free base forms. Pharmaceutically acceptable acid salts include hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Suitable base salts include aluminum, calcium, lithium, magnesium, potassium, sodium, zinc, and diethanolamine salts The agents are used in a regime (i.e., dose, frequency, route of administration) effective to achieve the intended purpose (e.g., reduction of damage effect of ischemia). A therapeutically effective regime means a regime that reduces or at least inhibits further deterioration of at least one symptom or sign of disease in a population of patients (or animal models) treated with the agent relative to a control population of patients (or animal models) not treated with the agent. Signs and symptoms of disease include infarctions (in the case of ischemic diseases), delayed neuronal death, and cognitive deficits, e.g., in memory, in ischemic and other neurologic disease, and reduced proliferation, toxicity and/or metastasis for cancer. The regime is also considered therapeutically effective if an individual treated patient achieves an outcome more favorable than the mean outcome in a control population of comparable patients not treated by methods of the invention. In the context of stroke, a regime is also considered therapeutically effective if an individual treated patient shows a disability of two or less on the Rankin scale and 75 or more on the Barthel scale. A regime is also considered therapeutically effective if a population of treated patients shows a significantly improved (i.e., less disability) distribution of scores on a disability scale than a comparable untreated population, see Lees et at 1., N Engl J Med 2006; 354:588-600. A prophylactically effective regime means a regime that delays the onset, reduces the frequency of onset, and/or reduces severity of at least one sign or symptom of disease in a population of patients (or animal models) treated with the agent relative to a control population of patients (or animal models) not treated with the agent. An effective regime refers to a regime that is effective therapeutically, prophylactically or both.

The amount of agent administered depends on the subject being treated, on the subject's weight, the severity of the affliction, the manner of administration and the judgment of the prescribing physician. The therapy can be repeated intermittently while symptoms detectable or even when they are not detectable. The therapy can be provided alone or in combination with other drugs.

Therapeutically effective dose of the present agents can provide therapeutic benefit without causing substantial toxicity. Toxicity of the chimeric peptides can be determined by standard pharmaceutical procedures in cell cultures or experimental animals, e.g., by determining the LD50 (the dose lethal to 50% of the population) or the LD100 (the dose lethal to 100% of the population). The dose ratio between toxic and therapeutic effect is the therapeutic index. Chimeric peptides or peptidomimetics exhibiting high therapeutic indices are preferred (see, e.g., Fingl et al., 1975, In: The Pharmacological Basis of Therapeutics, Ch. 1, p. 1).

EXAMPLES

Example 1

Assay for Screening for a Bioactive Agent that Modulates TRPM7 Activity

Introduction

An assay for screening for a bioactive agent that modulates TRPM7 activity can be created in which TRPM7 activity is evoked in cells, and then a bioactive agent that inhibits TRPM7 activity is tested to determine whether or not it prevents cell death in the assay. The cell may be expressing native (wild-type) TRPM7, or a recombinant TRPM7 which is transfected into the cell. In the present example, human embryonic kidney (HEK293 Trex) cells were stably transfected with a tetracycline inducible Flag-tagged TRPM7 construct.

Figure 17:
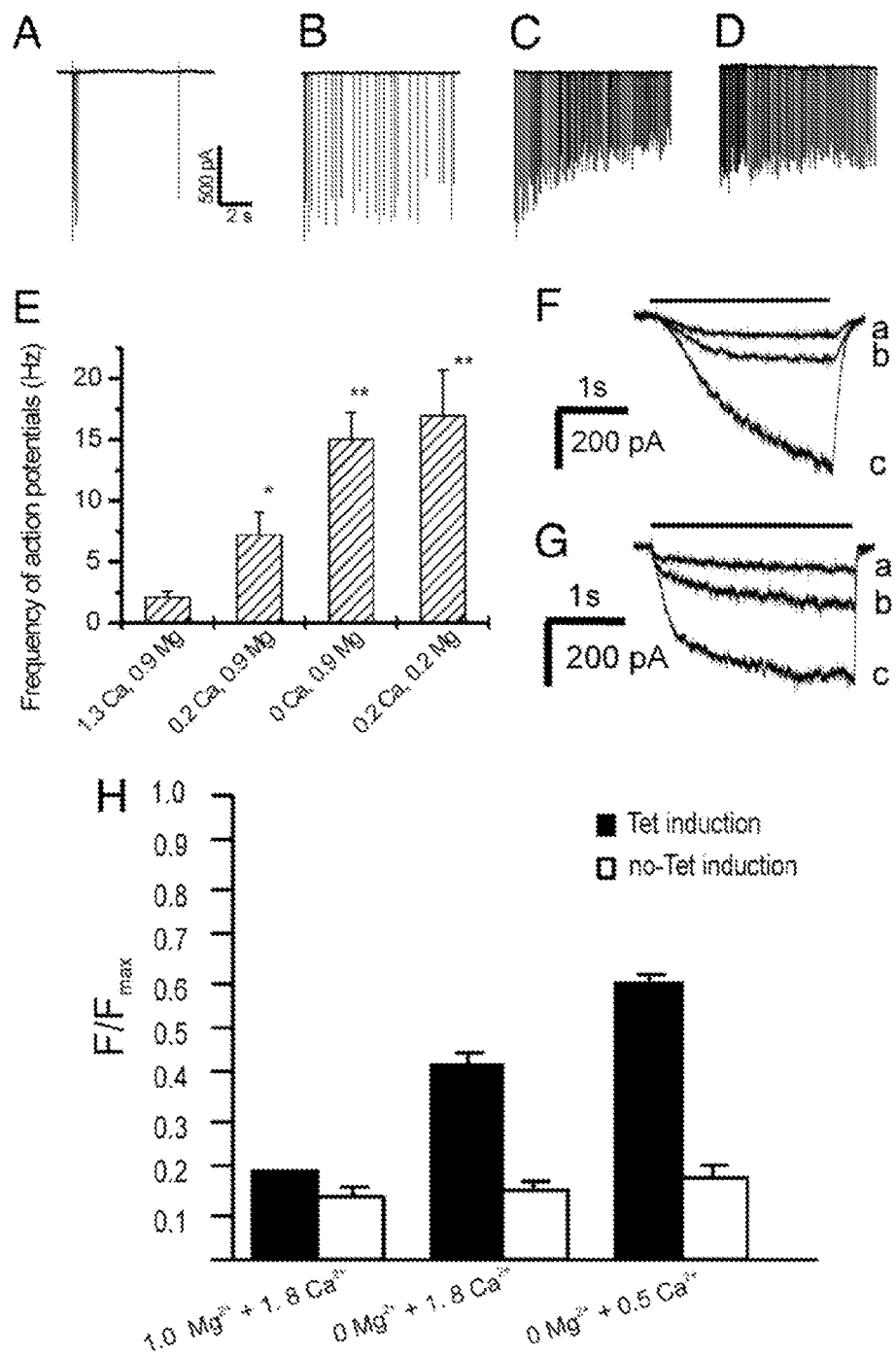
FIG. 17: Cultured hippocampal neurons demonstrate graded responses to reductions in extracellular divalents. (A-D) Graded increases in action potential firing frequency are detected when sequentially applying solutions containing 1.3 mM Ca2+ and 0.9 mM Mg2+ (standard solution) (A), 0.2 mM Ca2+ and 0.9 mMMg2+ (low Ca2+) (B), 0 mMCa2+ and 0.9 mMMg2+ (Ca2+-free) (C), or 0.2 mM Ca2+ and 0.2 mM Mg2+ (low divalent) (D). (E) For each of these conditions, the change in action potential firing frequency is plotted for a series of six cells and shows the graded excitation. *, P<0.05; **, P<0.01. (F and G) Whole-cell patch-clamp recordings of currents generated at 60 mVin a cultured (F) and isolated (G) neuron in response to a change to low Ca2+ (a), low divalent (b), low Ca2+, noMg2+ (c). (H) In HEK293 cells expressing TRPM7 (Tet induction), a graded increase in cell death is observed when extracellular divalents are progressively reduced. No similar increase is detected in HEK293 cells that do not express TRPM7 (no-Tet induction). Increased cell death is indicated by an increase in the fluorescent ratio F/Fmax, which represents the estimated fraction of total HEK293 cells that took up propidium iodide.

To activate TRPM7 channels, TRPM7 ion channel activity may be increased by lowering extracellular divalent cation concentrations, especially Ca2+ and Mg2+ (Wei et al., 2007). This causes a marked increase in the ionic current carried by TRPM7 channels (FIG. 17 A-G). Tet-induced TRPM7-expressing HEK293 cells that are exposed to a reduction in divalent undergo spontaneous TRPM7-activity-mediated cell death over a 24-48 hour period (FIG. 17H). This cell death can be measured, and the impact of a candidate TRPM7 modulator on this cell death can be measured. Exemplary assays that can be used for measuring cell death induced by TRPM7 activity include an assay for measuring lactate dehydrogenase (LDH), which is released from dying cells and an assay for measuring ATP in living cells, such as the CellTiter Glo kit® from Promega. Cell death can also be measured by fluorescent measurements of propidium iodide and dihydrorhodamine.

An exemplary screen for a Bioactive Agent that Modulates TRPM7 Activity is as follows.

Materials and Methods

Drugs, Solutions and Media

Tet-inducible Flag-murine TRPM7/pcDNA4-TO HEK293 Trex cells are cultured in: MEM (Invitrogen) supplemented with 10% fetal bovine serum, 20 mM GlutaMAX-1, 100 units/ml penicillin G sodium, 100 units/ml streptomycin sulfate, 0.25 ug/ml amphotericin B, 5 ug/ml blasticidin, 0.4 mg/ml zeocin. (All reagent were obtained from Invitrogen)

Screening experiments are conducted in Hank's Balanced Salt Solution (HBSS), containing (in mM): 121 NaCl, 5 KCl, 20 D-glucose, 10 HEPES acid, 10 HEPES-Na+, 1.8 CaCl2, 1 Na-pyruvate, 1MgCl2 (all from Sigma)

Mg2+-deficient HBSS used to activate TRPM7 contains: (in mM): 121 NaCl, 5 KCl, 20 D-glucose, 10 HEPES acid, 10 HEPES-Na, 1.8 CaCl2, 1 Na-pyruvate (all from Sigma)

Stably Transfected Flag-Tagged TPM7 HEK 293 Trex Cells

A HEK-293 cell line with a tetracycline-controlled expression of a Flag-tagged TRPM7 construct is used in the current example (Flag-murine TRPM7/pcDNA4-TO; (Aarts et al., 2003)).

Cell Cultures

Stably transfected Flag-murine TRPM7/pcDNA4-TO HEK293 Trex cells are thawed from frozen stock kept in liquid nitrogen, and cultured in culture medium for 5 days in 100 mm dishes (Costa). After the 5th day, they are trypsinized with 0.05% Trypsin (Invitrogen) for 5 min and then split into two 100 mm dishes, cultured for another 4-5 days, then trypsinized again as above and seeded into multi 96-well plates at $4-5 \times 10^4$/well/100 ul, or 384-well plate at $1.3-1.5 \times 10^4$ Cells/well/40 ul. Cells used in the present experiments are kept to three passages or less. The cells are maintained at 37° C. with 5% CO2 in a humidified incubator. All culture plates and multi-well plates (Costa) are coated with poly-D-lysine. The coating with poly-D-lysine is performed using 0.1 mg/ml poly-D-lysine (P1045 Sigma) for 12 h at 37C, followed by four washes with sterilized D-PBS (Invitrogen) without MgCl2 and CaCl2.).

Tetracycline Induction

When 384 well plates are used, Cells are seeded at $1.3-1.5 \times 10^4$ cells/well. When 96 well plates are used, cells are seeded at $4-5 \times 10^4$ Cells/well. After 24 h TRPM7 expression is induced by adding tetracycline (Tet; 1 ug/ml) (Invitrogen) for 24 h, followed by wash with Mg deficient HBSS.

Test Compounds

Test compounds for the current experiments were obtained from 3 sources:

LOPAC1280™, a library of 1280 pharmacologically-active compounds (Sigma, Prod. No. L01280)

The Prestwick Chemical Library® (Prestwick Chemical) contains 1120 small molecules, 90% being marketed drugs and 10% bioactive alkaloids or related substances. The active compounds were selected for their high chemical and pharmacological diversity as well as for their known bioavailability and safety in humans.

The Maybridge Screening collection, consisting of 53,000 organic compounds with drug-like properties that generally obey Lipinski's "rule of five" (Lipinski et al., 2001) and so demonstrate good ADME (absorption, distribution, metabolism and excretion) profiles.

The test compounds were plated in 96 or 384 well formats, and initially used at a concentration of: 4 µM for compounds of the LOPAC library and 5 µM for each of the Prestwick and Maybridge libraries. For the purpose of carrying out dose-response experiments, the compounds were used at concentrations ranging from 39 nM to 20 µM (obtained by performing two-fold serial dilutions 39 nM, 78 nM, 156 nM, 315 nM, 625 nM, 1.25 µM, 2.5 µM, 5 µM, 10 µM, 20 µM).

Calculation of Cell Death.

Cell death in the presence or absence of a test compound and/or under conditions of TRPM7 activation was determined by fluorescence measurements of PI (5-50 µg/ml).

In one approach, the "B score" method of Brideau et al (Brideau et al., 2003) was used to select hits from data generated by high-throughput screening (HTS) techniques. In brief, B scores are a relative potency score based on the raw sample PI fluorescence value. They are the ratio of an adjusted raw PI fluorescence value in the numerator to a measure of variability in the denominator. Details are provided by Brideau et al. (Supra).

In another approach, used manually to validate the results of the HTS method, a multiwell plate fluorescence scanner (Fluorskan Ascent; Thermo Scientific) was used. The fraction of dead cells in each culture was calculated as: fraction DEAD=(Ft−Fo)/Fmax Where Ft=PI fluorescence of the sample at time t, Fo=initial PI fluorescence and Fmax=background subtracted PI fluorescence the same cultures after exposure to 100 µM triton-X. An alternative to this formula is a Control-based formula wherein the fraction dead=$[Ft-F(-)t]/[F(+)t-F(-)_t]$ where Ft=PI fluorescence of the sample at time t, F(−)t is the PI fluorescence of the negative control sample at time t, F(+)t is the PI fluorescence of the positive control sample at time t.

Derivation of the Screening Assay Conditions

Derivation of Incubation Conditions:

Modifications of divalent cation concentrations in the HBSS described above were used to test the effect of varying divalent cations on TRPM7 ion channel activity and on TRPM7-mediated cell death.

Initially electrophysiological recordings were carried in cultured hippocampal neurons out as described in Wei et al. (2007). Direct measurements of a TRPM7-like current are made while neurons were exposed to solutions containing varying concentrations of Ca2+ and Mg2+ (FIG. 17A-G). This confirmed that conditions favoring low divalent, especially magnesium, enhance these currents.

Next, the impact of varying the extracellular concentrations of Ca2+ and Mg2+ was measured on the death of stably transfected Flag-murine TRPM7/pcDNA4-TO HEK293 Trex cells. Cells that have undergone Tet induction are compared with those that have not been induced with Tet to express recombinant TRPM7. As shown in the representative experiments of FIG. 17H, FIG. 18, FIG. 19, and FIG. 20, ionic conditions in which the HBSS contains reduced or absent Mg2+ consistently exhibited more cell death at the various time points examined as compared with cells that remain in 1 mM Mg2+.

Moreover, the impact of a CO2 is also tested. The death of Tet-induced cells was compared after placing them in either 0% CO2 or 5% CO2. Tet-induced Flag-murine TRPM7/pcDNA4-TO HEK293 Trex cells exhibit more cell death in 0% CO2 than when they are kept in a 5% CO2 environment (FIG. 18). Notably, there were no differences in cell death between cells kept in 0% vs 5% CO2 in the presence of MgCl2.

Figure 19:
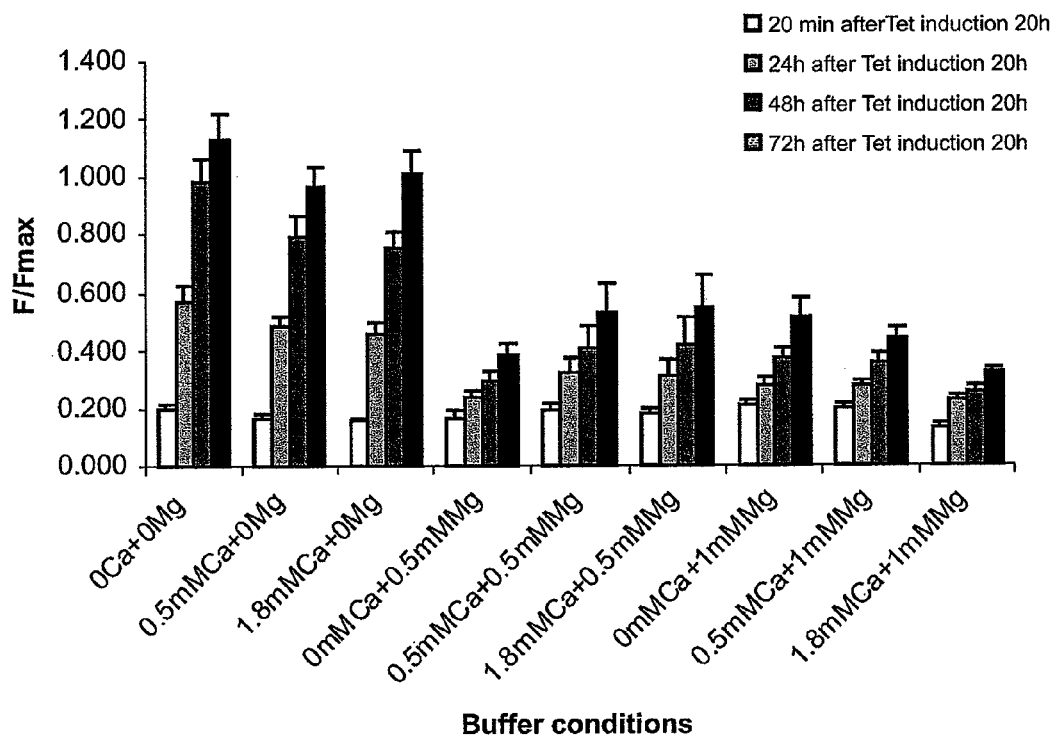
FIG. 19: Effect of Tet Induction and the indicated different buffer conditions on cell death as measured by propidium iodide (PI) fluorescence in TRPM7-expressing HEK293 cells at the indicated times in an assay performed in a 96 well plate format.
Figure 20:
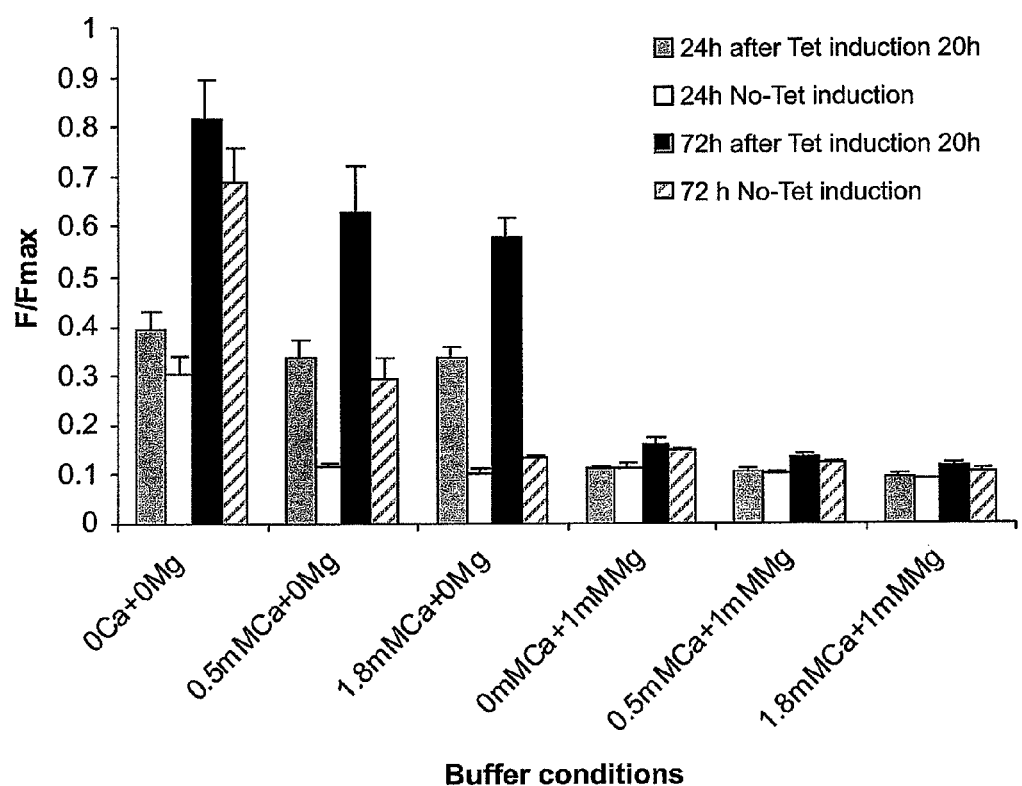
FIG. 20: Effect of Tet Induction and the indicated different buffer conditions on cell death as measured by propidium iodide (PI) fluorescence in TRPM7-expressing HEK293 cells at the indicated times in an assay performed in a 384 well plate format.

The optimal time-point for cell death determination is also examined in the 96 well and 384 well format. Tet-induced Flag-murine TRPM7/pcDNA4-TO HEK293 Trex cells exposed to MG2+-deficient HBSS for 48 hours exhibited significant amounts of cell death, whereas other controls remain viable. At 72 hours, Tet-induced Flag-murine TRPM7/pcDNA4-TO HEK293 Trex cells also exhibited large amounts of cell death, but controls also begin to demonstrate cell death. Thus cell death determination under the present conditions is best performed within 24-48 hours (FIGS. 19-20).

Screening of Compound Libraries

Screening was carried out in Tet-induced Flag-murine TRPM7/pcDNA4-TO HEK293 Trex cells. Tet-induction was omitted in certain controls. In some experiments, the test compounds were added to the cells simultaneously with Tet induction. In other experiments, the compounds were added 20-24 h after Tet induction. After a further 24 hours, cells with or without 1 ug/ml tetracycline induction, were washed 6 times using an EMBLA washer (Molecular Devices) with Mg2+-deficient HBSS. The test compounds were loaded into the 96 well or 384 well plates containing the cells using a Multimek™ 96/384 channel automated pipettor (Beckman) at the same time as Tet induction or 24 h after Tet induction as described above. Thereafter, the cells were incubated in Mg2+-containing, or Mg2+-deficient HBSS in order to activate TRPM7 channels. The HBSS also contains 10 ug/ml of propidium iodide (PI; Molecular Probes Inc), a fluorescent cell viability indicator. The cells remain at 37° C. in a 0-0.3% (ambient) CO2 atmosphere throughout the experiment. PI fluorescence readings were taken at t=20 min, 24 hours and 48 hours. PI fluorescence (F) was measured using a PHERAstar reader (BMG labtech) at λ excitation=530 nm, λ emission=620 nm. The following controls were used throughout against which the effect of a candidate compound on cell death can be determined: Negative control was the Tet-induced TRPM7-HEK cells in HBSS buffer. Positive control was the Tet-induced TRPM7-HEK cells in Mg-deficient HBSS buffer.

Results

Screening of the LOPAC and Prestwick Compound Libraries.

The LOPAC and Prestwick compound libraries were screened using test compounds at an initial concentration of 4 µM and 5 µM, respectively. Hits were determined using the B-score method (Table 2), and then manually replicated, including testing at a range of concentrations for the purpose of establishing dose-response relationships (Table 3). Among the compounds that were found to inhibit TRPM7-mediated cell injury were alpha 1 adrenoreceptor antagonists (Benoxathian hydrochloride, Naftopidil dihydrochloride), CDK1/cyclinB inhibitors (L-703,606 oxalate, CGP-74514A hydrochloride), modulators of the Na/K ATPase (Digoxin, Sanguinarine chloride), anthracycline antineoplastic agents/topoisomerase II inhibitors (Mitoxantrone, Daunorubicin hydrochloride, Doxorubicin hydrochloride) and other antineoplastic DNA intercalating agents (chelidamic acid, Quinacrine dihydrochloride), protein phosphatase inhibitors (Cantharidin—inhibits protein phosphatases 1 and 2A), inhibitors of protein synthesis (Puromycin dihydrochloride, anisomycine, Cephaleine), inhibitors of microtubule polymerization (colchicine), calcium channel blockers (Nicardipine), Agents that inhibit mitochondrial function (Ciclopirox ethanolamine, Betulinic acid), cation chelators (lasalocid, cicloprox), phosphodiesterase inhibitors (Ethaverine hydrochloride, Trequinsin hydrochloride), Phospholipase A2 inhibitor (Quinacrine), and natural alkaloids (Piperlongumine).

The impact of certain of the candidate compounds on the expression of FLAG-TRPM7 in the recombinant HEK293 cells was evaluated by Western blots (FIG. 21). The data suggested that incubating the tested compounds with the cells from the time of Tet induction does not adversely impact the cells' capacity to express recombinant TRPM7.

Screening of the Maybridge Library.

The Maybridge Screening collection, consisting of 53,000 organic compounds with drug-like properties. These are screened in 384 well plates using the HTS approach described above.

The "B-Score" method was used to define hits in the initial screen, which was performed using 5 µM concentrations of compound. Results of the 53,000 test compounds are graphically illustrated in FIG. 22.

Hits that exhibit cytotoxicity are excluded from further analysis. Thereafter, all hits having a "B-score" greater than 2 standard deviations from the mean B score were compiled. This provided 440 hits, which were then re-tested in triplicate. The re-test was considered positive if the test compound reduced cell death on at least 2 of three times. Using this approach, 339 candidate compounds were identified as potential inhibitors of TRPM7-mediated cell injury. The candidates were then classified as compounds having demonstrated >90%, >80%, >70%, >60%, >50%, >40% and >30% inhibition of TRPM7-mediated cell death. These are listed in Table 2 and the top 30 are shown in FIGS. 11-16.

Examination of the 339 candidate compounds revealed that a significant proportion of those having the best ability to inhibit TRPM7-mediated cell death (>=70% inhibition) belong to a few generic core structural groups (e.g., Formulae I-XIX).

Example 2

TRPM7 and Anoxic Cell Death in H9c2 Cardiac Myocites

Introduction

As a model of cardiac ischemia and reperfusion, a rat ventricular myoblast cell line H9c2 is used (Kimes and Brandt, 1976). H9c2 cells are morphologically similar to embryonic cardiocytes and possess several characteristics of the electrical and hormonal signal pathways found in adult cardiac cells (Hescheler et al., 1991). This cell line has previously been used in cardiac research (Levrand et al., 2006; Zordoky and El-Kadi, 2007), and more importantly, in culture models of myocyte ischemia and reperfusion (Sakamoto et al., 1998; Ekhterae et al., 1999; Bonavita et al., 2003; Fiorillo et al., 2006; Coaxum et al., 2007).

Materials and Methods

Cell Culture

The rat cardiomyoblast cell line H9c2 was obtained from the American Type Culture Collection (CRL-1446) and cultured in Dulbecco's Modified Eagle Medium supplemented with 10% (v/v) heat-inactivated fetal bovine serum and 1% antibiotic-antimycotic. Cells were grown in an atmosphere of 95% $O_2$/5% $CO_2$ in a humidified incubator.

RNA Preparation and RT-PCR

Total RNA was isolated from rat tissues and H9c2 cells using TRIzol reagent (Invitrogen, Burlington, ON, Canada) according to the manufacturer's protocol. One µg of isolated RNA is reverse-transcribed using the High Capacity cDNA Archive Kit (Applied Biosystems, Streetsville, ON, Canada) and PCR is carried out using REDTaq DNA polymerase (Sigma, Oakville, ON, Canada) and the following rat TRPM7-specific primers:

```
Forward:    5'-AGGAGAATGTCCCAGAAATCC-3'
Reverse:    5'-TCCTCCAGTTAAAATCCAAGC-3'
```

The PCR reactions were cycled for 5 mins at 94° C., followed by 30 cycles of 94° C. for 1 min, 57° C. for 30 sec, 72° C. for 45 sec, and 72° C. for 10 mins. PCR products were separated on a 1% agarose gel stained with ethidium bromide and visualized under UV light.

Oxygen Glucose Deprivation (OGD)

H9c2 cells were made anoxic by replacing the medium with de-oxygenated Ischemic buffer (in mM: 1.13 $CaCl_2$, 5 KCl, 0.3 $KH_2PO_4$, 0.5 $MgCl_2$, 0.4 $MgSO_4$, 128 NaCl, 10 HEPES) and by transferring them to an anaerobic chamber (5% $CO_2$, 10% $H_2$, 85% $N_2$) for 6 hrs or 16 hrs at 37° C. OGD was terminated by washing the cells with oxygenated glucose-containing Control buffer (in mM: 1.13 $CaCl_2$, 5 KCl, 0.3 $KH_2PO_4$, 0.5 $MgCl_2$, 0.4 $MgSO_4$, 128 NaCl, 10 HEPES 10 Glucose). Cultures were maintained for another 2 hrs at 37° C. in a humidified 5% $CO_2$ atmosphere. Normoxic cells were maintained in Control buffer for the duration of the experiment.

Propidium Iodide Uptake

Cell death was determined by fluorescence measurements of PI (5 µg/ml) using a multiwell plate fluorescence scanner. The fraction of dead cells in each culture was calculated as: fraction dead=$(F_t-F_0)/F_{max}$ where $F_t$=PI fluorescence at 2 hrs post-OGD, $F_0$=initial PI fluorescence immediately after the OGD treatment, and $F_{max}$=PI fluorescence of the same cultures following 20 mins incubation in 1% TritonX-100.

Results

RT-PCR analysis revealed that TRPM7 mRNA is detectable in most tissues examined in mouse and rat, including mouse and rat hearts. TRPM7 mRNA was also detectable in H9c2 cells (FIG. 23). Moreover, TRPM7 protein was detectable in the H9c2 cells by immunochemistry (FIG. 24), indicating that this myocardial cell line is appropriate for studying TRPM7-mediated anoxic damage in myocardial cells.

Figure 25:
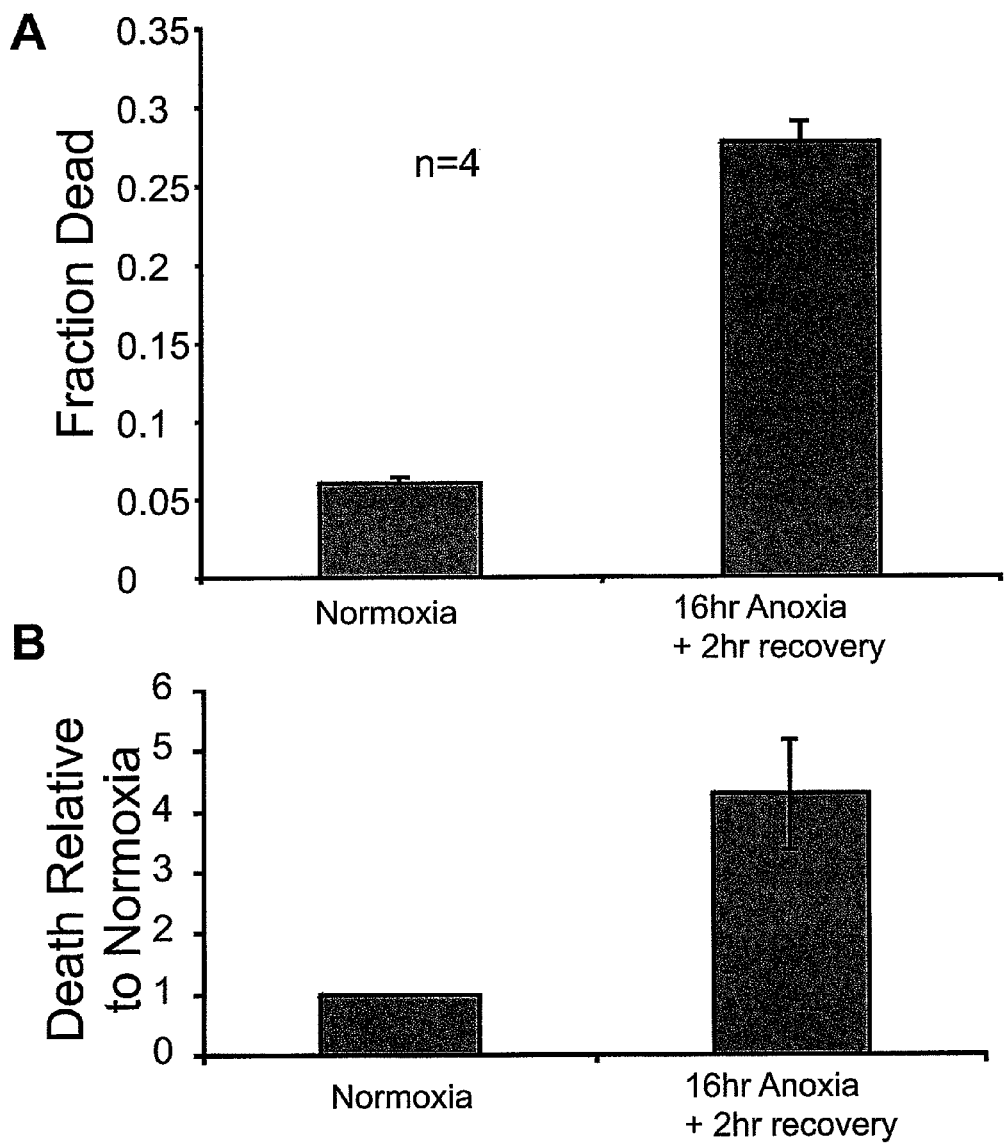
FIG. 25: Anoxic cell death in H9c2 cells. Exposure of H9c2 cells to 16 hr anoxia (5% CO2, 10% H2, 85% N2) and 2 hr recovery resulted in an approximately 4-fold increase in cell death as measured by PI uptake. Normoxic cultures were maintained at 37 degrees C. in a humidified 5% CO2 atmosphere. Results are presented as mean+/−SEM from four experiments. Data are analyzed as the fraction of dead cell (A), or as the amount of death relative to controls (B).
Figure 26:
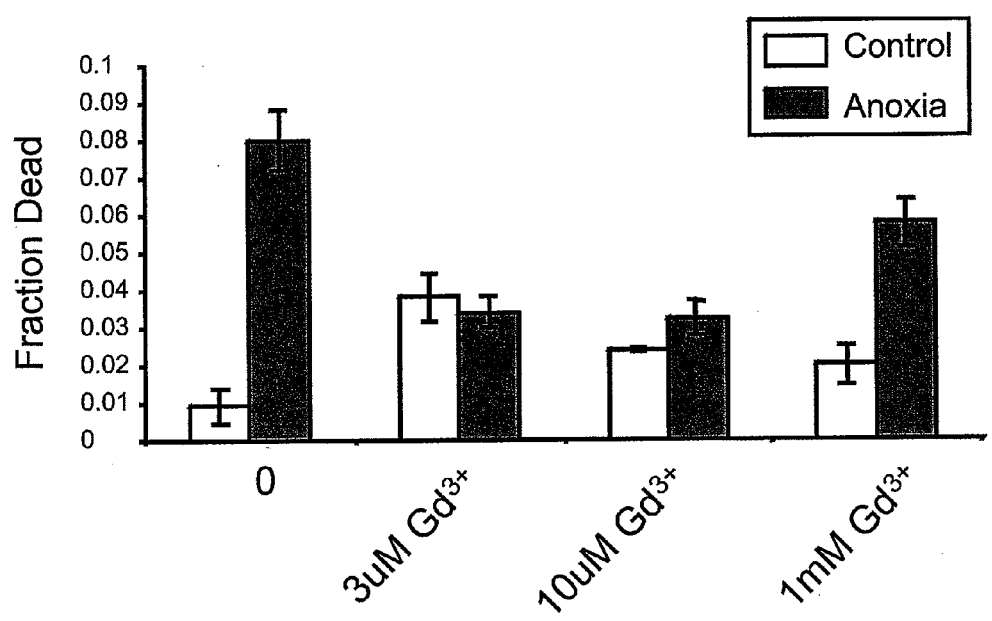
FIG. 26: Inhibition of anoxic (6 hr anoxia+2 hr recovery) cell death in H9c2 cells following exposure to the indicated quantity of gadolinium in HBSS buffer.

Exposing the H9c2 cells to OGD results in increased death of the cells (FIG. 25). OGD-mediated cell death was reduced by exposing cells to gadolinium (FIG. 26), a procedure that reduced TRPM7-mediated anoxic cell death (Aarts et al., 2003).

Conclusions

The findings show that TRPM7 is present in H9c2 cells, that these cells are vulnerable to cell death induced by OGD, and that this can be reduced by procedures that inhibit TRPM7. The data implicate TRPM7 as a factor in ischemic death of cardio myocites.

Example 3

An assay for detecting TRPM7-mediated Cellular Ion Flux and Cell Death mediated by Chemical Anoxia with NaCN.

Introduction

The TRPM7 channel provides a pathway for mono- and divalent cations into the cell, and is unique in that it contains a functional C-terminal α-kinase domain. Among the procedures known to activate TRPM7 channels, the TRPM7 channel has been shown to be activated by chemical anoxia using NaCN (Aarts et al., 2003). The induction of chemical anoxia in host cells such as recombinant HEK293 cells can be used to activate TRPM7. This activation is detectable with the use measurements of cellular calcium accumulation. This is achievable with the use of a fluorescent calcium indicator. Alternatively, this activation can also be measured using radiolabelled Ca2+ ($^{45}Ca^{2+}$) as described previously by Sattler et al. (Sattler et al., 1998) and Aarts et al. (Aarts et al., 2003).

Methods

Design of Specific TRPM7 Constructs

Flag-TRPM7/pBluescript II KS Construct

The TRPM7 construct was a Flag-TRPM7/pBluescript II KS construct (FIG. 27). The Flag-TRPM7 cDNA is comprised of the murine TRPM7 sequence (GenBank accession no. AY032591)) conjugated to a Flag epitope tag at its N-terminus, and was subcloned into the pBluescript vector from a Flag-TRPM7/pcDNA4/TO construct (Aarts et al., 2003). Restriction enzyme digest with EcoRI determined the direction of insert in the pBluescript vector. FIG. 27 illustrates that the banding pattern observed corresponded to a 3'→5' direction of insert (in bps): 3838, 3200, and 1592.

pTracer-CMV2 Constructs

For expression in a mammalian cell line, the TRPM7 sequence was subcloned into a modified pTracer-CMV2 vector (Promega, Madison Wis.) (FIG. 28). This vector had been modified such that the GFP cDNA of the original was replaced by enhanced GFP (eGFP) cDNA. The Flag-TRPM7/pTracer-CMV2 construct was generated by ligating the 5745 bp fragment of a SpeI/KpnI digest of Flag-TRPM7/pBluescript with the 6140 bp fragment of a KpnI/XbaI digest of pTracer, ensuring that the Flag tag is preserved through the subcloning and that the TRPM7 sequence is inserted into the pTracer vector in the correct orientation (5'→3') for expression. Selected transformants were screened by restriction enzyme digest with EcoRI, then with EcoRV, PmeI, and BamHI.

An additional pTracer construct was designed for use in calcium imaging experiments (FIG. 28). This construct does not contain the eGFP cDNA, as its excitation/emission spectrum (λexcitation=488 nm, λemission=509 nm) overlaps with that of the calcium dye used (fluo-3; λexcitation=506 nm, λemission=526 nm). The eGFP(−) construct was generated by digesting the Flag-TRPM7/pTracer or Flag-ΔPDZ/pTracer constructs with NgoMIV to excise the eGFP gene and a portion of the preceding EF-1a promoter, and religating the larger 10060 bp fragment. The ligated product was used to transform Subcloning Efficiency™ DH5α cells (Invitrogen) and selected transformants screened with EcoRI, PmeI, and BamHI.

Cell Culture

HEK-293 tSA (HEK-293T) cells were cultured in Dulbecco's Modified Eagle Medium with L-glutamine and sodium pyruvate (DMEM; Gibco, Burlington, ON), supplemented with 10% fetal bovine serum (FBS; Gibco) and 1% antibiotic-antimycotic (Gibco) on polystyrene cell culture dishes (Sarstedt, Montreal, QC). Cells were maintained in a humidified incubator (Steri-Cycle® CO2 incubator, model 370; Thermo Electron Corp.) set at 37° C. and 5% CO2. Media was replaced routinely in 60 mm and 35 mm dishes with 5 mL and 2 mL respectively. When cells reached 75-90% confluency, as estimated under a light microscope (NIKON Diaphot-TMD; Nikon Canada, Mississauga, ON), they were passaged into new dishes by the following method: media from the confluent dish was aspirated, the dish washed once with phosphate buffered saline (PBS), replaced with trypsin-EDTA (0.05% solution; Gibco) and incubated at 37° C. until cells could be dissociated by gentle shaking. Pre-warmed DMEM (Gibco) was added to the dish, then drawn up and dispensed several times from a pipette (Sarstedt) using a Pipet Aid® (Drummond, Broomall, Pa.) to dissociate any remaining cell clumps. Cells were divided into new dishes at 1:10 to 1:40 dilutions. Cells were used up to 15 passages from the time of thawing.

Determining Cell Count

Cells were dissociated with trypsin-EDTA (Gibco) and resuspended in DMEM. 50 μL of this suspension was mixed with 200 μL of Trypan Blue (Gibco) and 750 μL of PBS to create a 1:20 dilution of cells. Cells were loaded onto a hematocytometer and viewed under a light microscope (NIKON Diaphot-TMD; Nikon Canada). The following formula was used to determine cell count:

Cell count(/mL)=no. of viable cells×dilution×2500

Transient Transfection of Cell Cultures

Transient transfections were performed at 75% confluency, as estimated under a light microscope (NIKON Diaphot-TMD; Nikon Canada), using Lipofectamine 2000 (Invitrogen). Transfections were performed according to the manufacturer's instructions. For a 35 mm cell culture dish, 3 μg of DNA and 7.5 μL of Lipofectamine (a 1:2.5 ratio of DNA to reagent) was diluted in 500 μL OptiMEM® I reduced serum medium (Gibco). Media was replaced no sooner than 16 hours post-transfection.

Determining Transfection Efficiency

Transfection efficiency was quantified for cell cultures transfected with a construct containing the eGFP cDNA. Cells were counterstained with Hoechst (Molecular Probes Inc.) to allow for simultaneous visualization of untransfected cells. Hoechst and eGFP fluorescence were observed using a NIKON Eclipse TE2000 inverted microscope and TE-FM Epi-Fluorescence attachment (Nikon Canada), and images taken for later analysis. Transfection efficiency was determined by the following formula:

Transfection efficiency(%)=no. of eGFP-expressing cells/no. of Hoechst stained cells×100.

Staining with Hoechst and Propidium Iodide

Hoechst 33342 was purchased as a 10 mg/mL solution in water (Molecular Probes Inc., Eugene, Oreg.). Propidium iodide (PI) was purchased as a powder and prepared by dissolving in PBS at 1 mg/mL. PI solutions were stored at 4° C. until use. Hoechst and PI were added directly to cell culture to 5 µg/mL and 10 µg/mL respectively. Cells were incubated at room temperature or at 37° C. for 10 minutes to allow for adequate uptake, and fluorescence observed using a NIKON Eclipse TE2000 inverted microscope and TE-FM Epi-Fluorescence attachment (Nikon Canada).

Frozen Storage of Cells

To freeze cells, cells were dissociated with trypsin-EDTA (Gibco) and resuspended in DMEM. Cells were pelleted by centrifugation at 1500 rpm for 5 minutes in a tabletop centrifuge (Sorvall® GLC-1, Sorvall, Newtown, Conn.), the supernatant aspirated, and cells resuspended in a freezing solution (DMEM supplemented with 20% FBS and 10% dimethyl sulfoxide (DMSO)). Cells were dispensed into 2 mL cryovials (Sarstedt) at 106-107 cells/mL and placed in a "Mr. Frosty" freezing container (Nalgene) at −80° C. (Forma −86C ULT freezer, Thermo Electron Corp.) for at least 2 hours. The contents of the container, when filled with isopropanol, experience a cooling rate of 1° C. per minute. Cells were transferred to a −140° C. liquid nitrogen freezer (Cryoplus 1, Forma Scientific) for long-term storage.

To thaw cells, the contents of the cryovial were rapidly warmed to 37° C. in a water bath (Precision® model 282, Thermo Electron Corp.) and added to pre-warmed DMEM (Gibco). Cells were pelleted by centrifugation at 1500 rpm for 5 minutes in a tabletop centrifuge (Sorvall® GLC-1, Sorvall), the supernatant aspirated, and cells resuspended in DMEM supplemented with 10% FBS (Gibco) and 1% antibiotic-antimycotic (Gibco).

Preparing poly-D-lysine Coated Plates

Poly-D-lysine (mw >300,000; Sigma-Aldrich) was purchased in its lyophilized powder form and stored at −20° C. until use. For 24-well plates, poly-D-lysine was diluted in water at 0.1 mg/mL and 250 µL dispensed into each well. Plates were incubated at 37° C. in a humidified incubator for at least 4 hours, the solution aspirated, wells washed twice with water, and allowed to dry. Coated plates were stored at 4° C. for up to three months.

Calcium Uptake and Cell Death Assays

Calcium Imaging with Fluo-3

Fluo-3 was purchased from Molecular Probes Inc. in its acetoxymethyl (AM) ester form. A 5 mM fluo-3 AM stock was prepared in DMSO and stored at −20° C. for up to several days. Pluronic® F-127 was purchased as a 10% solution in water (Molecular Probes Inc.). On the day of the experiment, a loading solution containing 5 µM fluo-3 AM and 0.02% pluronic in a HEPES buffered salt solution (HBSS; 121 mM NaCl, 5 mM KCl, 20 mM D-glucose, 10 mM HEPES acid, 10 mM HEPES-Na salt, 3 mM NaHCO$_3$, 1 mM Na-pyruvate, and 1.8 mM CaCl$_2$, pH adjusted to 7.4 with NaOH) was prepared by brief vortex followed by sonication (FS5; Fisher Scientific) for at least 2 minutes. Cells were washed with HBSS, loaded with fluo-3 AM by incubation at 37° C. for 30 minutes, and washed again to remove excess dye. Fluo-3 fluorescence was visualized using a NIKON Eclipse TE2000 inverted microscope and TE-FM Epi-Fluorescence attachment (Nikon Canada) or measured using a Fluoroskan Ascent FL microplate reader (λexcitation=485 nm, λemission=527 nm) and accompanying Ascent software (Thermo Electron Corp.).

Calcium Uptake Assay

Untransfected cells or cells transfected with the TRPM7/pTracer or ΔPDZ/pTracer construct were plated onto 24-well plates, 24-hours post-transfection. Untransfected cells were plated at 0.75×10$^6$ cells/well and transfected cells at 1×10$^6$ cells/well. The plates were coated with poly-D-lysine to strengthen cell adhesion and to minimize cell loss during washes. Cells were loaded by incubation with 5 µM fluo-3 AM and 0.02% pluronic in HBSS at 37° C. for 30 minutes. Following loading, cells were washed with an aglycaemic HBSS containing, in mM: 20 N-methyl-D-glucamine (NMDG), 121 NaCl, 5 KCl, 10 HEPES acid, 10 HEPES-Na salt, 3 NaHCO$_3$, 1 Na-pyruvate, and 1.8 CaCl$_2$, pH adjusted to 7.4 with HCl. Calcium uptake, as assessed by fluo-3 fluorescence, was measured in response to 0, 5, 10, 15, 20, or 25 mM sodium cyanide (NaCN; Mallinckrodt Baker Inc., Phillipsburg, N.J.) dissolved in aglycaemic HBSS. A 250 mM NaCN stock was prepared in water and stored at room temperature for up to 2 weeks. Measurements of fluo-3 fluorescence were taken over a 2 hour period at 10 minutes intervals at room temperature (22-25° C.). Calcium uptake assays were performed 48 hours post-transfection.

Cell Death Assay

Cell death, as assessed by PI uptake, was examined at the end of the 2 hour calcium uptake assay. Cells were stained with 10 µg/mL PI and PI fluorescence measured using the Fluoroskan microplate reader (λexcitation=590 nm, λemission=630 nm) and accompanying Ascent software (Thermo Electron Corp.). To obtain a reading of maximal fluorescence (Fmax), 0.5% Triton X-100 was added to each well and allowed to incubate for 20 minutes. Cell death assays were performed 48 hours post-transfection.

Data Analysis

Data was entered into Excel (Microsoft, Seattle, Wash.) or SigmaPlot (SPSS Inc., Chicago, Ill.) for analysis. Pooled data are presented as the mean of at least 3 separate experiments±sem. Calcium uptake is expressed as a fraction of baseline uptake: $\Delta Ft=(Ft-Fo)/Fo$ where Ft is the fluorescence at time t, and Fo is the fluorescence at baseline. Cell death is expressed as a percentage of total cell death: cell death (%)=Ft/Fmax×100 where Ft is the fluorescence at time t and Fmax is the maximal fluorescence obtained by permeabilization with Triton X-100. Concentration-response curves were fit by nonlinear regression with a 4 parameter logistic curve represented by the following equation: $y=min+\{(max-min)/[1+(x/EC50)n]\}$ where y is the response at concentration x, min is the minimal response, max is the maximal response, EC50 is the concentration required for half-maximal response, and n is the Hill slope. Statistical analysis of data was carried out with a two-tailed Student's t test, or a one-way analysis of variance (ANOVA) followed by post hoc pairwise multiple comparisons testing using the Holm-Sidak method, where appropriate.

Microscopy

Fluorescent and Light Microscopy

Cell cultures were observed using a NIKON Eclipse TE2000 inverted microscope (Nikon Canada), and images taken with a Hamamatsu ORCA-ER digital camera and SimplePCI© software (Compix, Cranberry Township, Pa.). Fluorescence was observed using the TE-FM Epi-Fluorescence attachment (Nikon Canada).

Results

Generation of TRPM7 Constructs

A Flag-TRPM7/pBluescript II KS construct (FIG. 27), containing the murine TRPM7 sequence (GenBank accession no. AY032591) conjugated to an in-frame N-terminal Flag epitope tag, was used as the basis for all manipulations in this project. For expression in a mammalian system, the full-length TRPM7 and ΔPDZ sequences were subcloned into the pTracer-CMV2 eukaryotic expression vector, in which transgene expression is driven by the cytomegalovirus (CMV) promoter (FIG. 28). The sequences were excised from their original pBluescript II KS cloning vectors and ligated with pTracer to generate the Flag-TRPM7/pTracer-CMV2 and Flag-ΔPDZ/pTracer-CMV2 constructs (hereafter abbreviated to TRPM7/pTracer and ΔPDZ/pTracer). The pTracer vector contains cDNA for enhanced green fluorescent protein (eGFP), allowing for visual identification of transfectants. eGFP expression is driven by a separate EF-1α promoter. An additional nonfluorescent construct was generated for the full-length TRPM7 sequence in which the eGFP gene and a portion of the preceding EF-1α promoter was excised from the pTracer vectors to generate TRPM7/pTracereGFP-(FIG. 28). This allowed for the use of the fluo-3 AM calcium indicator ($\lambda_{max\ of\ excitation/emission}$ at 506/526 nm respectively) in subsequent calcium imaging experiments.

Heterologous Expression in a Recombinant System

The HEK-293 tSA (293T) cell line was selected for heterologous expression of the TRPM7 constructs by transient transfection. Cells were transfected with one of the TRPM7/pTracer, or TRPM7/pTracereGFP-, constructs. Cells transfected with the eGFP-containing construct were used in assessing transfection efficiency while cells transfected with the corresponding nonfluorescent construct were used in calcium uptake and cell death assays. Because calcium uptake and cell death assays were performed 48 hours post-transfection, transfection efficiency was also assessed at this time point. FIG. 29 illustrates the transfection efficiencies that were achieved with TRPM7/pTracer in the 293T cell line. Cells were counterstained with Hoechst 33342 to allow for simultaneous visualization of eGFP expression and of untransfected cells. Transfection efficiency was quantified by cell count and expressed as a percentage of the total number of cells. Transfection efficiencies were approximately 60% of cells exhibiting eGFP expression.

It has been reported that heterologous overexpression of the full-length TRPM7 channel in a recombinant system results in swelling of cells, detachment from the culture surface, and subsequent cell death with 18-72 hours (Nadler et al., 2001; Su et al., 2006). Accordingly, we examined transfected cells by light microscopy at 24 and 48 hours post-transfection to assess cell health and general cell morphology. FIG. 29 illustrates the characteristic flat, triangular shape of untransfected 293T cells. The morphology of cells transfected with the TRPM7/pTracer, and TRPM7/pTracereGFP-constructs remained consistent with wild-type morphology for up to 48 hours post-transfection (FIG. 29). The difference in observation may be due to lower levels of TRPM7 expression in our system, or to the presence of Mg2+ in the culture medium.

Calcium Uptake Induced by Chemical Anoxia

We studied the effect of the TRPM7 constructs on calcium uptake induced by oxidative stress by using fluo-3 AM, a cell-permeant fluorescent calcium indicator. Untransfected 293T cells or cells transfected with the TRPM7/pTracereGFP- construct were loaded with fluo-3 AM and treated with 0, 5, 10, 15, 20, or 25 mM sodium cyanide (NaCN) in a glucose-free HEPES buffered salt solution (HBSS; glucose substituted with an equimolar amount of N-methyl-D-glucamine (NMDG)) to simulate anoxia/aglycaemia. Assessments of calcium uptake were performed 48 hours post-transfection.

Effect of the Full-length TRPM7 Construct

We began by comparing calcium uptake in cells expressing the TRPM7 construct (TRPM7/pTracereGFP-) to that in wild-type, untransfected cells. FIG. 30 and FIG. 31 and illustrate calcium uptake induced by NaCN treatment at 1 and 2 hour incubations. Data were analyzed by 2 separate means: by Student's t test, and by nonlinear regression with a 4-parameter logistic curve to determine the EC50 of the calcium uptake response. NaCN-induced calcium uptake occurs in a time- and concentration-dependent manner. Both untransfected cells and cells transfected with TRPM7/pTracereGFP-exhibited steady increases in intracellular Ca2+ levels over the 2 hour time period examined (time-dependence data not shown), with higher concentrations of NaCN inducing higher levels of [Ca2+]i.

Differences in calcium uptake between untransfected and TRPM7-transfected cells were also evident. At the 1 hour incubation, cells transfected with TRPM7/pTracereGFP-showed significantly higher levels of [Ca2+]i than untransfected cells at the 10 and 15 mM NaCN concentrations (FIG. 30). At 15 mM NaCN, for example, TRPM7-transfected cells exhibited a 1.12±0.07 fold increase in fluo-3 fluorescence while untransfected cells exhibited a 0.43±0.04 fold increase (p=1.08×10-5; data represent mean±sem of 5 and 4 separate experiments respectively). At 1 hour, the fitted dose-response curves for NaCN-induced calcium uptake yielded an EC50 value of 17.6±1.1 mM NaCN in TRPM7-transfected cells and 13.1±1.1 mM NaCN in untransfected cells (FIG. 30), indicating that the TRPM7 channel is more sensitive to activation by chemical anoxic stimuli than endogenous routes of calcium entry present in wild-type 293T cells. Likewise, at the 2 hour incubation, cells transfected with TRPM7/pTracereGFP-showed significantly higher levels of [Ca2+]i than untransfected cells at 5, 10, and 15 mM NaCN (FIG. 31). At 2 hours, the fitted dose-response curves for TRPM7-transfected and for untransfected cells yielded EC50 values of 12.5±1.1 mM NaCN and 15.7±1.0 mM NaCN respectively (FIG. 31). Heterologous expression of the TRPM7 channel in 293T cells likely confers greater sensitivity to NaCN treatment, resulting in greater increases in intracellular Ca2+ levels than those observed in untransfected cells.

At the 20 and 25 mM NaCN concentrations, cells transfected with TRPM7/pTracereGFP-exhibited lower or similar levels of [Ca2+]i than untransfected cells. At 25 mM NaCN, TRPM7-transfected cells exhibited a 2.11±0.05 fold increase in fluo-3 fluorescence while untransfected cells exhibited a 2.59±0.13 fold increase (p=0.006; data represent mean±sem of 5 and 4 separate experiments respectively). This result can be rationalized by examining the levels of cell death in TRPM7-transfected cells at 2 hours at these NaCN concentrations (FIG. 32). PI uptake, used as a measure of cell death, occurs when a cell exhibits compromised membrane integrity as in, for example, necrotic forms of cell death. Compromised membrane integrity also allows the cleaved form of the fluo-3 AM ester to leak out of cells, thereby resulting in inaccurate measurements of intracellular Ca2+ levels. The fluo-3 fluorescence measured at the 20 and 25 mM NaCN concentrations may only represent [Ca2+]i in the subset of viable cells remaining, and as such may not be directly comparable to the fluorescence measurements obtained for untransfected cells.

Cell Death Induced by Chemical Anoxia

We studied the effect of the TRPM7 construct on cell death induced by NaCN treatment by monitoring propidium iodide (PI) uptake. PI is a cell-impermeant molecule that is able to cross the lipid bilayer only when membrane integrity has been compromised (i.e. by cellular degeneration in response to oxidative stress). PI exhibits a 20- to 30-fold increase in fluorescence intensity upon associating with nucleic acids, and is commonly employed as an indicator of cell death. Untransfected cells and cells transfected with the TRPM7/pTracereGFP-construct were stained with PI following a 2 hour NaCN treatment. The same cells were used in both the calcium uptake and cell death assays, such that PI uptake was assessed immediately after the last fluo-3 measurement at 2 hours. Cells were then exposed to 0.5% Triton X-100 to permeabilize all cell membranes, allowing for the quantification of maximal PI fluorescence as a measure of complete (100%) cell death to which all PI uptake values were subsequently normalized.

Effect of the TRPM7 Construct

FIG. 32 illustrates the levels of cell death that were observed at 2 hours of NaCN treatment for untransfected and TRPM7-transfected cells. Statistical comparisons were made with one-way ANOVA followed by post hoc testing using the Holm-Sidak method for pairwise multiple comparisons where appropriate (P<0.05). At all concentrations of NaCN, cells transfected with TRPM7/pTracereGFP-exhibited significantly higher levels of cell death in comparison to untransfected cells. At 25 mM NaCN, for example, NaCN treatment induced 43.2±4.2% cell death in TRPM7-transfected cells while only 20.6±4.6% in untransfected cells (P=0.024, data represent the mean±sem of 5 and 4 separate experiments respectively). At 15 mM NaCN, untransfected cells exhibited 6.13±1.1%, and TRPM7-transfected cells 14.1±1.4% (data represent mean±sem of 4-5 experiments).

Membrane Translocation Sequences

A membrane translocation sequence/domain (MTD) is coupled to a fragment of the small molecule, preferably but not exclusively at fragment E. If the small molecule terminates at fragments D, C, or B, then an MTD may be covalently attached to fragments D, C, or B, respectively. The MTD may be coupled to the small molecule via an amide linkage, an ester linkage, a thioamide linkage or other form of covalent attachment. However, the MTD may not be attached to the P(0) carboxylate or phenyl since these functional groups are important modulating TRPM7 activity.

Example 4

TRPM7 Inhibitors can Block Ion Channel Function

To further understand the structure function relationships between the TRPM7 inhibitors identified in the TRPM7-dependent HEK death assay, the activity of a subset of these inhibitors described herein were tested for their ability to inhibit TRPM7 currents in cell systems. Whole-cell patch clamp recordings were used essentially as described to test the TRPM7 inhibitors in HEK293 cells, H9c2 cardiomyocytes and cultured neurons. Each test compound was tested at 0.3, 1, 3, 10 and 30 µM, or as high as solubility permits. FIGS. 34-40 show the TRPM7 currents in HEK 293 cells expressing TRPM7. FIG. 34 shows the baseline TRPM7 shaped curve, while FIGS. 35-40 show the effect of extracellular application of TRPM7 inhibitors M5, M6, M7, M11, M14 and M21. Results were similar for other cell lines. Each of these inhibitors reduces current through the TRPM7 channel, with M11 and M21 showing the highest level of inhibition. It should be noted, however, that TRPM7 is a large membrane protein that interacts with a number of other proteins and which contains a kinase domain. Thus, inhibition of channel activity is not a requisite activity for a TRPM7 inhibitor, and indeed some of the inhibitors identified in the HEK293 TRPM7-dependent death assay increase survival but do not appear to block TRPM7 currents at the concentrations tested (data not shown).

To examine selectivity of a subset of these TRPM7 inhibitors, experiments were performed to determine whether TRPM7 antagonists cross-react with other ionic channels and receptors. These results show the value of the compounds for studies of TRPM7 physiology, as the interpretation of results depends on target specificity. From a therapeutic perspective, knowledge of cross-reactivity of candidate drugs could shed light on other ischemic mechanisms and raise awareness of potential side effects. M21 has no effect on voltage-sensitive Na+, and Ca2+ currents in cultured cortical neurons of TRPM7-expressing HEK293 cells, but inhibits K+ currents by about 20% at membrane potentials of −10 mV. M21 had no effect on agonist-induced Ca2+ changes in HEK293 cells transfected with constructs for TRPM2, TRPM4, TRPM6, TRPV1, TRPC2 and TRPA1. M21 also has no effect on NMDA and AMPA receptor currents in cultured neurons. Thus, at concentrations sufficient to inhibit TRPM7 channel activity, M21 does not appear to block other ion channels tested aside from potassium currents. Similar experiments were performed with other TRPM7 inhibitors including M5 and M11. Both also displayed slight inhibition of potassium currents but did not affect sodium or calcium currents. Thus, these results suggest that inhibition of TRPM7 itself is likely the mechanism for the protection from ischemia and anti-proliferative effects observed for TRPM7 inhibitors. They also suggest that these inhibitors are unlikely to display side effects due to the blockade of other currents/ion channels at concentrations that inhibit TRPM7 activity.

To assess whether the M-compounds were inhibiting TRPM7 currents from an intracellular or extracellular location, M21 and M6 were dissolved in DMSO at 10 mM as stock, then diluted into intracellular recording fluid (ICF) to final concentration of 2 mM Immediately start recording of the TRPM7 like currents to RAMP change of membrane potentials after making the whole cell. Recording lasts for 10-20 minutes to compare the currents between control and test group. M21 and M6 applied intracellularly do not affect TRPM7 currents. The results indicate that the inhibitory effects of M21 and M6 we previously observed, when M compounds were applied extracellularly, were mainly via the interaction of M compounds on TRPM7 ion channels extracellular binding sites.

Representative Whole Cell Patch Clamp Buffer Compositions:

TRPM7 Currents Recording in HEK293 Cells

| Internal Solution (mM) | | Bath Solution (mM) | |
| --- | --- | --- | --- |
| Cs—Me—SO4 | 145 | NaCl | 140 |
| NaCl | 8 | KCl | 5 |
| KCl | 1 | CaCl2 | 2 |
| CaCl2 | 4.1 | HEPEs | 20 |
| EGTA | 10 | Glucose | 10 |
| HEPEs | 10 | pH 7.4 with NaOH | |
| ATP | 5 | 315 mOsm | |
| pH 7.4 with CsOH | | | |
| 300 mOsm | | | |

TRPM7 Currents Recording in H9c2 Cells

| Internal Solution (mM) | | Bath Solution (mM) | |
|---|---|---|---|
| Cs—Me—SO4 | 130 | NaCl | 135 |
| CsCl | 25 | CsCl | 5.4 |
| MgCl2 | 1 | CaCl2 | 1.8 |
| ATP-Na2 | 5 | NaH2PO4 | 0.33 |
| GTP-Na2 | 0.1 | MgCl2 | 0.9 |
| EGTA | 1 | HEPES | 10 |
| HEPES | 5 | Glucose | 10 |
| pH 7.4 with CsOH | | Nifedipine | 0.1 |
| 295 mOsm | | pH 7.4 with NaOH | |
| | | 320 mOsm | |

Example 5

Inhibition of TRPM7 in Cells Subjected to Oxygen and Glucose Deprivation Protects Cells from Dying Inhibition of TRPM7 has been described as a fundamental mechanism for the protection of neurons from anoxic damage (Aarts et al, 2003; Sun et al, 2009), which provides a wider time window of neuroprotection that other glutamate or L-type calcium channel inhibitors in models of anoxic damage to neurons. This application discloses that TRPM7 is fundamental to anoxic/ischemic damage in all cell lineages and that inhibition of TRPM7 in tissues of all lineages provides protection from cell death following anoxia, as well as compounds for said inhibition.

TRPM7 is expressed in all cell lines and tissues tested to date by RT-PCR or western blot (FIGS. 23, 24 and P).

Small Molecules M5, M6, M7, M11, M14 and M21 Block Anoxic Death in Murine Primary Neuronal Cell Cultures.

TRPM7 inhibitors were tested for their ability to reduce anoxic death in murine primary neuronal cell cultures subjected to 1 to 3 hours of OGD. This assay was generally performed as described by Aarts et al (2003). In brief, mixed cortical cultures enriched with neurons (85%) were prepared and used for experiments after 12-14 days in vitro. The cultures were transferred to an anaerobic chamber containing 5% CO2, 10% H and 85% N2. Cultures were washed 3× with 500 µl deoxygenated glucose free bicarbonate solution and maintained anoxic for the appropriate duration at 37° C. OGD was terminated by washing the cultures with oxygenated glucose-containing bicarbonate solution, and the cultures were further maintained 1-24 hours in a humidified 5% CO2 atmosphere. Cell death wash generally measured by fluorescence measurement of PI (50 ug/ml) in a multiwall plate reader (CytoFluor II, Perseptive Biosystems).

FIG. 69 shows that treatment of primary cultured mouse cortical cell cultures exposed to anoxic conditions with TRPM7 inhibitors can reduce the death associated with OGD in the presence or absence of MCN (a mixture of MK101, CNQX and Nimodipine to inhibit other glutamate channels). FIG. 69 shows that for M5, M6 and M21, protection of cultures from anoxic death is observed upon application of the TRPM7 inhibitor either prior to or following OGD. In a similar manner, FIGS. 55, 56 and 59 show that M5, M6 and M21 are able to provide protection to neuronal cultures following OGD. Although some of these experiments did not show the expected protection with the MCN cocktail, indicating that cells were not able to be rescued from death by blocking glutamate channels, we were able to observe benefit by TRPM7 inhibitors, indicating that TRPM7 inhibitors can provide protection even in cases where glutamate inhibitors are insufficient. This protection has been demonstrated for other TRPM7 inhibitors in this M series (M5, M6, M7, M11, M14 and M21).

TRPM7 Inhibitors Can Rescue Cells from Anoxic Death in a Large Number of Cell and Tissue Types.

The ability of TRPM7 inhibitors to protect other types of cell cultures following exposure to anoxia, including non-neuronal cell cultures, has also been tested. In general, cultures of growing cells are exposed to a 1-6 hour period of anoxia, followed by addition of a TRPM7 at a range of concentrations upon removal from anoxic conditions. FIGS. 41-44 demonstrate the ability of M5, M11 and M21 to promote survival of mixed retinal cell cultures (FIGS. 42, 43), H9c2 cardiomyocytes (FIG. 44) and cultured ex vivo retinal explants (FIG. 41) following exposure to OGD. FIG. 70 demonstrates that M5 and M21 can promote survival of hepatocyte cultures (AML12 cell line) exposed to either 2 hour, 4 hour or 6 hour anoxia. FIG. 71 demonstrates that M5, M6, M11 and M21 can all promote survival of H9c2 cardiomyocytes after exposure to anoxia, and that the addition of 1 µM Nifedipine, a calcium channel blocker used as an anti-anginal and anti-hypertensive medication, does not provide additional protection. FIG. 72 shows an additional example of the ability of M5 and M21 to promote survival of H9c2 cardiomyocytes exposed to anoxia, and demonstrates that the benefit is observed with either a 24 hour pre-treatment or post-treatment of the TRPM7 inhibitor M5. This implies that TRPM7 inhibitors may be useful both as a treatment for anoxic damage to patients presenting symptoms of a disorder associated with anoxic damage, or as a preventative measure. Such preventative measures can be chronic, such as treatment to protect against damage from heart attacks or strokes, or acute, to be given prior to or during surgical procedures, which may include but not be limited to procedures that involve endovascular invasion and have the possibility of dislodging material that may block blood flow through arteries. Other types of preventative measures can include the reduction of anoxic damage associated with cardiovascular issues (heart attack, myocardial infarction, acute ischemic attacks, atrial fibrillation, etc), brain disorders (stroke, neurotrauma, etc), diabetic disorders (blindness, deafness, neuropathy), retinal/eye disorders (glaucoma, macular degeneration, blindness), aural disorders (deafness, progressive deafness, hearing loss), muscle disorders (weakness, myodegenerative disease, disorders associated with mitochondrial depletion), and organ disorders (kidney, lung, liver disorders associated with ischemia or anoxic damage).

TRPM7 inhibitors are also shown herein to provide protection from anoxic damage in tissues. FIGS. 73 and 75 show that treatment with TRPM7 inhibitors reduces cell death associated with myocardial infarction and glaucoma, respectively, as described in subsequent examples.

Conclusions

TRPM7 is a fundamental mechanism through which ischemia occurs. Blocking TRPM7 reduces anoxic damage in all cell and tissue systems tested, and appears to be a fundamental method for protecting cells against the effects of oxygen and glucose deprivation. We have demonstrated that TRPM7 inhibitors are protective against anoxic damage in tissues derived from all tissue lineages (endodermal, mesodermal and ectodermal), including a wide range of differentiated cell types (neurons, fibroblasts, myocardial cells, hepatocytes, retinal ganglion cells, etc) and tissues (brain, heart, retina). Exemplary cells/tissue for each lineage in this invention include neurons/brain (ectodermal); heart, cardiomyocytes, and kidney (mesodermal) and hepatocytes/liver (endodermal). Thus, inhibition of TRPM7 is predicted to provide protection against all forms of anoxic damage, providing a broad spectrum of benefit across clinical indications involving anoxic damage or resulting in ischemia.

Example 6

Inhibition of TRPM7 Reduces Myocardial Ischemia

We examined the expression of various TRPM channels in different rat tissues including heart and brain (FIG. 23). TRPM2, 3 and 6 levels varied among the tissues, but TRPM7 expression was ubiquitous and, consistent with previous reports, showed high levels in heart. For in-vitro studies of cytoprotection we selected the H9c2 ventricular myoblast cell line. H9c2 cells are used extensively in studies of cardiac myocytes ischemia/reperfusion. Among the ischemic mechanisms elucidated to date are oxidative stress via ROS and reactive nitrogen species and the activation of pro-death signaling that parallel events triggered in neurons by TRPM7 activation. H9c2 cells exhibit TRPM7 expression by RT-PCR (FIG. 23), Western blotting and by immunochemistry (FIG. 24) and ionic currents that exhibit enhancement by low divalents, an outwardly rectifying I-V curve, and inhibition by TRPM7 antagonists (FIGS. 71 and 72), consistent with TRPM7. Treatment of cultured H9c2 cells with M5, M6, M11 or M21 (0.05-5.0 µM) enhanced their resilience to OGD (D) similarly to genetic TRPM7 suppression in neurons. Pre-treatment with M6 or M11 also provided protection against OGD-induced death; however, in the case of M6 it gave a comparable result to treatment after the onset of anoxia and in the case of M11 pre-treatment showed a less robust rescue of the OGD-induced death. Thus, inhibitors of TRPM7 are can prevent or reduce injury to cardiac tissues subjected to OGD or tissue ischemia.

In subsequent in-vivo testing, we evaluated the tolerability of increasing doses of compounds M5 and M21 applied intravenously to mice. No adverse effects were detected in all doses examined (up to 150 µM; IC50 for TRPM7 is ~1-2 µM), suggesting that systemic therapy with these compounds is feasible. Subsequently, mice aged 8-12 weeks were subjected to a mouse model of permanent LAD coronary artery ligation as described by Michael et al., *Am. J. Physiol.* 1995; 269: H2147-©-H2154) and modified by Yuan et alm *Journal of Medical Systems.* 2009:Internet Publication). M21 was applied as a single intravenous dose within 15 minutes of LAD occlusion. Infarct volume evaluation was performed at 24 h using routine methods. Treatment with M21 significantly reduced infarct volume across a range of doses as evaluated using triphenyl tetrazolium chloride (TTC; FIG. 33). A more detailed evaluation of the infarcted tissue using TUNEL staining revealed that M21 treatment also significantly reduced the number of cells exhibiting DNA fragmentation (FIG. 73). These groundbreaking data confirm the feasibility of addressing myocardial cell death in-vivo by blocking TRPM7 with small molecule inhibitors. Thus, inhibitors of TRPM7 can be used to treat any afflictions of the heart that result in ischemic damage. These can include, but are not limited to, myocardial infarction (MI), Heart attack, acute ischemic attacks, and acute coronary disorders.

Methods/Figures

H9c2 cells were cultured and subjected to OGD as described supra. FIG. 71 panels A and B show the results of exposure to M21 or M5 for 24 hours following 6 hours of OGD. FIG. 71 panels C and D show the results of H9c2cells were treated with either 1 mM $Mg^{2+}$, 5 µM M6, M11 (acute treatment) during the anoxic and recovery periods, or 1 µM nifedipine. Results are presented as mean±SEM (n=4). Treatment with Nifedipine does not appear to have an additive effect over treatment with TRPM7 inhibitors alone.

Example 7

Inhibition of TRPM7 Reduces Retinal Ischemic Damage

Acute and chronic retinal ischemia are major causes of blindness. Retinal damage from glaucoma, also termed "slow excitotoxicity" afflicts millions of people each year and is the second leading cause of blindness worldwide (after cataracts). Diabetic retinopathy is also very common, afflicting about 40% of diabetics and, while less commonly producing complete blindness, is a leading cause of visual impairment. The retina is an extension of the CNS, and was the first organ in which excitotoxicity was described. This invention discloses TPRM7 antagonists that can inhibit anoxic retinal damage. To examine this, we cultured primary retinal ganglion cells (RGCs) and organotypic whole retinas from neonatal rat pups by standard methods and exposed them to OGD (1 or 3 hours). Cell death was evaluated by PI fluorescence (shown) and by LDH release assays that showed similar results (not shown). Our data indicate that treating RGCs with TRPM7 antagonists after as much as a 3 h OGD insult provided dramatic cytoprotection, saving as much as 66% of the cell death when compared to cells having been exposed to a 3 hr OGD insult in the absence of TRPM7 inhibitors (FIG. 74 panel A). Treatment with 5 µM M5, M6 or M21 was more protective than treatment with an ERK inhibitor U0126 or a PSD-95 inhibitor (NA-1). Similarly, treating whole retinal explants with any of these TRPM7 antagonists enhanced their resilience to OGD (FIG. 74 panel B). These data illustrate, with multiple inhibitors of TRPM7, for the first time, that despite the major role of glutamate receptors in the retina, TRPM7 channels govern an overriding process that, when blocked, inhibits ischemic retinal cell death. This underscores our earlier discussion that inhibiting TRPM7 is a ubiquitous mechanism for the reduction of ischemic damage.

We next tested whether direct intraocular injection of M21 could reduce retinal damage evoked by raising the intraocular pressure (IOP) in rats (80 mm Hg 1 hour; Morrison J C. Elevated intraocular pressure and optic nerve injury models in the rat. *J Glaucoma.* 2005; 14:315-317). M21 was micro-injected into the vitreous humor directly, to control for any blood-brain-barrier penetration issues. Histological evaluation of the retina at 7-14 days revealed a significant reduction in retinal damage in the M21-treated eye (FIG. 75 panel B). These provocative data suggest that TRPM7 antagonists are useful in retinal diseases as well as strokes, cardiac disorders, ischemia and cancer. The compounds of this invention can be used for the treatment of retinal disorders. Preferably these compounds are delivered orally, as an injection (intravenous, intraocular), or administered topically. This model of glaucoma can be used to assess the different routes of administration for these compounds Example 8

TRPM7 Inhibitors for the Treatment of Cancer

We first observed that TRPM7 inhibitors can reduce proliferation of cancerous cells under standard growth conditions when using Y79 retinoblastoma cells. Treatment of these cells with 1-7.5 µM M6 resulted in the death of the cancer cells in 48-72 hours as measured by MTT assay (FIG. 76 panel A). In contrast, M6 is not toxic to either regular primary neurons in that concentration range (data not shown), or to NIH3T3 fibroblast cells (FIG. 82). This result was confirmed in a second retinoblastoma cell line (Weri cells), which also showed a similar dose response curve to M6 (FIG. 76 panel B).

This effect was next demonstrated in ex-vivo retinal explant models. Retinal explants were surgically dissected and cultured by standard methods. One hundred thousand Y79 retinoblastoma cells were then seeded onto the retinas in culture and allowed to grow for 2 weeks on inserts in the presence or absence of 5 µM M6. Y79 cells were fluorescently labeled and intensity was counted (arbitrary fluorescence units). M6 was able to reduce the amount of Y79 cells on the cultured retinas (FIG. 77 panel A). Further, M6 also significantly reduced the ability of Y79 cells to migrate off of the retina (FIG. 77 panel B). This suggests that M6, and other TRPM7 inhibitors, are effective at reducing both the proliferation and migration of cancer cells. TRPM7 inhibitors may be useful in the reduction of tumor metastasis in addition to either reducing the proliferation or killing of cancer cells. FIG. 78 is a repetition of the experiment, observing the distribution of Y79 cells after 12 days of migration off the retina. The darker bars of each pair indicate fluorescence intensity of cells that have migrated off the retina. M6 treated cultures (1 µM) have significantly lower Y79 fluorescence off of the retinal explant.

To determine the breadth of efficacy in cancers, we examined the efficacy of a range of TRPM7 inhibitors for their ability to inhibit cell proliferation in cancer cell lines. Representative figures are included as examples. FIG. 79 shows that both M6 and M7 can significantly reduce proliferation of both HeLa cervical cancer cells and SW13 adrenal carcinoma cells (as measured by BrDU incorporation). FIG. 80 shows that M6, M7 and M11 can all reduce proliferation of MCF-7 and MDA-MB231 breast cancer cells. FIG. 81 shows that M5, M6 and M11 can all reduce the proliferation of melanoma cell lines B16F1 and B16F10. Similar results were observed for the cell lines presented in Table 4 with >20% inhibition of proliferation at 48-96 hours observed at or less than or equal to a single 10 µM drug application, as determined by either MTT test, SRB test, luminescence (Cell-gro) or BrDU incorporation.

TABLE 4

| TRPM7 Inhibitor | Demonstrated Reduction of Proliferation at or below 10 µM Inhibitor concentration |
| --- | --- |
| M5 | Y79 and Weri retinoblastoma, MCF-7 and MDA-MB231 breast cancer, B16F1 and B16F10 melanoma, SW13 adrenal carcinoma, HeLa cervical cancer, |
| M6 | Y79 and Weri retinoblastoma, MCF-7 and MDA-MB231 breast cancer, B16F1 and B16F10 melanoma, SW13 adrenal carcinoma, HeLa cervical cancer, U2OS osteosarcoma, DMS53 Lung cancer, DMS456 lung cancer, H292 non small cell lung cancer, HCT-116 colon cancer, A375 melanoma, RXF-393 renal |
| M7 | Weri retinoblastoma |
| M11 | Y79 and Weri retinoblastoma, MCF-7 and MDA-MB231 breast cancer, B16F1 and B16F10 melanoma, SW13 adrenal carcinoma, HeLa cervical cancer, U2OS osteosarcoma, DMS53 Lung cancer, |
| M14 | Weri retinoblastoma |
| M21 | Weri retinoblastoma |

TABLE 5

Mean $IC_{50}$ for M6 in human and murine tumor cell lines

| Cell Line | | Test Agent M6 |
| --- | --- | --- |
| H292 | Exp 1 | 18.5 µM |
| | Exp 2 | 15.9 µM |
| | Mean $IC_{50}$ | 17.2 µM |
| RXF393 | Exp 1 | 5.3 µM |
| | Exp 2 | 8.1 µM |
| | Mean $IC_{50}$ | 6.7 µM |
| Y79 | Exp 1 | 36.3 µM |
| | Exp 2 | 38.6 µM |
| | Mean $IC_{50}$ | 37.5 µM |
| HCT-116 | Exp 1 | 14.7 µM |
| | Exp 2 | 17.2 µM |
| | Mean $IC_{50}$ | 16.0 µM |
| A375 | Exp 1 | 12.6 µM |
| | Exp 2 | 14.2 µM |
| | Mean $IC_{50}$ | 13.4 µM |
| B16-F10 | Exp 1 | 16.5 µM |
| | Exp 2 | 14.3 µM |
| | Mean $IC_{50}$ | 15.6 µM |

To differentiate between an anti-proliferative effect of the TRPM7 inhibitors and cellular toxicity, the compounds were added to various 'non-cancerous' cell lines at the same concentrations and the percentage of PI uptake was measured after 72 hours. No significant toxicity was observed in NIH3T3 fibroblasts (FIG. 82). This was also true for compounds tested in H9c2 cardiomyocytes, although slight toxicity was observed for M7 and M11 at 10 µM. No toxicity was observed at 5 µM.

Total protein was also isolated from all of the cell lines tested using standard methods and a western blot was performed using an anti-TRPM7 antibody. All cell lines displayed TRPM7 expression, suggesting that the TRPM7 inhibitors are acting through TRPM7 (FIG. 83). As a further confirmation, siRNA was used as described previously to knock down expression of TRPM7 in B16F1 and B16F10 melanoma cell lines. Both cell lines showed a dose dependent reduction in proliferation in TRPM7 knock down samples when compared to scrambled siRNA controls (FIG. 84). Thus, blocking or eliminating TRPM7 is useful for the treatment of cancer.

To evaluate the efficacy of TRPM7 inhibitors in vivo, M6 was selected to for a pilot evaluation of its ability to reduce tumor formation in a murine tumor model of B16F10 melanoma and a RXF-393 human renal cell carcinoma xenograft model of tumor proliferation. First, a maximum tolerated dose study was performed that demonstrated M6 was tolerated in mice at concentrations up to the highest tested (20 mg/kg). For each tumor model, an appropriate number of cells were injected into the right flank (~3-5 million cells per animal in 0.1 ml 50% matrigel/50% media). When tumor sizes reached 100-150 mg, animals were randomized into control (vehicle only), positive control or M6. M6 was given by intravenous injection to 20 mg/kg once daily. Tumors were measured and the weights were calculated by standard means. FIG. 85 shows the results of daily M6 injection on melanoma tumor growth. M6 reduces tumor growth in animals with active melanomas. A similar trend was observed in the renal cancer xenograft tumor formation model, further supporting that TRPM7 inhibitors have broad anti-proliferative activity across cancer types.

General Methods
Cell Proliferation Studies

Cells (Table 1) were grown to 70% confluency, trypsinized, counted, and seeded in 96-well flat-bottom plates at a final concentration of $2.5 \times 10^3$-$5.0 \times 10^3$ cells/well in growth media containing 5% FBS (Day 0). Other well sizes and cell densities were used successfully as well. Cells were allowed to incubate in growth media for 24 hours to allow for maximum adhesion. Treatment with the test agent began on Day 1 and continued for 72 hours either with or without retreatment. At the 72 hour time point, viable cell numbers are quantified by the CellTiter-Glo® cell viability assay as described above, or using standard MTT, SRB or BrDU assays. Experiments were repeated at least twice with the same concentrations to determine growth inhibitory activity. Results from the dose response of these studies were used to calculate an $IC_{50}$ value (concentration that effectively inhibits cell growth by 50 percent of control) for each agent.

Data Collection—For the cell proliferation studies, data from each experiment was collected and expressed as % Cell Growth using the following calculation:

% Cell Growth=$(f_{test}/f_{vehicle}) \times 100$

Where $f_{test}$ is the luminescent signal of the tested sample, and $f_{vehicle}$ is the luminescence of the vehicle in which the drug is dissolved (or appropriate measure for the other viability/proliferation measures). Dose response graphs and $IC_{50}$ values were generated using standard software using the following variable slope equation:

$$Y = \frac{(Top - Bottom)}{(1 + 10^{((logIC50-X)-HillSlope)})}$$

Where X is the logarithm of concentration and Y is the response. Y starts at the Bottom and goes to Top with a sigmoid shape.

Conclusion

Inhibition of TRPM7 with small molecule inhibitors reduce the proliferation of a wide range of cancers at non-toxic concentrations, and thus are effective anti-cancer agents for cancers arising from many different mechanisms. Similar to the role of TRPM7 in ischemia, the data suggest that TRPM7 plays a fundamental role in cancer cell proliferation, and that inhibition of TRPM7 provides an effective treatment for a wide range of cancers including all of those demonstrated herein.

Example 9

TRPM7 Inhibitors for the Treatment of Pain

In addition to the assays described above, TRPM7 inhibitors have been tested in a rodent model of formalin induced inflammatory pain. M21 treatment provided a statistically significant reduction in pain behaviors in rats after intravenous administration. FIG. 68 demonstrates that the TRPM7 inhibitor M21 suppresses formalin-induced pain behaviors in rats with i.v. administration. FIG. 68 shows a time course of flinches induced by formalin (2.5%; 50 μL into the plantar hindpaw) with M21 or with saline as a negative control. M21 significantly reduced formalin-induced phase 2 pain (9-60 min) but showed little effect at the concentrations tested in reducing phase 1 (0-8 min) flinches.

M21 and other TRPM7 inhibitors are able to treat pain. This model is indicative of both neuropathic and inflammatory pain, and thus would be suitable for the treatment of these types of pain in humans. It is likely that these inhibitors are effective in other types of pain as well.

TABLE 1

Baseline Properties of TRPM7 post-ischemic, and Age-matched, non-ischemic, non TRPM7 deficient, neurons.

|  | shTRPM7 + 4VO (n = 8) | Age-matched controls (n = 8) | P = (t-test, unpaired, 2-tailed) |
|---|---|---|---|
| $V_m$ | −60.5 ± 1.0 | −58.9 ± 0.85 | 0.23 |
| $R_m$ | 94.2 ± 10.5 | 121.6 ± 14.3 | 0.14 |
| $C_m$ | 288.0 ± 41.9 | 340.2 ± 28.2 | 0.32 |
| AP amplitude | 82.0 ± 4.3 | 96.3 ± 2.5 | 0.01 |
| AP half-width | 2.21 ± 0.08 | 2.00 ± 0.08 | 0.08 |
| Threshold for AP | 135.0 ± 62.5 | 126.9 ± 23.8 | 0.81 |
| AHP amplitude | −6.0 ± 0.6 | −6.5 ± 0.7 | 0.59 |
| Depolarizing sag | 7.8 ± 0.5 | 10.7 ± 1.5 | 0.09 |

TABLE 2

Screens of LOPAC and Prestwick Libraries

| | | LOPAC | | | |
|---|---|---|---|---|---|
| | | | Verification | | Overlap with |
| ID | Name | B Score | Ratio | P-value | Dose-Response | Prestwick |
| 1 | Benoxathian hydrochloride | −10.32 | 0.358996 | <0.01 | Yes | |
| 3 | Cantharidin | −10.178 | 0.772445 | <0.05 | | |
| 5 | CGP-74514A hydrochloride | −7.96 | 0.654331 | <0.01 | Yes | |
| 6 | Chelidamic acid | −12.502 | 1.286922 | <0.05 | Yes | |
| 11 | L-703,606 oxalate | −8.636 | 0.372984 | <0.01 | Yes | |
| 12 | Mitoxantrone | −7.587 | 0.249987 | <0.01 | Yes | Yes |
| 17 | Naftopidil dihydrochloride | −7.535 | 0.223104 | <0.01 | Yes | |
| 19 | Quinacrine dihydrochloride | −5.516 | 0.825398 | <0.01 | Yes | |
| 20 | Sanguinarine chloride | −6.158 | 0.802864 | <0.01 | | |
| 22 | Trequinsin hydrochloride | −8.81 | 0.253421 | <0.01 | Yes | |

TABLE 2-continued

Screens of LOPAC and Prestwick Libraries

Prestwick

| ID | Name | B Score | Verification Ratio | P-value | Dose-Response | Overlap with Lopac |
|----|------|---------|--------------------|---------|---------------|--------------------|
| p1 | Colchicine | −7.343 | 0.672327 | <0.01 | | |
| p2 | Nicardipine hydrochloride | −7.543 | 0.665052 | <0.01 | Yes | |
| p3 | Mitoxantrone dihydrochloride | −10.068 | 0.138097 | <0.01 | | Yes |
| p4 | Anisomycin | −6.683 | 0.426478 | <0.01 | Yes | |
| p5 | Betulinic acid | −6.069 | 0.883082 | <0.05 | Yes | |
| p7 | Cephaeline dihydrochloride heptahydrate | −7.927 | 0.227091 | <0.01 | | |
| p8 | Digoxin | −5.938 | 0.724764 | <0.01 | Yes | |
| p9 | Doxorubicin hydrochloride | −9.315 | 0.458793 | <0.01 | Yes | |
| p11 | Puromycin dihydrochloride | −5.573 | 0.590477 | <0.01 | Yes | |
| p12 | Daunorubicin hydrochloride | −5.68 | 0.459813 | <0.01 | Yes | |
| p13 | Ciclopirox ethanolamine | −5.075 | 0.422749 | <0.01 | Yes | |
| p15 | Piperlongumine | −9.599 | 0.735448 | <0.05 | Yes | |
| p22 | Lasalocid sodium salt | −5.54 | 0.689066 | <0.01 | | |
| p23 | Ethaverine hydrochloride | −9.238 | 0.081422 | <0.01 | Yes | |
| p24 | Cantharidin | −9.671 | 0.374645 | <0.01 | | Yes |
| p26 | Naftopidil dihydrochloride | −8.736 | 0.13459 | <0.01 | | Yes |

All of the compositions and methods disclosed and claimed herein can be made and executed without undue experimentation in light of the present disclosure. While the compositions and methods of this invention have been described in terms of preferred embodiments, variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. All citations including literature, patent documents, accession numbers and the like are incorporated by reference in their entirety for all purposes to the same extent as so individually denoted. If more than one sequence is associated with an accession number at different times, the sequence associated with the accession number as of Dec. 11, 2009 is meant. Unless otherwise apparent from the context any step, embodiment, or feature of the invention can be used in combination with any other.

Reference List

Aarts et al., (2003) Cell 115, 863-877.
Aarts et al., (2002) Science 298, 846-850.
Aarts & Tymianski (2005a). Neuroscientist. 11, 116-123.
Aarts & Tymianski (2005b) Pflugers Arch.
Alvarez et al. (2006) J. Neurosci. 26, 7820-7825.
Bennett et al. (1996) Cold Spring Harbor Symposia on Quantitative Biology 61, 373-384.
Block (1999) Prog. Neurobiol. 58, 279-295.
Bonavita et al. (2003) FEBS Lett. 536, 85-91.
Brideau et al., (2003) J. Biomol. Screen. 8, 634-647.
Bridge et al., (2003). Nat. Genet. 34, 263-264.
Cheng et al., (2006). J. Neurosci. 26, 3713-3720.
Coaxum et al. (2007) Am. J. Physiol Heart Circ. Physiol 292, H2220-H2226.
Corish and Tyler-Smith (1999) Protein Eng 12, 1035-1040.
Davis et al. (1997) Lancet 349, 32.
Du et al. (1996) J. Cereb. Blood Flow Metab 16, 195-201.
Ekht et al. (1999) Circ. Res. 85, e70-e77.
Elbashir et al. (2001) Nature 411, 494-498.
Fanselow (1980) Pavlov. J. Biol. Sci. 15, 177-182.
Fiorillo et al. (2006) Cell Mol. Life. Sci. 63, 3061-3071.
Gavrieli et al. (1992). J Cell Biol 119, 493-501.
Hanano et al. (2004) J. Pharmacol. Sci 95, 403-419.
Harteneck et al. (2000) Trends Neurosci. 23, 159-166.
Hausenloy and Scorrano (2007) Clin. Pharmacol. Ther. 82, 370-373.
Hescheler et al. (1991) Circ. Res. 69, 1476-1486.
Jiang et al. (2008) Brain Res. Bull. 76, 124-130.
Jiang, Li, and Yue (2005) J. Gen. Physiol 126, 137-150.
Kimes and Brandt (1976) Exp. Cell Res. 98, 367-381.
Kirino, T (2000) Neuropathology. 20 Suppl, S95-S97.
Kumar et al. (2001). J. Neurochem. 77, 1418-1421.
Lawlor et al. (2007) Mol. Neurodegener. 2, 11.
Lees et al. (2000) Lancet 355, 1949-1954.
Levrand et al. (2006) Free Radic. Biol. Med. 41, 886-895.
Lin et al. (2004) J. Am. Coll. Nutr. 23, 556S-560S.
Lipinski et al. (2001) Adv. Drug Deliv. Rev. 46, 3-26.
Lipton (1999). Physiol Rev. 79, 1431-1568.
Lisman et al. (2002) Nat. Rev. Neurosci. 3, 175-190.
Lo et al. (2003) Nat. Rev. Neurosci. 4, 399-415.
Lo et al. (2005) Stroke 36, 189-192.
Mastakov et al. (2001). Mol. Ther. 3, 225-232.
Monteilh-Zoller et al. (2003). J. Gen. Physiol 121, 49-60.
Montell et al. (2002) Cell 108, 595-598.
Morris et al. (1999) J. Neurosurg. 91, 737-743.
Morris et al. (1984) J. Neurosci. Methods 11, 47-60.
Mullen et al. (1992) Development 116, 201-211.
Nadler et al. (2001) Nature 411, 590-595.
Paxinos and Watson (1998). The Rat Brain in Stereotaxic Coordinates. Academic Press).
Petito et al. (1987) Neurology 37, 1281-1286.
Pulsinelli and Brierly (1979). Stroke 10, 267-272.
Pulsinelli et al. (1982). Ann Neurol 11, 491-498.
Rod and Auer (1992). Stroke 23, 725-732.
Rothman and Olney (1986). Ann Neurol 19, 105-111.
Runnels et al. (2001). Science 291, 1043-1047.
Runnels et al. (2002). Nat. Cell Biol. 4, 329-336.
Sakamoto et al. (1998) Biochem. Biophys. Res. Commun. 251, 576-579.
Sattler (1998) J Neurochem 71, 2349-2364.

Schmitz et al. (2005) J. Biol. Chem. 280, 37763-37771.
Schmitz et al. (2003). Cell 114, 191-200.
Schwarze et al. (1999) Science 285, 1569-1572.
Silver and Erecinska (1990) J Gen Physiol 95, 837-866.
Sledz et al. (2003) Nat. Cell Biol. 5, 834-839.
Su et al. (2006) J. Biol. Chem. 281, 11260-11270.
Sun et al. (2006) J. Neurophysiol. 95, 2590-2601.
Tian et al. (2007) Neurosci. Lett. 419, 93-98.
Volpe et al. (1985) Neurology 35, 1793-1797.
Volpe et al. (1984) Stroke 15, 558-562.
Wei et al. (2007) Proc. Natl. Acad. Sci. U.S.A 104, 16323-16328.
Whitlock et al. (2006) Science 313, 1093-1097.
Zordoky and El-Kadi (2007) J. Pharmacol. Toxicol. Methods 56, 317-322.

What is claimed is:

1. A method of inhibiting, reducing or delaying neuronal cell death or a cognitive deficit resulting from ischemia in a patient, comprising administering to a patient having or at risk of ischemia an effective regime of a compound or a pharmaceutically acceptable salt thereof or a pharmaceutically acceptable composition comprising the compound wherein the compound is of Formula VI

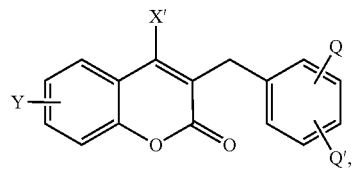

wherein
X' is hydrogen, or $C_1$-$C_6$ alkyl,
Y is hydroxyl or $C_1$-$C_6$ alkoxy, and
Q and Q' are halogen.

2. The method of claim 1, wherein said compound is

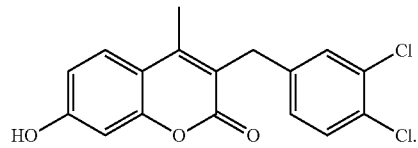 [SMILES: Cc1c(Cc2ccc(Cl)c(Cl)c2)c(=O)oc2cc(O)ccc12]

3. The method of claim 1, wherein the ischemia is cardiac, renal, retinal or CNS ischemia.

* * * * *